United States Patent
Song et al.

(10) Patent No.: US 10,988,519 B2
(45) Date of Patent: Apr. 27, 2021

(54) COMPOSITION AND METHOD FOR TREATING COMPLEMENT-MEDIATED DISEASE

(71) Applicant: The Trustees of the University of Pennsylvania, Philadelphia, PA (US)

(72) Inventors: Wenchao Song, Bryn Mawr, PA (US); Damodar Gullipalli, Philadelphia, PA (US); Takashi Miwa, Bala Cynwyd, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 452 days.

(21) Appl. No.: 15/762,721

(22) PCT Filed: Sep. 23, 2016

(86) PCT No.: PCT/US2016/053347
§ 371 (c)(1),
(2) Date: Mar. 23, 2018

(87) PCT Pub. No.: WO2017/053732
PCT Pub. Date: Mar. 30, 2017

(65) Prior Publication Data
US 2019/0177381 A1 Jun. 13, 2019

Related U.S. Application Data

(60) Provisional application No. 62/232,008, filed on Sep. 24, 2015.

(51) Int. Cl.
| | | |
|---|---|---|
| C12N 15/85 | (2006.01) | |
| C07K 14/47 | (2006.01) | |
| A61K 48/00 | (2006.01) | |
| A61K 47/69 | (2017.01) | |
| A61P 7/04 | (2006.01) | |

(52) U.S. Cl.
CPC ........ *C07K 14/472* (2013.01); *A61K 47/6911* (2017.08); *A61K 48/00* (2013.01); *A61K 48/005* (2013.01); *A61P 7/04* (2018.01); *C12N 15/85* (2013.01); *C12N 2750/14143* (2013.01); *C12N 2750/14171* (2013.01)

(58) Field of Classification Search
CPC .. A61K 47/6911; A61K 48/00; A61K 48/005; A61P 7/04; C12N 15/85; C12N 2750/14143
See application file for complete search history.

(56) References Cited

U.S. PATENT DOCUMENTS

| | | |
|---|---|---|
| 5,139,941 A | 8/1992 | Muzyczka et al. |
| 5,478,745 A | 12/1995 | Samulski et al. |
| 5,741,683 A | 4/1998 | Zhou et al. |
| 6,057,152 A | 5/2000 | Samulski et al. |
| 6,204,059 B1 | 3/2001 | Samulski et al. |
| 6,268,213 B1 | 7/2001 | Samulski et al. |
| 6,491,907 B1 | 12/2002 | Rabinowitz et al. |
| 6,596,535 B1 | 7/2003 | Carter |
| 6,660,514 B1 | 12/2003 | Zolotukhin et al. |
| 6,951,753 B2 | 10/2005 | Shenk et al. |
| 7,094,604 B2 | 8/2006 | Snyder et al. |
| 7,125,717 B2 | 10/2006 | Carter |
| 7,172,893 B2 | 2/2007 | Rabinowitz et al. |
| 7,201,898 B2 | 4/2007 | Monahan et al. |
| 7,229,823 B2 | 6/2007 | Samulski et al. |
| 7,282,199 B2 | 10/2007 | Gao et al. |
| 7,439,065 B2 | 10/2008 | Ferrari et al. |
| 7,456,683 B2 | 11/2008 | Takano et al. |
| 7,588,772 B2 | 9/2009 | Kay et al. |
| 7,790,449 B2 | 9/2010 | Gao et al. |
| 7,906,111 B2 | 3/2011 | Wilson et al. |
| 8,319,480 B2 | 11/2012 | Ko et al. |
| 8,962,330 B2 | 2/2015 | Gao et al. |
| 8,962,332 B2 | 2/2015 | Gao et al. |
| 2007/0036760 A1 | 2/2007 | Wilson et al. |
| 2008/0221011 A1 | 9/2008 | Gilkeson et al. |
| 2009/0197338 A1 | 8/2009 | Vandenberghe et al. |
| 2010/0009393 A1* | 1/2010 | Morgan .............. C07K 16/18 435/7.92 |
| 2013/0045186 A1 | 2/2013 | Gao et al. |
| 2013/0296255 A1 | 11/2013 | Hageman |

(Continued)

FOREIGN PATENT DOCUMENTS

| | | |
|---|---|---|
| EP | 1310571 | 2/2006 |
| RU | 2417099 C2 | 4/2011 |

(Continued)

OTHER PUBLICATIONS

Duffy et al entitled "The Human Complement Regulator Factor H Binds Pneumococcal Surface Protein PspC via Short Consensus Repeats 13 to 15" (Infection And Immunity, Oct. 2002, vol. 70, No. 10, pp. 5604-5611). (Year: 2002).*

Kumar-Singh et al. entitled "Rescue of Complement Mediated Pathology in a Murine Model of Macular Degeneration by Adenovirus-Mediated Delivery of the Alternative Pathway Regulator, Factor H". (Invest Ophthalmol Vis Sci.; Apr. 2014, vol. 55, p. 1319). (Year: 2014).*

Barata et al., Deletion of Crry and DAF on murine platelets stimulates thrombopoiesis and increases fH-dependent resistance of peripheral platelets to complement attack, J. Immunol, vol. 190(6):2886-95, Feb. 2013.

(Continued)

*Primary Examiner* — Catherine S Hibbert
(74) *Attorney, Agent, or Firm* — Howson & Howson LLP

(57) ABSTRACT

Provided herein is a recombinant viral vector having packaged therein an expression cassette comprising an engineered complement regulator factor H (fH), wherein the gene encodes a hfH protein variant comprising short consensus repeats (SCRs) 1-4, 6-8, and 17-20. Pharmaceutical compositions containing this vector and plasmids comprising nucleic acid sequences that encode the fH protein variant are also provided.

23 Claims, 38 Drawing Sheets
Specification includes a Sequence Listing.

(56) References Cited

U.S. PATENT DOCUMENTS

| | | | |
|---|---|---|---|
| 2015/0110766 A1* | 4/2015 | Lambris | A61P 43/00 424/94.5 |
| 2015/0139975 A1 | 5/2015 | Schmidt et al. | |
| 2017/0190753 A1* | 7/2017 | Abache | A01K 67/0275 |
| 2018/0230488 A1 | 8/2018 | Hinderer et al. | |

FOREIGN PATENT DOCUMENTS

| | | | |
|---|---|---|---|
| WO | WO-2003/042397 | 5/2003 | |
| WO | WO-2005/033321 | 4/2005 | |
| WO | WO-2006/088950 | 8/2006 | |
| WO | WO-2006/110689 | 10/2006 | |
| WO | WO 2007056227 A2 | 5/2007 | |
| WO | WO-2011/107591 | 9/2011 | |
| WO | WO-2011/126808 | 10/2011 | |
| WO | WO-2011/163412 | 12/2011 | |
| WO | WO-2011163412 A1 * | 12/2011 | A61P 3/10 |
| WO | WO-2013/049493 | 4/2013 | |
| WO | WO-2013/142362 | 9/2013 | |
| WO | WO-2013142362 A1 * | 9/2013 | C07K 14/472 |
| WO | WO-2014/124282 | 8/2014 | |
| WO | WO-2015/012924 | 1/2015 | |
| WO | WO 2015/092335 | 6/2015 | |
| WO | WO 2017/072515 | 5/2017 | |
| WO | WO 2020/210480 | 10/2020 | |

OTHER PUBLICATIONS

Beltran et al., rAAV2/5 gene-targeting to rods:dose-dependent efficiency and complications associated with different promoters, Gene Therapy, vol. 17(9):1162-74, Apr. 2010.

Buning et al., Recent developments in adeno-associated virus vector technology, J. Gene Med., vol. 10(7):717-733, Jul. 2008.

Cai et al., A 350 bp region of the proximal promoter of Rds drives cell-type specific gene expression, Exp Eye Res., vol. 91(2):186-94, Aug. 2010.

Dunkelberger, et al., C5aR Expression in a Novel GFP Reporter Gene Knockin Mouse: Implications for the Mechanism of Action of C5aR Signaling in T Cell Immunity, J Immunol., vol. 188(8):4032-4042, Apr. 2012.

Fakhouri et al., Treatment with human complement factor H rapidly reverses renal complement deposition in factor H-deficient mice, Kidney International, vol. 78(3):279-286, May 2010.

Fee et al., PEG-proteins: Reaction engineering and separation issues, Chemical Engineering Science, vol. 61(3):924-939, Feb. 2006.

Fridkis-Hareli et al., Design and development of TT30, a novel C3d-targeted C3/C5 convertase inhibitor for treatment of human complement alternative pathway-mediated diseases, vol. 118(17):4705-13, Aug. 2011.

Gao, et al., Adeno-associated viruses undergo substantial evolution in primates during natural infections, Proc. Natl. Acad. Sci. U.S.A., vol. 100(10):6081-6086, May 2003.

GenBank Accession No. AY327580, *Homo sapiens* rhodopsin kinase gene, promoter region, exon 1 and partial cds, Jul. 2016.

GenBank Accession No. YP_077180, capsid protein [Adeno-associated virus-8], Aug. 2018.

Mowat et al., Tyrosine capsid-mutant AAV vectors for gene delivery to the canine retina from a subretinal or intravitreal approach, Gene Therapy, vol. 21:96-105, Jan. 2014.

Grieger & Samulski, Adeno-associated virus as a gene therapy vector: Vector development, production and clinical applications, Adv. Biochem. Engin/Biotechnol., vol. 99:119-145, Oct. 2005.

Fisher et al., J. Virol., Transduction with recombinant adeno-associated virus for gene therapy is limited by leading-strand synthesis, vol. 70:520-532, Jan. 1996.

Kachi et al., Equine Infectious Anemia Viral Vector-Mediated Codelivery of Endostatin and Angiostatin Driven by Retinal Pigmented Epithelium-Specific VMD2 Promoter Inhibits Choroidal Neovascularization, Human Gene Therapy, vol. 20(1):31-9, Jan. 2009.

Kay et al, Targeting Photoreceptors via Intravitreal Delivery Using Novel, Capsid-Mutated AAV Vectors, PLoS One., vol. 8(4): e62097, Apr. 2013.

Kimura et al., Genetic and therapeutic targeting of properdin in mice prevents complement-mediated tissue injury, J Clin Invest., vol. 120(10):3545-54, Oct. 2010.

Kimura et al., Activator-specific requirement of properdin in the initiation and amplification of the alternative pathway complement, Blood, vol. 111(2):732-40, Jan. 2008 (Epub Oct. 2007).

Kumar-Singh et al., Rescue of Complement Mediated Pathology in a Murine Model of Macular Degeneration by Adenovirus-Mediated Delivery of the Alternative Pathway regulator, Factor H, Invest Opthalmol Vis. Sci., vol. 55:1319, Apr. 2014.

Lambard et al., Expression of Rod-Derived Cone Viability Factor: Dual Role of CRX in Regulating Promoter Activity and Cell-Type Specificity, PLoS One, vol. 5(10):e13025, Oct. 2010.

Lesher et al., Combination of factor H mutation and properdin deficiency causes severe C3 glomerulonephritis, J Am Soc Nephrol., vol. 24(1):53-65, Jan. 2013 (Epub Nov. 2012).

Liu et al, Enhancing the secretion of recombinant proteins by engineering N-glycosylation sites, Biotech Prog, vol. 25(5): 1468-1475, Sep.-Oct. 2009.

McCarty et al., Self-complementary recombinant adeno-associated virus (scAAV) vectors promote efficient transduction independently of DNA synthesis, Gene Therapy, vol. 8(16):1248-1254, Aug. 2001.

Miyatake et al., Transcriptional targeting of herpes simplex virus for cell-specific replication, J. Virol., vol. 71:5124-32, Jul. 1997.

Morrissey et al., PRE-1, a cis element sufficient to enhance cone- and rod-specific expression in differentiating zebrafish photoreceptors, BMC Dev. Biol, vol. 11:3, Jan. 2011.

Mussolino et al., AAV-mediated photoreceptor transduction of the pig cone-enriched retina, Gene Ther, vol. 18(7):637-45, Mar. 2011.

Nichols et al., An extended mini-complement factor H molecule ameliorates experimental C3 glomerulopathy, Kidney Int., vol. 88(6):1314-1322, Dec. 2015 (ePub Jul. 2015).

Nicoud et al., Development of photoreceptor-specific promoters and their utility to investigate EIAV lentiviral vector mediated gene transfer to photoreceptors, J. Gene Med, vol. 9(12):1015-23, Dec. 2007.

Sola et al., Glycosylation of therapeutic proteins: an effective strategy to optimize efficacy, BioDrugs, vol. 24(1):9-21, Feb. 2010.

Sandig et al., Hbv-derived promoters direct liver-specific expression of an adenovirally transduced LDL receptor gene, Gene Ther., vol. 3(11):1002-9, Nov. 1996.

Shu et al., Functional Characterization of the Human RPGR Proximal Promoter, IOVS, vol. 53:3951-3958, Jun. 2012.

Miwa et al., Complement-dependent T-cell lymphopenia caused by thymocyte deletion of the membrane complement regulator Crry, Blood, vol. 113(12):2684-2694, Mar. 2009.

Thomson et al, A comprehensive comparison of multiple sequence alignments, Nucl. Acids. Res., vol. 27(13):2682-2690, Jul. 1999.

Zhang et al., Adenovirus-adeno-associated virus hybrid for large-scale recombinant adeno-associated virus production, Human Gene Therapy, vol. 20(9):922-929, Sep. 2009.

International Search Report issued on International Patent Application No. PCT/US2016/053347, dated Mar. 23, 2017.

Written Opinion issued on International Patent Application No. PCT/US2016/053347, dated Mar. 23, 2017.

Examination Report dated Jun. 26, 2020 in European Patent Application No. 16849709.7.

Office Action dated Jul. 22, 2020 in Japanese Patent Application No. 2018-515539.

Gullipalli, et al., Therapeutic efficacy of AAV-mediated factor H gene transfer in a murine model of lethal C3 glomerulopathy, Molecular Immunology, 102, Oct. 2018, p. 157.

Search Report and Office Action dated Feb. 25, 2020 in Russian Patent Application No. 2018114907.

Response to Communication in European Patent Application No. 16849709.7, filed Feb. 11, 2020.

(56) References Cited

OTHER PUBLICATIONS

Estaller et al, Human complement factor H: Two factor H proteins are derived from alternatively spliced transcripts, Eur J Immunol., vol. 21(3):799-802, Mar. 1991.

Rodríguez et al., High-efficiency deleter mice show that FLPe is an alternative to Cre-loxP, Nat Genet., vol. 25(2):139-40, Jun. 2000.

Hebecker et al., An engineered construct combining complement regulatory and surface-recognition domains represents a minimal-size functional factor H. J Immunol. Jul. 15, 2013;191(2):912-21. doi: 10.4049/jimmunol.1300269. Published online Jul. 3, 2013.

A partial supplementary European search report issued in the corresponding European counterpart Application No. 16849709.7 and dated Feb. 27, 2019.

Supplementary European Search Report and Search Opinion issued in European Patent Application No. 16849709.7, dated Jul. 17, 2019.

Applicant's Reply to Communication pursuant to Article 94(3) EPC in European Patent Application 16 849 709.7, filed Oct. 28, 2020.

\* cited by examiner

Fig 1A

Fig 1B

```
Atgagacttctagcaaagattatttgccttatgttatgggctatttgtgtagcagaagat    signal peptide
 M  R  L  L  A  K  I  I  C  L  M  L  W  A  I  C  V  A  E  D
tgcaatgaacttcctccaagaagaaatacagaaattctgacaggttcctggtctgaccaa
 C  N  E  L  P  P  R  K  N  T  E  I  L  T  G  S  W  S  D  Q
Acatatccagaaggcacccaggctatctataaatgcagccctggatatagatctcttgga   SCR1
 T  Y  P  E  G  T  Q  A  I  Y  K  C  R  P  G  Y  R  S  L  G
aatataataatggtatgcaggaagggagaatgggttgtctttaatccattaaggaaatgt
 N  I  I  M  V  C  R  K  G  E  W  V  L  F  N  P  L  R  K  C
cagaaaaggccctgtggacatcctggagatactcctttttggtacttttacccttacagga
 Q  K  R  P  C  G  H  P  G  D  T  P  F  G  T  F  T  L  T  G
Ggaaatgtgtttgaatatggtgtaaaagctgtgtatacatgtaatgaggggtatcaattg   SCR2
 G  N  V  F  E  Y  G  V  K  A  V  Y  T  C  N  E  G  Y  Q  L
ctaggtgagattaattaccgtgaatgtgacacagatggatggaccaatgatattcctata
 L  G  E  I  N  Y  R  E  C  D  T  D  G  W  T  N  D  I  P  I
tgtgaagttgtgaagtgtttaccagtgacagcaccagagaatggaaaaattgtcagtagt
 C  E  V  V  K  C  L  P  V  T  A  P  E  N  G  K  I  V  S  S
Gcaatggaaccagatcgggaatacatttttggacaagcagtacggtttgtatgtaactca   SCR3
 A  M  E  P  D  R  E  Y  H  F  G  Q  A  V  R  F  V  C  N  S
ggctacaagattgaaggagatgaagaaatgcattgttcagacgatggttttggagtaaaa
 G  Y  K  I  E  G  D  E  E  M  H  C  S  D  D  G  F  W  S  K
gagaaaccaaagtgtgtggaaatttcatgcaaatcccagatgtatataaatggatctcct
 E  K  P  K  C  V  E  I  S  C  K  S  P  D  V  I  N  G  S  P
Atatctcagaagattatttataaggagaatgaacgatttcaatataaatgtaacatgggt   SCR4
 I  S  Q  K  I  I  Y  K  E  N  E  R  F  Q  Y  K  C  N  M  G
tatgaatacagtgaaagggaagatgctgtatgcactgaatctggatggcgtccgttgcct
 Y  E  Y  S  E  R  G  D  A  V  C  T  E  S  G  W  R  P  L  P
tcatgtgaagaaaaatcatgtgataatccttatattccaaatggtgactactcacctta
 S  C  E  E  K  S  C  D  N  P  Y  I  P  N  G  D  Y  S  P  L
Aggattaaacacagaactggagatgaaatcacgtaccagtgtagaaatggtttttatcct  SCR5
 R  I  K  H  R  T  G  D  E  I  T  Y  Q  C  R  N  G  F  Y  P
gcaacccggggaaatacagccaaatgcacaagtactggctggatacctgctccagatgt
 A  T  R  G  N  T  A  K  C  T  S  G  W  I  P  A  P  R  C
accttgaaaccttgtgattatccagacattaaacatggaggtctatatcatgagaatatg
 T  L  K  P  C  D  Y  P  D  I  K  H  G  G  L  Y  H  E  N  M
```

FIG 1C

```
Cgtagaccatactttccagtagctgtaggaaaatattactcctattactgtgatgaacat      SCR6
 R  R  P  Y  F  P  V  A  V  G  K  Y  Y  S  Y  Y  C  D  E  H
tttgagactccgtcaggaagttactgggatcacattcattgcacacaagatggatggtcg
 F  E  T  P  S  G  S  Y  W  D  H  I  H  C  T  Q  D  G  W  S
ccagcagtaccatgcctcagaaaatgttatttccttatttggaaaatggatataatcaa
 P  A  V  P  C  L  R  K  C  Y  F  P  Y  L  E  N  G  Y  N  Q
Aattatggaagaaagtttgtacagggtaaatctatagacgttgctgccatcctggctac      SCR7
 N  Y  G  R  K  F  V  Q  G  K  S  I  D  V  A  C  H  P  G  Y
gctcttccaaaagcgcagaccacagttacatgtatggagaatggctggtctcctactcca
 A  L  P  K  A  Q  T  T  V  T  C  M  E  N  G  W  S  P  T  P
agatgcatccgtgtcaaaacatgttccaaatcaagtatagatattgagaatgggtttatt
 R  C  I  R  V  K  T  C  S  K  S  S  I  D  I  E  N  G  F  I
Tctgaatctcagtatacatatgccttaaaagaaaaagcaaaatatcaatgcaaactagga    SCR8
 S  E  S  Q  Y  T  Y  A  L  K  E  K  A  K  Y  Q  C  K  L  G
tatgtaacagcagatggtgaaacatcaggatcaattacatgtgggaaagatggatggtca
 Y  V  T  A  D  G  E  T  S  G  S  I  T  C  G  K  D  G  W  S
gctcaaccacgtgcattaaatcttgtgatatccagtatttatgaatgccagaactaaa
 A  Q  P  T  C  I  K  S  C  D  I  P  V  F  M  N  A  R  T  K
Aatgacttcacatggtttaagctgaatgacacattggactatgaatgccatgatggttat    SCR9
 N  D  F  T  W  F  K  L  N  D  T  L  D  Y  E  C  H  D  G  Y
gaaagcaatactggaagcaccactggttccatagtgtgtggttacaatggttggtctgat
 E  S  N  T  G  S  T  T  G  S  I  V  C  G  Y  N  G  W  S  D
ttacccatatgttatgaaagagaatgcgaacttcctaaaatagatgtacacttagttcct
 L  P  I  C  Y  E  R  E  C  E  L  P  K  I  D  V  H  L  V  P
gatcgcaagaaagaccagtataaagttggagaggtgttgaaattctcctgcaaaccagga
 D  R  K  K  D  Q  Y  K  V  G  E  V  L  K  F  S  C  K  P  G   SCR10
tttacaatagttggacctaattccgttcagtgctaccactttggattgtctcctgacctc
 F  T  I  V  G  P  N  S  V  Q  C  Y  H  F  G  L  S  P  D  L
ccaatatgtaaagagcaagtacaatca gtggtcaacctcctgacctccaatgggaa
 P  I  C  K  E  Q  V  Q  S  C  G  P  P  P  E  L  L  N  G  N
Gttaaggaaaaacgaaggagaatatgcacagtgaagtggtggaatattattgcaat       SCR11
 V  K  E  K  T  K  E  E  Y  G  H  S  E  V  V  E  Y  Y  C  N
cctagatttctaatgaagggacctaataaatccatgtgttgatggagagtggacaat
 P  R  F  L  M  K  G  P  N  K  I  Q  C  V  D  G  E  W  T  T
ttaccagtgtgt attgtggaggagagtacctgtggagatataccctgaacttgaacatgga
 L  P  V  C  I  V  E  E  S  T  C  G  D  I  P  E  L  E  H  G
Tggcccagctttcttcccctccttattactatggagattcagtggaattcaattgctca    SCR12
```

FIG 1D

```
         W  A  Q  L  S  S  P  P  Y  Y  Y  G  D  S  Y  F  N  C  S
gaatcatttacaatgattggacacagatcaattacgtgtattcatggagtatggacccaa
         E  S  F  T  M  I  G  H  R  S  I  T  C  I  N  G  V  W  Q
cttccccagtgtgtggcaatagataaacttaagaagtgcaaatcatcaaatttaattata
         L  P  Q  C  V  A  I  D  K  L  K  K  C  K  S  S  N  L  I  I
Cttgagaacatttaaaaaacaagaaggaattcgatcataattctaacataaggtacaga    SCR13
         L  E  N  L  K  N  K  K  E  F  D  H  N  S  N  I  R  Y  R
tgtagaggaaaagaaggatggatacacacagtctgcataaatggaagatgggatccagaa
         C  R  G  K  E  G  W  I  H  T  V  C  I  N  G  R  W  D  P  E
gtgaactgctcaatggcacaaatacaattatgcccacctccacctcagattcccaattct
         V  N  C  S  M  A  Q  I  Q  L  C  P  P  P  P  Q  I  P  N  S
Cacaatatgacaaccacactgaattatcgggatggagaaaaagtatctgttctttgccaa    SCR14
         H  N  M  T  T  L  N  Y  R  D  G  E  K  V  S  V  L  C  Q
gaaaattatctaattcaggaaggagaagaaattacatgcaaagatggaagatggcagtca
         E  N  Y  L  I  Q  E  G  E  E  I  T  C  K  D  G  R  W  Q  S
ataccactctgtgttgaaaaaattccatgttcacaaccacctcagatagaacacggaacc
         I  P  L  C  V  E  K  I  P  C  S  Q  P  P  Q  I  E  H  G  T
Attaattcatccaggtcttcacaagaaagttatgcacatgggactaaattgagttatact    SCR15
         I  N  S  S  R  S  S  Q  E  S  Y  A  H  G  T  K  L  S  Y  T
tgtgagggtggtttcaggatatctgaagaaaatgaaacaacatgctacatgggaaaatgg
         C  E  G  G  F  R  I  S  E  E  N  E  T  T  C  Y  M  G  K  W
agttctccacctcagtgtgaaggccttccttgtaaatctccacctgagatttctcatggt
         S  S  P  P  Q  C  E  G  L  P  C  K  S  P  P  E  I  S  H  G
Gttgtagctcacatgtcagacagttatcagtatggagaagaagttacgtacaaatgttt    SCR16
         V  V  A  H  M  S  D  S  Y  Q  Y  G  E  E  V  T  Y  K  C  F
gaaggttttggaattgatgggcctgcaattgcaaaatgcttaggagaaaaatggtctcac
         E  G  F  G  I  D  G  P  A  I  A  K  C  L  G  E  K  W  S  H
cctccatcatgcataaaaacagattgtctcagtttacctagctttgaaaatgccataccc
         P  P  S  C  I  K  T  D  C  L  S  L  P  S  F  E  N  A  I  P
Atgggagagaagaaggatgtgtataaggcgggtgagcaagtgacttacacttgtgcaaca    SCR17
         M  G  E  K  K  D  V  Y  K  A  G  E  Q  V  T  Y  T  C  A  T
tattacaaaatggatggagccagtaatgtaacatgcattaatagcagatggacaggaagg
         Y  Y  K  M  D  G  A  S  N  V  T  C  I  N  S  R  W  T  G  R
ccaacatgcagagacacctcctgtgtgaatccaccaacagtacaaaatgcttatatagtg
         P  T  C  R  D  T  S  C  V  N  P  P  T  V  Q  N  A  Y  I  V
Tcgagacagatgagtaaatacccatctggtgagagagtaaggtatcaatgtaggagccct    SCR18
         S  R  Q  M  S  K  Y  P  S  G  E  R  V  R  Y  Q  C  R  S  P
```

Fig 1E

```
catgaaatgtttggggatgaagaagtgatgtgttaaatggaaactggacggaaccacct
 Y  E  M  F  G  D  E  V  M  C  L  N  G  N  W  T  E  P  P
caatgcaaagattctacaggaaaatgtgggcccctccacctattgacaatggggacatt
 Q  C  K  D  S  T  G  K  C  G  P  P  P  I  D  N  G  D  I
Acttcattcccgttgtcagtatatgctccagcttcatcagttgagtaccaatgccagaac     SCR19
 T  S  F  P  L  S  V  Y  A  P  A  S  S  V  E  Y  Q  C  Q  N
ttgtatcaacttgagggtaacaagcgaataacatgtagaaatggacaatggtcagaacca
 L  Y  Q  L  E  G  N  K  R  I  T  C  R  N  G  Q  W  S  E  P
ccaaaatgcttacatccgtgtgtaatatcccgagaaattatggaaaattataacatagca
 P  K  C  L  H  P  C  V  I  S  R  E  I  M  E  N  Y  N  I  A
Ttaaggtggacagccaaacagaagctttattcgagaacaggtgaatcagttgaatttgtg     SCR20
 L  R  W  T  A  K  Q  K  L  Y  S  R  T  G  E  S  V  E  F  V
tgtaaacggggatatcgtctttcatcacgttctcacacattgcgaacaacatgttgggat
 C  K  R  G  Y  R  L  S  S  R  S  H  T  L  R  T  T  C  W  D
gggaaactggagtatccaacttgtgcaaaaagatag
 G  K  L  E  Y  P  T  C  A  K  R  -
```

Fig 2A

FIG 2B

```
Atgagacttctagcaaagattatttgccttatgttatgggctatttgtgtagcagaagat    SignalPeptide
 M  R  L  A  K  I  I  C  L  M  L  W  A  I  C  V  A  E  D
tgcaatgaacttcctccaagaagaaatacagaaattctgacaggttcctggtctgaccaa
 C  N  E  L  P  P  R  N  T  E  I  L  T  G  S  W  S  D  Q
Acatatccagaaggcacccaggctatctataaatgccgccctggatatagatctcttgga   SCR1
 T  Y  P  E  G  T  Q  A  I  Y  K  C  R  P  G  Y  R  S  L  G
aatataataatggtatgcaggaaggagaatgggttgctcttaatccattaaggaaatgt
 N  I  I  M  V  C  R  K  G  E  W  V  A  L  N  P  L  R  K  C
cagaaaaggccctgtggacatcctggagatactccttttggtacttttaccttacagga
 Q  K  R  P  C  G  H  P  G  D  T  P  F  G  T  F  T  L  T  G
Ggaaatgtgtttgaatatggtgtaaaagctgtgtatacatgtaatgagggggtatcaattg
 G  N  V  F  E  Y  G  V  K  A  V  Y  T  C  N  E  G  Y  Q  L   SCR2
ctaggtgagattaattaccgtgaatgtgacacagatggatggaccaatgatattcctata
 L  G  E  I  N  Y  R  E  C  D  T  D  G  W  T  N  D  I  P  I
tgtgaagttgtgaagtgtttaccagtgacagcaccagagaatggaaaaattgtcagtagt
 C  E  V  V  K  C  L  P  V  T  A  P  E  N  G  K  I  V  S  S
Gcaatggaaccagatcgggaataccattttggacaagcagtacggtttgtatgtaactca
 A  M  E  P  D  R  E  Y  H  F  G  Q  A  V  R  F  V  C  N  S   SCR3
ggctacaagattgaaggagatgaagaaatgcattgttcagacgatggttttggagtaaa
 G  Y  K  I  E  G  D  E  E  M  H  C  S  D  D  G  F  W  S  K
gagaaaccaaagtgtgtggaaatttcatgcaaatccccagatgttataaatggatctcct
 E  K  P  K  C  V  E  I  S  C  K  S  P  D  V  I  N  G  S  P
Atatctcagaagatttattaaggagaatgaacgatttcaatataaatgtaacatgggt
 I  S  Q  K  I  I  Y  K  E  N  E  R  F  Q  Y  K  C  N  M  G   SCR4
tatgaatacagtgaaagaggagatgctgtatgcactgaatctggatggcgtccgttgcct
 Y  E  Y  S  E  R  G  D  A  V  C  T  E  S  G  W  R  P  L  P
Tcatgtgaagaaaaatca
 S  C  E  E  K  S
accttgaaacctgtgattatccagacattaaacatggaggtctatatcatgagaatatg
 T  L  K  P  C  D  Y  P  D  I  K  H  G  G  L  Y  H  E  N  M
cgtagaccatacttccagtagctgtaggaaaatattactcctattactgtgatgaacat
 R  R  P  Y  F  P  V  A  V  G  K  Y  Y  S  Y  Y  C  D  E  H   SCR6
tttgagactccgtcaggaagttactgggatcacattcattgcacacaagatggatggtcg
```

FIG 2C

```
ccagcagtaccatgcctcagaaaatgttatttccttatttggaaaatggatataatcaa
 P  A  V  P  C  L  R  K  C  Y  F  P  Y  L  E  N  G  Y  N  Q
Aattatggaagaaagtttgtacagggtaaatctatagacgttgcctgccatcctggctac
 N  Y  G  R  K  F  V  Q  G  K  S  I  D  V  A  C  H  P  G  Y      SCR7
gctcttccaaaagcgcagaccacagttacatgtatggagaatggctggtctcctactcc
 A  L  P  K  A  Q  T  T  V  T  C  M  E  N  G  W  S  P  T  P
agatgcatccgtgtcaaaacatgttccaaatcaagtatagatattgagaatggtttatt
 R  C  I  R  V  K  T  C  S  K  S  S  I  D  I  E  N  G  F  I
Tctgaatctcagtatacatatgccttaaaagaaaaagcaaaatatcaatgcaaactagga
 S  E  S  Q  Y  T  Y  A  L  K  E  K  A  K  Y  Q  C  K  L  G      SCR8
tatgtaacagcagatggtgaaacatcaggatcaattacatgtgggaaagatggatggtca
 Y  V  T  A  D  G  E  T  S  G  S  I  T  C  G  K  D  G  W  S
gctcaaccacgtgcattaaatctaaagattctacaggaaaatgtgggcccctccacct
 A  Q  P  T  C  I  K  S  K  D  S  T  G  K  C  G  P  P  P
attgacaatggggacattActtcattcccgttgtcagtatatgctccagcttcatcagtt
 I  D  N  G  D  I  T  S  F  P  L  S  V  Y  A  P  A  S  S  V
gagtaccaatgccagaacttgtatcaacttgagggtaacaagcgaataacatgtagaaat
 E  Y  Q  C  Q  N  L  Y  Q  L  E  G  N  K  R  I  T  C  R  N     SCR19
ttgtatcaacttgagggtaacaagcgaataacatgtagaaatggacaatggtcagaacca
 L  Y  Q  L  E  G  N  K  R  I  T  C  R  N  G  Q  W  S  E  P
ccaaaatgcttacatccgtgtgtaatatcccgagaaattatggaaaattataacatagca
 P  K  C  L  H  P  C  V  I  S  R  E  I  M  E  N  Y  N  I  A
Ttaaggtggacagccaaacagaagctttattcgagaacaggtgaatcagttgaatttgtg
 L  R  W  T  A  K  Q  K  L  Y  S  R  T  G  E  S  V  E  F  V     SCR20
tgtaaacggggatatcgtctttcatcacgttctcacacattgcgaacaacatgttggat
 C  K  R  G  Y  R  L  S  S  R  S  H  T  L  R  T  T  C  W  D
gggaaactggagtatccaacttgtgcaaaaagatag
 G  K  L  E  Y  P  T  C  A  K  R  -
```

FIG 3A

```
1 GGACGTTGTGAACAGAGTTAGCTGGTAAATGTCCTCTTAAAAGATCCAAAAA     52
  atgagactTctagcaaagattatttgccttatgttatgggctatttgtgtagcagaagattgcaatgaac  122
  ttcctccaagaagaaatacagaaattctgacaggttcctggtctgaccaaacatatccagaaggcaccca  192
  Ggctatctataaatgccgccctggatatagatctcttggaaatataataatggtatgcaggaaggagaa  262
  Tggqttgctcttaatccattaaggaaatgtcagaaaaggccctgtggacatcctggagatactccttttg  332
  gtacttttacccttacaggaggaaatgtGtttgaatatggtgtaaaagctgtgtatacatgtaatgaggg  402
  gtatcaattgctaggtgaGattaattaccgtgaatgtgacacagatggatggaccaatgatattcctata  472
  tgtgaagttgtgaagtgtttaccagtgacagcaccagagaatggaaaaattgtcagtagtgcaatggaac  542
  cagatcgggaataccattttggacaagcagtacggtttgtatgtaactcaggctacaagattgaaggaga  612
  tgaagaaatgcattgttcagacgatggttttggagtaaagagaaaccaaagtgtgtggaaatttcatgc  682
  aaatccccagatgttataaatggatctcctatatctcagaagattatttataaggagaatgaacgatttc  752
  aatataaatgtaacatgggttatgaatacagtgaaagaggagatgctgtatgcactgaatctggatggcg  822
  tccgttgccttcatgtgaagaaaaatcaaccttgaaaccttgtgattatccagacattaaacatggaggt  892
  ctatatcatgagaatatgcgtagaccatactttccagtagctgtaggaaaatattactcctattactgtg  962
  atgaacattttgagactccgtcaggaagttactgggatcacattcattgcacacaagatggatggtcgcc  1032
  agcagtaccatgcctcagaaaatgttatttccttatttggaaaatggatataatcaaaattatggaaga  1102
  aagtttgtacagggtaaatctatagacgttgcctgccatcctggctacgctcttccaaaagcgcagacca  1172
  cagttacatgtatggagaatggctggtcTcctactcccagatgcatccgtgtcaaacatgttccaaatc  1242
```

FIG 3B

Aagtatagatattgagaatgggtttatttctgaatctcagtatacatatgccttaaaagaaaaagcgaaa 1312
Tatcaatgcaaactaggatatgtaacagcagatggtgaaacatcaggatcaattagatgtgggaaagatg 1382
Gatggtcagctcaacccacgtgcattaaatctaaagattctacaggaaaatgtgggccccctccacctat 1452
Tgacaatggggacattacttcattcccgttgtcagtatatgctccagcttcatcagttgagtaccaatgc 1522
Cagaacttgtatcaacttgagggtaacaagcgaataacatgtagaaatggacaatggtcagaaccaccaa 1592
Aatgcttacatccgtgtgtaatatccgagaaattatggaaaattataacatagcattaaggtggacagc 1662
Caaacagaagctttattcgagaacaggtgaatcagttgaatttgtgtgtaaacggggatatcgtctttca 1732
Tcacgttctcacacattgcgaacaacatgttgggatgggaaactggagtatccaacttgtgcaaaaagat 1802
agAATCAATCATAAAGTGCACACCTTTATTCAGAACTTTAGTATTAAATCAGTTCTCAATTTCATTTTTT 1872
ATGTATTGTTTTACTCCTTTTTATTCATACGTAAAATTTTGGATTAATTTGTGAAAATGTAATTATAAGC 1942
TGAGACCGGTGGCTCTCTTCTTAAAAGCACCATATTAAATCCTGGAAAACTAAAAAAAAAAAAAAAAAAA 2012
AAAAAAAAAAAAAAAAAAAAAAAAAAAAAAAAAAAAAAAAAAAAAAAAAAAAAAA 2068

Fig 4 hfH1-4.678.19-20 protein amino acid sequence

<u>MRLLAKIICLMLWAICVA</u>EDCNELPPRRNTEILTGSWSDQTYPEGTQAIYKCRPGYRSLGNVIMVCRKGE
WVALNPLRKCQKRPCGHPGDTPFGTFTLTGGNVFEYGVKAVYTCNEGYQLLGEINYRECDTDGWTNDI
PICEVVKCLPVTAPENGKIVSSAMEPDREYHFGQAVRFVCNSGYKIEGDEEMHCSDDGFWSKEKPKCVE
ISCKSPDVINGSPISQKIIYKENERFQYKCNMGYEYSERGDAVCTESGWRPLPSCEEKSTLKPCDYPDKHG
GLYHENMRRPYFPVAVGKYYSYYCDEHFETPSGSYWDHIHCTQDGWSPAVPCLRKCYFPYLENGYNQN
HGRKFVQGKSIDVACHPGYALPKAQTTVTCMENGWSPTPRCIRVKTCSKSSIDIENGFISESQYTYALKEK
AKYQCKLGYVTADGETSGSIRCGKDGWSAQPTCIKSKDSTGKCGPPPPIDNGDITSFPLSVYAPASSVEYQ
CQNLYQLEGNKRITCRNGQWSEPPKCLHPCVISREIMENYNIALRWTAKQKLYSRTGESVEFVCKRGYRL
SSRSHTLRTTCWDGKLEYPTCAKR

Fig 5A

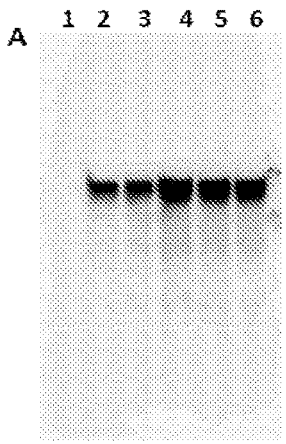

1: Con
2: pCMV Sport6-1
3: pCMV Sport6-2
4: pCBARBG-1
5: pCBARBG-2
6: pCBARBG-3

Fig 5B

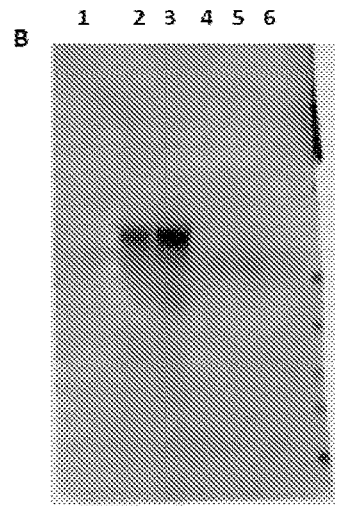

1: Con
2: pCBARBG-1
3: pAAV Cl1
4: pAAV Cl2
5: pAAV Cl3
6: pAAV Cl4

1: hfH 0.5ug
2: hfH 1-4.678.19-20 0.5ug(prep1)
3: hfH 1-4.678.19-20 0.5ug(prep2)
4: hfH 0.25ug
5: hfH 1-4.678.19-20 0.25ug(prep1)
6: hfH 1-4.678.19-20 0.25ug(prep2)
7: hC3b +fI Control FIG 10
FIG 11
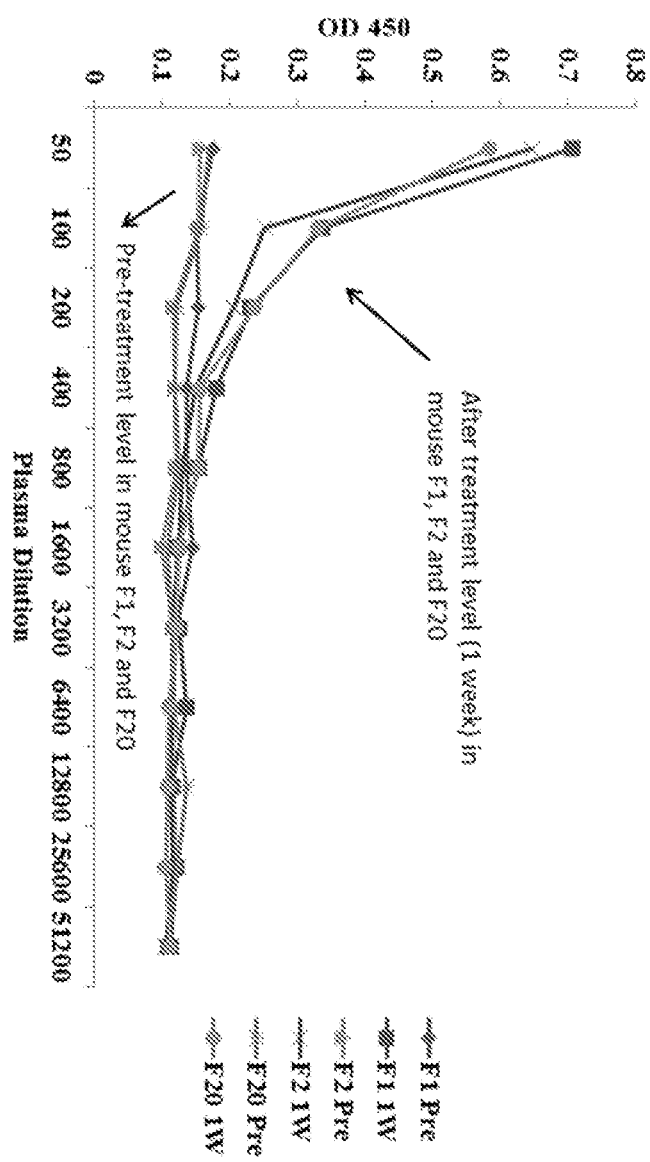
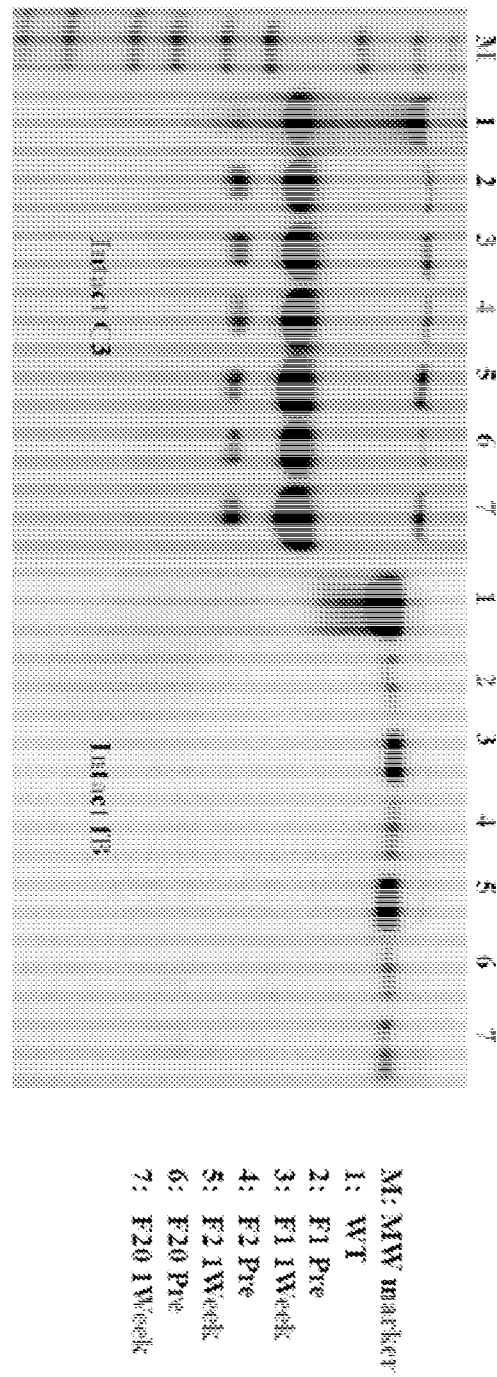

FIG 12B

```
Atgagacttctagcaaagattatttgccttatgttatgggctatttgtgtagcagaagat    SignalPeptide
 M  R  L  L  A  K  I  I  C  L  M  L  W  A  I  C  V  A  E  D
tgcaatgaacttcctccaagaagaaatacagaaattctgacaggttcctggtctgaccaa
 C  N  E  L  P  P  R  R  N  T  E  I  L  T  G  S  W  S  D  Q
acatatccagaaggcacccaggctatctataaatgccgccctggatatagatctcttgga    SCR1
 T  Y  P  E  G  T  Q  A  I  Y  K  R  P  G  Y  R  S  L  G
aatataataatggtatgcaggaaggagaatgggttgctcttaatccattaagaaatgt
 N  I  I  M  V  C  R  K  G  E  W  V  A  L  N  P  L  R  K  C
cagaaaaggccctgtggacatcctggagatactccttttggtacttttacccttacagga
 Q  K  R  P  C  G  H  P  G  D  T  P  F  G  T  F  T  L  T  G
ggaaatgtgtttgaatatggtgtaaaagctgtgtatacatgtaatgagggggtatcaattg    SCR2
 G  N  V  F  E  Y  G  V  K  A  V  Y  T  C  N  E  G  Y  Q  L
ctaggtgagattaattaccgtgaatgtgacacagatggatggaccaatgatattcctata
 L  G  E  I  N  Y  R  E  C  D  T  D  G  W  T  N  D  I  P  I
tgtgaagttgtgaagtgtttaccagtgacagcaccagagaatggaaaaattgtcagtagt
 C  E  V  V  K  C  L  P  V  T  A  P  E  N  G  K  I  V  S  S
gcaatggaaccagatcgggaataccattttggacaagcagtacggtttgtatgtaactca    SCR3
 A  M  E  P  D  R  E  Y  H  F  G  Q  A  V  R  F  V  C  N  S
ggctacaagattgaaggagatgaagaaatgcattgttcagacgatggttttggagtaaa
 G  Y  K  I  E  G  D  E  E  M  H  C  S  D  D  G  F  W  S  K
gagaaaccaaagtgtgtggaaatttcatgcaaatcccagatgttataaatggatctcct
 E  K  P  K  C  V  E  I  S  C  K  S  P  D  V  I  N  G  S  P
atatctcagaagatattttataagagaatgaacgatttcaatataaatgtaacatgggt    SCR4
 I  S  Q  K  I  I  Y  K  E  N  E  R  F  Q  Y  K  C  N  M  G
tatgaatacagtgaaggaggagatgctgtatgcactgaatctggatggcgtccgttgcct
 Y  E  Y  S  E  R  G  D  A  V  C  T  E  S  G  W  R  P  L  P
tcatgtgaagaaaaatcaaccttgaaaccttgtgattatccagacattaaacatggaggt
 S  C  E  E  K  S  T  L  K  P  C  D  Y  P  D  I  K  H  G  G
ctatatcatgagaatatgcgtagaccatactttccagtagctgtaggaaaatattactcc    SCR6
 L  Y  H  E  N  M  R  R  P  Y  F  P  V  A  V  G  K  Y  Y  S
tattactgtgatgaacattttgagactccgtcaggaagttactgggatcacattcattgc
 Y  Y  C  D  E  H  F  E  T  P  S  G  S  Y  W  D  H  I  H  C
acacaagatggatggtcgccagcagtaccatgcctcagaaaatgttatttttccttatttg
 T  Q  D  G  W  S  P  A  V  P  C  L  R  K  C  Y  F  P  Y  L
gaaaatggatataatcaaaattatggaagaaagtttgtacagggtaaatctatagacgtt    SCR7
 E  N  G  Y  N  Q  N  Y  G  R  K  F  V  Q  G  K  S  I  D  V
gcctgccatcctggctacgctcttccaaaagcgcagaccacagttacatgtatggagaat
 A  C  H  P  G  Y  A  L  P  K  A  Q  T  T  V  T  C  M  E  N
ggctggtctcctactccagatgcatccgtgtcaaaacatgttccaaatcaagtatagat
 G  W  S  P  T  P  R  C  I  R  V  K  T  C  S  K  S  S  I  D
attgagaatgggtttatttctgaatctcagtatacatatgccttaaaagaaaaagcaaaa    SCR8
 I  E  N  G  F  I  S  E  S  Q  Y  T  Y  A  L  K  E  K  A  K
tatcaatgcaaactaggatatgtaacagcagatggtgaaacatcaggatcaattcatgt
 Y  Q  C  K  L  G  Y  V  T  A  D  G  E  T  S  G  S  I  T  C
gggaaagatggatggtcagctcaacccacgtgcattaaatctataaaaacagatgtctc
 G  K  D  G  W  S  A  Q  P  T  C  I  K  S  I  K  T  D  C  L
```

Fig 12C

```
agtttaacctagctttgaaaatgccatacccatgggagagaagaaggatgtgtataaggcg
 S  L  P  S  F  E  N  A  I  P  M  G  E  K  K  D  V  Y  K  A
ggtgagcaagtgacttacacttgtgcaacatattacaaaatggatggagccagtaatgta        SCR17
 G  E  Q  V  T  Y  T  C  A  T  Y  Y  K  N  G  A  S  N  V
acatgcattaatagcagatggacaggaagtccaacatgcagagacacctcc
 T  C  I  N  S  R  W  T  Q  R  P  T  C  R  D  T  S

SCR18 aaagattctacaggaaaatgtggg
                                             K  D  S  T  G  K  C  G
cccctccacctattgacaatggggacattacttcattcccgttgtcagtatatgctcca         SCR19
 P  P  P  I  D  N  G  D  I  T  S  F  P  L  S  V  Y  A  P
gcttcatcagttgagtaccaatgccagaacttgtatcaacttgagggtaacaagcgaata
 A  S  S  V  E  Y  Q  C  Q  N  L  Y  Q  L  E  G  N  K  R  I
acatgtagaaatggacaatggtcagaaccaccaaaatgcttacatccgtgtgtaatatcc
 T  C  R  N  G  Q  W  S  E  P  P  K  C  L  H  P  C  V  I  S
cgagaaattatggaaaattataacatagcattaaggtggacagccaaacagaagctttat
 R  E  I  M  E  N  Y  N  I  A  L  R  W  T  A  K  Q  K  L  Y
tcgagaacaggtgaatcagttgaattTgtgtgtaaacggggatatcgtctttcatcacgt        SCR20
 S  R  T  G  E  S  V  E  F  V  C  K  R  G  Y  R  L  S  S  R
tctcacacattgcgaacaacatgtttgggatgggaaactggagtatccaacttgtgcaaaa
 S  H  T  L  R  T  T  C  W  D  G  K  L  E  Y  P  T  C  A  K
agatag
 R  -
```

```
GGACGTTGTGAACAGAGTTAGCTGGTAAATGTCCTCTTAAAAGATCCAAAAAatgagactctcagcaaagattatttgccttatgtt
atgggctattctgtgtagcagaagattgcaatgaacttcctcaagaagaaatacagaaattctgacagttcctggtctgaccaaac
atatccagaaggcaccaggctatctataaatgccgtcctggatatagatctcttggaaatataataatggtatgcaggaagggaga
atgggttgctcttaatcattaaggaaatgtcagaaaaggccctgtggacatcctggagatactccttttggtactttttaccettac
aggaggaaatgtgtttgaatatggtgtaaaagctgtgtatacatgtaatgaggggtatcaattgctaggtgagattaattaccgtga
atgtgacacagatggatggaccaatgatattcctatatgtgaagttgtgaagtgtttaccagtgacagcaccagagaatggaaaat
tgtcagtagtgcaatggaaccagatcgggaataccattttggacaagcagtacggttgtatgtaactcaggctacaagattgaagg
agatgaagaaatgcattgttcagacgatggtttttggagtaaagagaaaccaaagtgtgtggaaatttcagcaaatccccagatgt
tatataatggatctcctatatctcaagagatttcattaaggagaatgaacgatttcaacatatatgtaacatgggttatgactcaag
tgaaagcgagatgctgtatgcctgaatctggatggcatccagtgcctatctgtgaagaaaaatcaaccttgaaaccttgtgatta
tccagacattaaacatggaggtctatatcatgagaatatgcgtagaccatactttccagtagctgtaggaaaatattactcctatta
ctgtgatgaacattttgagactccgtcaggaagttactggatcacattcattgcacacaagatggatggtgccagcagtaccatg
cctcagaaaatgttatttccttattggaaaatggatataatcaaaattatggaagaaagtttgtacagggtaaatctatagacgt
tgcctgccatcctgctacgctcttcaaaagcgcagaccacagttacatgtatggagaatggctggtctcctactcccagatgcat
ccgtgtcaaaacatgttccaaatcaagtatagatattgagaatggggttattcttgaatctcagtatacatatgccttaaaagaaaa
agcaaaatatcaatgcaaactaggatatgtaacagcagatggtgaaacatcaggatcaattacatgtgggaaagatggatggtcagc
tcaacccacgtgcattaaatctataaaaacagatgtgtctcagtttaactagcttgaaatgccataccatgggagagaagaagga
tgtgtataaggcggggtgagcaagtgacttacactgtgcaacatattccaaaatggatggagccagtaatgtaacatgcattaatag
cagatggacaggaaggccaacatgcagagacacctccttgctgttgaattctcaggaaacaaccttgtctggacatgtagccagatt
gagcaacbcatcbactgctgagaactcccctatcatcgttaagagcatacbtgaacagtgtbtcggggatcaccagtcatcgtttaac
tcgaaactgctgccaacactgcgccagataaagattctacaggaaaatgtgggcccctccacctattgacaatggggacattacttc
attccgttgtcagtatatgctccagcttcatcagttgagtaccaatgccagaacttgtatcaacttgagggtaacaagcgaataac
atgtagaaatggacaatggtcagaaccaccaaaatgcttacatccgtgtgtaatatcccgagaattatggaaaattataacatago
attaaggtggacagccaaacagaagcttattcgagaacaggtgaatcagttgaatttgtgtgtaaacgggatatcgtctttcatc
acgttctcacacattgcgaacaacatgttggatgggaaactggagtatccaacttgtgcaaaaagatag
```

```
Atggtacagcacagatttctcttggagtcagttggtcccagaaagatccaaattatgaga    Signal Peptide
 M  V  Q  H  R  F  L  L  E  S  V  G  P  R  K  I  Q  I  M  R
Ctgtcagcaagaattatttggcttatattatggactgtttgtgcagcagaagattgtaaa    SCR1
 L  S  A  R  I  I  W  L  I  L  W  T  V  C  A  A  E  D  C  K
ggtcctcctccaagagaaaattcagaaattctctcaggctcgtggtcagaacaactatat
 G  P  P  P  R  E  N  S  E  I  L  S  G  S  W  S  E  Q  L  Y
ccagaaggcacccaggcatacctacaaatgccgccctggataccgaacacttggcactatt
 P  E  G  T  Q  A  Y  Y  K  C  R  P  G  Y  R  T  L  G  T  I
gtaaaagtatgcaagaatggaaaatgggtggcgtctaacccatccaggatatgtcggaaa
 V  K  V  C  K  N  G  K  W  V  A  S  N  P  S  R  I  C  R  K
Aagccttgtgggcatcccggagacacacccttttgggtcctttaggctggcagttggatct   SCR2
 K  P  C  G  H  P  G  D  T  P  F  G  S  F  R  L  A  V  G  S
caatttgagtttggtgcaaaaggttgtttataccctgtgatgatgggtatcaactattaggt
 Q  F  E  F  G  A  K  V  V  Y  T  C  D  D  G  Y  Q  L  L  G
gaaattgattaccgtgaatgtggtgcagatgggtggatcaatgatattccactatgtgaa
 E  I  D  Y  R  E  C  G  A  D  G  W  I  N  D  I  P  L  C  E
Gttgtgaagtgtctacctgtgacagaactcgagaatggaagaattgtgagtggtgcagca   SCR3
 V  V  K  C  L  P  V  T  E  L  E  N  G  R  I  V  S  G  A  A
gaaacagaccaggaatactatttggacaggtggtgtggtttgaatgcaattcaggcttc
 E  T  D  Q  E  Y  Y  L  D  R  W  C  G  L  N  A  I  Q  A  S
aagattgaaggacataaggaaattcattgctcagaaaatggcctttggagcaatgaaaag
 K  I  E  G  H  K  E  I  H  C  S  E  N  G  L  W  S  N  E  K
Ccacgatgtgtggaaattctctgcacaccaccgcgagtggaaaatggagatggtataaat   SCR4
 P  R  C  V  E  I  L  C  T  P  P  R  V  E  N  G  D  G  I  N
gtgaaaccagttttacaaggagaatgaaagataccactataagtgtaagcatggttatgtg
 V  K  P  V  Y  K  E  N  E  R  Y  H  Y  K  C  K  H  G  Y  V
cccaaagaaagaggggatgccgtctgcacaggctctggatggagtttctcagcctttctgt
 P  K  E  R  G  D  A  V  C  T  G  S  G  W  S  S  Q  P  F  C
Gaagaaaagagatgctcacctccttatattctaaatggtatctacacacctcacaggatt   SCR5
 E  E  K  R  C  S  P  P  Y  I  L  N  G  I  Y  T  P  H  R  I
atacacagaagtgatgatgaaatcagatatgaatgtaattatggcttctataccgtaact
 I  H  R  S  D  D  E  I  R  Y  E  C  N  Y  G  F  Y  P  V  T
ggatcaactgtttcaaagtgtacaccccactggctggatcccgttccaagatgtaccttg
 G  S  T  V  S  K  C  T  P  T  G  W  I  P  V  P  R  C  T  L
Aaaccatgtgaattccacaattcaaatatggacgtctgtattatgaagagagctgaga    SCR6
 K  P  C  E  F  P  Q  F  K  Y  G  R  L  Y  Y  E  E  L  R
cccaacttcccagtatctataggaaataagtacagctataagtgtgacaacgggttttca
 P  N  F  P  V  S  I  G  N  K  Y  S  Y  K  C  D  N  G  F  S
ccaacttctgggtattcctggactaccttcgttgcacagcacaagggtgggagcctgaa
 P  T  S  G  Y  S  W  D  Y  L  R  C  T  Q  G  W  E  P  E
Gtcccatgcgtcaggaaaatgtgttttccattatgtggagaatggagactctgcatactgg   SCR7
```

Fig 17B

```
                  V  P  C  V  R  K  C  V  F  H  Y  V  E  N  G  D  S  A  Y  W
gaaaaagtatatgtgcagggtcagtctttaaaagtccagtgttacaatggctatagtctt
   E  K  V  Y  V  Q  G  Q  S  L  K  V  Q  C  Y  N  G  Y  S  L
caaaatggtcaagacacaatgacatgtacagagaatggctggtcccctcctcccaaatgc
   Q  N  G  Q  D  T  M  T  C  T  E  N  G  W  S  P  P  P  K  C
Atccgtatcaagacatgttcagcatcagatatacacattgacaatggatttctttctgaa       SCR8
   I  R  I  K  T  C  S  A  S  D  I  H  I  D  N  G  F  L  S  E
tcttcttctatatatgctctaaatagagaaacatcctatagatgtaagcagggatatgtg
   S  S  S  I  Y  A  L  N  R  E  T  S  Y  R  C  K  Q  G  Y  V
acaaatactggagaaatatcaggatcaataacttgccttcaaaatggatggtcacctcaa
   T  N  T  G  E  I  S  G  S  I  T  C  L  Q  N  G  W  S  P  Q
Ccctcatgcattaagtcttgtgatatgcctgtatttgagaattctataactaagaatact       SCR9
   P  S  C  I  K  S  C  D  M  P  V  F  E  N  S  I  T  K  N  T
aggacatggtttaagctcaatgacaaattagactatgaatgtctcgttggatttgaaaat
   R  T  W  F  K  L  N  D  K  L  D  Y  E  C  L  V  G  F  E  N
gaatataaacataccaaaggctctataacatgtacttattatggatggtctgatacaccc
   E  Y  K  H  T  K  G  S  I  T  C  T  Y  Y  G  W  S  D  T  P
Tcatgttatgaaagagaatgcagtgttcccactctagaccgaaaactagtcgtttccccc       SCR10
   S  C  Y  E  R  E  C  S  V  P  T  L  D  R  K  L  V  V  S  P
agaaaagaaaaatacagagttggagatttgttggaattctcctgccattcaggacacaga
   R  K  E  K  Y  R  V  G  D  L  L  E  F  S  C  H  S  G  H  R
gttgggccagattcagtgcaatgctaccactttggatggtctcctggtttccctacatgt
   V  G  P  D  S  V  Q  C  Y  H  F  G  W  S  P  G  F  P  T  C
aaaggtcaagtagcatcatgtgcaccaacctcttgaaattcttaatggggaaataatgga       SCR11
   K  G  Q  V  A  S  C  A  P  P  L  E  I  L  N  G  E  I  N  G
gcaaaaaaagttgaatacagccatggtgaagtggtgaaatatgattgcaaacctagattc
   A  K  K  V  E  Y  S  H  G  E  V  V  K  Y  D  C  K  P  R  F
ctactgaagggacccaataaaatccagtgtgttgatgggaattggacaacctcgcctgta
   L  L  K  G  P  N  K  I  Q  C  V  D  G  N  W  T  T  L  P  V
Tgtattgaggaggagagaacatgtggagacattcctgaacttgaacatggctctgccaag       SCR12
   C  I  E  E  E  R  T  C  G  D  I  P  E  L  E  H  G  S  A  K
tgttctgttcctccctaccaccatggagattcagtggagttcatttgtgaagaaaacttc
   C  S  V  P  P  Y  H  H  G  D  S  V  E  F  I  C  E  E  N  F
acaatgattggacatgggtcagtttcttgcattagtggaaaatggaccagcttcctaaa
   T  M  I  G  H  G  S  V  S  C  I  S  G  K  W  T  Q  L  P  K
Tgtgttgcaacagaccaactggagaagtgtagagtgctgaagtcaactggcatagaagca       SCR13
   C  V  A  T  D  Q  L  E  K  C  R  V  L  K  S  T  G  I  E  A
ataaaaccaaaattgactgaatttacgcataactccaccatggattacaaatgtagagac
   I  K  P  K  L  T  E  F  T  H  N  S  T  M  D  Y  K  C  R  D
aagcaggagtacgaacgctcaatctgtatcaatggaaaatgggatcctgaaccaaactgt
   K  Q  E  Y  E  R  S  I  C  I  N  G  K  W  D  P  E  P  N  C
```

Fig 17C

```
Acaagcaaaacatcctgccctcctccaccgcagattccaaatacccaagtgattgaaacc          SCR14
 T  S  K  T  S  C  P  P  P  P  Q  I  P  N  T  Q  V  I  E  T
accgtgaaatacttggatggagaaaaattatctgttctttgccaagacaattacctaact
 T  V  K  Y  L  D  G  E  K  L  S  V  L  C  Q  D  N  Y  L  T
caggactcagaagaaatggtgtgcaaagatggaaggtggcagtcattacctcgctgcatt
 Q  D  S  E  E  M  V  C  K  D  G  R  W  Q  S  L  P  R  C  I
Gaaaaaattccatgttcccagccccctacaatagaacatggatctattaatttacccaga          SCR15
 E  K  I  P  C  S  Q  P  P  T  I  E  H  G  S  I  N  L  P  R
tcttcagaagaaaggagagattccattgagtccagcagtcatgaacatggaactacattc
 S  S  E  E  R  R  D  S  I  E  S  S  S  H  E  H  G  T  T  F
agctatgtctgtgatgatggtttcaggatacctgaagaaaataggataacctgctacatg
 S  Y  V  C  D  D  G  F  R  I  P  E  E  N  R  I  T  C  Y  M
Ggaaaatggagcactccacctcgctgtgttggacttcct...                            SCR16
 G  K  W  S  T  P  P  R  C  V  G  L  P  C  G  P  P  P  S  I
...
 P  L  G  T  V  S  L  E  L  E  S  Y  Q  E  G  E  E  V  T  Y
...
 H  C  S  T  G  F  I  D  G  P  A  F  I  I  C  E  G  G  K
...ataaaaacggattgtgacgttttacccacagttaaaaat                             SCR17
 W  S  D  P  E  K  C  I  K  T  D  C  D  V  L  P  T  V  K  N
gccataataagaggaaagagcaaaaaatcatataggacaggagaacaagtgacattcaga
 A  I  I  R  G  K  S  K  K  S  Y  R  T  G  E  Q  V  T  F  R
tgtcaatctccttatcaaatgaatggctcagacactgtgacatgtgtaatagtcggtgg
 C  Q  S  P  Y  Q  M  N  G  S  D  T  V  T  C  V  N  S  R  W
Attggacagccagtatgcaaagataattcc...                                     SCR18
 I  G  Q  P  V  C  K  D  N  S
...
...cgagactcaacagggaaa...                                              SCR19
          R  D  S  T  G  K
...
...ttacatgcatgtgtaataccagaaaacattatggaatcacac                         SCR20
 S  E  P  P  T  C  L  H  A  C  V  I  P  E  N  I  M  E  S  H
aatataattctcaaatggagacacactgaaaagatttattcccattcagggaggatatt
 N  I  I  L  K  W  R  H  T  E  K  I  Y  S  H  S  G  E  D  I
gaatttggatgtaaatatggatattataaagcaagagattcaccgccatttcgtacaaag
 E  F  G  C  K  Y  G  Y  Y  K  A  R  D  S  P  P  F  R  T  K
tgcattaatggcaccatcaattatcccacttgtgtataa
 C  I  N  G  T  I  N  Y  P  T  C  V  -
```

```
ccaccttctgggtattcctgggactaccttcgttgcacagcacaagggtgggagcctgaa
 P  P  S  G  Y  S  W  D  Y  L  R  C  T  A  Q  G  W  E  P  E
Gtcccatgcgtcaggaaatgtgttttccattatgtggagaatggagactctgcatactgg      SCR7
 V  P  C  V  R  K  C  V  F  H  Y  V  E  N  G  D  S  A  Y  W
gaaaaagtatatgtgcagggtcagtctttaaaagtccagtgttacaatggctatagtctt
 E  K  V  Y  V  Q  G  Q  S  L  K  V  Q  C  Y  N  G  Y  S  L
caaaatggtcaagacacaatgacatgtacagagaatggctggtcccctcctcccaaatgc
 Q  N  G  Q  D  T  M  T  C  T  E  N  G  W  S  P  P  P  K  C
Atccgtatcaagacatgttcagcatcagatatacacattgacaatggatttctttctgaa      SCR8
 I  R  I  K  T  C  S  A  S  D  I  H  I  D  N  G  F  L  S  E
tcttcttctatatatgctctaaatagagaaacatcctatagatgtaagcagggatatgtg
 S  S  S  I  Y  A  L  N  R  E  T  S  Y  R  C  K  Q  G  Y  V
acaaatactggagaaatatcaggatcaataacttgccttcaaaatggatggtcaccctcaa
 T  N  T  G  E  I  S  G  S  I  T  C  L  Q  N  G  W  S  P  Q
Ccctcatgcattaagtct
 P  S  C  I  K  S
cgagactcaacagggaaatgtggccctcctccacctatgacaat                      SCR19
 R  D  S  T  G  K  C  G  P  P  P  F  I  D  N
ggagacatcacctccttgtcattaccagtatatgaaccattatcatcagttgaatatcaa
 G  D  I  T  S  L  S  L  P  V  Y  E  P  L  S  S  V  E  Y  Q
tgccagaagtattatctcctaaagggaaagaagacaataacatgtagaaatggaaagtgg
 C  Q  K  Y  Y  L  L  K  G  K  K  T  I  T  C  R  N  G  K  W
tctgagccccaaactgcttacatgcatgtgtaataccagaaaacattatggaatcacac    SCR20
 S  E  P  P  T  C  L  H  A  C  V  I  P  E  N  I  M  E  S  H
aatataattctcaaatggagacacactgaaaagatttattcccattcaggggaggatatt
 N  I  I  L  K  W  R  H  T  E  K  I  Y  S  H  S  G  E  D  I
gaatttggatgtaaatatggatattataaagcaagagattcaccgccatttcgtacaaag
 E  F  G  C  K  Y  G  Y  Y  K  A  R  D  S  P  P  F  R  T  K
tgcattaatggcaccatcaattatcccacttgtgtataa
 C  I  N  G  T  I  N  Y  P  T  C  V  -
```

Fig 19

```
GGTCTACTATTTAGTTACTTTGCAGAAGTTGCTCATGGGCGGAGCAATCCTGATTTCCTAAACTGACTTCAACTTCCCTTGAAGCAAGTCTTT
CCTGCTGTGACCACAGTTCATAGCAGAGAAGAACTGGATTGTTGCACCGCAGATTCCTCTGGAGTCAGTGGTCAGTGTTCCCAGAAGATCCAAA
TTATGAGACTGTGCAGCAAGATTATATGGCTCGTGTTGTAGAACTACTATATCCAGAAGAAGATGTAGGTCCCAAATGCGCGATACCGAACA
TTCAGAAGATTCTCTCGGCTCACAGAAATGCAAGAATATGGCCTTTGGCTGGCCTACAAGGCGTACCACTGGAATTGTCCGGATCGGATCGGG
CTTGGGCTACTATTGTGAAATCGGGTCCTTTGGGCTGATTGAATCCGTGCAGAATGGTCAGATGTGGTTGCAAGGTTGTTACCTGTGATGATGG
CCGGAGCACACCCCTTTGAAATGCAAGGTCGAAATGTACCGTGAATCCGCCAACCACACCAGAACCACCACTATTGTGAAGTGTGAAGTGT
GTATCAACTATTAGGTGAATGCTGATTGATTACCCTGGAGAATGCACCAGAAACCAGGAATAGTCGCTGGAATCAGGACAGGTGGTCCGT
CATACCTCTGTGACAGAACTGGAGGTTCAGAGTCCCAATATGCCACAACCAATGCCCTTGGACATAGAGAAGAATGAAAGCCACAGGATCCAC
TTGAATCGAATTCTGCAGCTGGGAAATTGGAGCATAAGGATCAGGCCAAAGTATGAGAGAAACCTGGAAATCGGAACCAGTTCTGAGCTTCCGTGTAG
TGTGGAAATCGTAGCCATGGTAGCCTGACTGCCCAAATGAATTCCACACAAATGCCTGTCGTGTATTATGAGCCTGAGCACCACTTCCCAGT
AAAGGACAAGGACCTGATATGGCATTCCAACAATCGACAACGCCTACAATGTTCAAGGTTTTCACCACCACTAGTAGTGCAACAAGCACTGA
ATCCTATAGGAATATACACCTGAAGTCGACTGCCCAAATGTGCAGCATAGTCGAGAATGCAAGCACTCTGCGACTACCTGGAAAGTAT
CAAGGGATGGACGCTCAGTGTCTAAAGTCACTTTAAAATGTACAATGGCAAATGTCAAGGACACACACTGGATCACGACATGAGAATGG
ATGTGCAGGGTCCAGTCCCCAAATGCTATATCAGCACATGTCAAGCACAGTATCACACAGAAATCACTAACATGGCAACAATTCCTGAATCTCT
CTGGTCCCTCCCCAATATGCACTCCAGATGACACATCAGAATCTTAGAGACTCAGTGTGGAATATCCACGAGAAATATCAGGATCAATACTTI
TCTATATATAGCTCTAAATGCAGAAACACTCGTCAAAGGTCCAAATGCCATTAAATGCCATTAATCAGCACACACTCCTATCTCAGGCTTGACAA
GCCTTCAAATGCTAGGGTCACCCGATACCGCCTCCAGACACAAAAGCCATTAAGCTCATGAAACTCCGAAATGTGGGCCCTCCACCATTGACCA
TCGACACATAAGTCATCCTCTCGCATTGAGCCGTGAATGCATTATGGACTTGAATCATGCCTGAATATCATGAATATCGTAAGCATTATTCAAGAT
AAGACACAATATACATGTTCTTTGTTATATGGTGATTAATTGCAAAACTGTGCTTGGTTAATCTTAAAAACTATTTAAAACTATTCAATGACAGTAATT
CACACAATATACATGTTCTTTGTTATATGGTGATTAATTGCAAAACTATTTAAAACTATTCAATCACAGTAAT
TTTATTAGTTGATTTTATTGTTTAGAAAGGCACATGGTGATATTTAAAACCATGAAGCAAATGCCCTCAATATCAATCACACAGATCC
TTCTCAATAAATATAAACATTTTGTTATATGGTGATTAATTGTAACTTTAAAAACTATTTAAAACTATTCCAAAATGCAAAGCAGTAATTCAAAA
CTCCTAATCAAAATATAGATATGTCAAGGACAAACTATTCAATCAAGAAAGTAGATAGTTCAACATCGTTTCTATTCAG
AACTTTCCAGATTTCCTGATACCTTTGATGTAAGTACCTGATTACAAGGAATTACAGAAGATTAACGCAAGCAA
TATGATTTCCAAAGCATGTAACAACCAAACTATCATATATTATTATGACTAATAAATTAATTAATAATACTATATAATACTATATAAATA
AAAGAATCTAAGAACTTC
```

Fig 20

MVQHRFLLESVGPRKIQIMRLSARIIWLILWTVCAAEDCKGPPPREN
SEILSGSWSEQLYPEGTQATYKCRPGYRTLGTIVKVCKNGKWVASNP
SRICRKKPCGHPGDTPFGSFRLAVGSQFEGAKVVYTCDDGYQLLGEI
DYRECGADGWINDIPLCEVVKCLPVTELENGRIVSGAAETDQEYYFG
QVVRFECNSGFKIEGHKEIHCSENGLWSNEKPRCVEILCTPPRVENG
DGINVKPVYKENERYHYKCKHGYVPKERGDAVCTGSGWSSQPFCEEK
RTLKPCEFPQFKYGRLYEESLRPNFPVSIGNKYSYKCDNGFSPPSGYS
WDYLRCTAQGWEPEVPCVRKCVFHYVENGDSAYWEKVYVQGQSLK
VQCYNGYSLQNGQDTMTCTENGWSPPPKCIRIKTCSASDIHIDNGFL
SESSSIYALNRETSYRCKQGYVTNTGEISGSITCLQNGWSPQPSCIKSR
DSTGKCGPPPIDNGDITSLSLPVYEPLSSVEYQCQKYLLLKGKKTITC
RNGKWSEPPTCLHACVIPENIMESHNIILKWRHTEKIYSHSGEDIEFG
CKYGYYKARDSPPFRTKCINGTINYPTCV

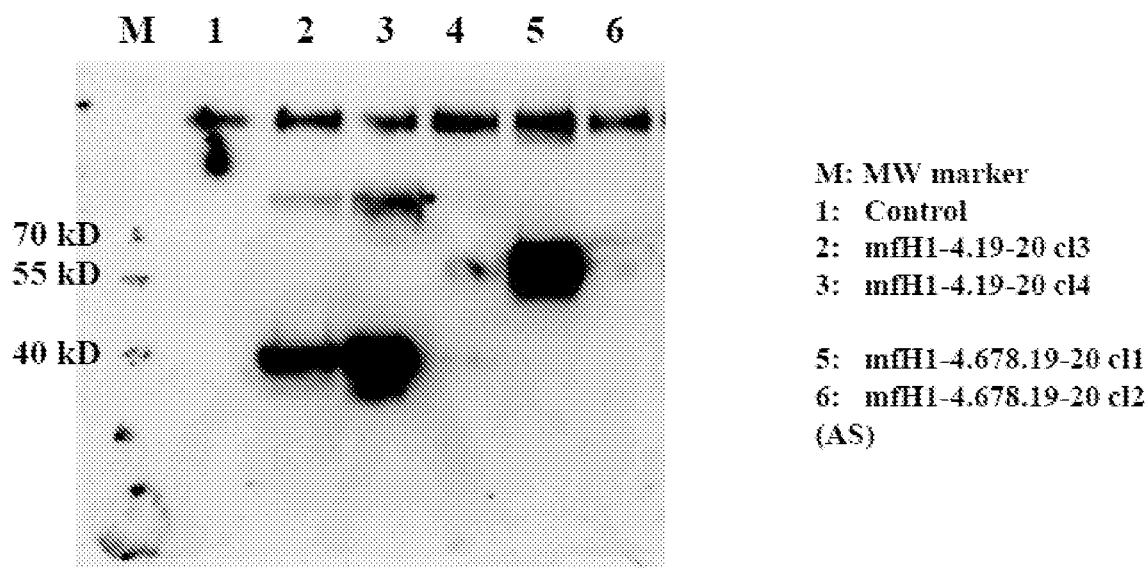
FIG. 21
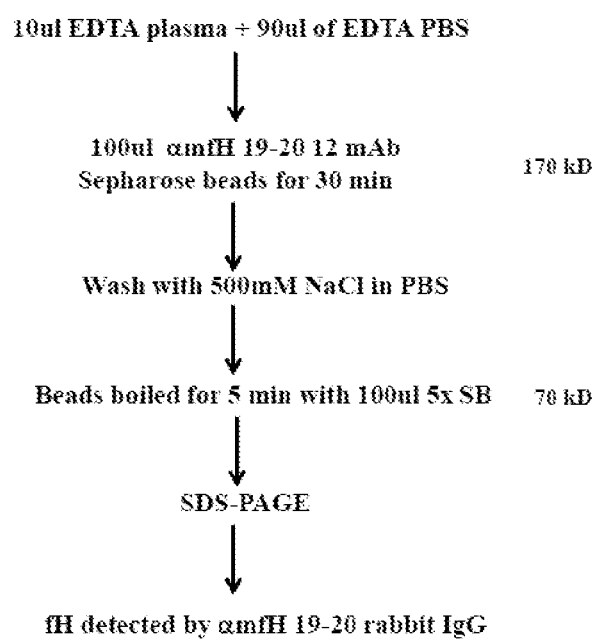
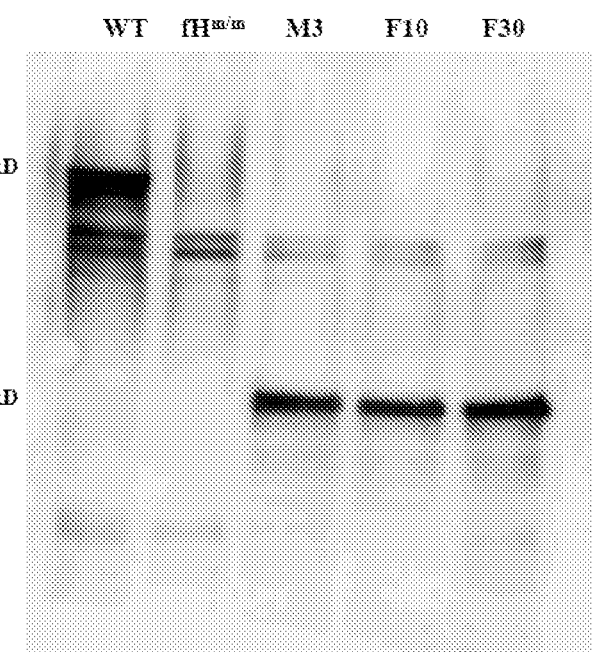
FIG 22A
FIG 22B

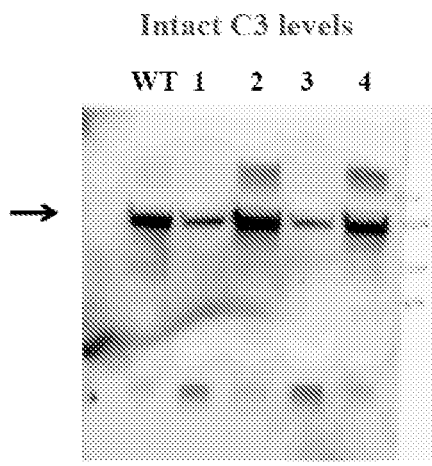
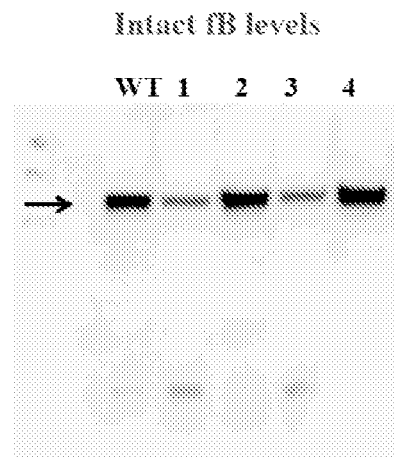
FIG 28A
FIG 28B
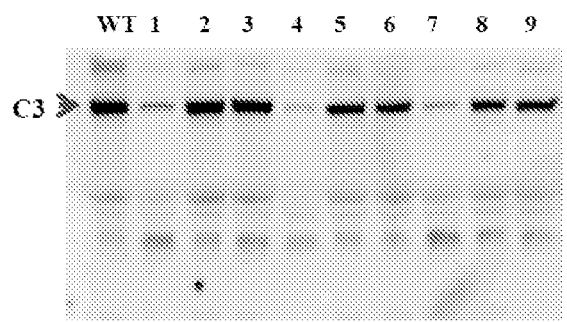
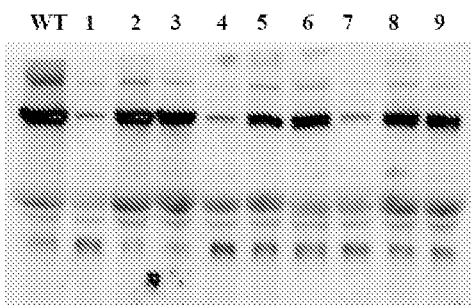
FIG 29A
FIG 29B

FIG. 34A  FIG. 34B  FIG. 34C
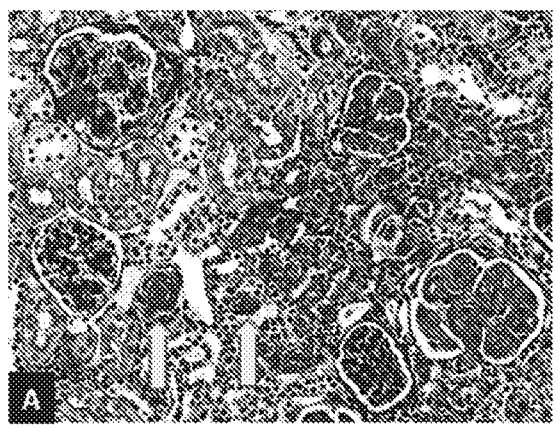  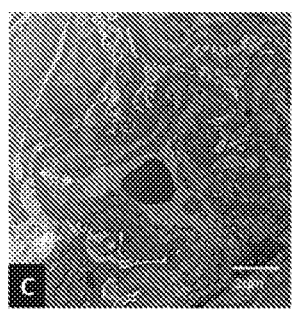
FIG 35A   FIG 35B
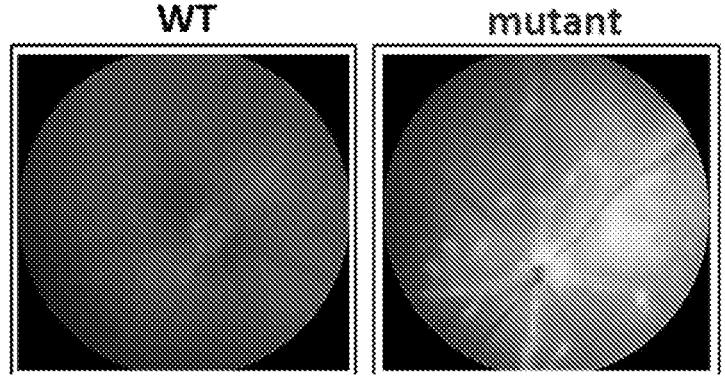
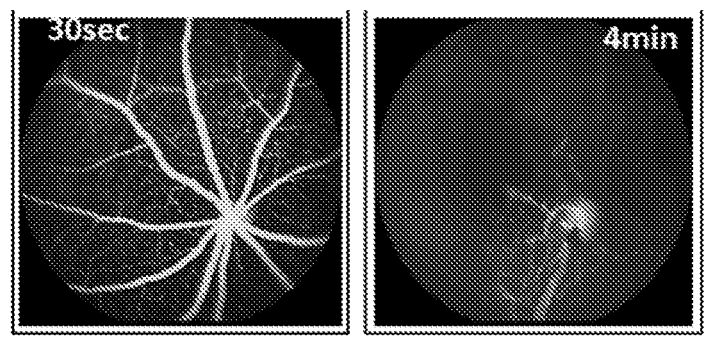
FIG 35C   FIG 35D

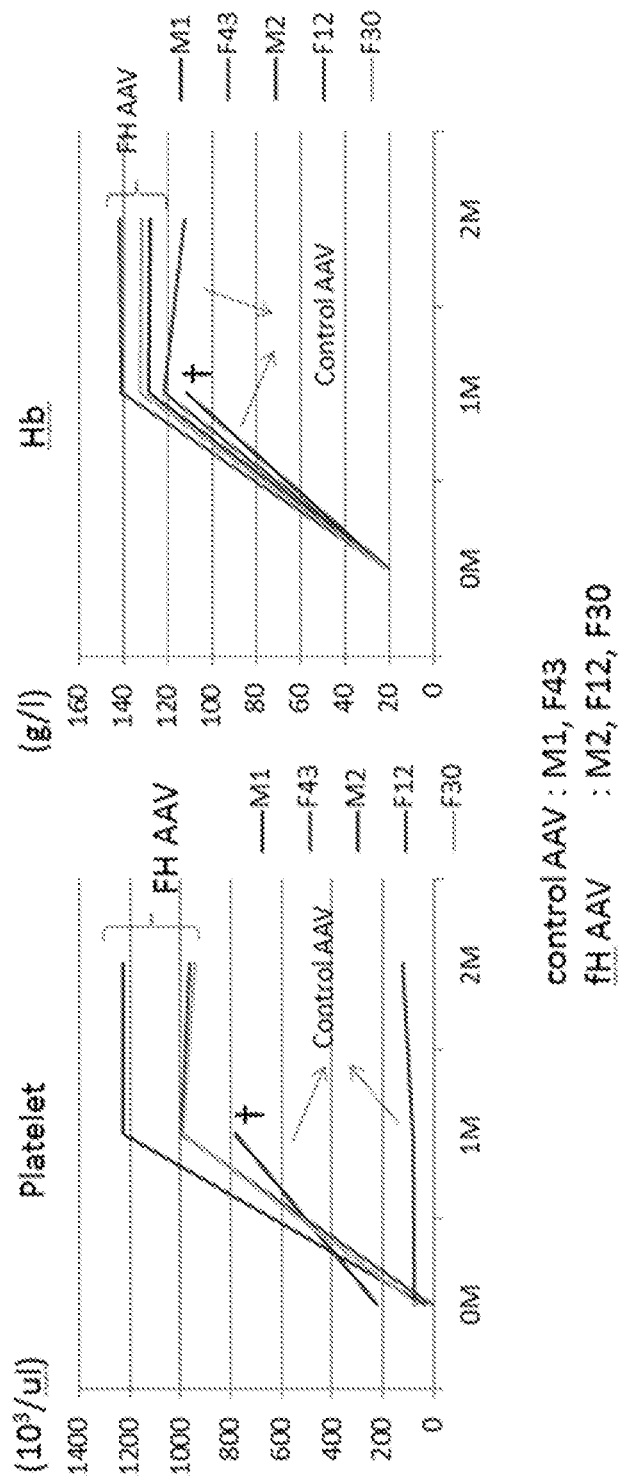

COMPOSITION AND METHOD FOR TREATING COMPLEMENT-MEDIATED DISEASE

STATEMENT REGARDING FEDERALLY SPONSORED RESEARCH OR DEVELOPMENT

This invention was made with government support under Grant No. AI085596 awarded by the National Institutes of Health. The government has certain rights in the invention.

INCORPORATION-BY-REFERENCE OF MATERIAL SUBMITTED IN ELECTRONIC FORM

The sequence listing labeled "16-7640PCT_ST25" created Sep. 21, 2016, and which is 141,325 bytes in size, is incorporated by reference herein.

BACKGROUND OF THE INVENTION

The complement system is a part of innate immunity that plays a key role in host defense. Complement can be activated by three different pathways, the classical, alternative and lectin pathways. Among them, the alternative pathway is unique in that it not only represents an independent pathway by which complement is activated by the "tick-over" mechanism, but also it amplifies complement activation initiated by the other two pathways. The alternative pathway requires the participation of C3, factor B (fB), factor D (fD) and properdin (fP). All pathways converge at the C3 activation step from where the alternative pathway amplification loop comes into play. Regardless of which pathway complement activation occurs, activated complement produces three types of effector functions: opsonization of targets with C3b/iC3b/C3d to facilitate phagocytosis and clearance, production of pro-inflammatory mediators C3a and C5a, and direct cellular attack by the terminal complement activation effector C5b-9, also known as membrane attack complex (MAC). Through activation of complement receptors (CRs) such as CR2 on B cells and follicular dendritic cells, and anaphylatoxin receptors C3a receptor (C3aR) and C5a receptor (C5aR) on leuckocytes such as macrophages and monocytes, complement also interacts with and cross-regulates the adaptive immune systems and thus plays a modulatory role in B and T cell immunology.

A number of human diseases are caused by complement dysregulation, resulting in complement-mediated autologous tissue injury. The complement dysregulation may arise from mutations, either somatic or germline, in complement regulator or regulator-related genes such that these regulators no longer function normally. Examples of this category include mutations in hematopoietic stem cells of the PIG-A gene that encodes for a key enzyme in the GPI anchor biosynthesis and such mutations result in the lack of expression of DAF and CD59 on blood cells of paroysmal nocturnal hemoglobinuria (PNH) patients. As a result, PNH patient's red blood cells and platelets are not protected from complement attack and they develop intravascular hemolysis and platelet activation, leading to anemia and thrombotic attacks. A second example is mutation in the membrane regulator MCP or fluid phase regulators fH or fI which render over-activation of the alternative pathway of complement in the kidney, leading to the pathogenesis of C3 glomerulopathy or atypical hemolytic uremic syndrome (aHUS). In addition to such rare and high penetrant mutations leading to absence of expression or dysfunction of DAF, CD59, fH, fI and MCP, there are single nucleotide polymorphisms (SNP) in fH that are more prevalent and less penetrant but nevertheless have been identified to contribute to disease pathogenesis via a complement-mediated mechanism. A very well characterized example is the strong association of Y420H polymorphism in fH with age-related macular degeneration (AMD). Thus, complement regulator dysfunction or sequence variation may lead to common as well as rare human diseases.

Complement dysregulation may arise not only from regulatory mutation/polymorphism but also from mutations in genes that encode the critical components of the alternative pathway, namely C3 and fB, as well as by the presence of autoantibodies against regulators or complement proteins such as fH, C3 or fB. It is now understood that certain mutations in C3 or fB will result in proteins which, when activated, form an unusually stable alternative pathway C3 convertase C3bBb that is resistant to regulation by the regulatory proteins, which in turn can lead to complement dysregulation and over-activation. In the case of autoantibodies against complement regulators, they often mimic mutations in genes encoding such proteins with the result being reduced functional potency of such proteins in the fluid phase or on the cell surface. Separately, autoantibodies against C3b called C3 nephritic factors (C3nef) are capable of binding and stabilizing the alternative pathway C3 convertase C3bBb, thus achieving the same effect of prolonging the half-life and activity of the convertase as that produced by C3 or fB gene mutations. Overall, there are common and rare human diseases that are caused by excessive complement activation resulting from dysregulation of the complement activation cascade. The underlying mechanism of complement dysregulation are variable, some are due to gene mutations and others to autoantibodies, and the mutated genes or targets of autoantibodies could be regulatory proteins or components of the alternative pathway.

Current therapeutic approaches are focused on the development of reagents such as mAbs, peptides or other small molecules that bind and block specific alternative pathway or terminal pathway complement components. A clinically validated example is Eculizumab, a humanized mAb against complement C5 which has been approved for the treatment of PNH and aHUS. Other approaches that have been described include mAbs against fB, fD, or fP, and a cyclic peptide that binds and inhibits C3. The limitation of these approaches is that they require repeated and inconvenient IV dosing of patients. Further, since they block the alternative pathway or terminal pathway, they run the risk of compromising host defense. Indeed, patients on Eculizumab therapy have to be vaccinated against bacteria strains that cause lethal meningitis and these patients are also put on prophylactic antibiotic therapy before being treated with the approved mAb drug.

In other approaches, recombinant regulatory proteins such as soluble DAF, CR1, CRIg and proteins comprising minimal domains of fH (N-terminal short consensus repeat [SCR] 1-5 and C-terminal SCR19-20) or fusion proteins between fH and CR2 (TT30) have been tested. See, e.g., US Patent Publication No. US2013/0296255; US Patent Publication No. 2008/0221011. However, large scale heterologous expression of such proteins as therapeutic drugs requires significant effort, and animal studies have shown their in vivo clearance rate after administration to be fast (Nichols E M, Barbour T D, Pappworth I Y, Wong E K, Palmer J M, Sheerin N S, Pickering M C, Marchbank K J. Kidney Int. 2015 Jul. 29. doi: 10.1038/ki.2015.233; Fridkis- Hareli M, Storek M, Mazsaroff I, Risitano A M, Lundberg A S, Horvath C J, Holers V M, Blood. 2011 Oct. 27; 118(17): 4705-13. doi: 10.1182/blood-2011-06-359646. Epub 2011 Aug. 22.), making such therapeutic strategies cumbersome and less practical as multiple and frequent administrations of such protein drugs would be required.

A need remains in the art for compositions useful for treating complement-mediated diseases with greater and longer-lasting efficacy.

SUMMARY OF THE INVENTION

In one aspect, the invention provides a recombinant vector having packaged therein an expression cassette comprising an engineered human complement regulator factor H (fH) gene operably linked to expression control sequences which direct expression thereof, wherein said hfH gene encodes a soluble hfH protein variant that retains complement regulatory function, wherein said fH variant comprises short consensus repeat (SCR) 1, 2, 3, 4, 19 and 20 and at least one of SCR7, SCR17 and/SCR18, wherein following administration of the vector to a subject and expression, detectable plasma levels of the hfH variant are present in the subject for at least a week.

In another aspect, the invention provides a recombinant AAV vector having packaged therein an expression cassette comprising an engineered human complement regulator factor H (fH) gene operably linked to expression control sequences which direct expression thereof, wherein said hfH gene encodes a soluble hfH protein variant that retains complement regulatory function, wherein said fH variant comprises short consensus repeat (SCR) 1, 2, 3, 4, 19 and 20, wherein following administration of the vector to a subject and expression, detectable therapeutically useful plasma levels of the hfH variant are present in the subject for at least about a month.

In a further aspect, a pharmaceutical composition is provided which comprises a carrier and/or excipient and a recombinant vector as described herein which expresses an fH variant.

In yet another aspect, a method is provided for treating a complement related disorder by delivering to the subject a vector as described herein. The complement related disorder may be, among others, membranoproliferative glomerulonephritis, atypical hemolytic uremic syndrome (aHUS), age related macular degeneration (AMD), microangiopathic haemolytic anemia, thrombocytopenia, acute renal failure, paroxysmal nocturnal hemoglobinuria (PNH), schizophrenia, ischemic stroke, and/or bacterial infections caused by recruitment of bacterial pathogens.

In a further aspect, use of a recombinant vector for treating AMD is provided. In another aspect, use of a rAAV vector for treating PNH, aHUS, or another complement associated disorder is described.

In another aspect, an engineered hfH variant is provided which comprises a leader sequence and human complement receptor SCRs consisting of: (a) SCR1-4, 7, and 19-20; (b) SCR1-4, 6, 7, and 19-20; (c) SCR1-4, 7, 8, and 19-20; (d) SCR1-4, 6, 7, 8, and 19-20; (e) SCR1-4, 17, and 19-20; (f) SCR1-4, and 18-20; (g) SCR1-4, and 17-20. Other embodiments include, e.g., SCR1-4, 7, and 18-20; SCR1-4, 6, 7, and 18-20; SCR1-4, 7, 8, and 18-20; or SCR1-4, 6, 7, 8, and 18-20, SCR1-4, 7, and 17-20; SCR1-4, 6, 7, and 17-20; SCR1-4, 7, 8, and 17-20; or SCR1-4, 6, 7, 8, and 17-20. Optionally, at least one glycosylation site is engineered into at least one of the SCRs. In another aspect, one of the engineered hfH variants is pegylated.

In still another aspect, a pharmaceutical composition comprising at least one type of the engineered hfH variant, a carrier and/or an excipient is provided. Such a composition may be used on its own, or in combination with another therapy, particularly, e.g., the vector therapy described herein.

Other aspects and advantages of the invention will be readily apparent from the following detailed description of the invention.

BRIEF DESCRIPTION OF THE DRAWINGS

FIG. 1A provides a schematic of the domain structure of mature human factor H protein.

FIGS. 1B-1E provide the nucleic acid and amino acid sequences of the leader peptide and identifies the locations of the 20 Short Consensus Repeat (SCR) domains used in generating the fH variants illustrated in the examples below. SEQ ID NO:1 provides the nucleic acid sequences; SEQ ID NO: 2 provides the amino acid sequence of the signal peptide. The amino acid sequences of the SCR1-20 are provided in SEQ ID NO: 3 (SCR1), 5 (SCR2), 7 (SCR3), 9 (SCR4), 11 (SCR5), 13 (SCR6), 14 (SCR7), 16 (SCR8), 17 (SCR9), 19 (SCR10), 21 (SCR11), 23 (SCR12), 25(SCR13), 27 (SCR14), 29 (SCR15), 31 (SCR16), 33 (SCR17), 35 (SCR18), 37 (SCR19), and 38 (SCR20) respectively. The locations of these domains in the fH isoform 1 are based on the convention described in C. Estaller et al, Eur J Immunol. 1991 March; 21(3):799-802. The amino acids sequences between the defined SCRs are linker sequences that afford fH flexibility [SEQ ID NO: 4, 6, 8, 10, 12, 15, 18, 20, 22, 24, 26, 28, 30, 32, 34, and 36], respectively]. The linker between SCR19 and SCR20 is only three amino acids (Leu-His-Pro), and thus not generated by the features in the Sequence Listing.

FIG. 2A provides a schematic domain structure of human factor H variant containing SCR1-4, 6-8, and 19-20.

FIGS. 2B-2C provide the nucleic acid [nt 53-1804 of SEQ ID NO: 41] and amino acid sequences [SEQ ID NO: 42] of the leader peptide and 9 short consensus repeat (SCR) domains of the fH variant SCR1-4, 6-8 and 19-20.

FIGS. 3A-3B are the complete cDNA [nt 53-1804 of SEQ ID NO: 41] and 5'-[nt 1-52 of SEQ ID NO:41] and 3'-UTR [nt 1805-2068 of SEQ ID NO: 41] sequences of the human factor H truncation construct containing the leader peptide and SCR1-4, 6-8, and 19-20 (hfH1-4.678.19-20).

FIG. 4 is the amino acid sequence of the factor H truncation construct containing the leader peptide (underlined) and SCR1-4, 6-8, 19-20 (hfH1-4.678.19-20) [SEQ ID NO: 42].

FIGS. 5A and 5B are gels which provide confirmation of protein expression and stability of hfH1-4.678.19-20. The cDNA sequence shown in FIG. 2 of human fH truncation variant containing SCR1-4, 6-8, and 19-20 [SEQ ID NO: 41] was cloned into eukaryotic expression vectors which were then used to transfect HEK cells. Cell culture supernatant was used for western blot analysis to detect truncated fH protein expression. Panel A: Lane 1, untransfected HEK cells; Lane 2 and 3, HEK cells transfected with a pCMV Sport6 vector containing the fH truncation variant cDNA; Lane 4-6, HEK cells transfected with a pCBARBG vector containing the fH variant cDNA. The pCBARBG vector contains the same 5' and 3' regulatory elements as the pAAV vector construct shown in FIG. 4. Panel B: Lane 1, untransfected HEK cells; Lane 2, HEK cells transfected with a pCBARG vector containing the truncated fH variant cDNA as a control; Lane 3, HEK cells transfected with the AAV8 plasmid containing the truncated fH variant cDNA.

FIG. 10 is a line graph showing ELISA detection of hfH1-4.678.19-20 in the blood of 3 different fH mutant mice (fH$^{m/m}$; F1, F2, F20) one week after AAV8-mediated fH gene therapy. The fH$^{m/m}$ mouse is a strain of fH mutant mice that carry premature stop codons at the beginning of SCR19. These mice produce trace amount of truncated fH (lacking SCR19-20) and has uncontrolled fluid phase alternative pathway complement activation and consumption (secondary C3 and fB deficiency). Mice were infected by retro-orbital I.V. with an AAV8 virus containing hfH1-4.678.19-20 ($3\times10^{11}$ gene copies/mouse) and after one week, blood samples were collected and processed for human fH protein detection. For ELISA assay, the mAb OX-23 was used as a capture antibody (recognizing an epitope in human fH SCR2-3) and biotinylated mAb L20/3 was used as a detection antibody (recognizing human fH SCR19). As shown in the figure, there is no hfH1-4.678.19-20 in the blood of 3 fH$^{m/m}$ mice (F1, F2, F20) before AAV-hfH1-4.678.19-20 treatment (Pre), but hfH1-4.678.19-20 was detected one week (1 W) after treatment.

FIG. 11 is western blot analysis demonstrating that AAV8-mediated human fH gene therapy in fH$^{m/m}$ mice inhibits alternative pathway complement activation due to the lack of sufficient endogenous mouse fH expression, untreated fH$^{m/m}$ mice have uncontrolled fluid phase alternative pathway complement activation, and as a result they consume plasma C3 and fB (compare Lane 1 of WT with Lanes 2, 4, 6 of three fH$^{m/m}$ mice before gene therapy). One week after fH$^{m/m}$ mice were treated with AAV8-hfH1-4.678.19-20, plasma C3 and fB levels significantly increased compared with pre-treatment levels, suggesting that AAV8-mediated human fH gene therapy inhibited uncontrolled alternative pathway complement activation and C3 and fB consumption. All three mice (F1, F2 and F20) received $3\times10^{11}$ gene copies each via retro-orbital I.V.

FIGS. 12B-12C provide the nucleic acid and amino acid sequences of the leader peptide and 11 short consensus repeat (SCR) domains of the fH variant SCR1-4, 6-8 and 17-20 [SEQ ID NO: 45 and 46, respectively].

FIG. 13 is the complete cDNA and 5'UTR sequences of the human factor H variant containing the leader peptide and SCR1-4, 6-8 and 17-20 (hfH1-4.678.17-20) (5'UTR is in capital letters) [SEQ ID NO: 47].

FIGS. 17A-17C show the nucleic acid and amino acid sequences of the leader peptide and the 20 Short Consensus Repeat (SCR) domains in mice [SEQ ID NO: 79 and 80, respectively]. Amino acid sequences between the defined SCRs are linker sequences that afford fH flexibility.

Figure 18A:
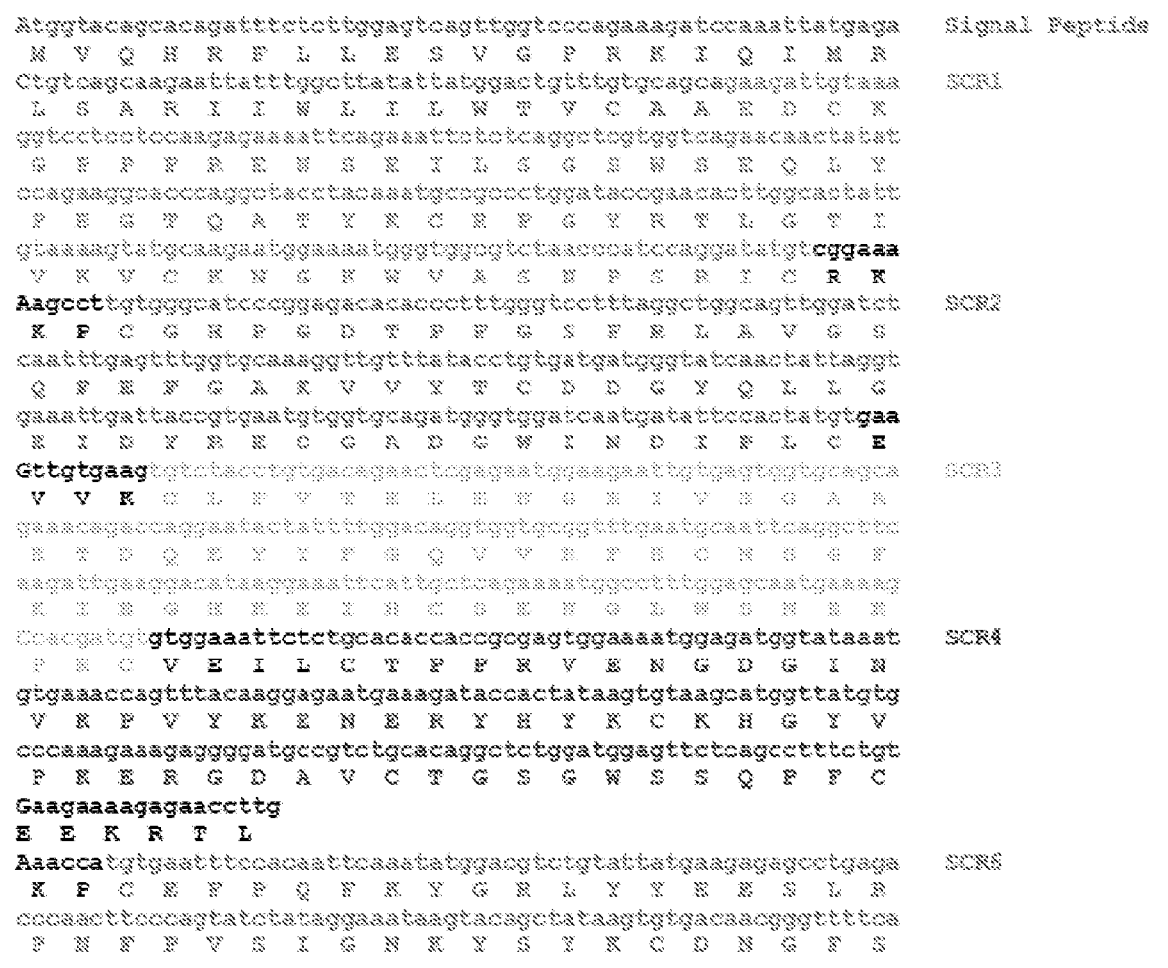

FIGS. 18A-18B provide the nucleic acid and amino acid sequences of the leader peptide and 9 Short Consensus Repeat (SCR) domains of the mouse fH variant [SEQ ID NO: 81 and 82, respectively]. Amino acid sequences between the defined SCRs are linker sequences that afford fH protein flexibility. This variant of mouse fH is used as a surrogate for testing the in vivo function of hfH1-4.678.19-20 in subsequent studies.

FIG. 19 provides the coding and 5' and 3'-UTR sequences of the mouse factor H truncation construct containing the leader peptide (underlined) and SCR1-4, 6-8, 19-20 (mfH1-4.678.19-20) [SEQ ID NO: 43].

FIG. 20 provides the amino acid sequence of the mouse factor H truncation construct containing the leader peptide (underlined) and SCR1-4, 6-8, and 19-20 (mfH1-4.678.19-20) [SEQ ID NO:44].

FIG. 21 is a gel showing confirmation of protein expression and stability of mfH1-4.19-20 and mfH1-4.678.19-20. The cDNA sequence of mouse fH truncation variant containing SCR1-4, 678, and 19-20 or that of another fH truncation variant containing SCR1-4, and 19-20 was cloned into a eukaryotic expression vector pCBARBG which was then used to transfect a mouse liver cell line, Hepa1C1C7 cells. Cell culture supernatant was used for western blot analysis to detect truncated mouse fH protein expression. M: molecular weight markers; Lane 1, untransfected Hepa1C1C7 cells (Control); Lane 2 and 3, Hepa1C1C7 cells transfected with pCBARBG-mfH1-4.19-20 clone 3 or clone 4; Lanes 5 and 6, HepaC1C7 cells transfected with pCBARBG-mfH1-4.678.19-20 clone 1 (sense) or clone 2 (antisense).

FIG. 22A is a fl ow chart showing how blood samples were collected and processed for fH protein detection. The fH$^{m/m}$ mouse is a strain of fH mutant mice that carry premature stop codons at the beginning of SCR19. These mice produce trace amount of truncated fH (lacking SCR19-20) and has uncontrolled fluid phase alternative pathway complement activation and consumption (secondary C3 and fB deficiency). Mice were infected by retro-orbital I.V. with an AAV8 virus containing mfH1-4.678.19-20 ($3 \times 10^{12}$ gene copies/mouse) and after one week, blood samples were collected, processed and analyzed as shown in the fl ow chart.

FIG. 22B is a western blot detection of mfH1-4.678.19-20 in the blood of a fH mutant mouse (fH$^{m/m}$) one week after AAV8-mediated fH gene therapy. As shown in the figure, there was no mfH1-4.678.19-20 (approximately 70 kd) in WT and non-treated fH$^{m/m}$ mice. In three virus-infected fH$^{m/m}$ mice, M3, F10, F30 (M indicates male and F indicates female), mfH1-4.678.19-20 was clearly detected.

FIGS. 28A and 28B demonstrate that AAV8-mfH1-4.678.19-20 gene therapy prevents alternative pathway complement activation caused by membrane regulator dysfunction. In this experiment, mice deficient in two membrane regulators, DAF and Crry, were treated with AAV8-mfH1-4.678.19-20 (retro-orbital route, I.V., $3\times10^{12}$ gene copies/mouse). Plasma samples were collected before and 1 week (1 W) after gene therapy to analyze plasma C3 (A) and fB (B) levels by western blot. As shown by the data, the DAF/Crry double mutant mice had excessive alternative pathway complement activation with low C3 and fB levels (Pre). After AAV8-mfH1-4.678.19-20 treatment, both C3 and fB were restored to wild-type mouse levels, suggesting that AAV8-mfH1-4.678.19-20 treatment can correct pathologies caused by membrane complement regulators. This data suggested that AAV8-mfH1-4.678.19-20 treatment was broadly effective for complement-mediated diseases caused by uncontrolled alternative pathway complement regulation, irrespective of the underlying regulatory mechanism defect. DAF/Crry double mutant mice used in this study is a crossbreed species between DAF knockout mice and a Crry$^{flox/flox}$-Tie-2Cre$^+$ mice. Because Tie-2-Cre is expressed in germ cells, it led to germline deletion of Crry gene in some progenies, leading to global Crry deletion.

FIGS. 29A-29B provide a dosage comparison of AAV8-mfH1-4.678.19-20 gene therapy using C3 recovery as a readout. In this experiment, different doses of AAV8-mfH1-4.678.19-20 were administered to fH$^{m/m}$ mice (retro-orbital route, IV.). Two mice each was given the following dosages: $1\times10^{12}$ gene copies/mouse (M #1, M #2), $3\times10^{11}$ gene copies/mouse (M #3, M #6) and $1\times10^{11}$ gene copies/mouse (M #4, M #5). Western blot was performed to analyze plasma C3 levels before (Pre) and one week (1 W) or 1 month (1M) after gene therapy. As shown, all doses tested were able to increase plasma C3 levels when examined at 1 W and 1M time points.

FIGS. 34A-34C show kidney sections of W1206R mutant mice showed pathologies characteristic of aHUS. The pathological features included mesangial expansion and narrowing of capillary lumens (Panel A), thrombi in small vessels as indicated by arrows in Panel A and Panel C. Electron microscopy showed that the glomerular capillary wall exhibited sub-endothelial expansion with fluffy granular electron-lucent material, and formation of double contours and new glomerular basement membrane.

FIGS. 35A-35D show that mice carrying W1206R mutation in fH also developed retinal injury and blood clotting in the eye. Compared with normal looking retinas of wild-type mice (FIG. 35A), there were many white patches, retinal edema and dilated vessels in the retina of the fH W1206R mutant mouse (FIG. 35B). In addition, fluorscien angiography showed the mutant mouse retina was not well perfused as the dye reached all blood vessels in the wild-type mouse eye within 30 seconds (FIG. 35C) but it did not reach out to much of the area in the mutant mouse retina even at 4 min (FIG. 35D).

FIGS. 37A and 37B are line graphs showing the treatment of fH$^{W1206R/W1206R}$ mice with AAV8-mfH1-4.678.19-20 vector at $3\times10^{11}$ GC/mouse normalized their platelet counts. All 3 fH$^{W1206R/W1206R}$ mice treated with AAV8-mfH1-4.678.19-20 were alive and healthy. Their platelet counts (FIG. 37A) and hemoglobin levels (Hb, FIG. 37B), increased and were maintained at normal range. In contrast, 1 of 2 fH$^{W1206R/W1206R}$ mice treated with control AAV vector died (at 4 weeks after treatment) and the remaining mouse had consistent low platelet counts and fluctuating hemoglobin level that was below that of mice treated with AAV8-mfH1-4.678.19-20.

DETAILED DESCRIPTION OF THE INVENTION

Figure 6:
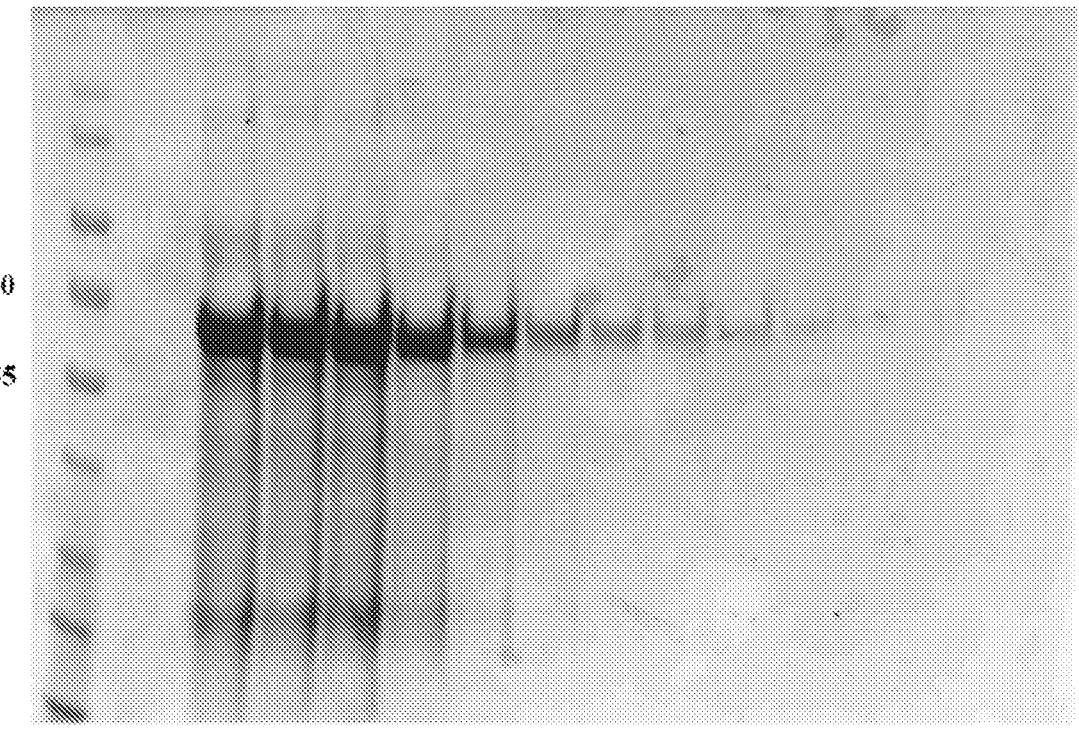
FIG. 6 is an SDS-gel which shows purification of recombinant hfH1-4.678.19-20. SDS-gel analysis was performed via Coomasie blue staining of human fH truncation variant containing SCR1-4, 6-8, and 19-20 that was expressed by transfecting HEK cells using the pCBARBG vector. The recombinant fH truncation protein was purified from the supernatant by passing through an affinity column that was prepared using a mAb against human factor H (clone OX-23) that recognizes an epitope in SCR2-3. Size and location of protein molecular weight markers are shown on the left side.
Figure 7:
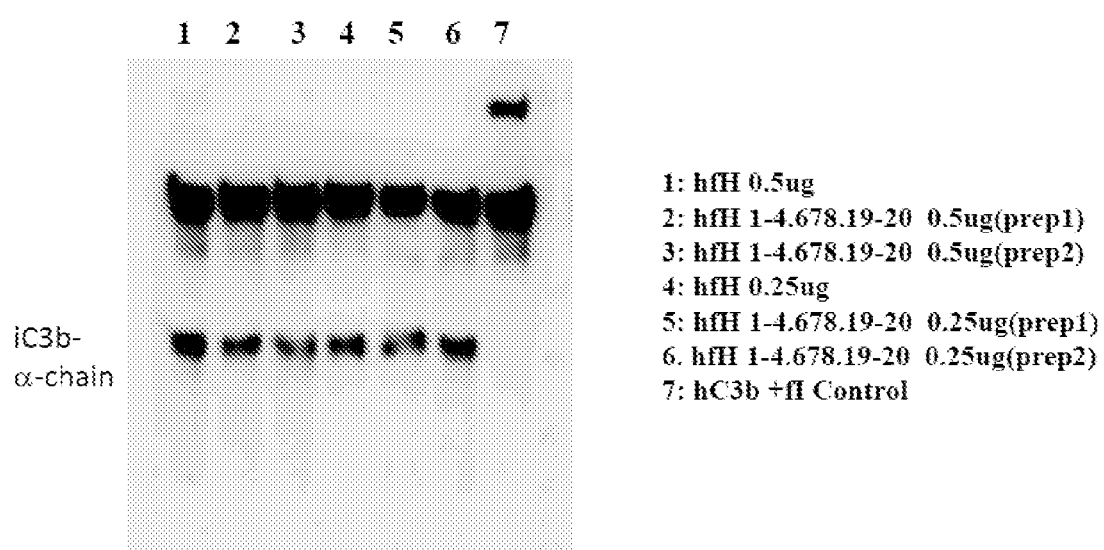
FIG. 7 is a gel showing recombinant hfH1-4.678.19-20 retains complement regulating activity (cofactor activity). The human fH truncation variant containing SCR1-4, 6-8, and 19-20 was tested for cofactor activity for factor I-mediated C3b cleavage. For this assay, human C3b was mixed with factor I in the presence (Lane 1-6) or absence (Lane 7) of full-length fH (hfH) or the truncated fH variant (hfH1-4.678.19-20). The reaction mixture was incubated and then analyzed by SDS-PAGE and western blot analysis. Cofactor activity is indicated by the appearance of the iC3b α-chain fragment.
Figure 8:
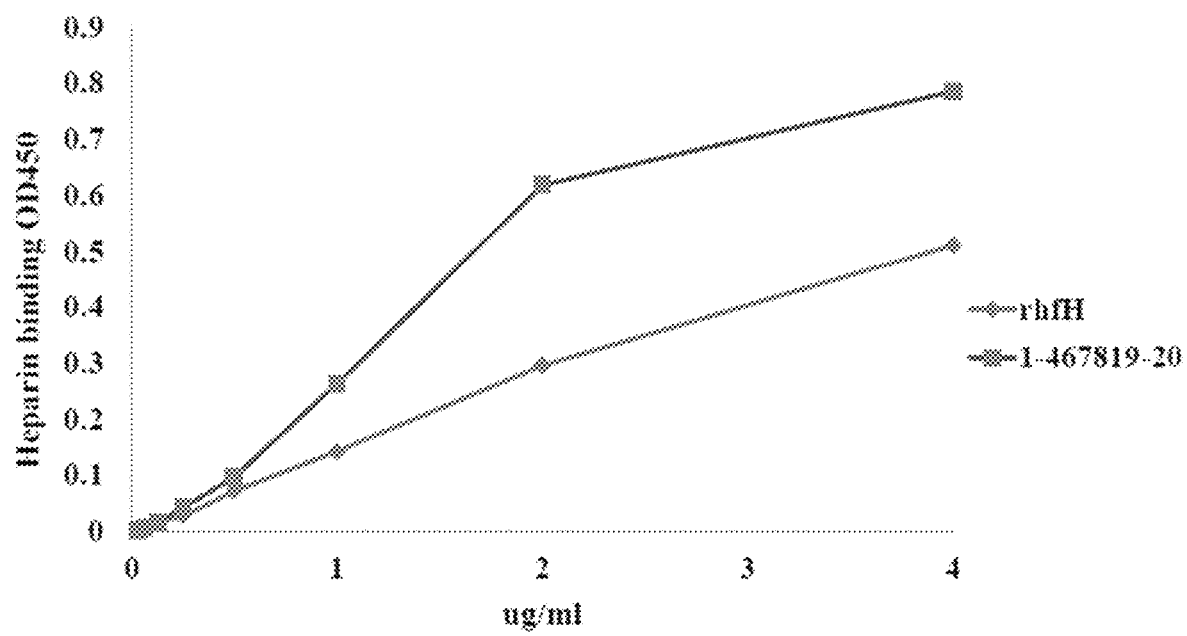
FIG. 8 is a line graph showing that recombinant hfH1-4.678.19-20 (square, top line) has strong heparin-binding activity. The human fH truncation variant containing SCR1-4, 6-8, and 19-20 retains heparin-binding activity. Its heparin-binding activity is dose-dependent, and when compared with full-length human fH (diamond, lower line) on a µg/ml basis, it showed higher activity. Heparin-binding activity was assessed by ELISA using plate-coated heparin, overlay of a full-length or truncated fH protein solution and, after washing, detection of bound fH or truncated fH by the mAb OX-23 (against an epitope in SCR2-3).
Figure 9:
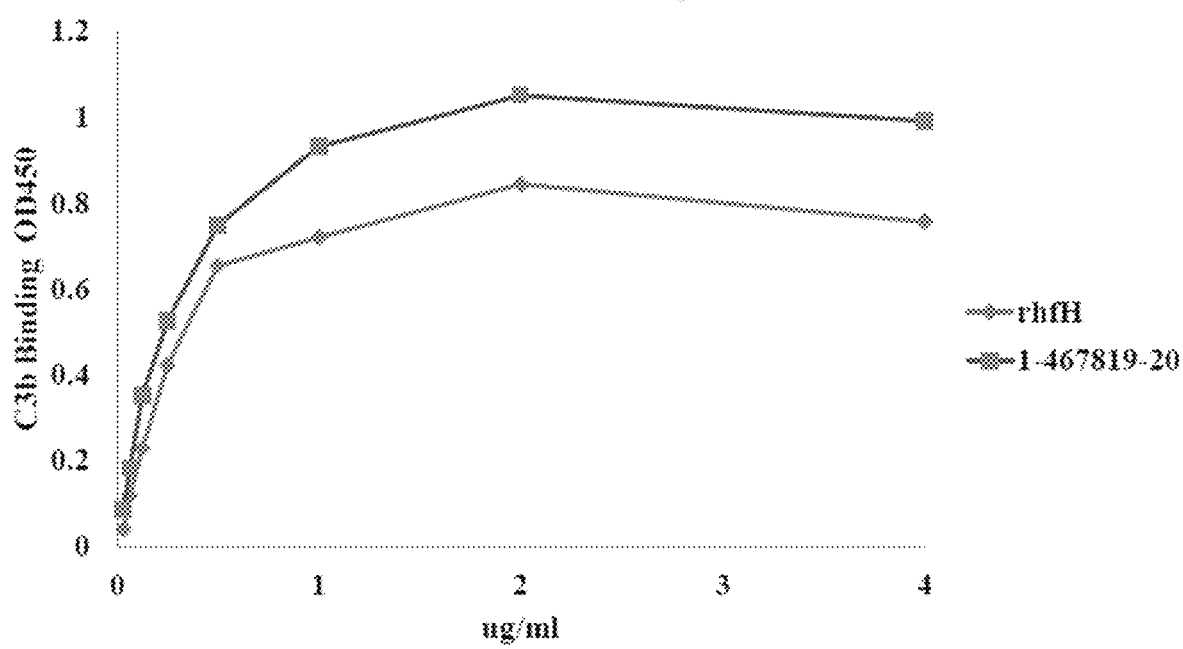
FIG. 9 is a line graph showing recombinant hfH1-4.678.19-20 (square, top line) has strong C3b-binding activity. The human fH truncation variant containing SCR1-4, 6-8, and 19-20 retains C3b-binding activity. Its C3b-binding activity is dose-dependent, and when compared with full-length human fH (diamond, bottom line) on a µg/mL basis, it showed higher activity. C3b-binding activity was assessed by ELISA using plate-coated C3b, overlay of a full-length or truncated fH protein solution and, after washing, detection of bound fH or truncated fH by the mAb OX-23 (against an epitope in SCR2-3).
Figure 12A:
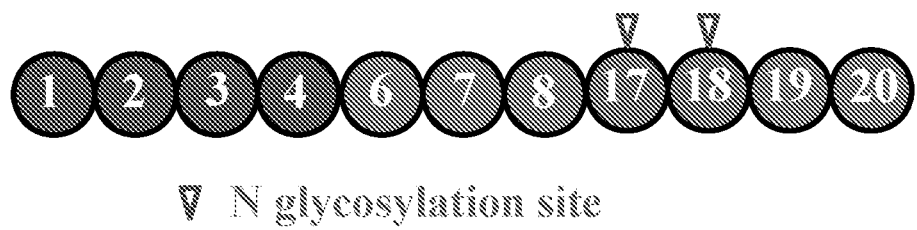
FIG. 12A provides a schematic domain structure of human factor H variant containing SCR1-4, 6-8, and 17-20, with the locations of N-glycosylatioins sites illustrated by arrows.
Figure 14:
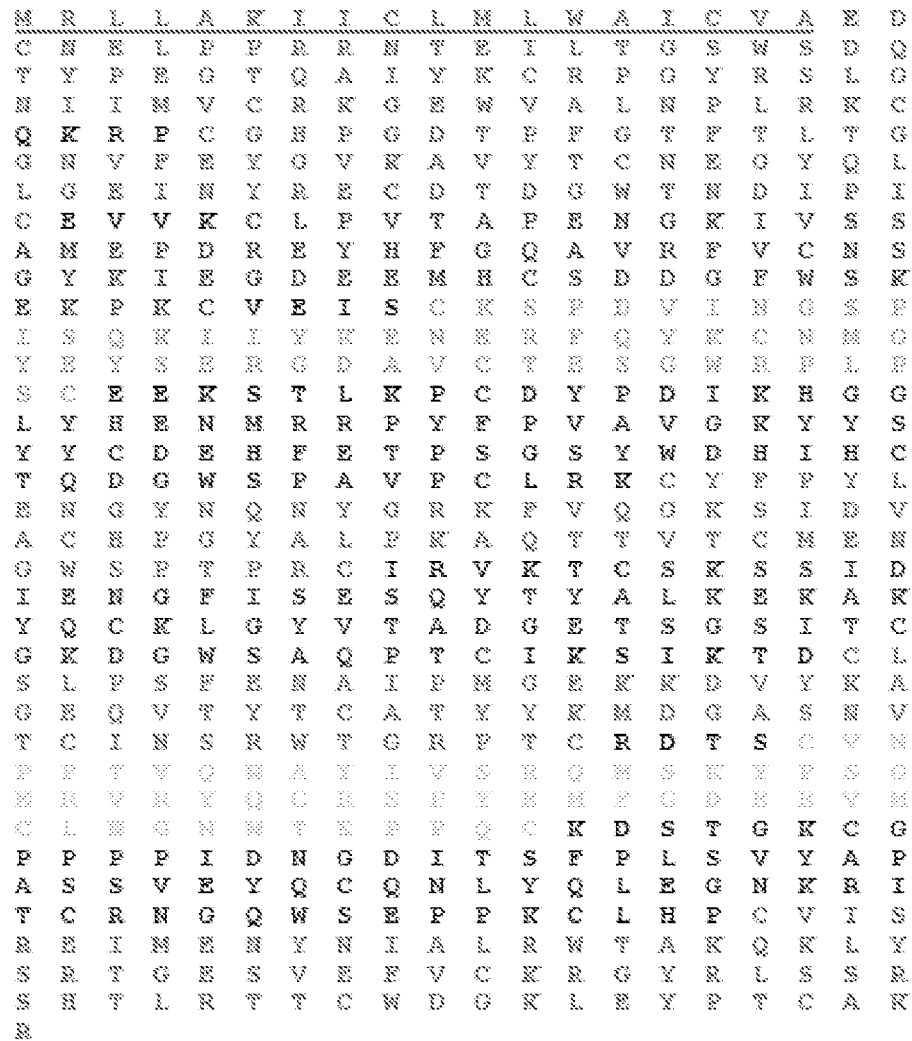
FIG. 14 is the amino acid sequence of the factor H truncation construct containing the leader peptide (underlined) and SCR1-4, 6-8, and 17-20 (hfH1-4.678.17-20) [SEQ ID NO 48].
Figure 15A:
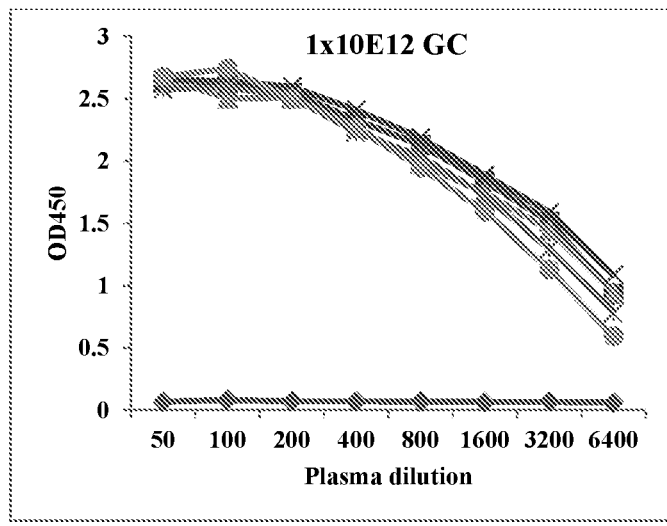
FIGS. 15A-15C show ELISA detection of hfH1-4.6-8.17-20 protein level in the plasma of 3 fH mutant mice treated with varying doses of AAV8-hfH1-4.678.17-20. The fH$^{m/m}$ mouse is a strain of fH mutant mice that carry premature stop codons at the beginning of SCR19. These mice produce trace amount of truncated fH (lacking SCR19-20) and has uncontrolled fluid phase alternative pathway complement activation and consumption (secondary C3 and fB deficiency). Mice were infected by retro-orbital I.V. with a AAV8 virus containing hfH11-4.678.17-20 at three doses, $1\times10^{12}$ gene copies (GC)/mouse, $3\times10^{11}$ GC/mouse and $1\times10^{11}$ GC/mouse, respectively. Plasma samples were collected for ELISA assay before AAV treatment (Pre) or at one week (W1), two weeks (W2), one month (M1), two months (M2) or 3 months (M3) after AAV treatment. For ELISA assay, the mAb OX-23 was used as a capture antibody (recognizing an epitope in human fH SCR2-3) and biotinylated mAb L20/3 was used as a detection antibody (recognizing human fH SCR19). As shown in the figure, there is no hfH1-4.678.17-20 in the blood of fH$^{m/m}$ mice before AAV-hfH1-4.678.17-20 treatment (Pre), but high level of hfH11-4.678.17-20 was detected after AAV treatment and hfH1-4.678.17-20 expression remained stable for at least 3 months.
Figure 15B:
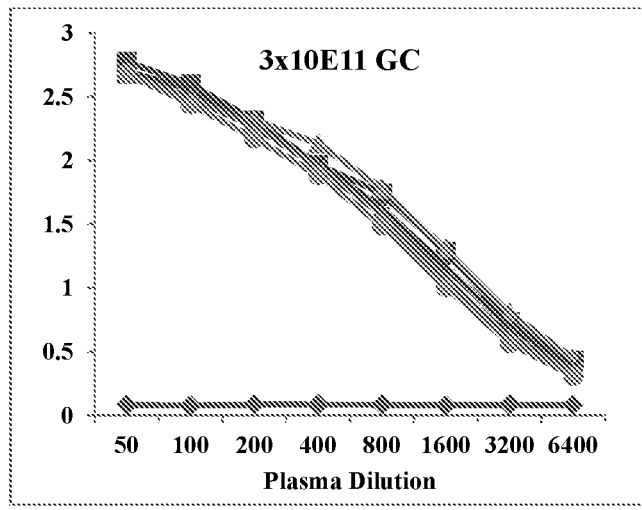
Figure 15C:
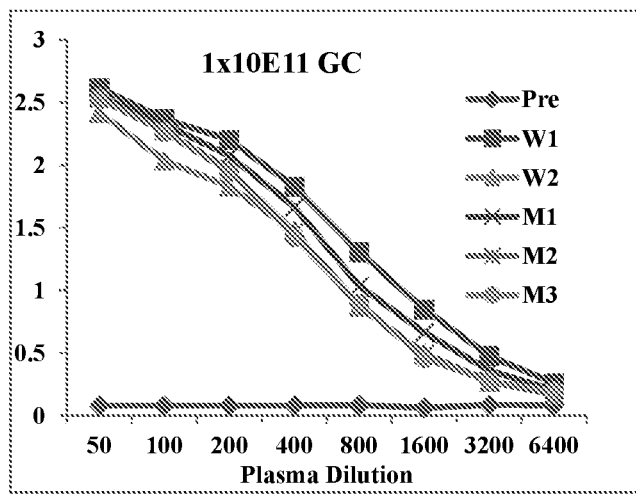
Figure 16A:
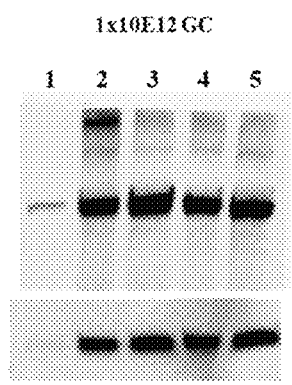
FIGS. 16A-16C are western blot analysis demonstrating that treatment with AAV8-hfH1-4.678.17-20 gene therapy of fH$^{m/m}$ mice inhibits alternative pathway complement activation. Due to the lack of sufficient endogenous mouse fH expression, untreated fH$^{m/m}$ mice have uncontrolled fluid phase alternative pathway complement activation, and as a result they consume plasma C3 and fB (Lane 1). In three fH$^{m/m}$ mice treated with $1\times10^{12}$ gene copies (GC)/mouse (FIG. 16A), $3\times10^{11}$ gene copies (GC)/mouse (FIG. 16B) and $1\times10^{11}$ gene copies (GC)/mouse (FIG. 16C), respectively, through retro-orbital I.V., alternative pathway complement activation was prevented with corresponding recovery of plasma C3 and fB when the treated mice were examined at one week (W1), one month (M1), 2 months (M2) and 3 months (M3) after AAV8-hfH1-4.678.17-20 gene therapy. In every treatment dosage and time point (Lanes 2, 3, 4, 5), plasma C3 and fB were markedly higher after AAV8-hfH11-4.678.17-20 gene therapy than before treatment (Pre, Lane 1).
Figure 16B:
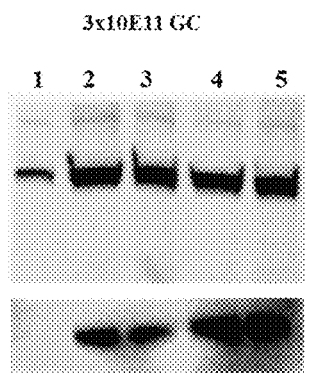
Figure 16C:
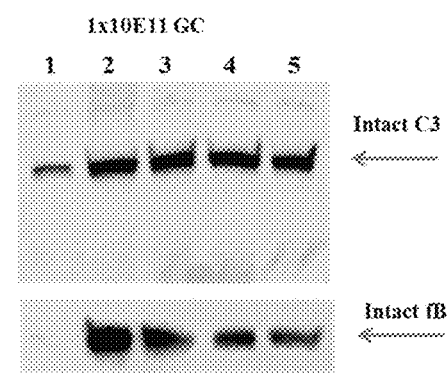
Figure 23:
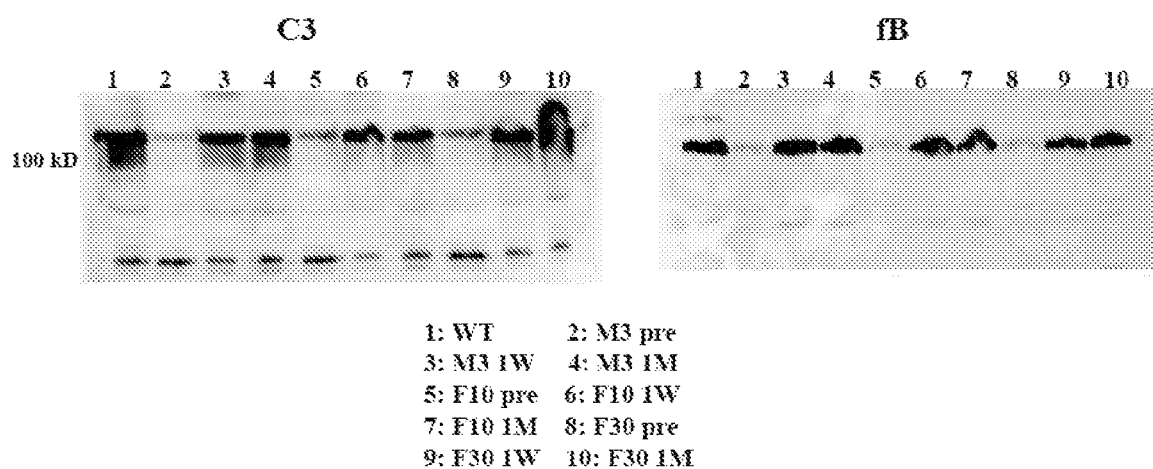
FIG. 23 is a western blot analysis demonstrating that AAV8-mediated fH gene therapy in fH$^{m/m}$ mice prevents uncontrolled alternative pathway complement activation. Due to the lack of sufficient endogenous fH expression, untreated fHm/m mice have uncontrolled fluid phase alternative pathway complement activation, and as a result they consume plasma C3 and fB (compare Lane 1 of WT with Lanes 2, 5, 8 of fH$^{m/m}$ mice before gene therapy). After fH$^{m/m}$ mice were treated with AAV8-mfH1-4.678.19-20, at one week (1 W, Lanes 3, 6, 9) and one month (1M, Lanes 4, 7, 10), plasma C3 and fB levels were recovered to WT levels, suggesting that AAV8-mediated fH gene therapy prevented uncontrolled alternative pathway complement activation and C3 and fB consumption, and that the therapeutic effect was evident as early as one week and last at least one month.
Figure 24:
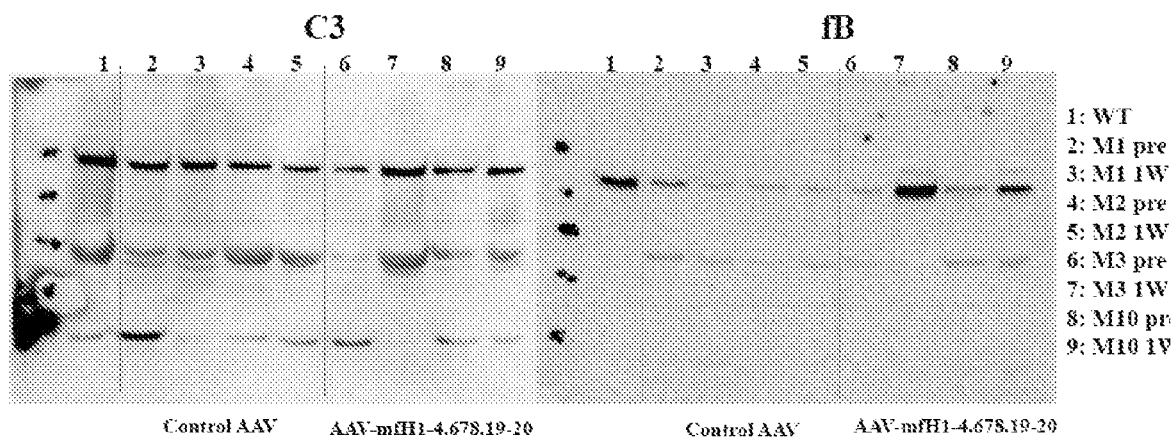
FIG. 24 is a western blot analysis demonstrating that AAV8-mediated fH gene therapy prevents uncontrolled alternative pathway complement activation in a mouse model of lethal C3 glomerulopathy. In fH$^{m/m}$ mice that are also deficient in properdin (fH$^{m/m}$ P$^{-/-}$), a similar uncontrolled alternative pathway complement activation with C3 and fB consumption occurs. Compared with fH$^{m/m}$ mice, fHm/mP-/- mice develop a lethal form of C3G and they die by the age of 10-12 weeks old. In this experiment, two fH$^{m/m}$ P$^{-/-}$ mice aged around 7-weeks old each were treated with AAV8-mfH1-4.678.19-20 or empty AAV8 vector (pAAV.TBG.rBG) as a control group (Control AAV). One week after AAV8 gene therapy, blood samples were collected and analyzed by western blot for C3 and fB levels. As shown in the panels, compared with blood samples before AAV8 treatment (pre), there was no difference in intact C3 or fB levels one week (1 W) after control AAV8 treatment (Lanes 2-5). However, plasma C3 and fB levels in mice one week after treatment with AAV8-mfH1-4.678.19-20 were significantly increased (Lanes 6-9), suggesting uncontrolled alternative pathway complement activation was inhibited by gene therapy. Mice were treated with AAV8 ($3 \times 10^{12}$ gene copies/mouse) via retro-orbital I.V. injection.
Figure 25:
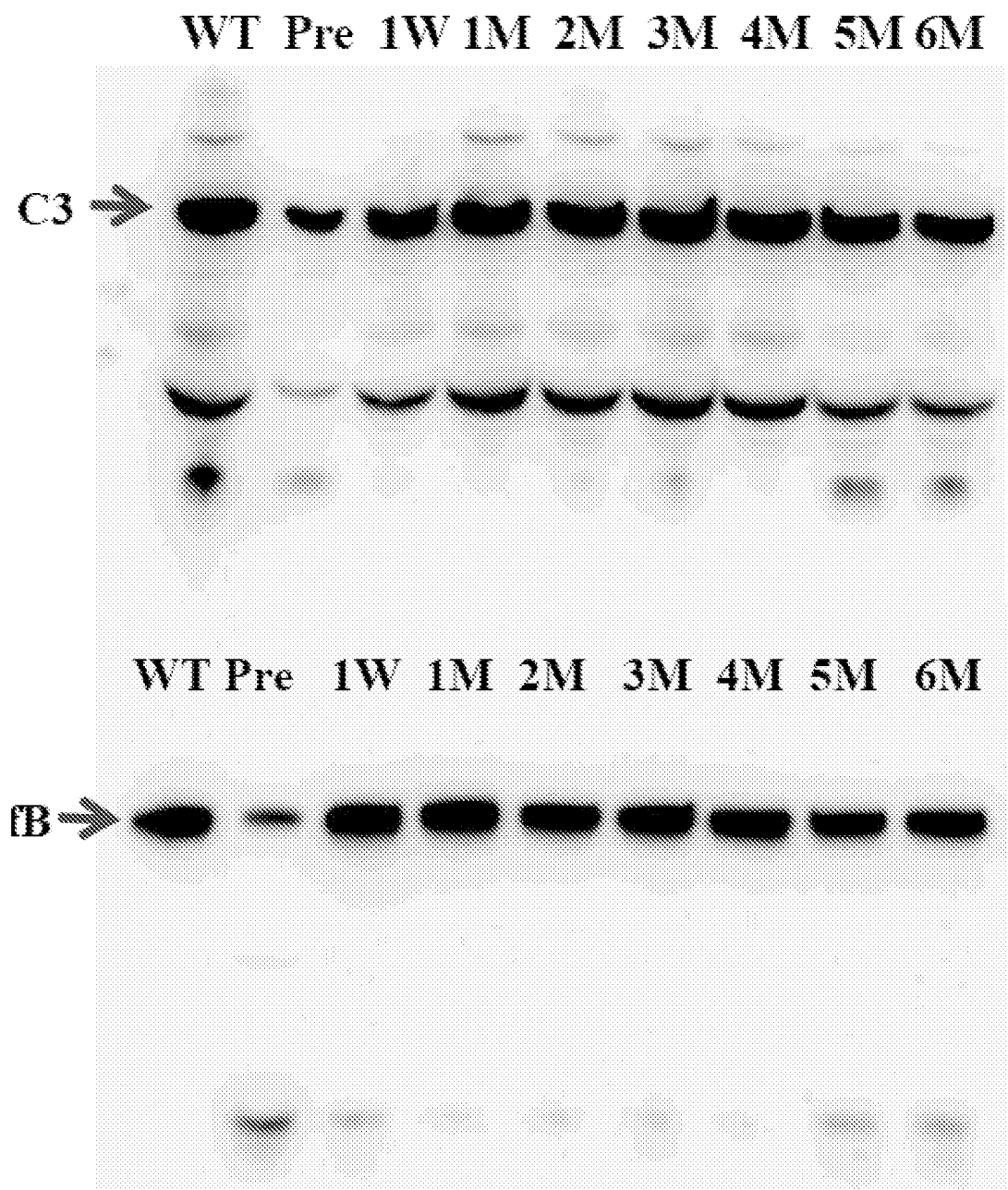
FIG. 25 shows long term follow-up of an fH$^{m/m}$ P$^{-/-}$ (M3 from FIG. 24)-treated with AAV8-mfH1-4.678.19-20 gene therapy. Western blot analysis of plasma C3 and fB levels before gene therapy (Pre) and at 1 week (1 W), 1, 2, 3, 4, 5 and 6 months (1M, 2M, 3M, 4M, 5M, 6M) after treating with AAV8-mfH1-4.678.19-20 showing C3 and fB were persistently elevated to wild-type mouse levels after gene therapy, suggesting that the therapeutic effect was long-lasting.
Figure 26:
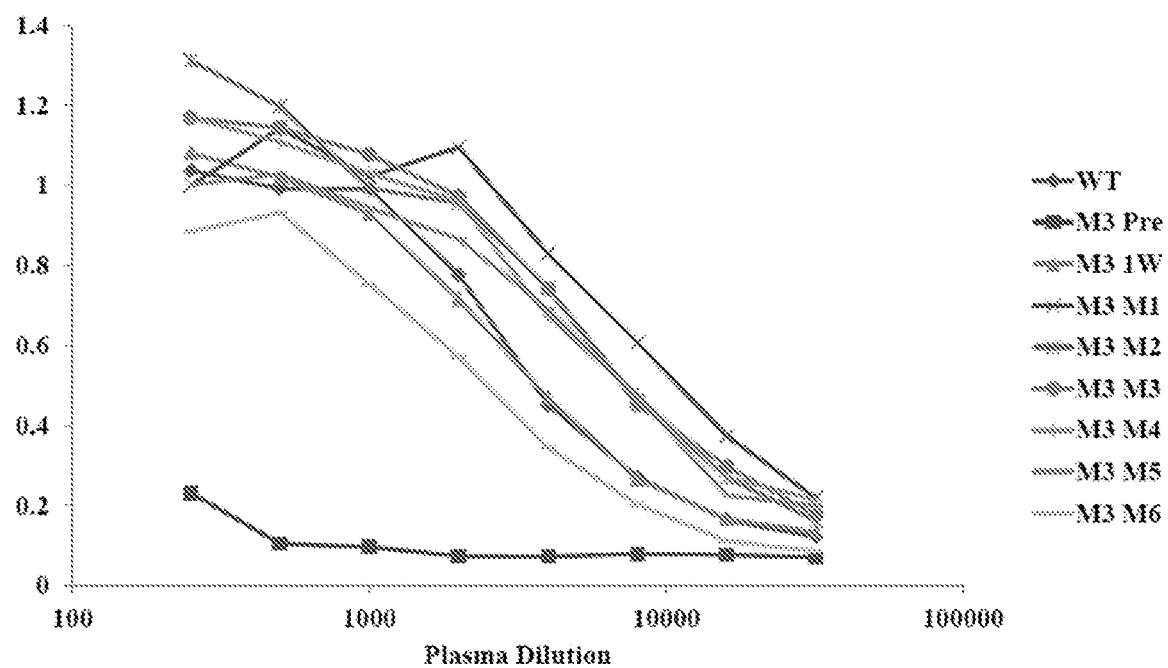
FIG. 26 shows long term follow-up of an fH$^{m/m}$P$^{-/-}$ (M3 from FIG. 24) treated with AAV8-mfH1-4.678.19-20 gene therapy. ELISA analysis of plasma levels of mfH1-4.678.19-20 protein before (Pre) and 1 week, 1, 2, 3, 4, 5 and 6 months (M) after treating with AAV8-mfH1-4.678.19-20 showing that mfH1-4.678.19-20 as a therapeutic protein drug was persistently expressed.
Figure 27:
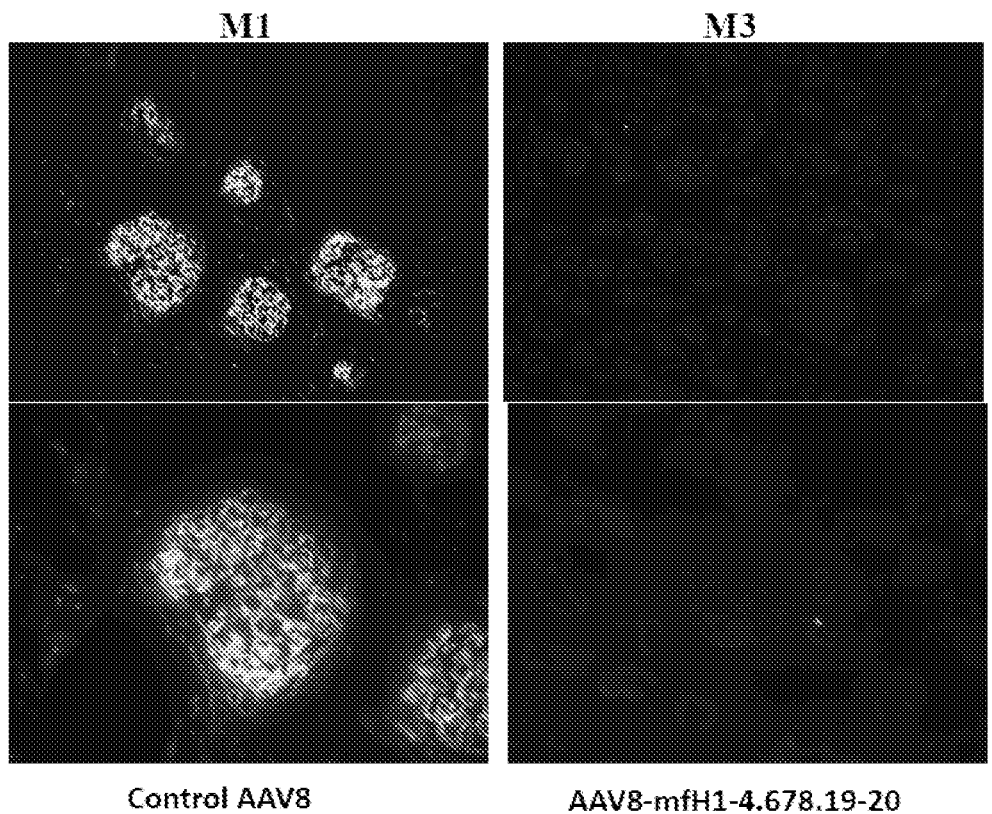
FIG. 27 shows the efficacy of AAV8-mfH1-4.678.19-20 gene therapy in preventing renal pathology in C3 glomerulopathy. An fH$^{m/m}$ P$^{-/-}$ mouse treated with control AAV8 vector (mouse M1 from FIG. 24) was moribund within 2 weeks of treatment and immunostaining of its kidney showed strong glomerular C3 deposition as previously described for untreated fH$^{m/m}$ P$^{-/-}$ mice (left panels). In contrast, a fH$^{m/m}$ P$^{-/-}$ mouse treated with the AAV8-mfH1-4.678.19-20 vector (M3 from FIG. 23) survived and was still healthy at 6 month after treatment, at which time it was sacrificed and analyzed for kidney histology. No glomerular C3 deposition was detected in this mouse (right panels), suggesting C3 glomerulopathy was prevented by AAV8-mfH1-4.678.19-20 gene therapy.
Figure 30:
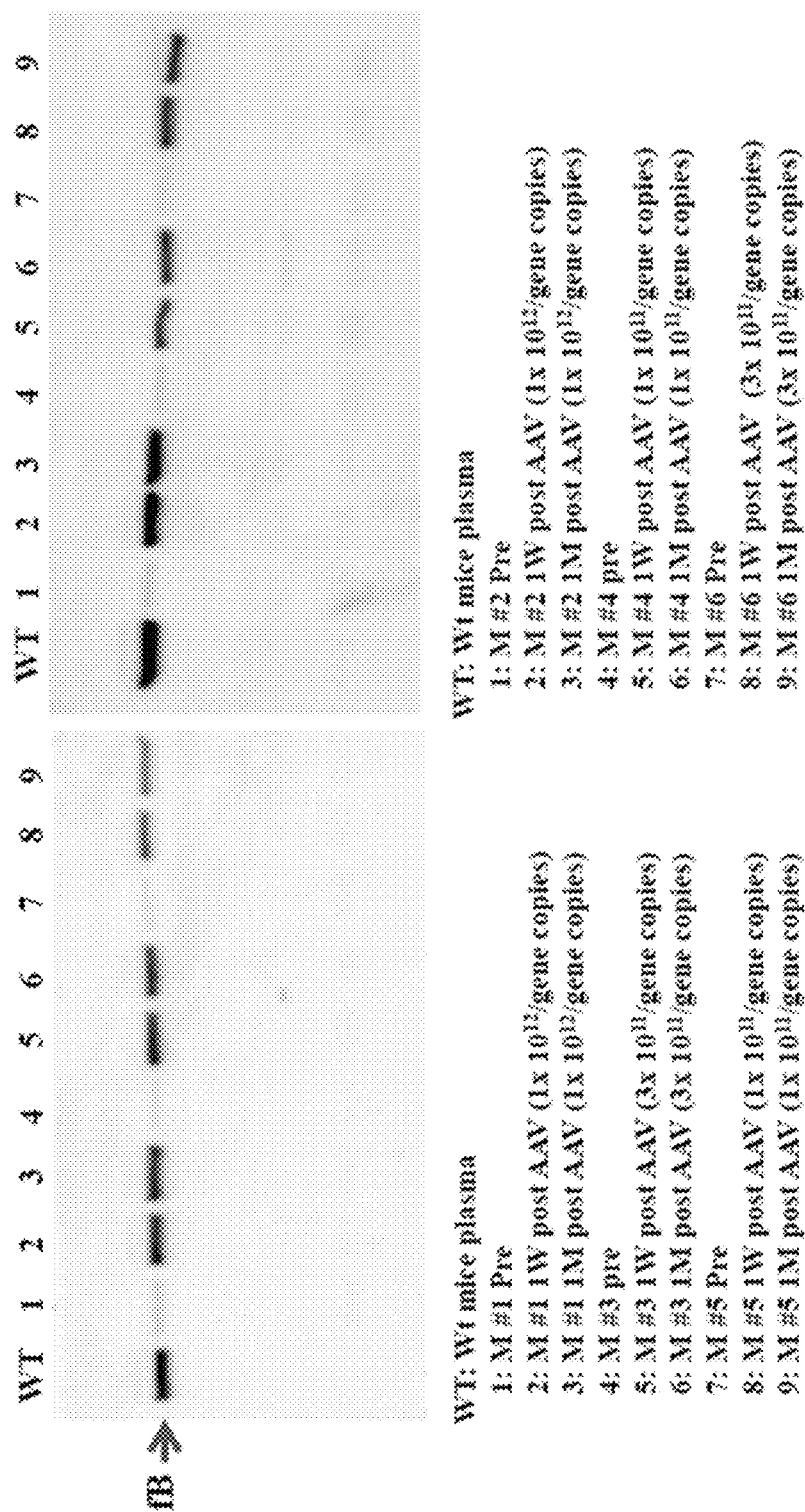
FIG. 30 provides a dosage comparison of AAV8-mfH1-4.678.19-20 gene therapy using fB recovery as a readout. The Western analysis was performed essentially as described in FIG. 29A-B where C3 was used as a readout. As shown, all doses tested were able to increase plasma fB levels when examined at 1 W and 1M time points.
Figure 31:
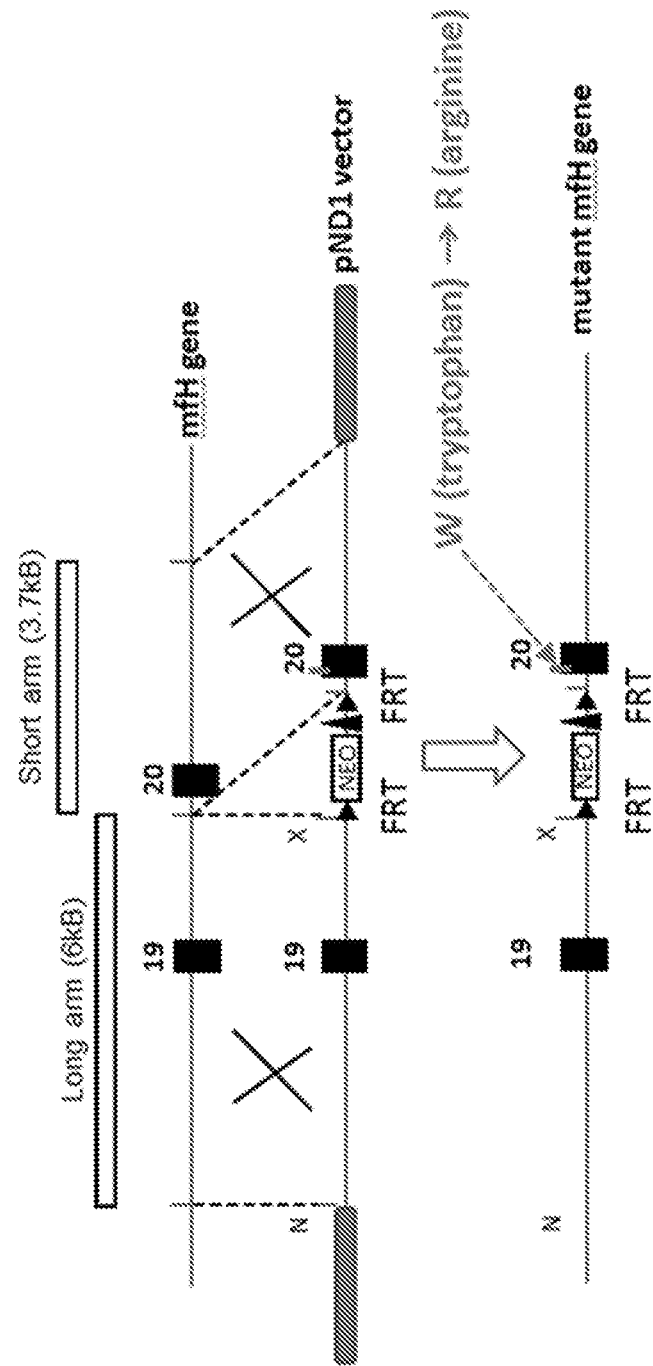
FIG. 31 is a schematic diagram showing the gene targeting strategy used to introduce a W to R mutation in SCR20 of mouse fH (position 1206, corresponding to position 1183 in human fH).
Figure 32:
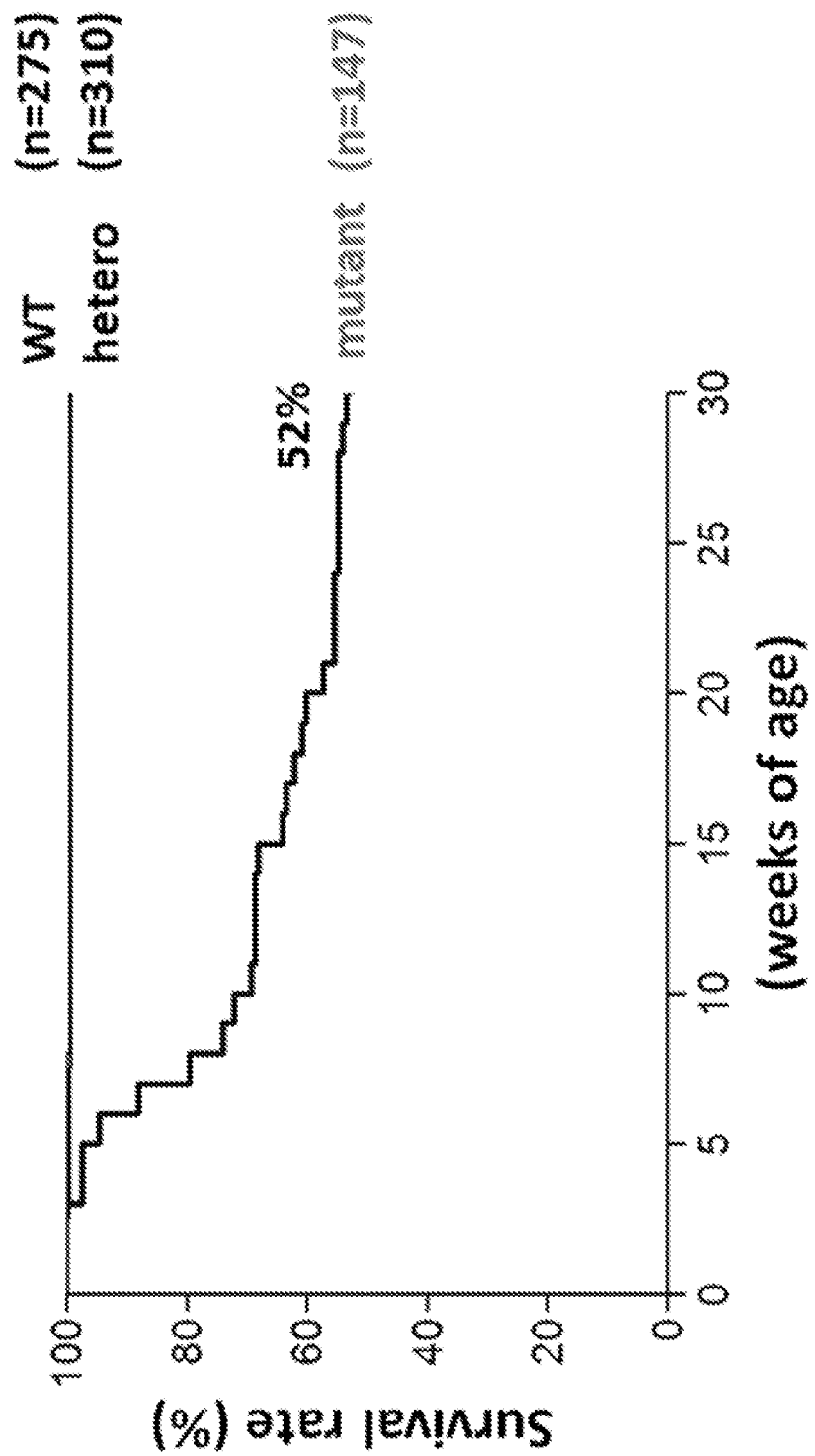
FIG. 32 shows the survival curves of wild-type littermate mice and mutant mice carrying W1206R mutation in fH. The fH mutant mice developed characteristic pathologies of aHUS and close to half of them died by 30 weeks of age.
Figures 33A, 33B:
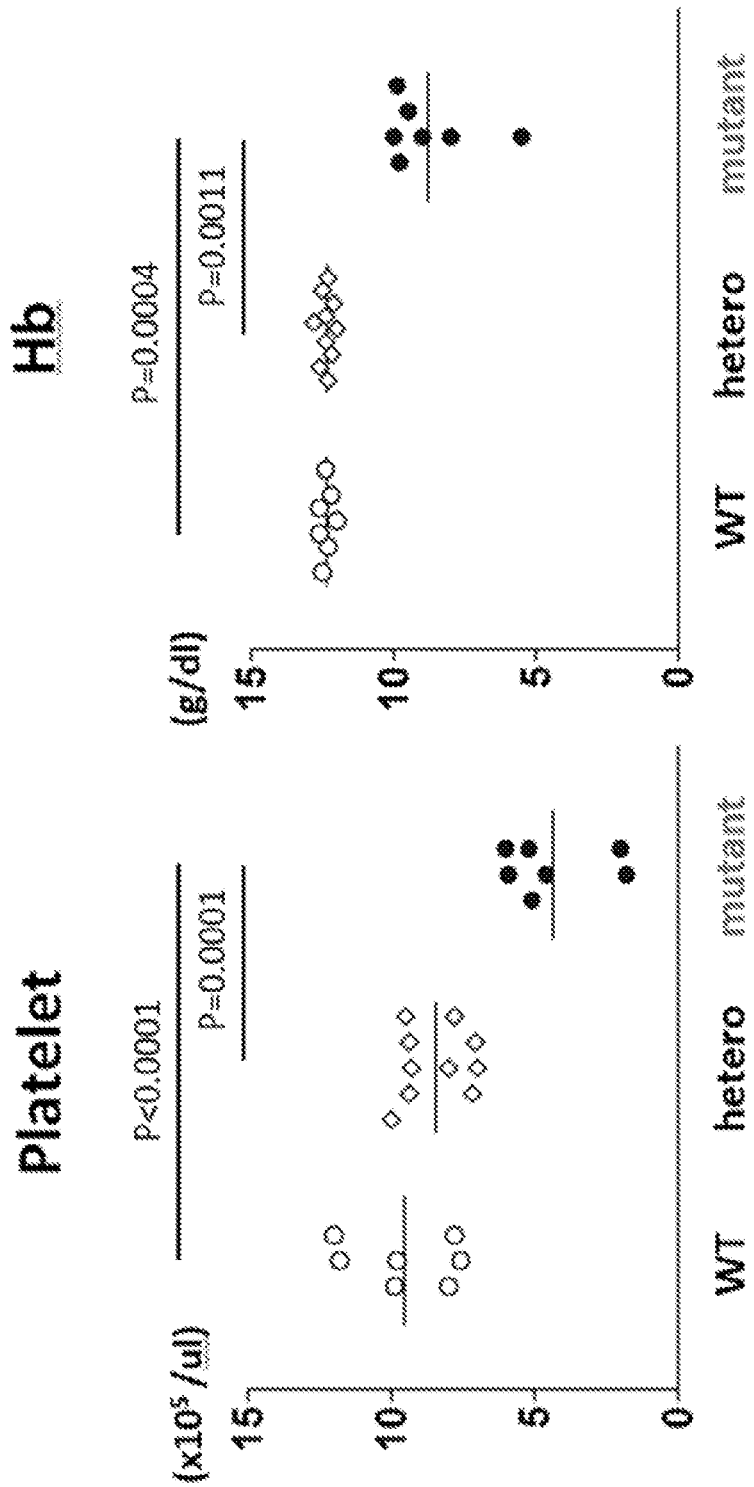
FIG. 33A shows a comparison of platelet counts in wild-type, heterozygous, and homozygous mutant mice. The homozygous mutant mice showed low platelet counts, suggesting that they were suffering from chronic thrombocytopenia.
FIG. 33B shows a comparison of hemoglobin levels in wild-type, heterozygous, and homozygous mutant mice. The homozygous mutant mice show low hemoglobin levels, suggesting that they are suffering from chronic hemolytic anemia.
Figure 36:
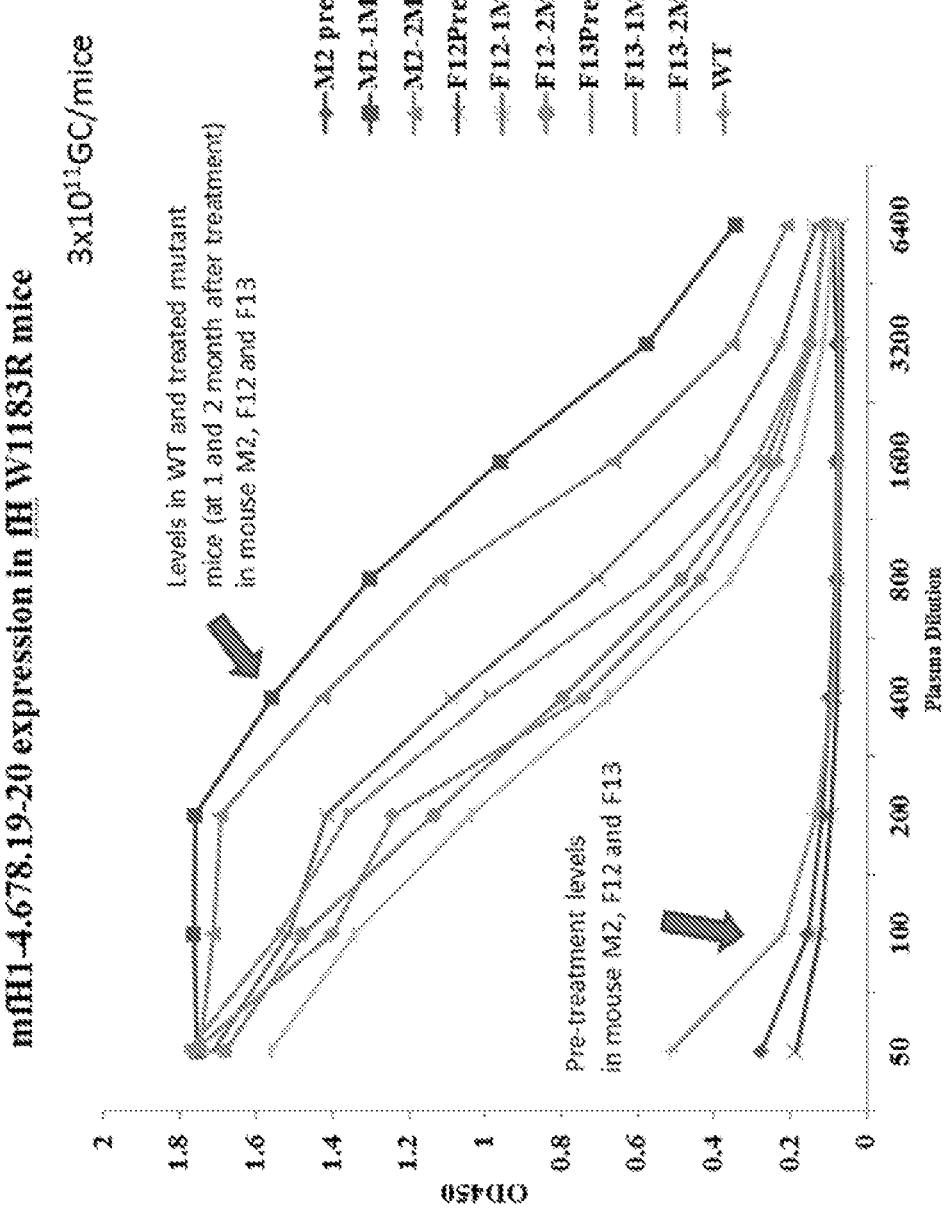
FIG. 36 shows that mfH1-4.678.19-20 protein was detected by ELISA in the blood of fH$^{W1206R/W1206R}$ mice at 1 month and 2 months after treatment with AAV8-mfH1-4.678.19-20 vector at $3\times10^{11}$ GC/mouse but not in the blood of these mice before AAV gene therapy.

Novel engineered factor H (fH) genes and protein variants are described herein. These variants are characterized by increased half-life and increased efficacy in treating conditions associated with factor H and other complement disorders.

Delivery of these variants to subjects in need thereof via a number of routes, and particularly by expression in vivo mediated by a recombinant vector such as a rAAV vector, are described. Also provided are methods of using these variants in regimens for treating factor H associated disorders. Advantageously, compositions provided herein are useful for simultaneously targeting multiple pathways and/or treating or modulating uncontrolled alternative pathway complement regulation caused by a variety of factors.

As used herein, the term "treating complement factor H disorders" may encompass alleviating, reducing, and/or ameliorating symptoms, and/or preventing the development of additional symptoms associated with complement factor H disorder, which can manifest as several different phenotypes, including asymptomatic, recurrent bacterial infections, and renal failure. This is typically characterized by decreased serum levels of factor H, complement component C3, and a decrease in other terminal complement components, indicating activation of the alternative complement pathway. This disorder is associated with a number of renal diseases with variable clinical presentation and progression, including C3 glomerulopathy and atypical hemolytic uremic syndrome. Also provided herein are compositions and methods for treating one or more of age related macular degeneration (AMD), atypical hemolytic uremic (including, e.g., syndrome microangiopathic haemolytic anemia, thrombocytopenia, acute renal failure), paroxysmal nocturnal hemoglobinuria (PNH), schizophrenia, ischemic stroke, and/or preventing or treating bacterial infections caused by recruitment of bacterial pathogens (e.g., *Aspergillus* spp.; *Borrelia burgdorferi*; *B. duttonii*; *B. recurrentis*; *Candida albicans*; *Francisella tularensis*; *Haemophilus influenzae*; *Neisseria*

*meningitidis; Streptococcus pyogenes*, or one of the five factor H binding proteins of *B. burgdorferi* (CRASP-1, CRASP-2, CRASP-3, CRASP-4, or CRASP-5), among others.

As used herein, the term "treating complement associated disorders" includes alleviating, reducing, and/or ameliorating symptoms, both of the complement factor H disorders identified above, but also other disorders associated with uncontrolled alternative pathway complement regulation. More particularly, the data provided herein suggests that at least one AAV-mediated fH variant is broadly effective for complement-mediated diseases caused by uncontrolled alternative pathway complement regulation, irrespective of the underlying regulatory mechanism defect. See, e.g. FIG. 23.

"Complement-mediated disorders" may encompass symptoms associated with complement dysregulation which can manifest as several different phenotypes, including asymptomatic, recurrent bacterial infections, and various tissue injuries including but not limited to renal diseases. Unless otherwise specified, both homozygous subjects and heterozygous subjects are encompassed within this definition. Complement dysregulation is typically caused by loss of function mutations in, or auto-antibodies against, complement regulatory proteins including but not limited to fH, factor I (fI) and membrane cofactor protein (MCP) or by gain of function mutations in other complement proteins including but not limited to C3 and factor B (fB). Complement dysregulation is typically, though not always, characterized by decreased serum levels of factor H, complement component C3, fB and a decrease in other terminal complement components, indicating activation of the alternative and/or the terminal complement pathway. Complement-mediated pathologies that can be treated by the present invention of composition and method include but are not limited to the following diseases with variable clinical presentation and progression: C3 glomerulopathy (formally called membranoproliferative glomerulonephritis type II or MPGNII), of which there are two known forms—dense deposit disease (DDD) and C3 glomerulonephritis (C3GN); thrombotic microangiopathy (TMA) including but not limited to atypical hemolytic uremic syndrome (aHUS), Shiga-like toxin-producing *E. coli* HUS (STEC-HUS) and thrombotic thrombocytopenia purpura (TTP); retinal degenerative eye disease including age related macular degeneration (AMD), RPE degeneration, chorioretinal degeneration, photoreceptor degeneration, paroxysmal nocturnal hemoglobinuria (PNH), ischemia reperfusion injury of all organs and settings, rheumatoid arthritis, hemodialysis, diabetic nephropathy, diabetic vasculopathy, asthma, systemic lupus erythematosus (SLE), ischemic stroke, abdominal aortic aneurysm (AAA), anti-neutrophil cytoplasmic antibody (ANCA) mediated vasculitis (ANCA vasculitis), ANCA-mediated hemorrhagic lung injury and disease, ANCA glomerulonephritis, graft versus host disease (GvHD), acute or delay graft rejection in organ transplantation, Crohn's disease, psoriasis, multiple sclerosis, anti-phospholipid syndrome, preeclampsia, atherosclerosis, neuromyelitis optica (NMO), autoimmune skin-blistering disease, Bullous pemphigoid (BP), Alzheimer's disease (AD), as well as bacterial infections caused by recruitment of bacterial pathogens (e.g., *Aspergillus* spp.; *Borrelia burgdorferi; B. duttonii; B. recurrentis; Candida albicans; Francisella tularensis; Haemophilus influenzae; Neisseria meningitidis; Streptococcus pyogenes*. Other examples of such disorders are discussed in more details below.

The amino acid sequence of the mature "wild-type" human complement factor H (isoform 1) is provided herein and serves as a reference for the amino acid numbering of the hfH isoform 1 [reproduced in SEQ ID NO: 39]. The leader sequence is located at amino acids 1 to 18 of factor H, with reference to SEQ ID NO: 39. The amino acid sequence of the leader is provided in SEQ ID NO: 2. The mature (secreted) hfH protein is located at amino acids 19 to 1231, with reference to SEQ ID NO: 39. There are alternative methods of determining the location of the 20 short complement repeats (SCRs). The location of the domains used in the experiments provided below is annotated in FIG. 1 and is based on the numbering used in C. Estaller et al, Eur J Immunol. 1991 March; 21(3):799-802.

The amino acid sequence of the wild-type human complement factor H, isoform 1, is reproduced in SEQ ID NO: 39. The features section of SEQ ID NO: 1 also illustrates an alternative system for identifying the start/stop of each of the 20 Short Consensus Repeat (SCR) domains. In this system, linker sequences are not present between each of the SCRs.

Optionally, an engineered hfH variant provided herein may have a heterologous leader sequence substituted for the native hfH leader sequence. In the following descriptions, substitutions may be written as (first amino acid identified by single letter code)–residue position #–(second amino acid identified by single letter code) whereby the first amino acid is the substituted amino acid and the second amino acid is the substituting amino acid at the specified position with reference to isoform 1; however, by conventional alignment steps, the corresponding amino acid residues identified herein with respect to the numbering of isoform 1 can be located in isoform 2 and non-disease causing natural variants of the SCRs of isoform 1 or 2 of fH.

As used herein, when reference is made to SCR #-##, the domains are inclusive of the endpoints and is the same as "SCR #, . . . SCR ##". In certain embodiments, periods are used between the domains. For example, SCR1-4, refers to "SCR1, SCR2, SCR3, and SCR4" and is the same as "SCR1,2,3,4" or "SCR1.2.3.4.". SCR19-20, refers to SCR19 and SCR20 and is the same as "SCR19,20". For example, "SCR6-8", "SCR6.7.8" and "SCR6,7,8" refer to the same domains.

As used herein, the term "functional fH variant" includes fH variants which are characterized by having complement regulating activity (cofactor activity) located in SCR1-4 and optionally, a functional C3b-binding and GAG-binding ability (located within wild-type SCR7 and SCR19-20) characteristic of wild-type fH. In some embodiments, the engineered fH variants have more than 100% of wild-type fH cofactor activity and/or GAG-binding ability. See, e.g., FIG. 8 and the examples below which demonstrate that a fH variant described herein has GAG- and C3b-binding activity statistically higher than full-length human fH, e.g., about 10% to 40% higher. In another embodiment, the engineered fH variant has less than about 95% to about 100% of wild-type functional fH. For example, an engineered fH variant may have at least 50% of the cofactor activity present in functional wild-type fH, and more desirably at least about 60%, at least about 75%, at least about 80%, at least about 85%, at least about 90%, at least about 95%, or at least about 99%. In another embodiment, the engineered fH variant may alternatively or additionally have at least at least 50% of the GAG-binding ability of functional fH, and more desirably at least about 60%, at least about 75%, at least about 80%, at least about 85%, at least about 90%, at least about 95%, or at least about 99%. Methods of determining cofactor activity, binding and/or determining increased circulating half-life as compared to the hfH proteins are known in the art, and at least one these assays is illustrated in the examples below.

Examples of functional fH variants include those having SCR1-4 and 19-20 of the fH protein, with one or more of an SCR7, SCR17 or SCR18 domain. Further variants include those having one or more of SCR6, SCR8, SCR16, SCR17, SCR18, or fragments thereof, and combinations thereof. For example, such variants may include, e.g., fH SCR1-4, 6-8, 19-20; fH SCR1-4, 6-8, 18-20; fH SCR1-4, 6-8, 17-20; fH SCR1-4, 6-7, 19-20; fH SCR1-4,6-7,18-20; fH SCR1-4,6-7,17-20; fH SCR1-4, 7-8, 19-20; fH SCR1-4, 7-8, 18-20; fH SCR1-4,7-8,17-20; fH SCR1-4, 7, 19-20; fH SCR1-4,7, 18-20; fH SCR1-4,7, 17-20; SCR1-4, 17, 19-20; SCR1-4, 18-20; SCR1-4, 17-20 and/or fH SCR1-4,7, 16-20, among others. In certain embodiments, the hfH variant further comprises additional hfH SCRs, e.g., SCR6, SCR8, SCR16, or combinations thereof. In preferred embodiments, hfH SCR5 is absent. However, in certain embodiments, hfH SCR5 may be present in whole or a fraction thereof. In certain embodiments, hfH SCR9, SCR10, SCR11, SCR12, SCR13, SCR14, and/or SCR15 are absent, or are at least functionally deleted. Optionally, one or more of the SCRs in these variants may be a "functional fragment" of the SCRs, rather than a full-length SCR as shown in FIG. 1 or the features of SEQ ID NO: 1. By "functional fragment" is meant an amino acid sequence (or coding sequence therefor) less than the full-length SCR which is characterized by having one or more of complement inhibiting activity, the ability to bind, heparin, and/or C3b-binding activity.

These and other variants may include other fH sequences. For example, when expressed from a viral vector the coding sequence of the fH variant also includes a leader sequence. Such a leader sequence may be an fH leader. Optionally, the leader sequence can be from another source, e.g., an IL-2 leader. In one embodiment, the leader sequence selected is less than about 26 amino acids in length (e.g., from about 1 to about 26 amino acids), more preferably less than 20 amino acids (from about 1 to about 20 amino acids), and most preferably, less than about 18 amino acids in length (from about 1 to about 18 amino acids). By "functional deletion" is meant an amino acid sequence (or coding sequence therefor) which lacks complement inhibiting activity, the C3b-binding activity, and optionally also further lacks heparin binding activity.

With the variants, domains may be located immediately adjacent to one another (e.g., the carboxy terminus of one domain may immediately follow the amino terminus of the preceding domain). Alternatively, one or more of the SCR domains may have a linker composed of one to about 12 to 18 amino acids located between them. For example, a variant may contain SCR1-(L1)-SCR2-(L2)-SCR3-(L3)-SCR4-(L4)-(SCR6-(L4'))-SCR7-(L5)-(SCR8-(L5'))-(SCR16-(L5''))-(SCR17-(L5'''))-(SCR18-(L5''''))-SCR 19-(L6)-SCR20, wherein the ( ) indicate optional component, "L" refers to a linker, and each of L1, L2, L3, L4, L4', L5, L5', L5'', L5''', L5'''', and L6 may be absent or independently selected from an amino acid sequence of about 1 to about 12-18 amino acids. In other words, where a variant contains multiple linkers, each of the linkers may have the same sequence or a different sequence. In certain embodiments, a variant contains at least one, at least two, at least three, at least four, at least five linkers, at least six linkers. Examples of suitable linkers include the natural linkers identified in FIG. 1 or FIG. 17, SEQ ID NO: 4, 6, 8, 10, 12, 15, 18, 20, 22, 24, 26, 28, 30, 32, 34 and 36, or synthetic linkers. Each of these wild-type linkers may be located in their native position. Alternatively, one or more of these wild-type linkers may be used in a different linker position, or in multiple different linker positions.

Optionally, one or more of these linkers may be fH sequences and are independently selected. Alternatively, one or more of the linkers may be heterologous to fH, e.g., from a different source, whether artificial, synthetic, or from a different protein which confers suitable flexibility to the fH variant. Examples of other suitable linkers may include, e.g., a poly Gly linker and other linkers providing suitable flexibility. In certain embodiments, the linkers lack any fH function.

The term "amino acid substitution" and its synonyms described above are intended to encompass modification of an amino acid sequence by replacement of an amino acid with another, substituting, amino acid. The substitution may be a conservative substitution. It may also be a non-conservative substitution. The term conservative, in referring to two amino acids, is intended to mean that the amino acids share a common property recognized by one of skill in the art. For example, amino acids having hydrophobic nonacidic side chains, amino acids having hydrophobic acidic side chains, amino acids having hydrophilic nonacidic side chains, amino acids having hydrophilic acidic side chains, and amino acids having hydrophilic basic side chains. Common properties may also be amino acids having hydrophobic side chains, amino acids having aliphatic hydrophobic side chains, amino acids having aromatic hydrophobic side chains, amino acids with polar neutral side chains, amino acids with electrically charged side chains, amino acids with electrically charged acidic side chains, and amino acids with electrically charged basic side chains. Both naturally occurring and non-naturally occurring amino acids are known in the art and may be used as substituting amino acids in embodiments. Methods for replacing an amino acid are well known to the skilled in the art and include, but are not limited to, mutations of the nucleotide sequence encoding the amino acid sequence. Reference to "one or more" herein is intended to encompass the individual embodiments of, for example, 1, 2, 3, 4, 5, 6, or more.

In addition to the fH protein variants provided herein, nucleic acid sequences encoding these fH protein variants are provided. The coding sequences for these variants may be from wild-type sequences of the leader sequence and/or one or more SCRs of isoform 1, isoform 2, or non-disease associated variants. Alternatively or additionally, web-based or commercially available computer programs, as well as service based companies may be used to back translate the amino acids sequences of the leader sequence, and/or one or more of the SCRs to nucleic acid coding sequences, including both RNA and/or cDNA. See, e.g., backtranseq by EMBOSS; Gene Infinity; and ExPasy. In one embodiment, the RNA and/or cDNA coding sequences are designed for optimal expression in human cells.

Codon-optimized coding regions can be designed by various different methods. This optimization may be performed using methods which are available on-line, published methods, or a company which provides codon optimizing services. One codon optimizing method is described, e.g., in WO 2015/012924 A2, which is incorporated by reference herein. Briefly, the nucleic acid sequence encoding the product is modified with synonymous codon sequences. Suitably, the entire length of the open reading frame (ORF) for the product is modified. However, in some embodiments, only a fragment of the ORF may be altered. By using one of these methods, one can apply the frequencies to any given polypeptide sequence, and produce a nucleic acid fragment of a codon-optimized coding region which encodes the polypeptide.

The terms "percent (%) identity", "sequence identity", "percent sequence identity", or "percent identical" in the context of nucleic acid sequences refers to the bases in the two sequences which are the same when aligned for correspondence. The length of sequence identity comparison may be over the full-length of the genome, the full-length of a gene coding sequence, or a fragment of at least about 500 to 5000 nucleotides, or as desired. However, identity among smaller fragments, e.g. of at least about nine nucleotides, usually at least about 20 to 24 nucleotides, at least about 28 to 32 nucleotides, at least about 36 or more nucleotides, may also be desired. Multiple sequence alignment programs are also available for nucleic acid sequences. Examples of such programs include, "Clustal W", "CAP Sequence Assembly", "BLAST", "MAP", and "MEME", which are accessible through Web Servers on the internet. Other sources for such programs are known to those of skill in the art. Alternatively, Vector NTI utilities are also used. There are also a number of algorithms known in the art that can be used to measure nucleotide sequence identity, including those contained in the programs described above. As another example, polynucleotide sequences can be compared using Fasta™, a program in GCG Version 6.1. Fasta™ provides alignments and percent sequence identity of the regions of the best overlap between the query and search sequences. For instance, percent sequence identity between nucleic acid sequences can be determined using Fasta™ with its default parameters (a word size of 6 and the NOPAM factor for the scoring matrix) as provided in GCG Version 6.1, herein incorporated by reference.

The terms "percent (%) identity", "sequence identity", "percent sequence identity", or "percent identical" in the context of amino acid sequences refers to the residues in the two sequences which are the same when aligned for correspondence. Percent identity may be readily determined for amino acid sequences over the full-length of a protein, polypeptide, about 32 amino acids, about 330 amino acids, or a peptide fragment thereof or the corresponding nucleic acid sequence coding sequencers. A suitable amino acid fragment may be at least about 8 amino acids in length, and may be up to about 700 amino acids. Generally, when referring to "identity", "homology", or "similarity" between two different sequences, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence. Alignments are performed using any of a variety of publicly or commercially available Multiple Sequence Alignment Programs. Sequence alignment programs are available for amino acid sequences, e.g., the "Clustal X", "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, Nucl. Acids. Res., "A comprehensive comparison of multiple sequence alignments", 27(13):2682-2690 (1999).

In one embodiment, the nucleic acid sequences encoding the fH variants (e.g., hfH variant gene) described herein are engineered into any suitable genetic element, e.g., naked DNA, phage, transposon, cosmid, RNA molecule (e.g., mRNA), episome, etc., which transfers the hfH sequences carried thereon to a host cell, e.g., for generating nanoparticles carrying DNA or RNA, viral vectors in a packaging host cell and/or for delivery to a host cells in subject. In one embodiment, the genetic element is a plasmid. The selected genetic element may be delivered by any suitable method, including transfection, electroporation, liposome delivery, membrane fusion techniques, high velocity DNA-coated pellets, viral infection and protoplast fusion. The methods used to make such constructs are known to those with skill in nucleic acid manipulation and include genetic engineering, recombinant engineering, and synthetic techniques. See, e.g., Green and Sambrook, Molecular Cloning: A Laboratory Manual, Cold Spring Harbor Press, Cold Spring Harbor, N.Y. (2012).

As used herein, an "expression cassette" refers to a nucleic acid molecule which comprises the hfH variant coding sequences, promoter, and may include other regulatory sequences therefor (e.g., 5' and/or 3' UTR sequences), which cassette may be engineered into a genetic element and/or packaged into the capsid of a viral vector (e.g., a viral particle). Typically, such an expression cassette for generating a viral vector contains the hfH sequences described herein flanked by packaging signals of the viral genome and other expression control sequences such as those described herein.

The expression cassette typically contains a promoter sequence as part of the expression control sequences. The illustrative plasmid and vector described herein uses the chicken beta-actin. Alternatively, another constitutive promoter may be selected. In certain embodiments, de-targeting of undesirable target cells may be achieved by use of appropriate vector elements, e.g., microRNAs. Additionally or alternatively, the vector selected may have preferential targeting for the desired tissue, e.g., an AAV8, AAV9, or AAVrh10 for liver, an AAV8, AAV1, or other AAV for eye, or the like.

However, targeting the vector to a desired tissue may be desirable for maximizing expression of the protein. And as such, a liver-specific promoter may be selected. Examples of suitable promoters include, thyroxin binding globulin (TBG), alpha 1 anti-trypsin (A1AT); human albumin Miyatake et al., J. Virol., 71:5124 32 (1997), humAlb; and hepatitis B virus core promoter, Sandig et al., Gene Ther., 3:1002 9 (1996)]. TTR minimal enhancer/promoter, alpha-antitrypsin promoter, LSP (845 nt) 25 (requires intron-less scAAV). Alternatively, other liver-specific promoters may be used (see, e.g., The Liver Specific Gene Promoter Database, Cold Spring Harbor). Alternatively, where targeting to another tissue is desired, a different tissue-specific promoter may be selected. The promoter may be derived from any species. For example, for use in the eye, e.g., a retinal pigmented epithelium (RPE) promoter or a photoreceptor promoter may be selected. In another embodiment, the promoter is the human G-protein-coupled receptor protein kinase 1 (GRK1) promoter (Genbank Accession number AY327580). In another embodiment, the promoter is a 292 nt fragment (positions 1793-2087) of the GRK1 promoter (See also, Beltran et al, Gene Therapy 2010 17:1162-74, which is hereby incorporated by reference herein). In another preferred embodiment, the promoter is the human interphotoreceptor retinoid-binding protein proximal (IRBP) promoter. In another embodiment, promoter is the native promoter for the gene to be expressed. In one embodiment, the promoter is the RPGR proximal promoter (Shu et al, IOVS, May 2012, which is incorporated by reference herein). Other promoters useful in the invention include, without limitation, the rod opsin promoter, the red-green opsin promoter, the blue opsin promoter, the cGMP-β-phosphodiesterase promoter, the mouse opsin promoter (Beltran et al 2010 cited above), the rhodopsin promoter (Mussolino et al, Gene Ther, Jul. 2011, 18(7):637-45); the alpha-subunit of cone transducin (Morrissey et al, BMC Dev, Biol, Jan. 2011, 11:3); beta phosphodiesterase (PDE) promoter; the retinitis pigmentosa (RP) promoter (Nicord et al, J. Gene Med, Dec. 2007, 9(12):1015-23); the NXNL2/NXNL1 promoter (Lambard et al, PLoS One, Oct. 2010, 5(10):e13025), the RPE65 promoter; the retinal degeneration slow/peripherin 2 (Rds/perph2) promoter (Cai et al, Exp Eye Res. 2010 August; 91(2):186-94); and the VMD2 promoter (Kachi et al, Human Gene Therapy, 2009 (20:31-9)). Examples of photoreceptor specific promoters include, without limitation, the rod opsin promoter, the red-green opsin promoter, the blue opsin promoter, the inter photoreceptor binding protein (IRBP) promoter and the cGMP-β-phosphodiesterase promoter. Alternatively, other promoters, such as viral promoters, constitutive promoters, regulatable promoters [see, e.g., WO 2011/126808 and WO 2013/04943], or a promoter responsive to physiologic cues may be used may be utilized in the vectors described herein.

In addition to a promoter, an expression cassette and/or a vector may contain other appropriate transcription initiation, termination, enhancer sequences, efficient RNA processing signals such as splicing and polyadenylation (polyA) signals; sequences that stabilize cytoplasmic mRNA; sequences that enhance translation efficiency (e.g., Kozak consensus sequence); sequences that enhance protein stability; and when desired, sequences that enhance secretion of the encoded product. Examples of suitable polyA sequences include, e.g., SV40, bovine growth hormone (bGH), rabbit beta globulin, and TK polyA. Examples of suitable enhancers include, e.g., the alpha fetoprotein enhancer, the TTR minimal promoter/enhancer, LSP (TH-binding globulin promoter/alphal-microglobulin/bikunin enhancer), amongst others.

These control sequences are "operably linked" to the fH gene sequences. As used herein, the term "operably linked" refers to both expression control sequences that are contiguous with the gene of interest and expression control sequences that act in trans or at a distance to control the gene of interest.

The expression cassette may be engineered onto a plasmid which is used for drug delivery or for production of a viral vector. Suitable viral vectors are preferably replication-defective and selected from amongst those which target ocular cells. Viral vectors may include any virus suitable for gene therapy may be used, including but not limited to adenovirus; herpes virus; lentivirus; retrovirus; parvovirus, etc.

Suitably, where one of these vectors is generated, it is produced as a replication-defective viral vector. A "replication-defective virus" or "viral vector" refers to a synthetic or recombinant viral particle in which an expression cassette containing a gene of interest is packaged in a viral capsid or envelope, where any viral genomic sequences also packaged within the viral capsid or envelope are replication-deficient; i.e., they cannot generate progeny virions but retain the ability to infect target cells. In one embodiment, the genome of the viral vector does not include genes encoding the enzymes required to replicate (the genome can be engineered to be "gutless"—containing only the transgene of interest flanked by the signals required for amplification and packaging of the artificial genome), but these genes may be supplied during production. Therefore, it is deemed safe for use in gene therapy since replication and infection by progeny virions cannot occur except in the presence of the viral enzyme required for replication.

In one embodiment, the viral vector is an adeno-associated virus (AAV). An adeno-associated virus (AAV) viral vector is an AAV DNase-resistant particle having an AAV protein capsid into which is packaged nucleic acid sequences for delivery to target cells. An AAV capsid is composed of 60 capsid protein subunits, VP1, VP2, and VP3, that are arranged in an icosahedral symmetry in a ratio of approximately 1:1:10 to 1:1:20, depending upon the selected AAV.

The studies described herein utilize AAV8 as an illustrative vector. As used herein, "AAV8 capsid" refers to the AAV8 capsid having the encoded amino acid sequence of GenBank accession: YP_077180, which is incorporated by reference herein. Some variation from this encoded sequence is encompassed by the present invention, which may include sequences having about 99% identity to the referenced amino acid sequence in GenBank accession: YP_077180; U.S. Pat. Nos. 7,282,199, 7,790,449; 8,319,480; 8,962,330; 8,962,332, (i.e., less than about 1% variation from the referenced sequence). In another embodiment, the AAV8 capsid may have the VP1 sequence of the AAV8 variant described in WO2014/124282, which is incorporated by reference herein. Methods of generating the capsid, coding sequences therefore, and methods for production of rAAV viral vectors have been described. See, e.g., Gao, et al, Proc. Natl. Acad. Sci. U.S.A. 100 (10), 6081-6086 (2003), US 2013/0045186A1, and WO 2014/124282. In certain embodiments, an AAV8 variant which shows tropism for the desired target cell, e.g., liver, photoreceptors, RPE or other ocular cells is selected. For example, an AAV8 capsid may have Y447F, Y733F and T494V mutations (also called "AAV8(C&G+T494V)" and "rep2-cap8(Y447F+733F+T494V)"), as described by Kay et al, Targeting Photoreceptors via Intravitreal Delivery Using Novel, Capsid-Mutated AAV Vectors, PLoS One. 2013; 8(4): e62097. Published online 2013 Apr. 26, which is incorporated herein by reference. See, e.g., Mowat et al, Tyrosine capsid-mutant AAV vectors for gene delivery to the canine retina from a subretinal or intravitreal approach, Gene Therapy 21, 96-105 (January 2014), which is incorporated herein by reference. In another embodiment, the AAV capsid is an AAV8 bp capsid, which preferentially targets bipolar cells. See, WO 2014/024282, which is incorporated herein by reference.

Other AAV serotypes may be selected as sources for capsids of AAV viral vectors (DNase resistant viral particles) including, e.g., AAV1, AAV2, AAV3, AAV4, AAV5, AAV6, AAV6.2, AAV7, AAV8, AAV9, rh10, AAVrh64R1, AAVrh64R2, rh8 [See, e.g., US Published Patent Application No. 2007-0036760-A1; US Published Patent Application No. 2009-0197338-A1; EP 1310571]. See also, WO 2003/042397 (AAV7 and other simian AAV), U.S. Pat. Nos. 7,790,449 and 7,282,199 (AAV8), WO 2005/033321 and U.S. Pat. No. 7,906,111 (AAV9), and WO 2006/110689], and rh10 [WO 2003/042397], variants thereof, or yet to be discovered, or a recombinant AAV based thereon, may be used as a source for the AAV capsid. These documents also describe other AAV which may be selected for generating AAV and are incorporated by reference. In some embodiments, an AAV cap for use in the viral vector can be generated by mutagenesis (i.e., by insertions, deletions, or substitutions) of one of the aforementioned AAV Caps or its encoding nucleic acid. In some embodiments, the AAV capsid is chimeric, comprising domains from two or three or four or more of the aforementioned AAV capsid proteins. In some embodiments, the AAV capsid is a mosaic of VP1, VP2, and VP3 monomers from two or three different AAVs or recombinant AAVs. In some embodiments, a rAAV composition comprises more than one of the aforementioned Caps.

For packaging an expression cassette into virions, the ITRs are the only AAV components required in cis in the same construct as the gene. In one embodiment, the coding sequences for the replication (rep) and/or capsid (cap) are removed from the AAV genome and supplied in trans or by a packaging cell line in order to generate the AAV vector. For example, as described above, a pseudotyped AAV may contain ITRs from a source which differs from the source of the AAV capsid. Additionally or alternatively, a chimeric AAV capsid may be utilized. Still other AAV components may be selected. Sources of such AAV sequences are described herein and may also be isolated or obtained from academic, commercial, or public sources (e.g., the American Type Culture Collection, Manassas, Va.). Alternatively, the AAV sequences may be obtained through synthetic or other suitable means by reference to published sequences such as are available in the literature or in databases such as, e.g., GenBank®, PubMed®, or the like.

The minimal sequences required to package an expression cassette into an AAV viral particle are the AAV 5' and 3' ITRs, which may be of the same AAV origin as the capsid, or which are of a different AAV origin (to produce an AAV pseudotype). In one embodiment, the ITR sequences from AAV2, or the deleted version thereof (ΔITR), are used for convenience and to accelerate regulatory approval. However, ITRs from other AAV sources may be selected. Where the source of the ITRs is from AAV2 and the AAV capsid is from another AAV source, the resulting vector may be termed pseudotyped. Typically, an expression cassette for an AAV vector comprises an AAV 5' ITR, the coding sequences and any regulatory sequences, and an AAV 3' ITR. However, other configurations of these elements may be suitable. A shortened version of the 5' ITR, termed ΔITR, has been described in which the D-sequence and terminal resolution site (trs) are deleted. In other embodiments, the full-length AAV 5' and 3' ITRs are used.

The abbreviation "sc" refers to self-complementary. "Self-complementary AAV" refers a plasmid or vector having an expression cassette in which a coding region carried by a recombinant AAV nucleic acid sequence has been designed to form an intra-molecular double-stranded DNA template. Upon infection, rather than waiting for cell mediated synthesis of the second strand, the two complementary halves of scAAV will associate to form one double stranded DNA (dsDNA) unit that is ready for immediate replication and transcription. See, e.g., D M McCarty et al, "Self-complementary recombinant adeno-associated virus (scAAV) vectors promote efficient transduction independently of DNA synthesis", Gene Therapy, (August 2001), Vol 8, Number 16, Pages 1248-1254. Self-complementary AAVs are described in, e.g., U.S. Pat. Nos. 6,596,535; 7,125,717; and 7,456,683, each of which is incorporated herein by reference in its entirety.

Methods for generating and isolating AAV viral vectors suitable for delivery to a subject are known in the art. See, e.g., U.S. Pat. Nos. 7,790,449; 7,282,199; WO 2003/042397; WO 2005/033321, WO 2006/110689; and U.S. Pat. No. 7,588,772 B2]. In a one system, a producer cell line is transiently transfected with a construct that encodes the transgene flanked by ITRs and a construct(s) that encodes rep and cap. In a second system, a packaging cell line that stably supplies rep and cap is transiently transfected with a construct encoding the transgene flanked by ITRs. In each of these systems, AAV virions are produced in response to infection with helper adenovirus or herpesvirus, requiring the separation of the rAAVs from contaminating virus. More recently, systems have been developed that do not require infection with helper virus to recover the AAV—the required helper functions (i.e., adenovirus E1, E2a, VA, and E4 or herpesvirus ULS, UL8, UL52, and UL29, and herpesvirus polymerase) are also supplied, in trans, by the system. In these newer systems, the helper functions can be supplied by transient transfection of the cells with constructs that encode the required helper functions, or the cells can be engineered to stably contain genes encoding the helper functions, the expression of which can be controlled at the transcriptional or posttranscriptional level. In yet another system, the transgene flanked by ITRs and rep/cap genes are introduced into insect cells by infection with baculovirus-based vectors. For reviews on these production systems, see generally, e.g., Zhang et al., 2009, "Adenovirus-adeno-associated virus hybrid for large-scale recombinant adeno-associated virus production," Human Gene Therapy 20:922-929, the contents of each of which is incorporated herein by reference in its entirety. Methods of making and using these and other AAV production systems are also described in the following U.S. patents, the contents of each of which is incorporated herein by reference in its entirety: U.S. Pat. Nos. 5,139,941; 5,741,683; 6,057,152; 6,204,059; 6,268,213; 6,491,907; 6,660,514; 6,951,753; 7,094,604; 7,172,893; 7,201,898; 7,229,823; and 7,439,065. See generally, e.g., Grieger & Samulski, 2005, "Adeno-associated virus as a gene therapy vector: Vector development, production and clinical applications," Adv. Biochem. Engin/Biotechnol. 99: 119-145; Buning et al., 2008, "Recent developments in adeno-associated virus vector technology," J. Gene Med. 10:717-733; and the references cited below, each of which is incorporated herein by reference in its entirety. The methods used to construct any embodiment of this invention are known to those with skill in nucleic acid manipulation and include genetic engineering, recombinant engineering, and synthetic techniques. See, e.g., Green and Sambrook et al, Molecular Cloning: A Laboratory Manual, Cold Spring Harbor Press, Cold Spring Harbor, N.Y. (2012). Similarly, methods of generating rAAV virions are well known and the selection of a suitable method is not a limitation on the present invention. See, e.g., K. Fisher et al, (1993) J. Virol., 70:520-532 and U.S. Pat. No. 5,478,745.

Optionally, the fH genes described herein may be delivered via viral vectors other than rAAV. Such other viral vectors may include any virus suitable for gene therapy may be used, including but not limited to adenovirus; herpes virus; lentivirus; retrovirus; etc. Suitably, where one of these other vectors is generated, it is produced as a replication-defective viral vector.

A "replication-defective virus" or "viral vector" refers to a synthetic or artificial viral particle in which an expression cassette containing a gene of interest is packaged in a viral capsid or envelope, where any viral genomic sequences also packaged within the viral capsid or envelope are replication-deficient; i.e., they cannot generate progeny virions but retain the ability to infect target cells. In one embodiment, the genome of the viral vector does not include genes encoding the enzymes required to replicate (the genome can be engineered to be "gutless"—containing only the transgene of interest flanked by the signals required for amplification and packaging of the artificial genome), but these genes may be supplied during production. Therefore, it is deemed safe for use in gene therapy since replication and infection by progeny virions cannot occur except in the presence of the viral enzyme required for replication.

The pharmaceutical compositions described herein are designed for delivery to subjects in need thereof by any suitable route or a combination of different routes, e.g., direct delivery to the liver (optionally via intravenous, via the hepatic artery, or by transplant), oral, inhalation, intranasal, intratracheal, intraarterial, intraocular, intravenous, intramuscular, subcutaneous, intradermal, and other parental routes of administration. The viral vectors described herein may be delivered in a single composition or multiple compositions. Optionally, two or more different AAV may be delivered, or multiple viruses [see, e.g., WO 2011/126808 and WO 2013/049493]. In another embodiment, multiple viruses may contain different replication-defective viruses (e.g., AAV and adenovirus).

The replication-defective viruses can be formulated with a physiologically acceptable carrier for use in gene transfer and gene therapy applications. In the case of AAV viral vectors, quantification of the genome copies (GC) may be used as the measure of the dose contained in the formulation. Any method known in the art can be used to determine the genome copy (GC) number of the replication-defective virus compositions of the invention. One method for performing AAV GC number titration is as follows: purified AAV vector samples are first treated with DNase to eliminate un-encapsidated AAV genome DNA or contaminating plasmid DNA from the production process. The DNase resistant particles are then subjected to heat treatment to release the genome from the capsid. The released genomes are then quantitated by real-time PCR using primer/probe sets targeting specific region of the viral genome (usually polyA signal).

Also, the replication-defective virus compositions can be formulated in dosage units to contain an amount of replication-defective virus that is in the range of about $1.0 \times 10^9$ GC to about $1.0 \times 10^{15}$ GC (to treat an average subject of 70 kg in body weight), and preferably $1.0 \times 10^{12}$ GC to $1.0 \times 10^{14}$ GC for a human patient. In another embodiment, the dose is less than about $1.5 \times 10^{11}$ GC/kg. For example, the dose of AAV virus may be about $1 \times 10^9$ GC, about $5 \times 10^9$ GC, about $1 \times 10^{10}$ GC, about $5 \times 10^{10}$ GC, or about $1 \times 10^{11}$ GC. In another example, the variants may be delivered in an amount of about 0.001 mg to about 10 mg/kg.

The above-described recombinant vectors may be delivered to host cells according to published methods. The rAAV, preferably suspended in a physiologically compatible carrier, may be administered to a human or non-human mammalian subject. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present invention.

Optionally, the compositions of the invention may contain, in addition to the rAAV and/or variants and carrier(s), excipients, including other non-active conventional pharmaceutical ingredients, such as preservatives, chemical stabilizers, suspending agents, and/or surfactants. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin. Optionally, for protein-based or antibody-based compositions, excipients suitable for solid compositions may be selected, including, e.g., fillers, beads, bulking agents, disintegrants, glidants, fI avorants, colorants, or other components.

The viral vectors and other constructs described herein may be used in preparing a medicament for delivering a fH variant to a subject in need thereof, supplying fH variant having an increased half-life to a subject, and/or for treating complement related disorders.

A course of treatment may optionally involve repeat administration of the same viral vector (e.g., an AAV8 vector) or a different viral vector (e.g., an AAV8 and an AAVrh10). For example, where targeted to the liver, repeat administration may be desirable over 18 months, 2 years, or a longer time period due to dilution of expression caused by natural hepatocyte proliferation. Still other combinations of viral and protein-based treatment may be selected using the viral vectors described herein. Optionally, the composition described herein may be combined in a regimen involving other anti-complement drugs (e.g., monoclonal antibodies, etc), or protein-based therapies (including, e.g., delivery of a composition containing one or more fH variants as described herein).

For example, an engineered hfH variant as described herein may be delivered in protein form. Optionally, when delivered to a subject in protein form, a fH variant may have a leader sequence, or may lack all or a portion of the leader sequence. Optionally, protein-based therapy may be used in conjunction with administration of a viral-mediated hfH variant. In one embodiment, the fH protein can provide an immediate release form of the hfH to the subject, e.g., detectable plasma levels within 2 hours post-administration, which typically will begin to be cleared from the subject within about 24 hours to about 48 hours, or to about 72 hours, should any lag time in the onset of expression from the viral-mediated delivery system be found to exist. In another embodiment, the hfH variant is further modified to extend its half-life by engineering into the variant at least one glycosylation site is engineered into at least one of the SCRs present in the variant, at least two of the SCRs present in the variant, at least three of the SCRs present in the variant, or more. For example, the glycosylation site may be engineered into one or more of SCR1, SCR2, SCR3, SCR4, SCR19, and/or SCR20. In another embodiment, SCR17 and/or SCR18 are additionally or alternatively glycosylated. In still a further embodiment, SCR4, 17 and 18 are glycosylated. In certain embodiments, a glycosylation site may be engineered into a linker. However, in such instance, the linker is preferably at least six amino acids in length up to about 18 amino acids in length, e.g., 8-18, 10-15, or 12 amino acids. Additionally, or alternatively, the engineered hfH protein variant may be pegylated, i.e., modified with a polyethylene glycol moiety using known techniques [see, e.g., Fee, Conan J.; Van Alstine, James M. (2006). "PEG-proteins: Reaction engineering and separation issues". Chemical Engineering Science 61 (3): 924].

As used herein, a glycosylation site refers to the point of attachment of oligosaccharides to a carbon atom (C-linked), nitrogen atom (N-linked), or oxygen atom (O-linked), or glycation (non-enzymatic attachment of reducing sugars to the nitrogen atom of a protein (e.g., the nitrogen atom of an asparagine (Asn) side chain that is part of an Asn-X-Ser/Thr, wherein X is any amino acid except Pro). In certain embodiments, N-glycosylation sites are desired. A variety of techniques are known in the art for engineering N-glycosylation sites. See. e.g. Y Liu et al, Biotech Prog 2009 September-October; 25(5): 1468-1475; Sala R J, Griebenos K. Glycosylation of therapeutic proteins: an effective strategy to optimize efficacy. BioDrugs. 2010 Feb. 1; 24(1): 9-21.

Further, an engineered hfH variant as provided herein may be formulated with a suitable carrier and/or excipient for delivery to a subject by any suitable route. In addition to conventional suspension carriers, the carrier may be a liposome or a nanocarrier. Suitable doses of the hfH variant include those which achieve sufficient plasma levels to treat a complement related disorder. Examples of dosages of hfH variants include, but are not limited to, an effective amount within the dosage range of any of about 0.01 µg/kg to about 300 µg/kg, or within about 0.1 µg/kg to about 40 mg/kg, or with about 1 µg/kg to about 20 mg/kg, or within about 1 µg/kg to about 10 mg/kg. For example, when administered intraocularly, the composition may be administered at low microgram ranges, including for example about 0.1 µg/kg or less, about 0.05 µg/kg or less, or 0.01 µg/kg or less. In some embodiments, the amount of hfH variant administered to an individual is about 10 µg to about 500 mg per dose, or about 10 µg to about 50 µg, about 50 µg to about 100 µg, about 100 µg to about 200 µg, about 200 µg to about 300 µg, about 300 µg to about 500 µg, about 500 µg to about 1 mg, about 1 mg to about 10 mg, about 10 mg to about 50 mg, about 50 mg to about 100 mg, about 100 mg to about 200 mg, about 200 mg to about 300 mg, about 300 mg to about 400 mg, or about 400 mg to about 500 mg per dose.

The pharmaceutical compositions may be administered alone. Optionally, the compositions described herein may be administered in combination with other molecules known to have a beneficial effect. For example, useful cofactors include symptom-alleviating cofactors, including antiseptics, antibiotics, antiviral and antifungal agents and analgesics, anti-inflammatories, anesthetics. In another embodiment, where intra-ocular administration is contemplated, molecules helpful for retinal attachment or treatment of damaged retinal tissue may be desired. Examples of useful, cofactors include anti-VEGF agents (such as an antibody against VEGF), basic fibroblast growth factor (bFGF), ciliary neurotrophic factor (CNTF), axokine (a mutein of CNTF), leukemia inhibitory factor (LIF), neutrotrophin 3 (NT-3), neurotrophin-4 (NT-4), nerve growth factor (NGF), insulin-like growth factor II, prostaglandin E2, 30 kD survival factor, taurine, and vitamin A. Another suitable therapeutic may include an anti-complement antibody, e.g., an anti-complement regulator C3 (e.g., such as is commercially available as Eculizumab).

The compositions described herein (both vector-mediated and protein-based) may be administered to a subject via any route, including, but not limited to, intravenous (e.g., by infusion pumps), intraperitoneal, intraocular, intra-arterial, intrapulmonary, oral, inhalation, intravesicular, intramuscular, intra-tracheal, subcutaneous, intraocular (including, intravitreal, and intra-retinal), intrathecal, transdermal, transpleural, intraarterial, topical, inhalational (e.g., as mists of sprays), mucosal, (such as via nasal mucosa), subcutaneous, transdermal, gastrointestinal, intraarticular, intracisternal, intraventricular, rectal (i.e., via suppository), vaginal (i.e., via pessary), intracranial, intraurethral, intrahepatic, and intratumoral. In some embodiments, the compositions are administered systemically (for example by intravenous injection). In some embodiments, the compositions are administered locally (for example by intraarterial or intraocular injection).

Thus, in a further aspect, use of a pharmaceutical composition in treating a complement related disorder including, e.g., a complement factor H associated disorder such as described herein and other complement related disorders, including, without limitation: tissue damage due to ischemia-reperfusion following acute myocardial infarction, aneurysm, stroke, hemorrhagic shock, crush injury, multiple organ failure, hypovolemic shock intestinal ischemia, spinal cord injury, and traumatic brain injury; inflammatory disorders, e.g., burns, endotoxemia and septic shock, adult respiratory distress syndrome, cardiopulmonary bypass, hemodialysis; anaphylactic shock, severe asthma, angioedema, Crohn's disease, sickle cell anemia, poststreptococcal glomerulonephritis, membranous nephritis, and pancreatitis; transplant rejection, e.g., hyperacute xenograft rejection; pregnancy related diseases such as recurrent fetal loss and pre-eclampsia; adverse drug reactions, e.g., drug allergy, IL-2 induced vascular leakage syndrome and radiographic contrast media allergy; andautoimmune disorders including, but not limited to, myasthenia gravis, Alzheimer's disease, multiple sclerosis, emphysema, obesity, rheumatoid arthritis, systemic lupus erythematosus, multiple sclerosis, myasthenia gravis, insulin-dependent diabetes mellitus, acute disseminated encephalomyelitis, Addison's disease, antiphospholipid antibody syndrome, autoimmune hepatitis, Crohn's disease, Goodpasture's syndrome, Graves' disease, Guillain-Barre syndrome, Hashimoto's disease, idiopathic thrombocytopenic purpura, pemphigus, Sjogren's syndrome, and Takayasu's arteritis, post cardiopulmonary bypass complications; myocardial infarction; ischemia/reperfusion injury; stroke; acute respiratory distress syndrome (ARDS); sepsis; burn injury; inflammation associated with cardiopulmonary bypass and hemodialysis; plasmapheresis; plateletpheresis; leukophereses; extracorporeal; membrane oxygenation (ECMO); heparin-induced extracorporeal LDL precipitation (HELP); radiographic contrast media induced allergic response; transplant rejection.

It is to be noted that the term "a" or "an" refers to one or more. As such, the terms "a" (or "an"), "one or more", and "at least one" are used interchangeably herein.

The words "comprise", "comprises", and "comprising" are to be interpreted inclusively rather than exclusively. The words "consist", "consisting", and its variants, are to be interpreted exclusively, rather than inclusively. While various embodiments in the specification are presented using "comprising" language, under other circumstances, a related embodiment is also intended to be interpreted and described using "consisting of" or "consisting essentially of" language.

As used herein, the term "about" means a variability of 10% from the reference given, unless otherwise specified.

The term "regulation" or variations thereof as used herein refers to the ability of a composition to inhibit one or more components of a biological pathway.

Unless otherwise specified herein, both homozygous subjects and heterozygous subjects are encompassed within the phrase subject having a complement mediated disorder.

A "subject" is a mammal, e.g., a human, mouse, rat, guinea pig, dog, cat, horse, cow, pig, or non-human primate, such as a monkey, chimpanzee, baboon or gorilla.

As used herein, "disease", "disorder", "dysfunction" and "condition" are used interchangeably, to indicate an abnormal state in a subject, unless otherwise specified.

Unless defined otherwise in this specification, technical and scientific terms used herein have the same meaning as commonly understood by one of ordinary skill in the art and by reference to published texts, which provide one skilled in the art with a general guide to many of the terms used in the present application.

The following examples are illustrative only and are not intended to limit the present invention.

EXAMPLES

Engineering and Cloning of Human Factor H Truncation Variant (hfH1-4.678.19-20)

Truncation variants were generated by inverse PCR method using Phusion high-fidelity DNA polymerase (Cat #M0530S, New England Biolabs) according to manufacturer's protocol. Full-length human complement factor H cDNA pCMV Sport6 used as template for inverse PCR was obtained from Thermo Fisher Scientific (Cat #MHS6278-202800294, clone ID 40148771). PCR primers used for generation of hfH1-4.678.19-20 are listed in Table 1. After PCR fragments were separated on 0.8% agarose gel and extracted by AccuPrep gel extraction kit (Cat #K-3035, Bioneer), 50 ng of gel purified fragment was used for ligation by Rapid DNA ligation Kit (Cat #K-4123, Thermo Fisher Scientific) and transformed into DH5a competent cells (Cat #1825801, Invitrogen). Positive clones were confirmed either by restriction digestion or by PCR screening using specific primers. Then, the hfH11-4.678.19-20 insert from pCMV Sport6 was released by EcoR I and Not I digestion and gel purified fragment was blunted by End-repair module (Cat #E6050S, New England Biolabs) and purified. This fragment was sub-cloned into the pCBABG vector (which has a chicken beta-actin promoter with CMV enhancer and a partial intron sequence of the same gene, and a rabbit beta-globulin gene polyadenylation signal sequence) at EcoR V site. Positive clones were selected by restriction digestion and PCR methods.

TABLE 1 hfH Truncation variant Primers:

| | | |
|---|---|---|
| hfHdSCR5R SEQ ID NO: 49 | TGA TTT TTC TTC ACA TGA AGG CAA CGG | |
| hfHdSCR5F SEQ ID NO: 50 | ACC TTG AAA CCT TGT GAT TAT CCA GAC A | |
| hfHdSCR9-18R SEQ ID NO: 51 | AGA TTT AAT GCA CGT GGG TTG AGC | |
| hfHdSCR9-18F SEQ ID NO: 52 | AAA GAT TCT ACA GGA AAA TGT GGG CC | |

Engineering and Cloning of Human Factor H Truncation Variant hfH1-4.678.17-20:

Truncation variants were generated by inverse PCR method using Phusion high-fidelity DNA polymerase (Cat #M0530S, New England Biolabs) according to manufacturer's protocol. Full length human complement factor H cDNA pCMV Sport6 (used as template for inverse PCR) was obtained from Thermo Fisher Scientific (Cat #MHS6278-202800294, clone ID 40148771). PCR primers used for generation of hfH1-4.678.17-20 are listed in Table 1. After PCR fragments were separated on 0.8% agarose gel and extracted by AccuPrep gel extraction kit (Cat #K-3035, Bioneer), 50 ng of gel purified fragment was used for ligation by Rapid DNA ligation Kit (Cat #K-4123, Thermo Fisher Scientific) and transformed into DH5a competent cells (Cat #1825801, Invitrogen). Positive clones were confirmed either by restriction digestion or by PCR screening using specific primers. Then, the engineered hfH11-4.678.17-20 variant in pCMV Sport6 was sub-cloned into pCBABG vector at EcoRI site by infusion cloning method (Clontech Cat #638909). Primers for truncation protein preparation and cloning into expression vector were in Table 2.

TABLE 2 hfH Truncation variant Primers:

| | | |
|---|---|---|
| hfHdSCR5R SEQ ID NO: 49 | TGA TTT TTC TTC ACA TGA AGG CAA CGG | |
| hfHdSCR5F SEQ ID NO: 50 | ACC TTG AAA CCT TGT GAT TAT CCA GAC A | |
| hfHdSCR9-16R SEQ ID NO: 53 | AGA TTT AAT GCA CGT GGG TTG AGC | |
| hfHdSCR9-16F SEQ ID NO: 54 | ATAAAAACAGATTGTCTCAGTTTACCTAGCT | |
| pCBAGhfH-ORF F SEQ ID NO: 55 | TTTTGGCAAAGAATTGGACGTTGTGAACAGAGTT | |
| pCBAGhfH-ORF R SEQ ID NO: 56 | CCTGAGGAGTGAATTCTATCTTTTTGCACAAGTTGG | |

Expression and Purification of Recombinant hfH1-4.678.19-20 Protein:

Positive clones (hfH1-4.678.19-20 in pCBARBG vector) were transfected into HEK cells to assess the stability and functional activity of hfH1-4.678.19-20 protein. About 80% confluent HEK cells in a 6-well plate (Falcon, Cat #353046) were transfected with hfH1-4.678.19-20 cDNA in pCBARBG using Lipofectamine 2000 (Cat #11668019, Invitrogen) according to manufacturer's instructions. Protein expression was confirmed by western blotting using goat anti-human factor H IgG (Cat #A237, Complement tech). For large scale protein expression, 80% confluent HEK cells in 150 cm dishes (Falcon, Cat #353025) were transfected with endotoxin free hfH1-4.678.19-20 cDNA in pCBARBG plasmid with PEI (Cat #23966, Polysciences) according to manufacturer's instructions. Two days post-transfection, supernatant was collected from the plates and filtered through 0.2 m filter and loaded onto a PBS-equilibrated, Ox-23 (mouse anti-human fH mAb specific for SCR2/3, cat #10402-1VL, Sigma) sepharose affinity column. After washing with PBS containing 500 mM NaCl with 25 column volumes, bound hfH11-4.678.19-20 was eluted with 100 mM Glycine HCl pH2.7 and eluted fractions (2 ml per fraction) were neutralized with 200 ul of 1.5M Tris-HCl pH 8.5. Eluted protein purity was checked by SDS-PAGE and pure fraction were pooled and dialyzed with PBS with 2 changes overnight.

Engineering and Cloning of Mouse Factor H Truncation Variant (mfH1-4.678.19-20):

Truncation variants were generated by inverse PCR method using Phusion high-fidelity DNA polymerase according to manufacturer protocol. Full-length mouse complement factor H cDNA in pBluescript SK(−) used as template for inverse PCR was kindly provided by Dr M. Nonaka (University of Tokyo, Japan, Nucleotide 110-4361 of NCBI NM 009888.3). All PCR primers used for generation of mfH1-4.678.19-20 variant are listed in Table 3. After PCR fragments were separated on 0.8% agarose gel and extracted by AccuPrep gel extraction kit, 50 ng of gel purified fragment was used for ligation by Rapid DNA ligation Kit and transformed into DH5a competent cells. Positive clones were confirmed either by restriction digestion or by PCR screening using specific primers. Then, mfH1-4.678.-19-20 insert from pBluescript SK(-) was released by Sma I and EcoR V digestion and gel purified. This fragment was sub-cloned into pCBARBG vector at EcoR V site. Positive clones were selected by restriction digestion and PCR methods.

TABLE 3 mfH Truncation variant Primers:

| | |
|---|---|
| dSCR5R SEQ ID NO: 57 | TCTCTTTTCTTCACAGAAAGGCTGAGAACTCC |
| dSCR5F SEQ ID NO: 58 | ACC TTG AAA CCA TGT GAA TTT CCA CAA TTC |
| dSCR9-18F SEQ ID NO: 59 | CGA GAC TCA ACA GGG AAA TGT GG |
| dSCR9-18R SEQ ID NO: 60 | AGA CTT AAT GCA TGA GGG TTG AGG T |

Expression of Recombinant mfH1-4.678.19-20 Protein:

Positive clones (mfH1-4.678.19-20 in pCBARBG vector) were transfected into Hepa1C1C7 cells (mouse hepatoma cell line, ATCC® CRL-2026) to assess stability and functional activity of mfH1-4.678.19-20 protein. About 80% confluent cells in a 6-well plate were transfected with mfH1-4.678.19-20 cDNA using Lipofectamine 2000 according to manufacturer's instructions. Protein expression was confirmed by western blotting using rabbit anti-mouse fH IgG (Ref #1). Blots were visualized using Pierce ECL plus Western Blotting substrate (Cat #80196, Thermo Fisher Scientific).

Generation of AAV Transfer Plasmid and Virus:

mfH1-4.678.19-20 or hfH1-4.678.19-20 expression cassette from pCBARBG vector was released by Hinc II and Pst I digestion and gel purified fragment was blunted with the End Repair Module (cat #E6050S, NEB) and ligated into Nhe I- and Xho I-digested and blunted pAAV TBG-.PI.EGFP.WPRE.BGH vector (Cat #PL-C-PV0146) from the University of Pennsylvania Vector Core. Positive clones were screened by Sma I digestion.

pCBABG with hfH1-4.678.17-20 vector was modified into AAV transfer plasmid by inserting the ITRs (inverted terminal repeats) at 5' end (SEQ ID NO: 61: ctgcgc-gctcgctcgctcactgaggccgcccgggcaaagcccgggcgtcgggcgacct-ttggtcgcccggcctcagtgagc gagcgagcgcgcagagagg-gagtggcca-actcc-atcactaggggttccttgtagttaat, at HincII site) and 3'end (SEQ ID NO: 62: attaactacaaggaacccctagtgatggagttggcca-ctccctctctgcgcgctcgctcgctcactgaggccgggcgaccaaa ggtcgc-ccgacgcccgggctttgcccgggcggcctcagtgagcgagcgagcgcgcag, at Pst I site) of the expression cassette by using Infusion cloning method. Primers were used to amplify the AAV ITRs from the pENN.AAV.TBG.PI.RBG vector used as template listed in Table 4. The pENN.AAV.TBG.PI.RBG vector was obtained from the University of Pennsylvania Vector Core (Cat #PL-C-PV1015).

TABLE 4

ITR insertion primers

| | |
|---|---|
| Hinc II 5' ITR F SEQ ID NO: 63 | AAGTGCCACCTGGTCGACGCTGCGCGCTCGCT CGCT |
| Hinc II 5' ITR R SEQ ID NO: 64 | TCAATAATCAATGTCGACATTAACTACAAGGA ACCCCT |

TABLE 4-continued

ITR insertion primers

| | |
|---|---|
| Pst I 3'ITR F SEQ ID NO: 65 | GAAGATCCCTCGACCTGCAGATTAACTACAAG GAACCCCT |
| Pst I 3'ITR R SEQ ID NO: 66 | ACGCCAAGCTTGGGCTGCAGCTGCGCGCTCGC TCGCTC |

Super-coiled endotoxin-free AAV plasmid was prepared by Endo free plasmid kit (cat #12362, Qiagen), and was used for AAV virus production by the University of Pennsylvania Vector Core or the University of Massachusetts Gene Therapy Center Vector Core. The packaging, purification, and titer determination of AAV encoding mfH1-4.678.19-20, hfH11-4.678.19-20 or hfH1-4.678.17-20 was accomplished by using standard procedures.

Therapeutic Efficacy of hfH1-4.678.19-20 and hfH1-4.678.17-20 AAV in fH$^{m/m}$ Mice:

The generation of fH$^{m/m}$ mice which developed C3 glomerulopathy has been described previously in the paper by Lesher et al (2013) "Combination of factor H mutation and properdin deficiency causes severe C3 glomerulonephritis", J Am Soc Nephrol. 2013 January; 24(1):53-65. Epub 2012 Nov. 30. To test the expression levels, duration and therapeutic efficacy of hfH-4.678.19-20 and hfH11-4.678.17-20 in treating C3 glomerulopathy, 10-12 weeks old fH$^{m/m}$ mice were injected with $3 \times 10^{12}$ gene copies/mouse (for hfH1-4.678.19-20) or $1 \times 10^{11}$-$1 \times 10^{12}$ gene copies/mouse (for hfH1-4.678.17-20) by retro-orbital route. In separate groups of mice, a control AAV vector (pAAV.TBG.NULL.rBG) was used as a control. It is known from previous studies that natural human fH is functionally active in inhibiting alternative pathway (AP) complement activation in mice (Fakhouri, F., et al, Kidney International (2010) 78, 279-286; published online 5 May 2010). Blood was collected via retro-orbital bleed prior to injection and at 1 week after injection (for hfH1-4.678.19-20) or 1, 2 weeks, 1, 2, 3 months after injection (for hfH11-4.678.17-20). The fH$^{m/m}$ mice develop spontaneous C3 glomerulopathy characterized by uncontrolled plasma AP complement activation, leading to C3, factor B (fB) and C5 consumption and prominent glomerular deposition of C3 and C5b-9 (Lesher et al 2013). If hfH11-4.678.19-20 or hfH1-4.678.17-20 is functionally active in fH$^{m/m}$ mice, one would expect a reduction in C3 and fB consumption. Therefore, as a readout for the therapeutic efficacy of hfH1-4.678.19-20 and hfH1-4.678.17-20, we examined the levels of plasma C3 and fB by western blot before and after AAV injection into fH$^{m/m}$ mice. Mouse plasma (1 µl) was diluted with sample buffer and boiled before loading onto 4-20% gradient SDS-PAGE gels under reducing conditions. Samples were then transferred to PVDF membrane and probed with appropriate antibodies. For the detection of C3 and fB, HRP-conjugated goat anti-mouse C3 Ab (1:4000, MP Biomedicals Cat #0855557) or affinity-purified goat anti-human fB Ab (cross-reacts with mouse fB; 1:2500, cat #A235, Complement Technology) were used as primary antibodies, followed by HRP-conjugated rabbit anti-goat IgG (1:4000, Cat #1721034, Bio-Rad). Blots were visualized using Pierce ECL Plus Western Blotting substrate.

Detection of hfH1-4.678.19-20 or hfH1-4.678.17-20 Protein in Mouse Blood:

To detect the presence of hfH11-4.678.19-20 or hfH1-4.678.17-20 in AAV-treated fH$^{m/m}$ mice, an ELISA method was developed and used. Briefly, 96-well plates (MaxiSorp) were pre-coated with 4 µg/ml of anti-human factor-H mAb (OX-23) at RT for 2 hr. Un-occupied binding sites on the plates were blocked using 1% bovine serum albumin (BSA) in PBS at RT for 1 h. Serially diluted mouse plasma samples in blocking buffer containing 10 mM EDTA were added to the wells and incubated at RT for 1 h, followed by 2 ug/ml of biotin-labeled anti-hfH mAb (clone L20/3, specific for SCR19 of human factor-H, Cat #518504, Bio-Legend) and incubated at RT for 1 h. After washing, plates were then incubated with Avidin-HRP (1/1000, Cat 554058, BD Biosciences) at RT for 1 h, and developed using the TMB substrate reagent (Cat 51-2606KC and BD Cat 51-2607KC, BD Biosciences).

Therapeutic Efficacy of mfH1-4.678.19-20 Delivered by AAV in fH$^{m/m}$ or fH$^{m/m}$P$^{-/-}$ Mice:

To test the therapeutic efficacy of mfH1-4.678.19-20 as a surrogate for hfH1-4.678.19-20, fH$^{m/m}$ mice and fH$^{m/m}$ P$^{-/-}$ mice were infected with AAV vector containing the coding sequences for mfH1-4.678.19-20. As previously described by Lesher et al (Lesher et al, 2013, cited above), while fH$^{m/m}$ mice developed non-lethal C3 glomerulopathy with C3 and fB consumption, the double mutant fH$^{m/m}$ P$^{-/-}$ mice (fH$^{m/m}$ mice that were rendered deficient in properdin) developed an exacerbated and lethal form of C3 glomerulopathy and died by 10-12 week old (Lesher et al 2013). Therefore, the fH$^{m/m}$P$^{-/-}$ mice would also allow us to use mortality as another readout for the therapeutic efficacy of mfH1-4.678.19-20 AAV. 7-week old fH$^{m/m}$ or fH$^{m/m}$ P$^{-/-}$ mice were injected with either control AAV (pAAV.TBG.NULL.rBG) or mfH1-4.678.19-20 AAV at 3×10$^{12}$ gene copies/mouse by retro-orbital route. Blood was collected via retro-orbital bleeding prior to injection at various time points starting at 1 week after injection. To assess plasma C3 and fB levels, mouse plasma (1 µl) was diluted with sample buffer and boiled before loading onto 4-20% gradient SDS-PAGE gels under reducing conditions. Samples were then transferred to PVDF membrane and probed with appropriate antibodies. For C3 and fB, HRP-conjugated goat anti-mouse C3 Ab or affinity-purified goat anti-human fB Ab (cross reacts with mouse fB) were used as primary antibodies, followed by detection with HRP-conjugated rabbit-anti goat IgG. In some cases, the treated mice were followed for 6 or 10 months to observe the efficacy of mfH1-4.678.19-20 AAV in preventing death and/or AP complement activation using plasma C3 and fB levels as readouts.

Dosage Determination of mfH1-4.678.19-20 AAV in fH m/m Mice:

In experiments aimed at titrating the amount of mfH1-4.678.19-20 AAV copies needed to achieve therapeutic efficacy, 10-12 weeks old fH$^{m/m}$ mice (Lesher, 2013) were injected with 1×10$^{12}$, 3×10$^{11}$ or 1×10$^{11}$ gene copies/mouse of AAV by retro orbital route. Blood was collected via retro-orbital bleeds prior to injection and at indicated time points (1 week and 1 month after injection). Mouse plasma (1 µl) was diluted with sample buffer and boiled before loading onto 4-20% gradient SDS-PAGE gels under reducing conditions. Samples were then transferred to PVDF membrane and probed with appropriate antibodies. For the detection of C3 and fB, HRP-conjugated goat anti-mouse C3 Ab (1:4000, Cat #0855557, MP Biomedicals) or affinity-purified goat anti-human fB Ab (cross-reacts with mouse fB; 1:2500, cat #A235, Complement Technology, Inc.) were used as primary antibodies, followed by detection with HRP-conjugated rabbit anti-goat IgG (1:4000, Cat #1721034, Bio-Rad). Blots were visualized using Pierce ECL Plus Western Blotting substrate.

Detection of mfH1-4.678.19-20 Protein in Mouse Blood by ELISA:

To detect the presence of mfH1-4.678.19-20 protein in the mouse blood, an ELISA assay was developed and used. Briefly, 96-well plates were pre-coated with 2 µg/ml of mouse anti-mouse fH SCR19-20 mAb (clone-12, generated in-house by immunizing fH$^{m/m}$ mice with recombinant mouse fH SCR19-20 (Barata, L., et al, J. Immunol 190(6): 2886-95 (2013)) at 37° C. for 1-2 hr at room temperature. Un-occupied binding sites on the plates were blocked with 1% BSA in PBS at RT for 1 hr. Serially diluted mouse plasma samples in blocking buffer containing 10 mM EDTA were added to wells and incubated at RT for 1 hr, followed by biotin-labeled rabbit anti-mouse fH Ab (Lesher et al, 2013) at RT for 1 hr. Plates were incubated with Avidin-HRP at RT for 1 hr, then developed using the TMB substrate reagent.

Detection of mfH1-4.678.19-20 Protein in Mouse Plasma by Western Blotting:

To detect the presence of mfH1-4.678.19-20 protein in the mouse blood by western blot, 10 µl of mouse plasma was diluted with 90 ul of PBS containing 10 mM EDTA and incubated with anti-mouse fH mAb (clone-12)-coupled Sepharose® beads for 30 min at room temperature. After washing 2 times with PBS containing 500 mM NaCl, the Sepharose® beads were boiled with SDS-PAGE sample buffer for 5 min and run on SDS-PAGE. Samples were then transferred to PVDF membrane and mfH1-4.678.19-20 protein was detected by BSA pre-absorbed rabbit anti mouse fH 19-20 Ab (Lesher et al, 2013). Blots were visualized using Pierce ECL Plus Western Blotting substrate.

Immuno-Fluorescence Staining of C3 in Kidney:

Kidneys from control AAV- or mfH1-4.678.19-20 AAV-treated fH$^{m/m}$ or fHh$^{m/m}$P$^{-/-}$ mice were snap-frozen in OCT medium and stored at −80° C. For immunofluorescence studies, 4 µm sections were cut and used for staining. For C3 staining, FITC-conjugated goat anti-mouse C3 Ab was used (1:500, Cat #855500, MP Biomedicals) and the experiment was performed as described (Lesher et al 2013).

Mouse Survival Analysis:

The following Table provides a summary of survival data of fH$^{m/m}$P$^{-/-}$ mice treated with control AAV8 vector or AAV8-mfH1-4.678.19-20 vector. All 8 fH$^{m/m}$P$^{-/-}$ mice treated with control AAV8 vector died within 2-3 weeks of treatment, whereas 7 out of 9 fH$^{m/m}$P$^{-/-}$ mice treated with the AAV8-mfH1-4.678.19-20 vector were rescued from lethal C3 glomerulopathy. All mice were injected with 3×10$^{12}$ gene copies/mouse of the respective AAV virus through retro-orbital I.V. routes. Survival of control AAV- or mfH1-4.678.19-20 AAV-treated fH$^{m/m}$P$^{-/-}$ mice was recorded after AAV treatment for 10 months. Data were categorized as being censored (euthanized) or natural death and analyzed by GraphPad Prism (La Jolla, Calif.).

| AAV vector | Number of mice treated | Note |
| --- | --- | --- |
| AAV8-mfH1-4.678.19-20 | 9 mice | 4- healthy at 9 month after gene therapy (continuing) 2- healthy at 6 month after gene therapy (sacrificed at 6 month) 1- healthy at 5 month after gene therapy (continuing) 1- Moribund at 3 month after gene therapy 1- Moribund at 2 weeks after gene therapy |
| Con AAV8 | 8 mice | All died 2-3 W post injection |

Heparin-Binding Assay:

To test the Heparin-binding activity of hfH1-4.678.19-20 and mfH1-4.678.19-20 proteins, 96-well plates were pre-coated with 100 µg of Heparin (Sigma, H3393) in bicarbonate buffer (pH9.6) at 37° C. for 1 hr. The unoccupied binding sites on the plates were blocked with 1% BSA in PBS at RT for 1 hr. Different amounts of hfH-4.678.19-20 or mfH1-4.678.19-20 protein were added and incubated at RT for 1 hr, followed by 2 µg/ml of mouse anti-human fH mAb (OX-23) at RT for 1 hr. Plates were incubated with HRP-conjugated rabbit anti-mouse IgG (1/4000, Cat #A9044, Sigma) at RT for 1 hr, then developed using the TMB substrate reagent.

C3b-Binding Assay:

To test the C3b-binding activity of hfH11-4.678.19-20 and mfH1-4.678.19-20 proteins, 96-well plates were pre-coated with 2 µg/ml human C3b (Cat #A114, CompTech) at 37° C. for 1 hr. The unoccupied binding sites on the plates were blocked with 1% BSA in PBS at RT for 1 h. Different amounts of hfH1-4.678.19-20 or mfH1-4.678.19-20 protein were added and incubated at RT for 1 h, followed by 2 ug/ml of mouse anti-human fH mAb (OX-23) at RT for 1 hr. Plates were incubated with HRP-conjugated rabbit anti-mouse IgG at RT for 1 hr, then developed using the TMB substrate reagent.

Assay of Fluid-Phase Cofactor Activity of fH Protein in Factor I-Mediated C3b Cleavage:

To assess the fluid phase cofactor activity of hfH11-4.678.19-20 and mfH1-4.678.19-20 proteins in factor I-mediated cleavage of C3b, 0.5 or 0.25 µg of purified hfH1-4.678.19-20 or mfH1-4.678.19-20 protein was mixed with 2 µg of human C3b in 15 µl PBS, and 1 µg of human factor I (Cat #A138, CompTech) was subsequently added and incubated at 37° C. for 15 minutes. Reaction was stopped by adding 5× reducing SDS-PAGE sample buffer. Proteolysis of C3b was determined by analyzing the cleavage of the a chain and the generation of the a41 and u39 fragments using 4-20% Gradient SDS-PAGE gels under reducing conditions, followed by western blot detection using HRP-conjugated goat anti-human C3 IgG (1/4000, Cat #855237, MP biomedicals). Blots were visualized using Pierce ECL Plus Western Blotting substrate.

Assessment of Therapeutic Efficacy of mfH1-4.678.19-20 in Preventing AP Complement Activation Caused by Membrane Complement Regulator Defects:

To determine if fH1-4.678.19-20 AAV treatment may also be effective in preventing AP complement activation caused by defects in membrane complement regulators, mfH1-4.678.19-20 was tested in a strain of mouse that is deficient in two membrane complement regulators DAF and Crry (DAF/Crry double mutant mice). The generation of DAF/Crry double mutant mice (DAF$^{-/-}$-Crry$^{flox/flox}$-Tie-2Cre$^+$) was previously described with a phenotype of secondary complement deficiency due to excessive AP complement activation (Barata et al, 2013). Like fH$^{m/m}$ mice, there was C3 and fB consumption in the DAF/Crry double mutant mice (Barata et al, 2013). DAF/Crry double mutant mice (10-week old) were injected with mfH1-4.678.19-20 AAV at $3 \times 10^{12}$ gene copies/mouse by retro orbital route. Blood was collected via retro-orbital bleeds prior to injection and at 1 week after injection. Therapeutic efficacy was assessed by measuring plasma C3 and fB levels before and after mfH1-4.678.19-20 AAV treatment using western blot analysis. For western blot, mouse plasma (1 µl) was diluted with sample buffer and boiled before loading onto 4-20% gradient SDS-PAGE gels under reducing conditions. Samples were then transferred to PVDF membrane and probed with appropriate antibodies. For the detection of mouse C3 and fB, HRP-conjugated goat anti-mouse C3 Ab (1:4000, Cat #0855557, MP Biomedicals) or affinity-purified goat anti-human fB Ab (Cat #A235, CompTech, Texas, across reacts with mouse fB) were used as primary antibodies, followed by detection with HRP-conjugated rabbit anti-goat IgG. Blots were visualized using Pierce ECL Plus Western Blotting substrate.

Generation of aHUS Mouse Model:

To create a murine aHUS model for testing the therapeutic efficacy of AAV-mediated fH gene therapy, a mutant mouse strain carrying a fH point mutation in SCR20 corresponding to human fH W1183R mutation found in aHUS patients was created by homologous recombination-based gene targeting technique (Lesher et al, 2013; Dunkelberger, et al, J Immunol. 2012 Apr. 15; 188(8): 4032-4042; Takashi et al, Blood. 2009 Mar. 19; 113(12): 2684-2694; Kimura Y1, et al., Blood. 2008 Jan. 15; 111(2):732-40. Epub 2007 Oct. 4; Kimura Y1, et al, J Clin Invest. 2010 October; 120(10):3545-54). For this experiment, fH gene fragments were amplified from C57BL/6 mouse genomic DNA by using the Expand Long Template PCR system (Roche, Indianapolis, Ind.) in order to construct the gene targeting vector. The long arm of targeting vector was comprised of a 6 kb fragment containing the 21th exon and flanking intronic sequences of the mouse fH gene. It was amplified by PCR using the following primers: SEQ ID NO: 67: 5'-gcggccgccctatccattagtgagtgtgg-3' and SEQ ID NO: 68: 5'-ctcgaggacagcgatgtaagaacaatc-3'. The PCR product was ligated into PCR 2.1 vector (Invitrogen) and the insert was then released from PCR2.1 vector by with Not I and XhoI restriction digestion, purified and sub-cloned into the pND1 vector upstream of the NEO cassette. The use of pND1 vector has been described in previous publications of gene targeting experiments (Lesher et al (2013); Dunkelberger et al, 2012; Miwa et al, 2009; Kimura et al, 2008; Kimura et al 2012) and this vector contains neomycin (NEO) and diphtheria toxin (DT) cassettes for positive and negative selection, respectively (Lesher et al (2013); Dunkelberger et al, 2012; Miwa et al, 2009; Kimura et al, 2008; Kimura et al 2012). The pND1 vector also contains a loxP site and two flippase recognition target (FRT) sites flanking the NEO cassette for potential removal of NEO by FLPe recombinase (Rodriguez C I, et al, Nat Genet. 2000 June; 25(2):139-40.).

The short arm sequence was comprised of a 3.85 kb fragment containing the 22$^{th}$ exon encoding SCR20 and the flanking intronic sequences of the mouse fH gene. This sequence was PCR-amplified using the following primers: SEQ ID NO: 69: 5'-ggtaccaagcttattgaccagctacagacagta-3' and SEQ ID NO: 70: 5'-ggtaccctcactcaggtgtattactc-3'. The PCR product was cloned into PCR 2.1 vector and subsequently a tryptophan (W) to arginine (R) mutation at position 1206 corresponding to W1183R mutation of human fH in SCR20 was made by site-directed mutagenesis using the Stratagene QuickChange Site-Directed Mutagenesis kit (Agilent Technologies, CA) with the following two primers, SEQ ID NO: 71: 5'-GGAATCACACAATATAATTCT-CAAAAGGAGACACACTG-3' and SEQ ID NO: 72: 5'-CAGTGTGTCTCCTTTTGAGAATTATATTGTGTGAT-TCC-3'. After W to R mutation was confirmed, the short arm fragment was released from PCR2.1 by Kpn I digestion and sub-cloned into the pND1 vector downstream of the NEO cassette at the same restriction site. The targeting vector was then linearized by Not I digestion and transfected into C57BL/6 embryonic stem (ES) cells (EmbroMAX Embryonic stem cell line-strain C57BL/6, Cat #CMTI-2, Millipore) by electroporation-method. Transfected ES cells were subjected to G418 selection starting from 48 hours after electroporation. ES cells with homologous recombination were screened by Southern blot analysis of genomic DNA after HindIII digestion with a 480 bp 3' probe amplified using SEQ ID NO: 73: 5'-ATAGCATGTGCCAGGAGACAC-3' and SEQ ID NO: 83: 5'-AGTGTTGACTCGTGGAGACCA-3' as primers. Wild-type allele produced a 12.5 kb fragment, whereas the targeted allele produced a 10.2 kb fragment. Correctly targeted ES cells ($fH^{W1201R\ (Neo\text{-}positive)/+}$) were injected into 3.5-day post-coital C57BL/6J blastocysts to generate chimeras at the University of Pennsylvania School of Medicine Transgenic Core Facility. The resultant chimeras yielded germ line transmission, as assessed by a combination of coat color and PCR screening for the detection of NEO using the following two primers: Neo-4 primer: SEQ ID NO: 74: 5-CTTGGGTGGAGAGGCTATTC-3' and SEQ ID NO: 75: Neo-5 primer: 5'-AGGTGAGATGACAGGAGATC-3'. The neomycin-resistance cassette (NEO) in the targeting vector was flanked by 2 flippase (FLP) recombinase target (FRT) sites to allow its subsequent removal by FLP recombinase. Heterozygous FH-targeted mice ($fH^{W1206R\ (Neo\text{-}positive)/+}$) were crossed with FLPe transgenic mice (expressing the enhanced version of FLP, on C57BL/6 genetic background) to remove the NEO from the fH allele and generate a heterozygous fH mutant mouse without the NEO gene cassette ($fH^{W1206R/+}$) $fH^{W1206R/+}$ mice were intercrossed to generate $fH^{W1206R/W206R}$ homozygous mice on C57BL/6 genetic background. For genotyping, the following primers were used for detection of wild-type and mutated fH alleles by PCR: WR1 (FH-specific) SEQ ID NO: 76:5'-GATATGGTCAATTTAGGGAAAGT, SEQ ID NO: 77: Neo7 (NEO-specific) 5'-GGGTGGGATTAGATAAATGCC-3' and SEQ ID NO: 78: WR4 (FH-specific) 5'-TACTGTCTGTAGCTGGTCAAT 3'.

The following table summarizes the treatment outcome of $f^{W1206R/W1206R}$ mice receiving control AAV or AAV8-mfH1-4.678.19-20 vector at $3\times10^{11}$ GC/mouse.

| AAV vector | Number of mice treated | Outcome |
|---|---|---|
| AAV8-mfH1-4.678.19-20 (3 × 10^11 GC/mouse) | 3 mice | All 3 mice are alive and healthy as of date (2 months after gene therapy) All have normal platelet counts |
| Con AAV8 (3 × 10^11 GC/mouse) | 2 mice | 1 died after 4 weeks of treatment The remaining mouse is alive but has low platelet count |

Homozygous $fH^{W1206R/W1206R}$ mice failed to thrive with significantly lower bodyweights as evidenced at 4-6 weeks of age and a near 50% mortality rate by 30 weeks. All $fH^{W1206R/W1206R}$ mice showed one or more of the characteristic features of aHUS, i.e. renal injury (elevated blood urea nitrogen levels and/or histological signs of thrombotic microangiopathy in glomeruli), thrombocytopenia and anemia. About one third of $fH^{W1206R/W1206R}$ mice also developed severe neurological symptoms indicative of stroke. In addition to thrombotic microangiopathy in the kidney glomeruli, numerous large vessel thrombi in multiple organs (liver, lung, spleen, kidney, brain and eye) were present in $fH^{W1206R/W1206R}$ mice.

As of the timepoints reported above, all 3 $fH^{W1206R/W1206R}$ mice treated with AAV8-mfH1-4.678.19-20 were alive and healthy with normalized platelet counts, whereas 1 of 2 $fH^{W1206R/W1206R}$ mice treated with control AAV vector died (at 4 weeks after treatment) and remaining mouse was displaying symptoms of aHUS including thrombocytopenia.

Therapeutic efficacy of mfH1-4.678.19-20 delivered by AAV in $fH^{W1206R/W126R}$ Mice: To test the therapeutic efficacy of mfH1-4.678.19-20 as a surrogate for hfH1-4.678.19-20, we injected 4-week old homozygous $fH^{W1206R/W1206R}$ mice with $3\times10^{11}$ gene copies/mouse by retro-orbital route. If mfH1-4.678.19-20 is functionally active in $fH^{W1206R/W1206R}$ mice, one would expect a reduction in thrombocytopenia and renal injury. Therefore, as readouts for the therapeutic efficacy of mfH1-4.678.19-20, we counted the number of platelet and measured the level of serum blood urea nitrogen. Since $fH^{W1206R/W1206R}$ mice failed to thrive with significantly lower bodyweights evident at 4-6 weeks of age and a near 50% mortality rate by 30 weeks. The $fH^{W1206R/W1206R}$ mice would also allow us to use mortality as another readout for the therapeutic efficacy of mfH1-4.678.19-20 AAV.

Platelet Counts in Control AAV- and mfH1-4.678.19-20 AAV-Treated $fH^{W1206R/W1206R}$ mice To determine the platelet counts in control AAV- and mfH1-4.678.19-20 AAV-treated $fH^{W1206R/W1206R}$ mice, blood was collected with EDTA (final concentration: 0.02M) via retro-orbital bleeds prior to injection and at various time points starting at 1 month after injection and analyzed on the Sysmex XT-2000iV Automated Hematology Analyzer at the CTRC Translational Core Laboratory at the Children's Hospital of Philadelphia.

Blood Urea Nitrogen (BUN) Measurement in Control AAV- and mfH1-4.678.19-20 AAV-Treated $fH^{W1206R/W1206R}$ Mice:

To measure the serum level of blood urea nitrogen, blood samples were collected via retro-orbital bleeds prior to injection and at various time points starting at 1 month after injection. Serum BUN levels were measured using urea nitrogen reagents (Sigma-Aldrich) by following the manufacturer's instructions.

Histological Examination of Kidney and Other Organs of $fH^{W1206R/W1206R}$ Mice:

Paired kidneys and other organs were collected from $fH^{W1206R/W1206R}$ mice. One was fixed in formalin solution overnight and processed for paraffin embedding, and the other was snap-frozen in OCT compound (Sakura Finetek). Kidneys and other organs were evaluated histologically for signs of aHUS/thrombotic microangiopathy using light microscopy and immunohistochemistry including immunofluorescence and immunoperoxidase.

Sequence Listing Free Text

The following information is provided for sequences containing free text under numeric identifier <223>.

| SEQ ID NO: (containing free text) | Free text under <223> |
|---|---|
| 39 | <220> <221> SIGNAL <222> (1) ... (18) <220> <221> DOMAIN <222> (19) ... (82) <223> Sushi 1 <220> <221> DOMAIN <222> (83) ... (143) <223> Sushi 1 |

| SEQ ID NO: (containing free text) | Free text under <223> |
|---|---|
| | <220> |
| | <221> DOMAIN |
| | <222> (144) . . . (207) |
| | <223> Sushi 3 |
| | <220> |
| | <221> DOMAIN |
| | <222> (208) . . . (264) |
| | <223> Sushi 4 |
| | <220> |
| | <221> DOMAIN |
| | <222> (265) . . . (322) |
| | <223> Sushi 5 |
| | <220> |
| | <221> DOMAIN |
| | <222> (324) . . . (386) |
| | <223> Sushi 6 |
| | <220> |
| | <221> DOMAIN |
| | <222> (387) . . . (444) |
| | <223> Sushi 7 |
| | <220> |
| | <221> DOMAIN |
| | <222> (446) . . . (507) |
| | <223> Sushi 8 |
| | <220> |
| | <221> DOMAIN |
| | <222> (515) . . . (566) |
| | <223> Sushi 9 |
| | <220> |
| | <221> DOMAIN |
| | <222> (576) . . . (625) |
| | <223> Sushi 10 |
| | <220> |
| | <221> DOMAIN |
| | <222> (628) . . . (686) |
| | <223> Sushi 11 |
| | <220> |
| | <221> DOMAIN |
| | <222> (689) . . . (746) |
| | <223> Sushi 12 |
| | <220> |
| | <221> DOMAIN |
| | <222> (751) . . . (805) |
| | <223> Sushi 13 |
| | <220> |
| | <221> DOMAIN |
| | <222> (809) . . . (866) |
| | <223> Sushi 14 |
| | <220> |
| | <221> DOMAIN |
| | <222> (868) . . . (928) |
| | <223> Sushi 15 |
| | <220> |
| | <221> DOMAIN |
| | <222> (929) . . . (986) |
| | <223> Sushi 16 |
| | <220> |
| | <221> DOMAIN |
| | <222> (987) . . . (1045) |
| | <223> Sushi 17 |
| | <220> |
| | <221> DOMAIN |

| SEQ ID NO: (containing free text) | Free text under <223> |
|---|---|
| | <222> (1046) . . . (1104) |
| | <223> Sushi 18 |
| | <220> |
| | <221> DOMAIN |
| | <222> (1107) . . . (1165) |
| | <223> Sushi 19 |
| | <220> |
| | <221> DOMAIN |
| | <222> (1170) . . . (1230) |
| | <223> Sushi 20 |
| 41 | <223> engineered hfH1-4.678.19-20 variant cDNA |
| 42 | <223> hfH1-4.678.19-20 protein |
| 43 | <223> murine fH1-4.678.19-20 |
| 44 | <223> mouse factor H truncation construct mFH1-4.678.19-20 |
| 45 | <223> engineered fH SCR1-4, 6-8, 17-20 |
| 46 | <223> Synthetic Construct |
| 47 | <223> hfH1-4.678.17-20 containing leader and 5' UTR |
| 48 | <223> hFH 1-4.678.17-20 |
| 49 | <223> hfHdSCR5R truncation variant primer |
| 50 | <223> hfHdSCR5F truncation primer |
| 51 | <223> hfHdSCR9-18R truncation variant primer |
| 52 | <223> hfHdSCR9-18F truncation variant primer |
| 53 | <223> hfHdSCR9-16R truncation variant primer |
| 54 | <223> hfHdSCR9-16F truncation variant primer |
| 55 | <223> pCBAGhfH-ORF F truncation variant primer |
| 56 | <223> pCBAghfH-ORF R primer |
| 57 | <223> dSCR5R |
| 58 | <223> dSCR5F truncation varient primer |
| 59 | <223> dSCR9-18F truncation varient primer |
| 60 | <223> dSCR9-18R truncation primer |
| 61 | <223> AAV 5' ITR |
| 62 | <223> AAV 3' ITR |
| 63 | <223> Hinc II 5'ITR F insertion primer |
| 64 | <223> Hinc II 5'ITR R insertion primer |
| 65 | <223> Pst I 3'ITR F insertion primer |
| 66 | <223> Pst I 3'ITR R insertion primer |
| 67 | <223> mFH primer 21st exon + intron |
| 68 | <223> R primer mFH 21st exon + intron |
| 69 | <223> F primer mFH SCR20 (exon 22) |
| 70 | <223> R primer mFH SCR20 (exon 22) |
| 71 | <223> F primer W1183R mutation hFH |
| 72 | <223> R primer W1183R mutation |
| 73 | <223> F Primer for 480 bp 3' probe |
| 74 | <223> Neo-4 primer |
| 75 | <223> Neo-5 primer |
| 76 | <223> mfH 1-4.678.19-20 |
| 77 | <223> NEO-specific |
| 78 | <223> WR4 (FH-specific) |
| 81 | <223> mfH1-4.678.19-20 |

All publications cited in this specification are incorporated herein by reference. U.S. Provisional Application No. 62/232,008, filed Sep. 24, 2015, is also incorporated by reference. While the invention has been described with reference to particular embodiments, it will be appreciated that modifications can be made without departing from the spirit of the invention. Such modifications are intended to fall within the scope of the appended claims.

The invention claimed is:

1. A recombinant viral vector having packaged therein an expression cassette comprising a nucleic acid sequence that encodes SEQ ID NO: 48 operably linked to expression control sequences which direct expression thereof.

2. The recombinant viral vector according to claim 1, wherein the vector is an adeno-associated virus (AAV) vector, an adenovirus vector, an RNA virus vector, a lentivirus vector, or a vaccinia virus vector.

3. A recombinant AAV vector comprising an AAV capsid and having packaged therein an expression cassette comprising an engineered complement regulator factor H (fH) gene operably linked to expression control sequences which direct expression thereof, wherein said fH gene encodes the amino acid sequence of SEQ ID NO: 48.

4. The recombinant AAV vector according to claim 3, wherein the capsid is an AAV1, AAV2, AAV5, AAV8, rh64R1, AAV9, or rh10 capsid.

5. The recombinant AAV vector according to claim 3, wherein the expression control sequences comprise a liver-specific promoter.

6. The recombinant AAV vector according to claim 3, wherein the expression control sequences comprise a promoter that is tissue specific for the eye.

7. A pharmaceutical composition comprising a pharmaceutically acceptable carrier and the recombinant viral vector according to claim 1.

8. The recombinant AAV vector according to claim 3, wherein the expression control sequences comprise a Kozak sequence.

9. The recombinant AAV vector according to claim 3, wherein the expression control sequences comprise a chicken beta-actin promoter.

10. The recombinant AAV vector according to claim 3, wherein the expression control sequences comprise a polyadenylation (polyA) signal sequence.

11. The recombinant AAV vector according to claim 10, wherein the polyA signal sequence is a rabbit beta globin polyA signal sequence.

12. A pharmaceutical composition comprising a pharmaceutically acceptable carrier and the recombinant AAV vector according to claim 3.

13. A plasmid comprising an expression cassette comprising a nucleic acid sequence encoding a fH protein variant comprising SEQ ID NO: 48 operably linked to expression control sequences which direct expression thereof.

14. The plasmid according to claim 13, wherein the expression cassette further comprises a 5' ITR and a 3' ITR.

15. The plasmid according to claim 14, wherein the 5' ITR and 3' ITR are from AAV2.

16. The plasmid according to claim 13, wherein the expression control sequences comprise a Kozak sequence.

17. The plasmid according to claim 13, wherein the expression control sequences comprise a chicken beta-actin promoter.

18. The plasmid according to claim 13, wherein the expression control sequences comprise a polyA signal sequence.

19. The plasmid according to claim 18, wherein the polyA signal sequence is a rabbit beta-globin polyA signal sequence.

20. An isolated host cell comprising the plasmid according to claim 13.

21. A recombinant AAV vector comprising an AAV capsid having packaged therein an expression cassette comprising:
    (a) an AAV 5' ITR;
    (b) a chicken beta-actin promoter with CMV enhancer;
    (c) a nucleic acid sequence that encodes SEQ ID NO: 48;
    (d) a polyA signal sequence; and
    (e) an AAV 3' ITR.

22. The recombinant AAV vector according to claim 21, wherein the capsid is an AAV1, AAV2, AAV5, AAV8, rh64R1, AAV9, or rh10 capsid.

23. A pharmaceutical composition comprising a pharmaceutically acceptable carrier and the recombinant AAV vector according to claim 21.

* * * * *

SEQUENCE LISTING

<160> NUMBER OF SEQ ID NOS: 83

<210> SEQ ID NO 1
<211> LENGTH: 3696
<212> TYPE: DNA
<213> ORGANISM: Homo sapiens
<220> FEATURE:

```
<221> NAME/KEY: CDS
<222> LOCATION: (1)..(54)
<223> OTHER INFORMATION: signal peptide
<220> FEATURE:
<221> NAME/KEY: CDS
<222> LOCATION: (55)..(240)
<223> OTHER INFORMATION: SCR1
<220> FEATURE:
<221> NAME/KEY: CDS
<222> LOCATION: (241)..(252)
<223> OTHER INFORMATION: linker 1/2
<220> FEATURE:
<221> NAME/KEY: CDS
<222> LOCATION: (253)..(423)
<223> OTHER INFORMATION: SCR2
<220> FEATURE:
<221> NAME/KEY: CDS
<222> LOCATION: (424)..(435)
<223> OTHER INFORMATION: linker 2/3
<220> FEATURE:
<221> NAME/KEY: CDS
<222> LOCATION: (436)..(615)
<223> OTHER INFORMATION: SCR3
<220> FEATURE:
<221> NAME/KEY: CDS
<222> LOCATION: (616)..(627)
<223> OTHER INFORMATION: linker 3/4
<220> FEATURE:
<221> NAME/KEY: CDS
<222> LOCATION: (628)..(786)
<223> OTHER INFORMATION: SCR4
<220> FEATURE:
<221> NAME/KEY: CDS
<222> LOCATION: (787)..(798)
<223> OTHER INFORMATION: Linker 4/5
<220> FEATURE:
<221> NAME/KEY: CDS
<222> LOCATION: (799)..(960)
<223> OTHER INFORMATION: SCR5
<220> FEATURE:
<221> NAME/KEY: CDS
<222> LOCATION: (961)..(972)
<223> OTHER INFORMATION: linker 5/6
<220> FEATURE:
<221> NAME/KEY: CDS
<222> LOCATION: (973)..(1155)
<223> OTHER INFORMATION: SCR6
<220> FEATURE:
<221> NAME/KEY: CDS
<222> LOCATION: (1156)..(1164)
<223> OTHER INFORMATION: linker 6/7
<220> FEATURE:
<221> NAME/KEY: CDS
<222> LOCATION: (1165)..(1326)
<223> OTHER INFORMATION: SCR7
<220> FEATURE:
<221> NAME/KEY: CDS
<222> LOCATION: (1327)..(1341)
<223> OTHER INFORMATION: linker 7/8
<220> FEATURE:
<221> NAME/KEY: CDS
<222> LOCATION: (1342)..(1515)
<223> OTHER INFORMATION: SCR8
<220> FEATURE:
<221> NAME/KEY: CDS
<222> LOCATION: (1516)..(1524)
<223> OTHER INFORMATION: linker 8/9
<220> FEATURE:
<221> NAME/KEY: CDS
<222> LOCATION: (1525)..(1692)
<223> OTHER INFORMATION: SCR9
<220> FEATURE:
<221> NAME/KEY: CDS
<222> LOCATION: (1693)..(1704)
<223> OTHER INFORMATION: linker 9/10
<220> FEATURE:
<221> NAME/KEY: CDS
<222> LOCATION: (1705)..(1869)
<223> OTHER INFORMATION: SCR10
```

-continued

```
<220> FEATURE:
<221> NAME/KEY: CDS
<222> LOCATION: (1870)..(1887)
<223> OTHER INFORMATION: linker 10/11
<220> FEATURE:
<221> NAME/KEY: CDS
<222> LOCATION: (1888)..(2052)
<223> OTHER INFORMATION: SCR11
<220> FEATURE:
<221> NAME/KEY: CDS
<222> LOCATION: (2053)..(2070)
<223> OTHER INFORMATION: linker 11/12
<220> FEATURE:
<221> NAME/KEY: CDS
<222> LOCATION: (2071)..(2232)
<223> OTHER INFORMATION: SCR12
<220> FEATURE:
<221> NAME/KEY: CDS
<222> LOCATION: (2233)..(2256)
<223> OTHER INFORMATION: linker 12/13
<220> FEATURE:
<221> NAME/KEY: CDS
<222> LOCATION: (2257)..(2409)
<223> OTHER INFORMATION: SCR13
<220> FEATURE:
<221> NAME/KEY: CDS
<222> LOCATION: (2410)..(2430)
<223> OTHER INFORMATION: linker 13/14
<220> FEATURE:
<221> NAME/KEY: CDS
<222> LOCATION: (2431)..(2592)
<223> OTHER INFORMATION: SCR14
<220> FEATURE:
<221> NAME/KEY: CDS
<222> LOCATION: (2593)..(2607)
<223> OTHER INFORMATION: linker
<220> FEATURE:
<221> NAME/KEY: CDS
<222> LOCATION: (2608)..(2778)
<223> OTHER INFORMATION: SCR15
<220> FEATURE:
<221> NAME/KEY: CDS
<222> LOCATION: (2779)..(2790)
<223> OTHER INFORMATION: linker
<220> FEATURE:
<221> NAME/KEY: CDS
<222> LOCATION: (2791)..(2952)
<223> OTHER INFORMATION: SCR16
<220> FEATURE:
<221> NAME/KEY: CDS
<222> LOCATION: (2953)..(2964)
<223> OTHER INFORMATION: linker
<220> FEATURE:
<221> NAME/KEY: CDS
<222> LOCATION: (2965)..(3129)
<223> OTHER INFORMATION: SCR17
<220> FEATURE:
<221> NAME/KEY: CDS
<222> LOCATION: (3130)..(3141)
<223> OTHER INFORMATION: linker 17/18
<220> FEATURE:
<221> NAME/KEY: CDS
<222> LOCATION: (3142)..(3306)
<223> OTHER INFORMATION: SCR18
<220> FEATURE:
<221> NAME/KEY: CDS
<222> LOCATION: (3307)..(3324)
<223> OTHER INFORMATION: linker 18/19
<220> FEATURE:
<221> NAME/KEY: CDS
<222> LOCATION: (3325)..(3489)
<223> OTHER INFORMATION: SCR19
<220> FEATURE:
<221> NAME/KEY: CDS
<222> LOCATION: (3490)..(3498)
<223> OTHER INFORMATION: SCR19
<220> FEATURE:
<221> NAME/KEY: CDS
<222> LOCATION: (3499)..(3696)
```

<223> OTHER INFORMATION: SCR20

<400> SEQUENCE: 1

```
atg aga ctt cta gca aag att att tgc ctt atg tta tgg gct att tgt      48
Met Arg Leu Leu Ala Lys Ile Ile Cys Leu Met Leu Trp Ala Ile Cys
1               5                   10                  15 gta gca gaa gat tgc aat gaa ctt cct cca aga aga aat aca gaa att      96
Val Ala Glu Asp Cys Asn Glu Leu Pro Pro Arg Arg Asn Thr Glu Ile
            20                  25                  30 ctg aca ggt tcc tgg tct gac caa aca tat cca gaa ggc acc cag gct     144
Leu Thr Gly Ser Trp Ser Asp Gln Thr Tyr Pro Glu Gly Thr Gln Ala
        35                  40                  45 atc tat aaa tgc cgc cct gga tat aga tct ctt gga aat ata ata atg     192
Ile Tyr Lys Cys Arg Pro Gly Tyr Arg Ser Leu Gly Asn Ile Ile Met
50                  55                  60 gta tgc agg aag gga gaa tgg gtt gct ctt aat cca tta agg aaa tgt     240
Val Cys Arg Lys Gly Glu Trp Val Ala Leu Asn Pro Leu Arg Lys Cys
65                  70                  75                  80 cag aaa agg ccc tgt gga cat cct gga gat act cct ttt ggt act ttt     288
Gln Lys Arg Pro Cys Gly His Pro Gly Asp Thr Pro Phe Gly Thr Phe
                85                  90                  95 acc ctt aca gga gga aat gtg ttt gaa tat ggt gta aaa gct gtg tat     336
Thr Leu Thr Gly Gly Asn Val Phe Glu Tyr Gly Val Lys Ala Val Tyr
            100                 105                 110 aca tgt aat gag ggg tat caa ttg cta ggt gag att aat tac cgt gaa     384
Thr Cys Asn Glu Gly Tyr Gln Leu Leu Gly Glu Ile Asn Tyr Arg Glu
        115                 120                 125 tgt gac aca gat gga tgg acc aat gat att cct ata tgt gaa gtt gtg     432
Cys Asp Thr Asp Gly Trp Thr Asn Asp Ile Pro Ile Cys Glu Val Val
    130                 135                 140 aag tgt tta cca gtg aca gca cca gag aat gga aaa att gtc agt agt     480
Lys Cys Leu Pro Val Thr Ala Pro Glu Asn Gly Lys Ile Val Ser Ser
145                 150                 155                 160 gca atg gaa cca gat cgg gaa tac cat ttt gga caa gca gta cgg ttt     528
Ala Met Glu Pro Asp Arg Glu Tyr His Phe Gly Gln Ala Val Arg Phe
                165                 170                 175 gta tgt aac tca ggc tac aag att gaa gga gat gaa gaa atg cat tgt     576
Val Cys Asn Ser Gly Tyr Lys Ile Glu Gly Asp Glu Glu Met His Cys
            180                 185                 190 tca gac gat ggt ttt tgg agt aaa gag aaa cca aag tgt gtg gaa att     624
Ser Asp Asp Gly Phe Trp Ser Lys Glu Lys Pro Lys Cys Val Glu Ile
        195                 200                 205 tca tgc aaa tcc cca gat gtt ata aat gga tct cct ata tct cag aag     672
Ser Cys Lys Ser Pro Asp Val Ile Asn Gly Ser Pro Ile Ser Gln Lys
    210                 215                 220 att att tat aag gag aat gaa cga ttt caa tat aaa tgt aac atg ggt     720
Ile Ile Tyr Lys Glu Asn Glu Arg Phe Gln Tyr Lys Cys Asn Met Gly
225                 230                 235                 240 tat gaa tac agt gaa aga gga gat gct gta tgc act gaa tct gga tgg     768
Tyr Glu Tyr Ser Glu Arg Gly Asp Ala Val Cys Thr Glu Ser Gly Trp
                245                 250                 255 cgt ccg ttg cct tca tgt gaa gaa aaa tca tgt gat aat cct tat att     816
Arg Pro Leu Pro Ser Cys Glu Glu Lys Ser Cys Asp Asn Pro Tyr Ile
            260                 265                 270 cca aat ggt gac tac tca cct tta agg att aaa cac aga act gga gat     864
Pro Asn Gly Asp Tyr Ser Pro Leu Arg Ile Lys His Arg Thr Gly Asp
        275                 280                 285 gaa atc acg tac cag tgt aga aat ggt ttt tat cct gca acc cgg gga     912
Glu Ile Thr Tyr Gln Cys Arg Asn Gly Phe Tyr Pro Ala Thr Arg Gly
    290                 295                 300
```

| | | |
|---|---|---|
| aat aca gcc aaa tgc aca agt act ggc tgg ata cct gct ccg aga tgt<br>Asn Thr Ala Lys Cys Thr Ser Thr Gly Trp Ile Pro Ala Pro Arg Cys<br>305                         310                             315                       320 | | 960 |
| acc ttg aaa cct tgt gat tat cca gac att aaa cat gga ggt cta tat<br>Thr Leu Lys Pro Cys Asp Tyr Pro Asp Ile Lys His Gly Gly Leu Tyr<br>                       325                             330                       335 | | 1008 |
| cat gag aat atg cgt aga cca tac ttt cca gta gct gta gga aaa tat<br>His Glu Asn Met Arg Arg Pro Tyr Phe Pro Val Ala Val Gly Lys Tyr<br>                   340                             345                       350 | | 1056 |
| tac tcc tat tac tgt gat gaa cat ttt gag act ccg tca gga agt tac<br>Tyr Ser Tyr Tyr Cys Asp Glu His Phe Glu Thr Pro Ser Gly Ser Tyr<br>                       355                             360                       365 | | 1104 |
| tgg gat cac att cat tgc aca caa gat gga tgg tcg cca gca gta cca<br>Trp Asp His Ile His Cys Thr Gln Asp Gly Trp Ser Pro Ala Val Pro<br>               370                             375                             380 | | 1152 |
| tgc ctc aga aaa tgt tat ttt cct tat ttg gaa aat gga tat aat caa<br>Cys Leu Arg Lys Cys Tyr Phe Pro Tyr Leu Glu Asn Gly Tyr Asn Gln<br>385                         390                             395                       400 | | 1200 |
| aat tat gga aga aag ttt gta cag ggt aaa tct ata gac gtt gcc tgc<br>Asn Tyr Gly Arg Lys Phe Val Gln Gly Lys Ser Ile Asp Val Ala Cys<br>                       405                             410                       415 | | 1248 |
| cat cct ggc tac gct ctt cca aaa gcg cag acc aca gtt aca tgt atg<br>His Pro Gly Tyr Ala Leu Pro Lys Ala Gln Thr Thr Val Thr Cys Met<br>                   420                             425                       430 | | 1296 |
| gag aat ggc tgg tct cct act ccc aga tgc atc cgt gtc aaa aca tgt<br>Glu Asn Gly Trp Ser Pro Thr Pro Arg Cys Ile Arg Val Lys Thr Cys<br>               435                             440                       445 | | 1344 |
| tcc aaa tca agt ata gat att gag aat ggg ttt att tct gaa tct cag<br>Ser Lys Ser Ser Ile Asp Ile Glu Asn Gly Phe Ile Ser Glu Ser Gln<br>          450                             455                             460 | | 1392 |
| tat aca tat gcc tta aaa gaa aaa gca aaa tat caa tgc aaa cta gga<br>Tyr Thr Tyr Ala Leu Lys Glu Lys Ala Lys Tyr Gln Cys Lys Leu Gly<br>465                         470                             475                       480 | | 1440 |
| tat gta aca gca gat ggt gaa aca tca gga tca att aca tgt ggg aaa<br>Tyr Val Thr Ala Asp Gly Glu Thr Ser Gly Ser Ile Thr Cys Gly Lys<br>                       485                             490                       495 | | 1488 |
| gat gga tgg tca gct caa ccc acg tgc att aaa tct tgt gat atc cca<br>Asp Gly Trp Ser Ala Gln Pro Thr Cys Ile Lys Ser Cys Asp Ile Pro<br>               500                             505                             510 | | 1536 |
| gta ttt atg aat gcc aga act aaa aat gac ttc aca tgg ttt aag ctg<br>Val Phe Met Asn Ala Arg Thr Lys Asn Asp Phe Thr Trp Phe Lys Leu<br>                   515                             520                       525 | | 1584 |
| aat gac aca ttg gac tat gaa tgc cat gat ggt tat gaa agc aat act<br>Asn Asp Thr Leu Asp Tyr Glu Cys His Asp Gly Tyr Glu Ser Asn Thr<br>530                         535                             540 | | 1632 |
| gga agc acc act ggt tcc ata gtg tgt ggt tac aat ggt tgg tct gat<br>Gly Ser Thr Thr Gly Ser Ile Val Cys Gly Tyr Asn Gly Trp Ser Asp<br>545                         550                             555                       560 | | 1680 |
| tta ccc ata tgt tat gaa aga gaa tgc gaa ctt cct aaa ata gat gta<br>Leu Pro Ile Cys Tyr Glu Arg Glu Cys Glu Leu Pro Lys Ile Asp Val<br>                   565                             570                       575 | | 1728 |
| cac tta gtt cct gat cgc aag aaa gac cag tat aaa gtt gga gag gtg<br>His Leu Val Pro Asp Arg Lys Lys Asp Gln Tyr Lys Val Gly Glu Val<br>                       580                             585                       590 | | 1776 |
| ttg aaa ttc tcc tgc aaa cca gga ttt aca ata gtt gga cct aat tcc<br>Leu Lys Phe Ser Cys Lys Pro Gly Phe Thr Ile Val Gly Pro Asn Ser<br>               595                             600                       605 | | 1824 |
| gtt cag tgc tac cac ttt gga ttg tct cct gac ctc cca ata tgt aaa<br>Val Gln Cys Tyr His Phe Gly Leu Ser Pro Asp Leu Pro Ile Cys Lys | | 1872 |

```
                   610                 615                 620
gag caa gta caa tca tgt ggt cca cct cct gaa ctc ctc aat ggg aat      1920
Glu Gln Val Gln Ser Cys Gly Pro Pro Pro Glu Leu Leu Asn Gly Asn
625                 630                 635                 640 gtt aag gaa aaa acg aaa gaa gaa tat gga cac agt gaa gtg gtg gaa      1968
Val Lys Glu Lys Thr Lys Glu Glu Tyr Gly His Ser Glu Val Val Glu
                    645                 650                 655 tat tat tgc aat cct aga ttt cta atg aag gga cct aat aaa att caa      2016
Tyr Tyr Cys Asn Pro Arg Phe Leu Met Lys Gly Pro Asn Lys Ile Gln
            660                 665                 670 tgt gtt gat gga gag tgg aca act tta cca gtg tgt att gtg gag gag      2064
Cys Val Asp Gly Glu Trp Thr Thr Leu Pro Val Cys Ile Val Glu Glu
        675                 680                 685 agt acc tgt gga gat ata cct gaa ctt gaa cat ggc tgg gcc cag ctt      2112
Ser Thr Cys Gly Asp Ile Pro Glu Leu Glu His Gly Trp Ala Gln Leu
    690                 695                 700 tct tcc cct cct tat tac tat gga gat tca gtg gaa ttc aat tgc tca      2160
Ser Ser Pro Pro Tyr Tyr Tyr Gly Asp Ser Val Glu Phe Asn Cys Ser
705                 710                 715                 720 gaa tca ttt aca atg att gga cac aga tca att acg tgt att cat gga      2208
Glu Ser Phe Thr Met Ile Gly His Arg Ser Ile Thr Cys Ile His Gly
                    725                 730                 735 gta tgg acc caa ctt ccc cag tgt gtg gca ata gat aaa ctt aag aag      2256
Val Trp Thr Gln Leu Pro Gln Cys Val Ala Ile Asp Lys Leu Lys Lys
            740                 745                 750 tgc aaa tca tca aat tta att ata ctt gag gaa cat tta aaa aac aag      2304
Cys Lys Ser Ser Asn Leu Ile Ile Leu Glu Glu His Leu Lys Asn Lys
        755                 760                 765 aag gaa ttc gat cat aat tct aac ata agg tac aga tgt aga gga aaa      2352
Lys Glu Phe Asp His Asn Ser Asn Ile Arg Tyr Arg Cys Arg Gly Lys
    770                 775                 780 gaa gga tgg ata cac aca gtc tgc ata aat gga aga tgg gat cca gaa      2400
Glu Gly Trp Ile His Thr Val Cys Ile Asn Gly Arg Trp Asp Pro Glu
785                 790                 795                 800 gtg aac tgc tca atg gca caa ata caa tta tgc cca cct cca cct cag      2448
Val Asn Cys Ser Met Ala Gln Ile Gln Leu Cys Pro Pro Pro Pro Gln
                    805                 810                 815 att ccc aat tct cac aat atg aca acc aca ctg aat tat cgg gat gga      2496
Ile Pro Asn Ser His Asn Met Thr Thr Thr Leu Asn Tyr Arg Asp Gly
            820                 825                 830 gaa aaa gta tct gtt ctt tgc caa gaa aat tat cta att cag gaa gga      2544
Glu Lys Val Ser Val Leu Cys Gln Glu Asn Tyr Leu Ile Gln Glu Gly
        835                 840                 845 gaa gaa att aca tgc aaa gat gga aga tgg cag tca ata cca ctc tgt      2592
Glu Glu Ile Thr Cys Lys Asp Gly Arg Trp Gln Ser Ile Pro Leu Cys
    850                 855                 860 gtt gaa aaa att cca tgt tca caa cca cct cag ata gaa cac gga acc      2640
Val Glu Lys Ile Pro Cys Ser Gln Pro Pro Gln Ile Glu His Gly Thr
865                 870                 875                 880 att aat tca tcc agg tct tca caa gaa agt tat gca cat ggg act aaa      2688
Ile Asn Ser Ser Arg Ser Ser Gln Glu Ser Tyr Ala His Gly Thr Lys
                    885                 890                 895 ttg agt tat act tgt gag ggt ggt ttc agg ata tct gaa gaa aat gaa      2736
Leu Ser Tyr Thr Cys Glu Gly Gly Phe Arg Ile Ser Glu Glu Asn Glu
            900                 905                 910 aca aca tgc tac atg gga aaa tgg agt tct cca cct cag tgt gaa ggc      2784
Thr Thr Cys Tyr Met Gly Lys Trp Ser Ser Pro Pro Gln Cys Glu Gly
        915                 920                 925 ctt cct tgt aaa tct cca cct gag att tct cat ggt gtt gta gct cac      2832
```

```
Leu Pro Cys Lys Ser Pro Glu Ile Ser His Gly Val Val Ala His
        930             935             940 atg tca gac agt tat cag tat gga gaa gaa gtt acg tac aaa tgt ttt         2880
Met Ser Asp Ser Tyr Gln Tyr Gly Glu Glu Val Thr Tyr Lys Cys Phe
945                 950                 955                 960 gaa ggt ttt gga att gat ggg cct gca att gca aaa tgc tta gga gaa         2928
Glu Gly Phe Gly Ile Asp Gly Pro Ala Ile Ala Lys Cys Leu Gly Glu
            965                 970                 975 aaa tgg tct cac cct cca tca tgc ata aaa aca gat tgt ctc agt tta         2976
Lys Trp Ser His Pro Pro Ser Cys Ile Lys Thr Asp Cys Leu Ser Leu
        980                 985                 990 cct agc ttt gaa aat gcc ata ccc atg gga gag aag aag gat gtg tat         3024
Pro Ser Phe Glu Asn Ala Ile Pro Met Gly Glu Lys Lys Asp Val Tyr
    995                 1000                1005 aag gcg ggt gag caa gtg act tac act tgt gca aca tat tac aaa             3069
Lys Ala Gly Glu Gln Val Thr Tyr Thr Cys Ala Thr Tyr Tyr Lys
1010                1015                1020 atg gat gga gcc agt aat gta aca tgc att aat agc aga tgg aca             3114
Met Asp Gly Ala Ser Asn Val Thr Cys Ile Asn Ser Arg Trp Thr
1025                1030                1035 gga agg cca aca tgc aga gac acc tcc tgt gtg aat ccg ccc aca             3159
Gly Arg Pro Thr Cys Arg Asp Thr Ser Cys Val Asn Pro Pro Thr
1040                1045                1050 gta caa aat gct tat ata gtg tcg aga cag atg agt aaa tat cca             3204
Val Gln Asn Ala Tyr Ile Val Ser Arg Gln Met Ser Lys Tyr Pro
1055                1060                1065 tct ggt gag aga gta cgt tat caa tgt agg agc cct tat gaa atg             3249
Ser Gly Glu Arg Val Arg Tyr Gln Cys Arg Ser Pro Tyr Glu Met
1070                1075                1080 ttt ggg gat gaa gaa gtg atg tgt tta aat gga aac tgg acg gaa             3294
Phe Gly Asp Glu Glu Val Met Cys Leu Asn Gly Asn Trp Thr Glu
1085                1090                1095 cca cct caa tgc aaa gat tct aca gga aaa tgt ggg ccc cct cca             3339
Pro Pro Gln Cys Lys Asp Ser Thr Gly Lys Cys Gly Pro Pro Pro
1100                1105                1110 cct att gac aat ggg gac att act tca ttc ccg ttg tca gta tat             3384
Pro Ile Asp Asn Gly Asp Ile Thr Ser Phe Pro Leu Ser Val Tyr
1115                1120                1125 gct cca gct tca tca gtt gag tac caa tgc cag aac ttg tat caa             3429
Ala Pro Ala Ser Ser Val Glu Tyr Gln Cys Gln Asn Leu Tyr Gln
1130                1135                1140 ctt gag ggt aac aag cga ata aca tgt aga aat gga caa tgg tca             3474
Leu Glu Gly Asn Lys Arg Ile Thr Cys Arg Asn Gly Gln Trp Ser
1145                1150                1155 gaa cca cca aaa tgc tta cat ccg tgt gta ata tcc cga gaa att             3519
Glu Pro Pro Lys Cys Leu His Pro Cys Val Ile Ser Arg Glu Ile
1160                1165                1170 atg gaa aat tat aac ata gca tta agg tgg aca gcc aaa cag aag             3564
Met Glu Asn Tyr Asn Ile Ala Leu Arg Trp Thr Ala Lys Gln Lys
1175                1180                1185 ctt tat tcg aga aca ggt gaa tca gtt gaa ttt gtg tgt aaa cgg             3609
Leu Tyr Ser Arg Thr Gly Glu Ser Val Glu Phe Val Cys Lys Arg
1190                1195                1200 gga tat cgt ctt tca tca cgt tct cac aca ttg cga aca aca tgt             3654
Gly Tyr Arg Leu Ser Ser Arg Ser His Thr Leu Arg Thr Thr Cys
1205                1210                1215 tgg gat ggg aaa ctg gag tat cca act tgt gca aaa aga tag               3696
Trp Asp Gly Lys Leu Glu Tyr Pro Thr Cys Ala Lys Arg
1220                1225                1230
```

<210> SEQ ID NO 2
<211> LENGTH: 18
<212> TYPE: PRT
<213> ORGANISM: Homo sapiens

<400> SEQUENCE: 2

Met Arg Leu Leu Ala Lys Ile Ile Cys Leu Met Leu Trp Ala Ile Cys
1               5                   10                  15

Val Ala

<210> SEQ ID NO 3
<211> LENGTH: 62
<212> TYPE: PRT
<213> ORGANISM: Homo sapiens

<400> SEQUENCE: 3

Glu Asp Cys Asn Glu Leu Pro Pro Arg Arg Asn Thr Glu Ile Leu Thr
1               5                   10                  15

Gly Ser Trp Ser Asp Gln Thr Tyr Pro Glu Gly Thr Gln Ala Ile Tyr
            20                  25                  30

Lys Cys Arg Pro Gly Tyr Arg Ser Leu Gly Asn Ile Ile Met Val Cys
        35                  40                  45

Arg Lys Gly Glu Trp Val Ala Leu Asn Pro Leu Arg Lys Cys
    50                  55                  60

<210> SEQ ID NO 4
<211> LENGTH: 4
<212> TYPE: PRT
<213> ORGANISM: Homo sapiens

<400> SEQUENCE: 4

Gln Lys Arg Pro
1

<210> SEQ ID NO 5
<211> LENGTH: 57
<212> TYPE: PRT
<213> ORGANISM: Homo sapiens

<400> SEQUENCE: 5

Cys Gly His Pro Gly Asp Thr Pro Phe Gly Thr Phe Thr Leu Thr Gly
1               5                   10                  15

Gly Asn Val Phe Glu Tyr Gly Val Lys Ala Val Tyr Thr Cys Asn Glu
            20                  25                  30

Gly Tyr Gln Leu Leu Gly Glu Ile Asn Tyr Arg Glu Cys Asp Thr Asp
        35                  40                  45

Gly Trp Thr Asn Asp Ile Pro Ile Cys
    50                  55

<210> SEQ ID NO 6
<211> LENGTH: 4
<212> TYPE: PRT
<213> ORGANISM: Homo sapiens

<400> SEQUENCE: 6

Glu Val Val Lys
1

<210> SEQ ID NO 7
<211> LENGTH: 60
<212> TYPE: PRT

<213> ORGANISM: Homo sapiens

<400> SEQUENCE: 7

Cys Leu Pro Val Thr Ala Pro Glu Asn Gly Lys Ile Val Ser Ser Ala
1               5                   10                  15

Met Glu Pro Asp Arg Glu Tyr His Phe Gly Gln Ala Val Arg Phe Val
                20                  25                  30

Cys Asn Ser Gly Tyr Lys Ile Glu Gly Asp Glu Glu Met His Cys Ser
            35                  40                  45

Asp Asp Gly Phe Trp Ser Lys Glu Lys Pro Lys Cys
        50                  55                  60

<210> SEQ ID NO 8
<211> LENGTH: 4
<212> TYPE: PRT
<213> ORGANISM: Homo sapiens

<400> SEQUENCE: 8

Val Glu Ile Ser
1

<210> SEQ ID NO 9
<211> LENGTH: 53
<212> TYPE: PRT
<213> ORGANISM: Homo sapiens

<400> SEQUENCE: 9

Cys Lys Ser Pro Asp Val Ile Asn Gly Ser Pro Ile Ser Gln Lys Ile
1               5                   10                  15

Ile Tyr Lys Glu Asn Glu Arg Phe Gln Tyr Lys Cys Asn Met Gly Tyr
                20                  25                  30

Glu Tyr Ser Glu Arg Gly Asp Ala Val Cys Thr Glu Ser Gly Trp Arg
            35                  40                  45

Pro Leu Pro Ser Cys
        50

<210> SEQ ID NO 10
<211> LENGTH: 4
<212> TYPE: PRT
<213> ORGANISM: Homo sapiens

<400> SEQUENCE: 10

Glu Glu Lys Ser
1

<210> SEQ ID NO 11
<211> LENGTH: 54
<212> TYPE: PRT
<213> ORGANISM: Homo sapiens

<400> SEQUENCE: 11

Cys Asp Asn Pro Tyr Ile Pro Asn Gly Asp Tyr Ser Pro Leu Arg Ile
1               5                   10                  15

Lys His Arg Thr Gly Asp Glu Ile Thr Tyr Gln Cys Arg Asn Gly Phe
                20                  25                  30

Tyr Pro Ala Thr Arg Gly Asn Thr Ala Lys Cys Thr Ser Thr Gly Trp
            35                  40                  45

Ile Pro Ala Pro Arg Cys
        50

<210> SEQ ID NO 12
<211> LENGTH: 4
<212> TYPE: PRT
<213> ORGANISM: Homo sapiens

<400> SEQUENCE: 12

Thr Leu Lys Pro
1

<210> SEQ ID NO 13
<211> LENGTH: 61
<212> TYPE: PRT
<213> ORGANISM: Homo sapiens

<400> SEQUENCE: 13

Cys Asp Tyr Pro Asp Ile Lys His Gly Gly Leu Tyr His Glu Asn Met
1               5                   10                  15

Arg Arg Pro Tyr Phe Pro Val Ala Val Gly Lys Tyr Tyr Ser Tyr Tyr
                20                  25                  30

Cys Asp Glu His Phe Glu Thr Pro Ser Gly Ser Tyr Trp Asp His Ile
            35                  40                  45

His Cys Thr Gln Asp Gly Trp Ser Pro Ala Val Pro Cys
    50                  55                  60

<210> SEQ ID NO 14
<211> LENGTH: 54
<212> TYPE: PRT
<213> ORGANISM: Homo sapiens

<400> SEQUENCE: 14

Cys Tyr Phe Pro Tyr Leu Glu Asn Gly Tyr Asn Gln Asn Tyr Gly Arg
1               5                   10                  15

Lys Phe Val Gln Gly Lys Ser Ile Asp Val Ala Cys His Pro Gly Tyr
                20                  25                  30

Ala Leu Pro Lys Ala Gln Thr Thr Val Thr Cys Met Glu Asn Gly Trp
            35                  40                  45

Ser Pro Thr Pro Arg Cys
    50

<210> SEQ ID NO 15
<211> LENGTH: 5
<212> TYPE: PRT
<213> ORGANISM: Homo sapiens

<400> SEQUENCE: 15

Ile Arg Val Lys Thr
1               5

<210> SEQ ID NO 16
<211> LENGTH: 58
<212> TYPE: PRT
<213> ORGANISM: Homo sapiens

<400> SEQUENCE: 16

Cys Ser Lys Ser Ser Ile Asp Ile Glu Asn Gly Phe Ile Ser Glu Ser
1               5                   10                  15

Gln Tyr Thr Tyr Ala Leu Lys Glu Lys Ala Lys Tyr Gln Cys Lys Leu
                20                  25                  30

Gly Tyr Val Thr Ala Asp Gly Glu Thr Ser Gly Ser Ile Thr Cys Gly
            35                  40                  45

Lys Asp Gly Trp Ser Ala Gln Pro Thr Cys

<210> SEQ ID NO 17
<211> LENGTH: 56
<212> TYPE: PRT
<213> ORGANISM: Homo sapiens

<400> SEQUENCE: 17

Cys Asp Ile Pro Val Phe Met Asn Ala Arg Thr Lys Asn Asp Phe Thr
1               5                   10                  15

Trp Phe Lys Leu Asn Asp Thr Leu Asp Tyr Glu Cys His Asp Gly Tyr
            20                  25                  30

Glu Ser Asn Thr Gly Ser Thr Gly Ser Ile Val Cys Gly Tyr Asn
        35                  40                  45

Gly Trp Ser Asp Leu Pro Ile Cys
    50                  55

<210> SEQ ID NO 18
<211> LENGTH: 4
<212> TYPE: PRT
<213> ORGANISM: Homo sapiens

<400> SEQUENCE: 18

Tyr Glu Arg Glu
1

<210> SEQ ID NO 19
<211> LENGTH: 55
<212> TYPE: PRT
<213> ORGANISM: Homo sapiens

<400> SEQUENCE: 19

Cys Glu Leu Pro Lys Ile Asp Val His Leu Val Pro Asp Arg Lys Lys
1               5                   10                  15

Asp Gln Tyr Lys Val Gly Glu Val Leu Lys Phe Ser Cys Lys Pro Gly
            20                  25                  30

Phe Thr Ile Val Gly Pro Asn Ser Val Gln Cys Tyr His Phe Gly Leu
        35                  40                  45

Ser Pro Asp Leu Pro Ile Cys
    50                  55

<210> SEQ ID NO 20
<211> LENGTH: 6
<212> TYPE: PRT
<213> ORGANISM: Homo sapiens

<400> SEQUENCE: 20

Lys Glu Gln Val Gln Ser
1               5

<210> SEQ ID NO 21
<211> LENGTH: 55
<212> TYPE: PRT
<213> ORGANISM: Homo sapiens

<400> SEQUENCE: 21

Cys Gly Pro Pro Pro Glu Leu Leu Asn Gly Asn Val Lys Glu Lys Thr
1               5                   10                  15

Lys Glu Glu Tyr Gly His Ser Glu Val Val Glu Tyr Tyr Cys Asn Pro
            20                  25                  30

Arg Phe Leu Met Lys Gly Pro Asn Lys Ile Gln Cys Val Asp Gly Glu

```
                35                  40                  45

Trp Thr Thr Leu Pro Val Cys
    50                  55

<210> SEQ ID NO 22
<211> LENGTH: 6
<212> TYPE: PRT
<213> ORGANISM: Homo sapiens

<400> SEQUENCE: 22

Ile Val Glu Glu Ser Thr
1               5

<210> SEQ ID NO 23
<211> LENGTH: 54
<212> TYPE: PRT
<213> ORGANISM: Homo sapiens

<400> SEQUENCE: 23

Cys Gly Asp Ile Pro Glu Leu Glu His Gly Trp Ala Gln Leu Ser Ser
1               5                   10                  15

Pro Pro Tyr Tyr Tyr Gly Asp Ser Val Glu Phe Asn Cys Ser Glu Ser
            20                  25                  30

Phe Thr Met Ile Gly His Arg Ser Ile Thr Cys Ile His Gly Val Trp
        35                  40                  45

Thr Gln Leu Pro Gln Cys
    50

<210> SEQ ID NO 24
<211> LENGTH: 8
<212> TYPE: PRT
<213> ORGANISM: Homo sapiens

<400> SEQUENCE: 24

Val Ala Ile Asp Lys Leu Lys Lys
1               5

<210> SEQ ID NO 25
<211> LENGTH: 51
<212> TYPE: PRT
<213> ORGANISM: Homo sapiens

<400> SEQUENCE: 25

Cys Lys Ser Ser Asn Leu Ile Ile Leu Glu Glu His Leu Lys Asn Lys
1               5                   10                  15

Lys Glu Phe Asp His Asn Ser Asn Ile Arg Tyr Arg Cys Arg Gly Lys
            20                  25                  30

Glu Gly Trp Ile His Thr Val Cys Ile Asn Gly Arg Trp Asp Pro Glu
        35                  40                  45

Val Asn Cys
    50

<210> SEQ ID NO 26
<211> LENGTH: 7
<212> TYPE: PRT
<213> ORGANISM: Homo sapiens

<400> SEQUENCE: 26

Ser Met Ala Gln Ile Gln Leu
1               5
```

```
<210> SEQ ID NO 27
<211> LENGTH: 54
<212> TYPE: PRT
<213> ORGANISM: Homo sapiens

<400> SEQUENCE: 27

Cys Pro Pro Pro Gln Ile Pro Asn Ser His Asn Met Thr Thr Thr
1               5                   10                  15

Leu Asn Tyr Arg Asp Gly Glu Lys Val Ser Val Leu Cys Gln Glu Asn
                20                  25                  30

Tyr Leu Ile Gln Glu Gly Glu Glu Ile Thr Cys Lys Asp Gly Arg Trp
            35                  40                  45

Gln Ser Ile Pro Leu Cys
        50

<210> SEQ ID NO 28
<211> LENGTH: 5
<212> TYPE: PRT
<213> ORGANISM: Homo sapiens

<400> SEQUENCE: 28

Val Glu Lys Ile Pro
1               5

<210> SEQ ID NO 29
<211> LENGTH: 57
<212> TYPE: PRT
<213> ORGANISM: Homo sapiens

<400> SEQUENCE: 29

Cys Ser Gln Pro Pro Gln Ile Glu His Gly Thr Ile Asn Ser Ser Arg
1               5                   10                  15

Ser Ser Gln Glu Ser Tyr Ala His Gly Thr Lys Leu Ser Tyr Thr Cys
                20                  25                  30

Glu Gly Gly Phe Arg Ile Ser Glu Glu Asn Glu Thr Thr Cys Tyr Met
            35                  40                  45

Gly Lys Trp Ser Ser Pro Pro Gln Cys
        50                  55

<210> SEQ ID NO 30
<211> LENGTH: 4
<212> TYPE: PRT
<213> ORGANISM: Homo sapiens

<400> SEQUENCE: 30

Glu Gly Leu Pro
1

<210> SEQ ID NO 31
<211> LENGTH: 54
<212> TYPE: PRT
<213> ORGANISM: Homo sapiens

<400> SEQUENCE: 31

Cys Lys Ser Pro Pro Glu Ile Ser His Gly Val Val Ala His Met Ser
1               5                   10                  15

Asp Ser Tyr Gln Tyr Gly Glu Glu Val Thr Tyr Lys Cys Phe Glu Gly
                20                  25                  30

Phe Gly Ile Asp Gly Pro Ala Ile Ala Lys Cys Leu Gly Glu Lys Trp
            35                  40                  45

Ser His Pro Pro Ser Cys
```

50

<210> SEQ ID NO 32
<211> LENGTH: 4
<212> TYPE: PRT
<213> ORGANISM: Homo sapiens

<400> SEQUENCE: 32

Ile Lys Thr Asp
1

<210> SEQ ID NO 33
<211> LENGTH: 55
<212> TYPE: PRT
<213> ORGANISM: Homo sapiens

<400> SEQUENCE: 33

Cys Leu Ser Leu Pro Ser Phe Glu Asn Ala Ile Pro Met Gly Glu Lys
1               5                   10                  15
Lys Asp Val Tyr Lys Ala Gly Glu Gln Val Thr Tyr Thr Cys Ala Thr
            20                  25                  30
Tyr Tyr Lys Met Asp Gly Ala Ser Asn Val Thr Cys Ile Asn Ser Arg
        35                  40                  45
Trp Thr Gly Arg Pro Thr Cys
    50                  55

<210> SEQ ID NO 34
<211> LENGTH: 4
<212> TYPE: PRT
<213> ORGANISM: Homo sapiens

<400> SEQUENCE: 34

Arg Asp Thr Ser
1

<210> SEQ ID NO 35
<211> LENGTH: 55
<212> TYPE: PRT
<213> ORGANISM: Homo sapiens

<400> SEQUENCE: 35

Cys Val Asn Pro Pro Thr Val Gln Asn Ala Tyr Ile Val Ser Arg Gln
1               5                   10                  15
Met Ser Lys Tyr Pro Ser Gly Glu Arg Val Arg Tyr Gln Cys Arg Ser
            20                  25                  30
Pro Tyr Glu Met Phe Gly Asp Glu Glu Val Met Cys Leu Asn Gly Asn
        35                  40                  45
Trp Thr Glu Pro Pro Gln Cys
    50                  55

<210> SEQ ID NO 36
<211> LENGTH: 6
<212> TYPE: PRT
<213> ORGANISM: Homo sapiens

<400> SEQUENCE: 36

Lys Asp Ser Thr Gly Lys
1               5

<210> SEQ ID NO 37
<211> LENGTH: 55
<212> TYPE: PRT

<213> ORGANISM: Homo sapiens

<400> SEQUENCE: 37

```
Cys Gly Pro Pro Pro Ile Asp Asn Gly Asp Ile Thr Ser Phe Pro
1               5                   10                  15
Leu Ser Val Tyr Ala Pro Ala Ser Ser Val Glu Tyr Gln Cys Gln Asn
            20                  25                  30
Leu Tyr Gln Leu Glu Gly Asn Lys Arg Ile Thr Cys Arg Asn Gly Gln
        35                  40                  45
Trp Ser Glu Pro Pro Lys Cys
    50                  55
```

<210> SEQ ID NO 38
<211> LENGTH: 65
<212> TYPE: PRT
<213> ORGANISM: Homo sapiens

<400> SEQUENCE: 38

```
Cys Val Ile Ser Arg Glu Ile Met Glu Asn Tyr Asn Ile Ala Leu Arg
1               5                   10                  15
Trp Thr Ala Lys Gln Lys Leu Tyr Ser Arg Thr Gly Glu Ser Val Glu
            20                  25                  30
Phe Val Cys Lys Arg Gly Tyr Arg Leu Ser Ser Arg Ser His Thr Leu
        35                  40                  45
Arg Thr Thr Cys Trp Asp Gly Lys Leu Glu Tyr Pro Thr Cys Ala Lys
    50                  55                  60
Arg
65
```

<210> SEQ ID NO 39
<211> LENGTH: 1231
<212> TYPE: PRT
<213> ORGANISM: Homo sapiens
<220> FEATURE:
<221> NAME/KEY: SIGNAL
<222> LOCATION: (1)..(18)
<220> FEATURE:
<221> NAME/KEY: DOMAIN
<222> LOCATION: (19)..(82)
<223> OTHER INFORMATION: Sushi 1
<220> FEATURE:
<221> NAME/KEY: DOMAIN
<222> LOCATION: (83)..(143)
<223> OTHER INFORMATION: Sushi 1
<220> FEATURE:
<221> NAME/KEY: DOMAIN
<222> LOCATION: (144)..(207)
<223> OTHER INFORMATION: Sushi 3
<220> FEATURE:
<221> NAME/KEY: DOMAIN
<222> LOCATION: (208)..(264)
<223> OTHER INFORMATION: Sushi 4
<220> FEATURE:
<221> NAME/KEY: DOMAIN
<222> LOCATION: (265)..(322)
<223> OTHER INFORMATION: Sushi 5
<220> FEATURE:
<221> NAME/KEY: DOMAIN
<222> LOCATION: (324)..(386)
<223> OTHER INFORMATION: Sushi 6
<220> FEATURE:
<221> NAME/KEY: DOMAIN
<222> LOCATION: (387)..(444)
<223> OTHER INFORMATION: Sushi 7
<220> FEATURE:
<221> NAME/KEY: DOMAIN
<222> LOCATION: (446)..(507)
<223> OTHER INFORMATION: Sushi 8

```
<220> FEATURE:
<221> NAME/KEY: DOMAIN
<222> LOCATION: (515)..(566)
<223> OTHER INFORMATION: Sushi 9
<220> FEATURE:
<221> NAME/KEY: DOMAIN
<222> LOCATION: (576)..(625)
<223> OTHER INFORMATION: Sushi 10
<220> FEATURE:
<221> NAME/KEY: DOMAIN
<222> LOCATION: (628)..(686)
<223> OTHER INFORMATION: Sushi 11
<220> FEATURE:
<221> NAME/KEY: DOMAIN
<222> LOCATION: (689)..(746)
<223> OTHER INFORMATION: Sushi 12
<220> FEATURE:
<221> NAME/KEY: DOMAIN
<222> LOCATION: (751)..(805)
<223> OTHER INFORMATION: Sushi 13
<220> FEATURE:
<221> NAME/KEY: DOMAIN
<222> LOCATION: (809)..(866)
<223> OTHER INFORMATION: Sushi 14
<220> FEATURE:
<221> NAME/KEY: DOMAIN
<222> LOCATION: (868)..(928)
<223> OTHER INFORMATION: Sushi 15
<220> FEATURE:
<221> NAME/KEY: DOMAIN
<222> LOCATION: (929)..(986)
<223> OTHER INFORMATION: Sushi 16
<220> FEATURE:
<221> NAME/KEY: DOMAIN
<222> LOCATION: (987)..(1045)
<223> OTHER INFORMATION: Sushi 17
<220> FEATURE:
<221> NAME/KEY: DOMAIN
<222> LOCATION: (1046)..(1104)
<223> OTHER INFORMATION: Sushi 18
<220> FEATURE:
<221> NAME/KEY: DOMAIN
<222> LOCATION: (1107)..(1165)
<223> OTHER INFORMATION: Sushi 19
<220> FEATURE:
<221> NAME/KEY: DOMAIN
<222> LOCATION: (1170)..(1230)
<223> OTHER INFORMATION: Sushi 20

<400> SEQUENCE: 39

Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
                20                  25                  30

Leu Thr Gly Ser Trp Ser Asp Gln Thr Tyr Pro Glu Gly Thr Gln Ala
            35                  40                  45

Ile Tyr Lys Cys Arg Pro Gly Tyr Arg Ser Leu Gly Asn Val Ile Met
        50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
            100                 105                 110

Thr Cys Asn Glu Gly Tyr Gln Leu Leu Gly Glu Ile Asn Tyr Arg Glu
        115                 120                 125

Cys Asp Thr Asp Gly Trp Thr Asn Asp Ile Pro Ile Cys Glu Val Val
    130                 135                 140

Lys Cys Leu Pro Val Thr Ala Pro Glu Asn Gly Lys Ile Val Ser Ser
```

-continued

```
            145                 150                 155                 160
Ala Met Glu Pro Asp Arg Glu Tyr His Phe Gly Gln Ala Val Arg Phe
                    165                 170                 175

Val Cys Asn Ser Gly Tyr Lys Ile Glu Gly Asp Glu Met His Cys
                180                 185                 190

Ser Asp Asp Gly Phe Trp Ser Lys Glu Lys Pro Lys Cys Val Glu Ile
            195                 200                 205

Ser Cys Lys Ser Pro Asp Val Ile Asn Gly Ser Pro Ile Ser Gln Lys
    210                 215                 220

Ile Ile Tyr Lys Glu Asn Glu Arg Phe Gln Tyr Lys Cys Asn Met Gly
225                 230                 235                 240

Tyr Glu Tyr Ser Glu Arg Gly Asp Ala Val Cys Thr Glu Ser Gly Trp
                245                 250                 255

Arg Pro Leu Pro Ser Cys Glu Glu Lys Ser Cys Asp Asn Pro Tyr Ile
                260                 265                 270

Pro Asn Gly Asp Tyr Ser Pro Leu Arg Ile Lys His Arg Thr Gly Asp
            275                 280                 285

Glu Ile Thr Tyr Gln Cys Arg Asn Gly Phe Tyr Pro Ala Thr Arg Gly
    290                 295                 300

Asn Thr Ala Lys Cys Thr Ser Thr Gly Trp Ile Pro Ala Pro Arg Cys
305                 310                 315                 320

Thr Leu Lys Pro Cys Asp Tyr Pro Asp Ile Lys His Gly Gly Leu Tyr
                325                 330                 335

His Glu Asn Met Arg Arg Pro Tyr Phe Pro Val Ala Val Gly Lys Tyr
                340                 345                 350

Tyr Ser Tyr Tyr Cys Asp Glu His Phe Glu Thr Pro Ser Gly Ser Tyr
            355                 360                 365

Trp Asp His Ile His Cys Thr Gln Asp Gly Trp Ser Pro Ala Val Pro
    370                 375                 380

Cys Leu Arg Lys Cys Tyr Phe Pro Tyr Leu Glu Asn Gly Tyr Asn Gln
385                 390                 395                 400

Asn Tyr Gly Arg Lys Phe Val Gln Gly Lys Ser Ile Asp Val Ala Cys
                405                 410                 415

His Pro Gly Tyr Ala Leu Pro Lys Ala Gln Thr Thr Val Thr Cys Met
                420                 425                 430

Glu Asn Gly Trp Ser Pro Thr Pro Arg Cys Ile Arg Val Lys Thr Cys
            435                 440                 445

Ser Lys Ser Ser Ile Asp Ile Glu Asn Gly Phe Ile Ser Glu Ser Gln
    450                 455                 460

Tyr Thr Tyr Ala Leu Lys Glu Lys Ala Lys Tyr Gln Cys Lys Leu Gly
465                 470                 475                 480

Tyr Val Thr Ala Asp Gly Glu Thr Ser Gly Ser Ile Thr Cys Gly Lys
                485                 490                 495

Asp Gly Trp Ser Ala Gln Pro Thr Cys Ile Lys Ser Cys Asp Ile Pro
            500                 505                 510

Val Phe Met Asn Ala Arg Thr Lys Asn Asp Phe Thr Trp Phe Lys Leu
    515                 520                 525

Asn Asp Thr Leu Asp Tyr Glu Cys His Asp Gly Tyr Glu Ser Asn Thr
530                 535                 540

Gly Ser Thr Thr Gly Ser Ile Val Cys Gly Tyr Asn Gly Trp Ser Asp
545                 550                 555                 560

Leu Pro Ile Cys Tyr Glu Arg Glu Cys Glu Leu Pro Lys Ile Asp Val
                565                 570                 575
```

```
His Leu Val Pro Asp Arg Lys Lys Asp Gln Tyr Lys Val Gly Glu Val
            580                 585                 590
Leu Lys Phe Ser Cys Lys Pro Gly Phe Thr Ile Val Gly Pro Asn Ser
            595                 600                 605
Val Gln Cys Tyr His Phe Gly Leu Ser Pro Asp Leu Pro Ile Cys Lys
610                 615                 620
Glu Gln Val Gln Ser Cys Gly Pro Pro Glu Leu Leu Asn Gly Asn
625                 630                 635                 640
Val Lys Glu Lys Thr Lys Glu Tyr Gly His Ser Glu Val Val Glu
            645                 650                 655
Tyr Tyr Cys Asn Pro Arg Phe Leu Met Lys Gly Pro Asn Lys Ile Gln
            660                 665                 670
Cys Val Asp Gly Glu Trp Thr Thr Leu Pro Val Cys Ile Val Glu Glu
            675                 680                 685
Ser Thr Cys Gly Asp Ile Pro Glu Leu Glu His Gly Trp Ala Gln Leu
            690                 695                 700
Ser Ser Pro Pro Tyr Tyr Tyr Gly Asp Ser Val Glu Phe Asn Cys Ser
705                 710                 715                 720
Glu Ser Phe Thr Met Ile Gly His Arg Ser Ile Thr Cys Ile His Gly
            725                 730                 735
Val Trp Thr Gln Leu Pro Gln Cys Val Ala Ile Asp Lys Leu Lys Lys
            740                 745                 750
Cys Lys Ser Ser Asn Leu Ile Ile Leu Glu Glu His Leu Lys Asn Lys
            755                 760                 765
Lys Glu Phe Asp His Asn Ser Asn Ile Arg Tyr Arg Cys Arg Gly Lys
            770                 775                 780
Glu Gly Trp Ile His Thr Val Cys Ile Asn Gly Arg Trp Asp Pro Glu
785                 790                 795                 800
Val Asn Cys Ser Met Ala Gln Ile Gln Leu Cys Pro Pro Pro Gln
            805                 810                 815
Ile Pro Asn Ser His Asn Met Thr Thr Thr Leu Asn Tyr Arg Asp Gly
            820                 825                 830
Glu Lys Val Ser Val Leu Cys Gln Glu Asn Tyr Leu Ile Gln Glu Gly
            835                 840                 845
Glu Glu Ile Thr Cys Lys Asp Gly Arg Trp Gln Ser Ile Pro Leu Cys
850                 855                 860
Val Glu Lys Ile Pro Cys Ser Gln Pro Pro Gln Ile Glu His Gly Thr
865                 870                 875                 880
Ile Asn Ser Ser Arg Ser Ser Gln Glu Ser Tyr Ala His Gly Thr Lys
            885                 890                 895
Leu Ser Tyr Thr Cys Glu Gly Gly Phe Arg Ile Ser Glu Glu Asn Glu
            900                 905                 910
Thr Thr Cys Tyr Met Gly Lys Trp Ser Ser Pro Pro Gln Cys Glu Gly
            915                 920                 925
Leu Pro Cys Lys Ser Pro Pro Glu Ile Ser His Gly Val Val Ala His
            930                 935                 940
Met Ser Asp Ser Tyr Gln Tyr Gly Glu Glu Val Thr Tyr Lys Cys Phe
945                 950                 955                 960
Glu Gly Phe Gly Ile Asp Gly Pro Ala Ile Ala Lys Cys Leu Gly Glu
            965                 970                 975
Lys Trp Ser His Pro Pro Ser Cys Ile Lys Thr Asp Cys Leu Ser Leu
            980                 985                 990
```

```
Pro Ser Phe Glu Asn Ala Ile Pro Met Gly Glu Lys Lys Asp Val Tyr
        995                 1000                1005

Lys Ala Gly Glu Gln Val Thr Tyr Thr Cys Ala Thr Tyr Tyr Lys
        1010                1015                1020

Met Asp Gly Ala Ser Asn Val Thr Cys Ile Asn Ser Arg Trp Thr
        1025                1030                1035

Gly Arg Pro Thr Cys Arg Asp Thr Ser Cys Val Asn Pro Pro Thr
        1040                1045                1050

Val Gln Asn Ala Tyr Ile Val Ser Arg Gln Met Ser Lys Tyr Pro
        1055                1060                1065

Ser Gly Glu Arg Val Arg Tyr Gln Cys Arg Ser Pro Tyr Glu Met
        1070                1075                1080

Phe Gly Asp Glu Glu Val Met Cys Leu Asn Gly Asn Trp Thr Glu
        1085                1090                1095

Pro Pro Gln Cys Lys Asp Ser Thr Gly Lys Cys Gly Pro Pro Pro
        1100                1105                1110

Pro Ile Asp Asn Gly Asp Ile Thr Ser Phe Pro Leu Ser Val Tyr
        1115                1120                1125

Ala Pro Ala Ser Ser Val Glu Tyr Gln Cys Gln Asn Leu Tyr Gln
        1130                1135                1140

Leu Glu Gly Asn Lys Arg Ile Thr Cys Arg Asn Gly Gln Trp Ser
        1145                1150                1155

Glu Pro Pro Lys Cys Leu His Pro Cys Val Ile Ser Arg Glu Ile
        1160                1165                1170

Met Glu Asn Tyr Asn Ile Ala Leu Arg Trp Thr Ala Lys Gln Lys
        1175                1180                1185

Leu Tyr Ser Arg Thr Gly Glu Ser Val Glu Phe Val Cys Lys Arg
        1190                1195                1200

Gly Tyr Arg Leu Ser Ser Arg Ser His Thr Leu Arg Thr Thr Cys
        1205                1210                1215

Trp Asp Gly Lys Leu Glu Tyr Pro Thr Cys Ala Lys Arg
        1220                1225                1230

<210> SEQ ID NO 40
<211> LENGTH: 449
<212> TYPE: PRT
<213> ORGANISM: Homo sapiens

<400> SEQUENCE: 40

Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
                20                  25                  30

Leu Thr Gly Ser Trp Ser Asp Gln Thr Tyr Pro Glu Gly Thr Gln Ala
            35                  40                  45

Ile Tyr Lys Cys Arg Pro Gly Tyr Arg Ser Leu Gly Asn Val Ile Met
        50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
            100                 105                 110

Thr Cys Asn Glu Gly Tyr Gln Leu Leu Gly Glu Ile Asn Tyr Arg Glu
        115                 120                 125
```

Cys Asp Thr Asp Gly Trp Thr Asn Asp Ile Pro Ile Cys Glu Val Val
130                 135                 140

Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe
                165                 170                 175

Val Cys Asn Ser Gly Tyr Lys Ile Glu Gly Asp Glu Glu Met His Cys
                180                 185                 190

Ser Asp Asp Gly Phe Trp Ser Lys Glu Lys Pro Lys Cys Val Glu Ile
                195                 200                 205

Ser Cys Lys Ser Pro Asp Val Ile Asn Gly Ser Pro Ile Ser Gln Lys
210                 215                 220

Ile Ile Tyr Lys Glu Asn Glu Arg Phe Gln Tyr Lys Cys Asn Met Gly
225                 230                 235                 240

Tyr Glu Tyr Ser Glu Arg Gly Asp Ala Val Cys Thr Glu Ser Gly Trp
                245                 250                 255

Arg Pro Leu Pro Ser Cys Glu Glu Lys Ser Cys Asp Asn Pro Tyr Ile
                260                 265                 270

Pro Asn Gly Asp Tyr Ser Pro Leu Arg Ile Lys His Arg Thr Gly Asp
                275                 280                 285

Glu Ile Thr Tyr Gln Cys Arg Asn Gly Phe Tyr Pro Ala Thr Arg Gly
290                 295                 300

Asn Thr Ala Lys Cys Thr Ser Thr Gly Trp Ile Pro Ala Pro Arg Cys
305                 310                 315                 320

Thr Leu Lys Pro Cys Asp Tyr Pro Asp Ile Lys His Gly Gly Leu Tyr
                325                 330                 335

His Glu Asn Met Arg Arg Pro Tyr Phe Pro Val Ala Val Gly Lys Tyr
                340                 345                 350

Tyr Ser Tyr Tyr Cys Asp Glu His Phe Glu Thr Pro Ser Gly Ser Tyr
                355                 360                 365

Trp Asp His Ile His Cys Thr Gln Asp Gly Trp Ser Pro Ala Val Pro
370                 375                 380

Cys Leu Arg Lys Cys Tyr Phe Pro Tyr Leu Glu Asn Gly Tyr Asn Gln
385                 390                 395                 400

Asn Tyr Gly Arg Lys Phe Val Gln Gly Lys Ser Ile Asp Val Ala Cys
                405                 410                 415

His Pro Gly Tyr Ala Leu Pro Lys Ala Gln Thr Thr Val Thr Cys Met
                420                 425                 430

Glu Asn Gly Trp Ser Pro Thr Pro Arg Cys Ile Arg Val Ser Phe Thr
                435                 440                 445

Leu

<210> SEQ ID NO 41
<211> LENGTH: 2068
<212> TYPE: DNA
<213> ORGANISM: Artificial sequence
<220> FEATURE:
<223> OTHER INFORMATION: engineered hfH1-4.678.19-20 variant cDNA

<400> SEQUENCE: 41
ggacgttgtg aacagagtta gctggtaaat gtcctcttaa aagatccaaa aaatgagact    60
tctagcaaag attatttgcc ttatgttatg ggctatttgt gtagcagaag attgcaatga   120
acttcctcca agaagaaata cagaaattct gacaggttcc tggtctgacc aaacatatcc   180

-continued

| | |
|---|---|
| agaaggcacc caggctatct ataaatgccg ccctggatat agatctcttg gaaatataat | 240 |
| aatggtatgc aggaagggag aatgggttgc tcttaatcca ttaaggaaat gtcagaaaag | 300 |
| gccctgtgga catcctggag atactccttt tggtactttt acccttacag gaggaaatgt | 360 |
| gtttgaatat ggtgtaaaag ctgtgtatac atgtaatgag gggtatcaat tgctaggtga | 420 |
| gattaattac cgtgaatgtg acacagatgg atggaccaat gatattccta tatgtgaagt | 480 |
| tgtgaagtgt ttaccagtga cagcaccaga gaatggaaaa attgtcagta gtgcaatgga | 540 |
| accagatcgg aataccatt tggacaagc agtacggttt gtatgtaact caggctacaa | 600 |
| gattgaagga gatgaagaaa tgcattgttc agacgatggt ttttggagta agagaaacc | 660 |
| aaagtgtgtg gaatttcat gcaaatcccc agatgttata aatggatctc ctatatctca | 720 |
| gaagattatt tataaggaga atgaacgatt tcaatataaa tgtaacatgg gttatgaata | 780 |
| cagtgaaaga ggagatgctg tatgcactga atctggatgg cgtccgttgc cttcatgtga | 840 |
| agaaaaatca accttgaaac cttgtgatta tccagacatt aaacatggag gtctatatca | 900 |
| tgagaatatg cgtagaccat actttccagt agctgtagga aaatattact cctattactg | 960 |
| tgatgaacat tttgagactc cgtcaggaag ttactgggat cacattcatt gcacacaaga | 1020 |
| tggatggtcg ccagcagtac catgcctcag aaaatgttat tttccttatt ggaaaatgg | 1080 |
| atataatcaa aatcatggaa gaaagtttgt acagggtaaa tctatagacg ttgcctgcca | 1140 |
| tcctggctac gctcttccaa aagcgcagac acacagttaca tgtatggaga atggctggtc | 1200 |
| tcctactccc agatgcatcc gtgtcaaaac atgttccaaa tcaagtatag atattgagaa | 1260 |
| tgggtttatt tctgaatctc agtatacata tgccttaaaa gaaaaagcga atatcaatg | 1320 |
| caaactagga tatgtaacag cagatggtga acatcagga tcaattagat gtgggaaaga | 1380 |
| tggatggtca gctcaaccca cgtgcattaa atctaaagat tctacaggaa aatgtgggcc | 1440 |
| ccctccacct attgacaatg ggacattac ttcattcccg ttgtcagtat atgctccagc | 1500 |
| ttcatcagtt gagtaccaat gccagaactt gtatcaactt gagggtaaca agcgaataac | 1560 |
| atgtagaaat ggacaatggt cagaaccacc aaaatgctta catccgtgtg taatatcccg | 1620 |
| agaaattatg gaaaattata acatagcatt aaggtggaca gccaaacaga agctttattc | 1680 |
| gagaacaggt gaatcagttg aatttgtgtg taaacgggga tatcgtcttt catcacgttc | 1740 |
| tcacacattg cgaacaacat gttgggatgg gaaactggag tatccaactt gtgcaaaaag | 1800 |
| atagaatcaa tcataaagtg cacaccttta ttcagaactt tagtattaaa tcagttctca | 1860 |
| atttcatttt ttatgtattg ttttactcct ttttattcat acgtaaaatt ttggattaat | 1920 |
| ttgtgaaaat gtaattataa gctgagaccg gtggctctct tcttaaaagc accatattaa | 1980 |
| atcctggaaa actaaaaaaa aaaaaaaaaa aaaaaaaaa aaaaaaaaaa aaaaaaaaaa | 2040 |
| aaaaaaaaaa aaaaaaaaaa aaaaaaaa | 2068 |

<210> SEQ ID NO 42
<211> LENGTH: 583
<212> TYPE: PRT
<213> ORGANISM: Artificial sequence
<220> FEATURE:
<223> OTHER INFORMATION: hfH1-4.678.19-20 protein

<400> SEQUENCE: 42

Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
            20                  25                  30

-continued

```
Leu Thr Gly Ser Trp Ser Asp Gln Thr Tyr Pro Glu Gly Thr Gln Ala
         35                  40                  45
Ile Tyr Lys Cys Arg Pro Gly Tyr Arg Ser Leu Gly Asn Val Ile Met
 50                  55                  60
Val Cys Arg Lys Gly Glu Trp Val Ala Leu Asn Pro Leu Arg Lys Cys
 65                  70                  75                  80
Gln Lys Arg Pro Cys Gly His Pro Gly Asp Thr Pro Phe Gly Thr Phe
                 85                  90                  95
Thr Leu Thr Gly Gly Asn Val Phe Glu Tyr Gly Val Lys Ala Val Tyr
             100                 105                 110
Thr Cys Asn Glu Gly Tyr Gln Leu Leu Gly Glu Ile Asn Tyr Arg Glu
             115                 120                 125
Cys Asp Thr Asp Gly Trp Thr Asn Asp Ile Pro Ile Cys Glu Val Val
130                 135                 140
Lys Cys Leu Pro Val Thr Ala Pro Glu Asn Gly Lys Ile Val Ser Ser
145                 150                 155                 160
Ala Met Glu Pro Asp Arg Glu Tyr His Phe Gly Gln Ala Val Arg Phe
                 165                 170                 175
Val Cys Asn Ser Gly Tyr Lys Ile Glu Gly Asp Glu Glu Met His Cys
             180                 185                 190
Ser Asp Asp Gly Phe Trp Ser Lys Glu Lys Pro Lys Cys Val Glu Ile
             195                 200                 205
Ser Cys Lys Ser Pro Asp Val Ile Asn Gly Ser Pro Ile Ser Gln Lys
             210                 215                 220
Ile Ile Tyr Lys Glu Asn Glu Arg Phe Gln Tyr Lys Cys Asn Met Gly
225                 230                 235                 240
Tyr Glu Tyr Ser Glu Arg Gly Asp Ala Val Cys Thr Glu Ser Gly Trp
                 245                 250                 255
Arg Pro Leu Pro Ser Cys Glu Glu Lys Ser Thr Leu Lys Pro Cys Asp
             260                 265                 270
Tyr Pro Asp Ile Lys His Gly Gly Leu Tyr His Glu Asn Met Arg Arg
             275                 280                 285
Pro Tyr Phe Pro Val Ala Val Gly Lys Tyr Tyr Ser Tyr Tyr Cys Asp
             290                 295                 300
Glu His Phe Glu Thr Pro Ser Gly Ser Tyr Trp Asp His Ile His Cys
305                 310                 315                 320
Thr Gln Asp Gly Trp Ser Pro Ala Val Pro Cys Leu Arg Lys Cys Tyr
                 325                 330                 335
Phe Pro Tyr Leu Glu Asn Gly Tyr Asn Gln Asn His Gly Arg Lys Phe
             340                 345                 350
Val Gln Gly Lys Ser Ile Asp Val Ala Cys His Pro Gly Tyr Ala Leu
             355                 360                 365
Pro Lys Ala Gln Thr Thr Val Thr Cys Met Glu Asn Gly Trp Ser Pro
             370                 375                 380
Thr Pro Arg Cys Ile Arg Val Lys Thr Cys Ser Lys Ser Ser Ile Asp
385                 390                 395                 400
Ile Glu Asn Gly Phe Ile Ser Glu Ser Gln Tyr Thr Tyr Ala Leu Lys
                 405                 410                 415
Glu Lys Ala Lys Tyr Gln Cys Lys Leu Gly Tyr Val Thr Ala Asp Gly
             420                 425                 430
Glu Thr Ser Gly Ser Ile Arg Cys Gly Lys Asp Gly Trp Ser Ala Gln
             435                 440                 445
```

Pro Thr Cys Ile Lys Ser Lys Asp Ser Thr Gly Lys Cys Gly Pro Pro
450                 455                 460

Pro Pro Ile Asp Asn Gly Asp Ile Thr Ser Phe Pro Leu Ser Val Tyr
465                 470                 475                 480

Ala Pro Ala Ser Val Glu Tyr Gln Cys Gln Asn Leu Tyr Gln Leu
            485                 490                 495

Glu Gly Asn Lys Arg Ile Thr Cys Arg Asn Gly Gln Trp Ser Glu Pro
            500                 505                 510

Pro Lys Cys Leu His Pro Cys Val Ile Ser Arg Glu Ile Met Glu Asn
            515                 520                 525

Tyr Asn Ile Ala Leu Arg Trp Thr Ala Lys Gln Lys Leu Tyr Ser Arg
530                 535                 540

Thr Gly Glu Ser Val Glu Phe Val Cys Lys Arg Gly Tyr Arg Leu Ser
545                 550                 555                 560

Ser Arg Ser His Thr Leu Arg Thr Thr Cys Trp Asp Gly Lys Leu Glu
            565                 570                 575

Tyr Pro Thr Cys Ala Lys Arg
            580

<210> SEQ ID NO 43
<211> LENGTH: 2406
<212> TYPE: DNA
<213> ORGANISM: Artificial sequence
<220> FEATURE:
<223> OTHER INFORMATION: murine fH1-4.678.19-20

<400> SEQUENCE: 43
ggtctactat tttagtttac tttgcagaag ttgctcatgg gcggagcaat cctgatttcc         60
taaactgact ttcaacttcc ctttgaagca agtctttccc tgctgtgacc acagttcata        120
gcagagagga actggatggt acagcacaga tttctcttgg agtcagttgg tcccagaaag        180
atccaaatta tgagactgtc agcaagaatt atttggctta tattatggac tgtttgtgca        240
gcagaagatt gtaaaggtcc tcctccaaga gaaaattcag aaattctctc aggctcgtgg        300
tcagaacaac tatatccaga aggcacccag gctacctaca aatgccgccc tggataccga        360
acacttggca ctattgtaaa agtatgcaag aatggaaaat gggtggcgtc taacccatcc        420
aggatatgtc ggaaaaagcc ttgtgggcat cccggagaca cacccttt gg gtcctttagg        480 ctggcagttg gatctcaatt tgagtttggt gcaaggttg tttatacctg tgatgatggg        540
tatcaactat aggtgaaat tgattaccgt gaatgtggtg cagatgggtg gatcaatgat        600
attccactat gtgaagttgt gaagtgtcta cctgtgacag aactcgagaa tggaagaatt        660
gtgagtggtg cagcagaaac agaccaggaa tactattttg acaggtggt gcggtttgaa        720 tgcaattcag gcttcaagat tgaaggacat aaggaaattc attgctcaga aaatggcctt        780
tggagcaatg aaaagccacg atgtgtggaa attctctgca caccaccgcg agtggaaaat        840
ggagatggta taaatgtgaa accagtttac aaggagaatg aaagatacca ctataagtgt        900
aagcatggtt atgtgcccaa agaaagaggg gatgccgtct gcacaggctc tggatggagt        960
tctcagcctt tctgtgaaga aaagagaacc ttgaaaccat gtgaatttcc acaattcaaa       1020 tatgacgtc tgtattatga agagagcctg agacccaact tcccagtatc tataggaaat       1080
aagtacagct ataagtgtga acgggttt tcaccaccctt ctgggtattc ctgggactac       1140
cttcgttgca cagcacaagg gtgggagcct gaagtcccat gcgtcaggaa atgtgttttc       1200
cattatgtgg agaatggaga ctctgcatac tgggaaaag tatatgtgca gggtcagtct       1260

```
ttaaaagtcc agtgttacaa tggctatagt cttcaaaatg gtcaagacac aatgacatgt    1320
acagagaatg gctggtcccc tcctcccaaa tgcatccgta tcaagacatg ttcagcatca    1380
gatatacaca ttgacaatgg atttctttct gaatcttctt ctatatatgc tctaaataga    1440
gaaacatcct atagatgtaa gcagggatat gtgacaaata ctggagaaat atcaggatca    1500
ataacttgcc ttcaaaatgg atggtcacct caaccctcat gcattaagtc tcgagactca    1560
acagggaaat gtgggcctcc tccacctatt gacaatggag acatcacctc cttgtcatta    1620
ccagtatatg aaccattatc atcagttgaa tatcaatgcc agaagtatta tctccttaag    1680
ggaaagaaga caataacatg tagaaatgga aagtggtctg agccaccaac atgcttacat    1740
gcatgtgtaa taccagaaaa cattatggaa tcacacaata taattctcaa atggagacac    1800
actgaaaaga tttattccca ttcaggggag gatattgaat ttggatgtaa atatggatat    1860
tataaagcaa gagattcacc gccatttcgt acaaagtgca ttaatggcac catcaattat    1920
cccacttgtg tataaaatca taatacattt attagttgat tttattgttt agaaaggcac    1980
atgcatgtga ctaatatact ttcaatttgc attgaagtat tgtttaactc atgtcttctc    2040
ataaatataa acattttgt tatatggtga ttaatttgta actttaaaaa ctattgccaa    2100
aatgcaaaag cagtaattca aaactcctaa tctaaaatat gatatgtcca aggacaaact    2160
atttcaatca agaaagtaga tgtaagttct tcaacatctg tttctattca gaactttctc    2220
agattttcct ggatacctt tgatgtaagg tcctgattta cagtggataa aggatatatt    2280
gactgattct tcaaattaat atgatttccc aaagcatgta acaaccaaac tatcatatat    2340
tatatgacta atgcatacaa ttaattacta tataatactt tcaaataaaa gaatctaaga    2400
aacttc    2406
```

<210> SEQ ID NO 44
<211> LENGTH: 599
<212> TYPE: PRT
<213> ORGANISM: Artificial sequence
<220> FEATURE:
<223> OTHER INFORMATION: mouse factor H truncation construct
      mFH1-4.678.19-20

<400> SEQUENCE: 44

```
Met Val Gln His Arg Phe Leu Leu Glu Ser Val Gly Pro Arg Lys Ile
1               5                   10                  15

Gln Ile Met Arg Leu Ser Ala Arg Ile Ile Trp Leu Ile Leu Trp Thr
            20                  25                  30

Val Cys Ala Ala Glu Asp Cys Lys Gly Pro Pro Arg Glu Asn Ser
        35                  40                  45

Glu Ile Leu Ser Gly Ser Trp Ser Glu Gln Leu Tyr Pro Glu Gly Thr
    50                  55                  60

Gln Ala Thr Tyr Lys Cys Arg Pro Gly Tyr Arg Thr Leu Gly Thr Ile
65                  70                  75                  80

Val Lys Val Cys Lys Asn Gly Lys Trp Val Ala Ser Asn Pro Ser Arg
                85                  90                  95

Ile Cys Arg Lys Lys Pro Cys Gly His Pro Gly Asp Thr Pro Phe Gly
            100                 105                 110

Ser Phe Arg Leu Ala Val Gly Ser Gln Phe Glu Phe Gly Ala Lys Val
        115                 120                 125

Val Tyr Thr Cys Asp Asp Gly Tyr Gln Leu Leu Gly Glu Ile Asp Tyr
    130                 135                 140

Arg Glu Cys Gly Ala Asp Gly Trp Ile Asn Asp Ile Pro Leu Cys Glu
```

```
145                 150                 155                 160
Val Val Lys Cys Leu Pro Val Thr Glu Leu Glu Asn Gly Arg Ile Val
                165                 170                 175
Ser Gly Ala Ala Glu Thr Asp Gln Glu Tyr Tyr Phe Gly Gln Val Val
                    180                 185                 190
Arg Phe Glu Cys Asn Ser Gly Phe Lys Ile Glu Gly His Lys Glu Ile
                195                 200                 205
His Cys Ser Glu Asn Gly Leu Trp Ser Asn Glu Lys Pro Arg Cys Val
    210                 215                 220
Glu Ile Leu Cys Thr Pro Pro Arg Val Glu Asn Gly Asp Gly Ile Asn
225                 230                 235                 240
Val Lys Pro Val Tyr Lys Glu Asn Glu Arg Tyr His Tyr Lys Cys Lys
                    245                 250                 255
His Gly Tyr Val Pro Lys Glu Arg Gly Asp Ala Val Cys Thr Gly Ser
                    260                 265                 270
Gly Trp Ser Ser Gln Pro Phe Cys Glu Glu Lys Arg Thr Leu Lys Pro
                275                 280                 285
Cys Glu Phe Pro Gln Phe Lys Tyr Gly Arg Leu Tyr Tyr Glu Glu Ser
    290                 295                 300
Leu Arg Pro Asn Phe Pro Val Ser Ile Gly Asn Lys Tyr Ser Tyr Lys
305                 310                 315                 320
Cys Asp Asn Gly Phe Ser Pro Pro Ser Gly Tyr Ser Trp Asp Tyr Leu
                    325                 330                 335
Arg Cys Thr Ala Gln Gly Trp Glu Pro Glu Val Pro Cys Val Arg Lys
                    340                 345                 350
Cys Val Phe His Tyr Val Glu Asn Gly Asp Ser Ala Tyr Trp Glu Lys
                355                 360                 365
Val Tyr Val Gln Gly Gln Ser Leu Lys Val Gln Cys Tyr Asn Gly Tyr
                    370                 375                 380
Ser Leu Gln Asn Gly Gln Asp Thr Met Thr Cys Thr Glu Asn Gly Trp
385                 390                 395                 400
Ser Pro Pro Pro Lys Cys Ile Arg Ile Lys Thr Cys Ser Ala Ser Asp
                    405                 410                 415
Ile His Ile Asp Asn Gly Phe Leu Ser Glu Ser Ser Ser Ile Tyr Ala
                420                 425                 430
Leu Asn Arg Glu Thr Ser Tyr Arg Cys Lys Gln Gly Tyr Val Thr Asn
                    435                 440                 445
Thr Gly Glu Ile Ser Gly Ser Ile Thr Cys Leu Gln Asn Gly Trp Ser
    450                 455                 460
Pro Gln Pro Ser Cys Ile Lys Ser Arg Asp Ser Thr Gly Lys Cys Gly
465                 470                 475                 480
Pro Pro Pro Pro Ile Asp Asn Gly Asp Ile Thr Ser Leu Ser Leu Pro
                    485                 490                 495
Val Tyr Glu Pro Leu Ser Ser Val Glu Tyr Gln Cys Gln Lys Tyr Tyr
                500                 505                 510
Leu Leu Lys Gly Lys Lys Thr Ile Thr Cys Arg Asn Gly Lys Trp Ser
                515                 520                 525
Glu Pro Pro Thr Cys Leu His Ala Cys Val Ile Pro Glu Asn Ile Met
    530                 535                 540
Glu Ser His Asn Ile Ile Leu Lys Trp Arg His Thr Glu Lys Ile Tyr
545                 550                 555                 560
Ser His Ser Gly Glu Asp Ile Glu Phe Gly Cys Lys Tyr Gly Tyr Tyr
                    565                 570                 575
```

<210> SEQ ID NO 45
<211> LENGTH: 2106
<212> TYPE: DNA
<213> ORGANISM: Artificial Sequence
<220> FEATURE:
<223> OTHER INFORMATION: engineered fH SCR1-4, 6-8, 17-20
<220> FEATURE:
<221> NAME/KEY: CDS
<222> LOCATION: (1)..(2106)

<400> SEQUENCE: 45

```
atg aga ctt cta gca aag att att tgc ctt atg tta tgg gct att tgt        48
Met Arg Leu Leu Ala Lys Ile Ile Cys Leu Met Leu Trp Ala Ile Cys
1               5                   10                  15 gta gca gaa gat tgc aat gaa ctt cct cca aga aga aat aca gaa att        96
Val Ala Glu Asp Cys Asn Glu Leu Pro Pro Arg Arg Asn Thr Glu Ile
            20                  25                  30 ctg aca ggt tcc tgg tct gac caa aca tat cca gaa ggc acc cag gct       144
Leu Thr Gly Ser Trp Ser Asp Gln Thr Tyr Pro Glu Gly Thr Gln Ala
        35                  40                  45 atc tat aaa tgc cgc cct gga tat aga tct ctt gga aat ata ata atg       192
Ile Tyr Lys Cys Arg Pro Gly Tyr Arg Ser Leu Gly Asn Ile Ile Met
    50                  55                  60 gta tgc agg aag gga gaa tgg gtt gct ctt aat cca tta agg aaa tgt       240
Val Cys Arg Lys Gly Glu Trp Val Ala Leu Asn Pro Leu Arg Lys Cys
65                  70                  75                  80 cag aaa agg ccc tgt gga cat cct gga gat act cct ttt ggt act ttt       288
Gln Lys Arg Pro Cys Gly His Pro Gly Asp Thr Pro Phe Gly Thr Phe
                85                  90                  95 acc ctt aca gga gga aat gtg ttt gaa tat ggt gta aaa gct gtg tat       336
Thr Leu Thr Gly Gly Asn Val Phe Glu Tyr Gly Val Lys Ala Val Tyr
            100                 105                 110 aca tgt aat gag ggg tat caa ttg cta ggt gag att aat tac cgt gaa       384
Thr Cys Asn Glu Gly Tyr Gln Leu Leu Gly Glu Ile Asn Tyr Arg Glu
        115                 120                 125 tgt gac aca gat gga tgg acc aat gat att cct ata tgt gaa gtt gtg       432
Cys Asp Thr Asp Gly Trp Thr Asn Asp Ile Pro Ile Cys Glu Val Val
    130                 135                 140 aag tgt tta cca gtg aca gca cca gag aat gga aaa att gtc agt agt       480
Lys Cys Leu Pro Val Thr Ala Pro Glu Asn Gly Lys Ile Val Ser Ser
145                 150                 155                 160 gca atg gaa cca gat cgg gaa tac cat ttt gga caa gca gta cgg ttt       528
Ala Met Glu Pro Asp Arg Glu Tyr His Phe Gly Gln Ala Val Arg Phe
                165                 170                 175 gta tgt aac tca ggc tac aag att gaa gga gat gaa gaa atg cat tgt       576
Val Cys Asn Ser Gly Tyr Lys Ile Glu Gly Asp Glu Glu Met His Cys
            180                 185                 190 tca gac gat ggt ttt tgg agt aaa gag aaa cca aag tgt gtg gaa att       624
Ser Asp Asp Gly Phe Trp Ser Lys Glu Lys Pro Lys Cys Val Glu Ile
        195                 200                 205 tca tgc aaa tcc cca gat gtt ata aat gga tct cct ata tct cag aag       672
Ser Cys Lys Ser Pro Asp Val Ile Asn Gly Ser Pro Ile Ser Gln Lys
    210                 215                 220 att att tat aag gag aat gaa cga ttt caa tat aaa tgt aac atg ggt       720
Ile Ile Tyr Lys Glu Asn Glu Arg Phe Gln Tyr Lys Cys Asn Met Gly
225                 230                 235                 240
```

-continued

| | | |
|---|---|---|
| tat gaa tac agt gaa aga gga gat gct gta tgc act gaa tct gga tgg<br>Tyr Glu Tyr Ser Glu Arg Gly Asp Ala Val Cys Thr Glu Ser Gly Trp<br>                245                          250                          255 | 768 |
| cgt ccg ttg cct tca tgt gaa gaa aaa tca acc ttg aaa cct tgt gat<br>Arg Pro Leu Pro Ser Cys Glu Glu Lys Ser Thr Leu Lys Pro Cys Asp<br>260                          265                          270 | 816 |
| tat cca gac att aaa cat gga ggt cta tat cat gag aat atg cgt aga<br>Tyr Pro Asp Ile Lys His Gly Gly Leu Tyr His Glu Asn Met Arg Arg<br>            275                          280                          285 | 864 |
| cca tac ttt cca gta gct gta gga aaa tat tac tcc tat tac tgt gat<br>Pro Tyr Phe Pro Val Ala Val Gly Lys Tyr Tyr Ser Tyr Tyr Cys Asp<br>290                          295                          300 | 912 |
| gaa cat ttt gag act ccg tca gga agt tac tgg gat cac att cat tgc<br>Glu His Phe Glu Thr Pro Ser Gly Ser Tyr Trp Asp His Ile His Cys<br>305                          310                          315                          320 | 960 |
| aca caa gat gga tgg tcg cca gca gta cca tgc ctc aga aaa tgt tat<br>Thr Gln Asp Gly Trp Ser Pro Ala Val Pro Cys Leu Arg Lys Cys Tyr<br>                          325                          330                          335 | 1008 |
| ttt cct tat ttg gaa aat gga tat aat caa aat tat gga aga aag ttt<br>Phe Pro Tyr Leu Glu Asn Gly Tyr Asn Gln Asn Tyr Gly Arg Lys Phe<br>            340                          345                          350 | 1056 |
| gta cag ggt aaa tct ata gac gtt gcc tgc cat cct ggc tac gct ctt<br>Val Gln Gly Lys Ser Ile Asp Val Ala Cys His Pro Gly Tyr Ala Leu<br>                355                          360                          365 | 1104 |
| cca aaa gcg cag acc aca gtt aca tgt atg gag aat ggc tgg tct cct<br>Pro Lys Ala Gln Thr Thr Val Thr Cys Met Glu Asn Gly Trp Ser Pro<br>370                          375                          380 | 1152 |
| act ccc aga tgc atc cgt gtc aaa aca tgt tcc aaa tca agt ata gat<br>Thr Pro Arg Cys Ile Arg Val Lys Thr Cys Ser Lys Ser Ser Ile Asp<br>385                          390                          395                          400 | 1200 |
| att gag aat ggg ttt att tct gaa tct cag tat aca tat gcc tta aaa<br>Ile Glu Asn Gly Phe Ile Ser Glu Ser Gln Tyr Thr Tyr Ala Leu Lys<br>                    405                          410                          415 | 1248 |
| gaa aaa gca aaa tat caa tgc aaa cta gga tat gta aca gca gat ggt<br>Glu Lys Ala Lys Tyr Gln Cys Lys Leu Gly Tyr Val Thr Ala Asp Gly<br>                    420                          425                          430 | 1296 |
| gaa aca tca gga tca att aca tgt ggg aaa gat gga tgg tca gct caa<br>Glu Thr Ser Gly Ser Ile Thr Cys Gly Lys Asp Gly Trp Ser Ala Gln<br>                        435                          440                          445 | 1344 |
| ccc acg tgc att aaa tct ata aaa aca gat tgt ctc agt tta cct agc<br>Pro Thr Cys Ile Lys Ser Ile Lys Thr Asp Cys Leu Ser Leu Pro Ser<br>450                          455                          460 | 1392 |
| ttt gaa aat gcc ata ccc atg gga gag aag aag gat gtg tat aag gcg<br>Phe Glu Asn Ala Ile Pro Met Gly Glu Lys Lys Asp Val Tyr Lys Ala<br>465                          470                          475                          480 | 1440 |
| ggt gag caa gtg act tac act tgt gca aca tat tac aaa atg gat gga<br>Gly Glu Gln Val Thr Tyr Thr Cys Ala Thr Tyr Tyr Lys Met Asp Gly<br>                    485                          490                          495 | 1488 |
| gcc agt aat gta aca tgc att aat agc aga tgg aca gga agg cca aca<br>Ala Ser Asn Val Thr Cys Ile Asn Ser Arg Trp Thr Gly Arg Pro Thr<br>              500                          505                          510 | 1536 |
| tgc aga gac acc tcc tgt gtg aat ccg ccc aca gta caa aat gct tat<br>Cys Arg Asp Thr Ser Cys Val Asn Pro Pro Thr Val Gln Asn Ala Tyr<br>                515                          520                          525 | 1584 |
| ata gtg tcg aga cag atg agt aaa tat cca tct ggt gag aga gta cgt<br>Ile Val Ser Arg Gln Met Ser Lys Tyr Pro Ser Gly Glu Arg Val Arg<br>530                          535                          540 | 1632 |
| tat caa tgt agg agc cct tat gaa atg ttt ggg gat gaa gaa gtg atg<br>Tyr Gln Cys Arg Ser Pro Tyr Glu Met Phe Gly Asp Glu Glu Val Met | 1680 |

| | | | | |
|---|---|---|---|---|
| 545 | 550 | 555 | 560 | | tgt tta aat gga aac tgg acg gaa cca cct caa tgc aaa gat tct aca   1728
Cys Leu Asn Gly Asn Trp Thr Glu Pro Pro Gln Cys Lys Asp Ser Thr
                565                 570                 575 gga aaa tgt ggg ccc cct cca cct att gac aat ggg gac att act tca   1776
Gly Lys Cys Gly Pro Pro Pro Pro Ile Asp Asn Gly Asp Ile Thr Ser
        580                 585                 590 ttc ccg ttg tca gta tat gct cca gct tca tca gtt gag tac caa tgc   1824
Phe Pro Leu Ser Val Tyr Ala Pro Ala Ser Ser Val Glu Tyr Gln Cys
            595                 600                 605 cag aac ttg tat caa ctt gag ggt aac aag cga ata aca tgt aga aat   1872
Gln Asn Leu Tyr Gln Leu Glu Gly Asn Lys Arg Ile Thr Cys Arg Asn
                610                 615                 620 gga caa tgg tca gaa cca cca aaa tgc tta cat ccg tgt gta ata tcc   1920
Gly Gln Trp Ser Glu Pro Pro Lys Cys Leu His Pro Cys Val Ile Ser
625                 630                 635                 640 cga gaa att atg gaa aat tat aac ata gca tta agg tgg aca gcc aaa   1968
Arg Glu Ile Met Glu Asn Tyr Asn Ile Ala Leu Arg Trp Thr Ala Lys
                645                 650                 655 cag aag ctt tat tcg aga aca ggt gaa tca gtt gaa ttt gtg tgt aaa   2016
Gln Lys Leu Tyr Ser Arg Thr Gly Glu Ser Val Glu Phe Val Cys Lys
            660                 665                 670 cgg gga tat cgt ctt tca tca cgt tct cac aca ttg cga aca aca tgt   2064
Arg Gly Tyr Arg Leu Ser Ser Arg Ser His Thr Leu Arg Thr Thr Cys
        675                 680                 685 tgg gat ggg aaa ctg gag tat cca act tgt gca aaa aga tag            2106
Trp Asp Gly Lys Leu Glu Tyr Pro Thr Cys Ala Lys Arg
    690                 695                 700

<210> SEQ ID NO 46
<211> LENGTH: 701
<212> TYPE: PRT
<213> ORGANISM: Artificial Sequence
<220> FEATURE:
<223> OTHER INFORMATION: Synthetic Construct

<400> SEQUENCE: 46

Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
                20                  25                  30

Leu Thr Gly Ser Trp Ser Asp Gln Thr Tyr Pro Glu Gly Thr Gln Ala
            35                  40                  45

Ile Tyr Lys Cys Arg Pro Gly Tyr Arg Ser Leu Gly Asn Ile Ile Met
        50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
            100                 105                 110

Thr Cys Asn Glu Gly Tyr Gln Leu Leu Gly Glu Ile Asn Tyr Arg Glu
        115                 120                 125

Cys Asp Thr Asp Gly Trp Thr Asn Asp Ile Pro Ile Cys Glu Val Val
    130                 135                 140

Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe

```
            165                 170                 175
Val Cys Asn Ser Gly Tyr Lys Ile Glu Gly Asp Glu Met His Cys
            180                 185                 190

Ser Asp Asp Gly Phe Trp Ser Lys Glu Lys Pro Lys Cys Val Glu Ile
            195                 200                 205

Ser Cys Lys Ser Pro Asp Val Ile Asn Gly Ser Pro Ile Ser Gln Lys
    210                 215                 220

Ile Ile Tyr Lys Glu Asn Glu Arg Phe Gln Tyr Lys Cys Asn Met Gly
225                 230                 235                 240

Tyr Glu Tyr Ser Glu Arg Gly Asp Ala Val Cys Thr Glu Ser Gly Trp
            245                 250                 255

Arg Pro Leu Pro Ser Cys Glu Glu Lys Ser Thr Leu Lys Pro Cys Asp
            260                 265                 270

Tyr Pro Asp Ile Lys His Gly Gly Leu Tyr His Glu Asn Met Arg Arg
            275                 280                 285

Pro Tyr Phe Pro Val Ala Val Gly Lys Tyr Tyr Ser Tyr Tyr Cys Asp
            290                 295                 300

Glu His Phe Glu Thr Pro Ser Gly Ser Tyr Trp Asp His Ile His Cys
305                 310                 315                 320

Thr Gln Asp Gly Trp Ser Pro Ala Val Pro Cys Leu Arg Lys Cys Tyr
            325                 330                 335

Phe Pro Tyr Leu Glu Asn Gly Tyr Asn Gln Asn Tyr Gly Arg Lys Phe
            340                 345                 350

Val Gln Gly Lys Ser Ile Asp Val Ala Cys His Pro Gly Tyr Ala Leu
            355                 360                 365

Pro Lys Ala Gln Thr Thr Val Thr Cys Met Glu Asn Gly Trp Ser Pro
            370                 375                 380

Thr Pro Arg Cys Ile Arg Val Lys Thr Cys Ser Lys Ser Ser Ile Asp
385                 390                 395                 400

Ile Glu Asn Gly Phe Ile Ser Glu Ser Gln Tyr Thr Tyr Ala Leu Lys
            405                 410                 415

Glu Lys Ala Lys Tyr Gln Cys Lys Leu Gly Tyr Val Thr Ala Asp Gly
            420                 425                 430

Glu Thr Ser Gly Ser Ile Thr Cys Gly Lys Asp Gly Trp Ser Ala Gln
            435                 440                 445

Pro Thr Cys Ile Lys Ser Ile Lys Thr Asp Cys Leu Ser Leu Pro Ser
            450                 455                 460

Phe Glu Asn Ala Ile Pro Met Gly Glu Lys Lys Asp Val Tyr Lys Ala
465                 470                 475                 480

Gly Glu Gln Val Thr Tyr Thr Cys Ala Thr Tyr Tyr Lys Met Asp Gly
            485                 490                 495

Ala Ser Asn Val Thr Cys Ile Asn Ser Arg Trp Thr Gly Arg Pro Thr
            500                 505                 510

Cys Arg Asp Thr Ser Cys Val Asn Pro Pro Thr Val Gln Asn Ala Tyr
            515                 520                 525

Ile Val Ser Arg Gln Met Ser Lys Tyr Pro Ser Gly Glu Arg Val Arg
            530                 535                 540

Tyr Gln Cys Arg Ser Pro Tyr Glu Met Phe Gly Asp Glu Glu Val Met
545                 550                 555                 560

Cys Leu Asn Gly Asn Trp Thr Glu Pro Pro Gln Cys Lys Asp Ser Thr
            565                 570                 575

Gly Lys Cys Gly Pro Pro Pro Pro Ile Asp Asn Gly Asp Ile Thr Ser
            580                 585                 590
```

```
                Phe Pro Leu Ser Val Tyr Ala Pro Ala Ser Ser Val Glu Tyr Gln Cys
                    595                 600                 605

Gln Asn Leu Tyr Gln Leu Glu Gly Asn Lys Arg Ile Thr Cys Arg Asn
                610                 615                 620

Gly Gln Trp Ser Glu Pro Pro Lys Cys Leu His Pro Cys Val Ile Ser
                625                 630                 635                 640

Arg Glu Ile Met Glu Asn Tyr Asn Ile Ala Leu Arg Trp Thr Ala Lys
                                645                 650                 655

Gln Lys Leu Tyr Ser Arg Thr Gly Glu Ser Val Glu Phe Val Cys Lys
                            660                 665                 670

Arg Gly Tyr Arg Leu Ser Ser Arg Ser His Thr Leu Arg Thr Thr Cys
                        675                 680                 685

Trp Asp Gly Lys Leu Glu Tyr Pro Thr Cys Ala Lys Arg
                    690                 695                 700

<210> SEQ ID NO 47
<211> LENGTH: 2158
<212> TYPE: DNA
<213> ORGANISM: Artificial sequence
<220> FEATURE:
<223> OTHER INFORMATION: hfH1-4.678.17-20 containing leader and 5' UTR

<400> SEQUENCE: 47
ggacgttgtg aacagagtta gctggtaaat gtcctcttaa aagatccaaa aaatgagact    60
tctagcaaag attatttgcc ttatgttatg ggctatttgt gtagcagaag attgcaatga   120
acttcctcca agaagaaata cagaaattct gacaggttcc tggtctgacc aaacatatcc   180
agaaggcacc caggctatct ataaatgccg ccctggatat agatctcttg gaaatataat   240
aatggtatgc aggaagggag aatgggttgc tcttaatcca ttaaggaaat gtcagaaaag   300
gccctgtgga catcctggag atactccttt tggtactttt acccttacag gaggaaatgt   360
gtttgaatat ggtgtaaaag ctgtgtatac atgtaatgag gggtatcaat tgctaggtga   420
gattaattac cgtgaatgtg acacagatgg atggaccaat gatattccta tatgtgaagt   480
tgtgaagtgt ttaccagtga cagcaccaga gaatggaaaa attgtcagta gtgcaatgga   540
accagatcgg aataccatt ttggacaagc agtacggttt gtatgtaact caggctacaa   600
gattgaagga gatgaagaaa tgcattgttc agacgatggt ttttggagta agagaaaacc   660
aaagtgtgtg gaaatttcat gcaaatcccc agatgttata aatggatctc ctatatctca   720
gaagattatt tataaggaga atgaacgatt tcaatataaa tgtaacatgg ttatgaata   780 cagtgaaaga ggagatgctg tatgcactga atctggatgg cgtccgttgc cttcatgtga   840
agaaaaatca accttgaaac cttgtgatta tccagacatt aaacatggag gtctatatca   900
tgagaatatg cgtagaccat actttccagt agctgtagga aaatattact cctattactg   960
tgatgaacat tttgagactc cgtcaggaag ttactgggat cacattcatt gcacacaaga  1020
tggatggtcg ccagcagtac catgcctcag aaaatgttat tttccttatt tggaaaatgg  1080
atataatcaa aattatggaa gaaagtttgt acagggtaaa tctatagacg ttgcctgcca  1140
tcctggctac gctcttccaa aagcgcagac cacagttaca tgtatggaga atggctggtc  1200
tcctactccc agatgcatcc gtgtcaaaac atgttccaaa tcaagtatag atattgagaa  1260
tgggtttatt tctgaatctc agtatacata tgccttaaaa gaaaagcaa aatatcaatg  1320 caaactagga tatgtaacag cagatggtga aacatcagga tcaattacat gtgggaaaga  1380
tggatggtca gctcaaccca cgtgcattaa atctataaaa acagattgtc tcagtttacc  1440
```

-continued

```
tagctttgaa aatgccatac ccatgggaga gaagaaggat gtgtataagg cgggtgagca    1500
agtgacttac acttgtgcaa catattacaa aatggatgga gccagtaatg taacatgcat    1560
taatagcaga tggacaggaa ggccaacatg cagagacacc tcctgtgtga atccgcccac    1620
agtacaaaat gcttatatag tgtcgagaca gatgagtaaa tatccatctg gtgagagagt    1680
acgttatcaa tgtaggagcc cttatgaaat gtttggggat gaagaagtga tgtgtttaaa    1740
tggaaactgg acggaaccac ctcaatgcaa agattctaca ggaaaatgtg gccccctcc     1800 acctattgac aatggggaca ttacttcatt cccgttgtca gtatatgctc cagcttcatc    1860
agttgagtac caatgccaga acttgtatca acttgagggt aacaagcgaa taacatgtag    1920
aaatggacaa tggtcagaac caccaaaatg cttacatccg tgtgtaatat cccgagaaat    1980 tatgggaaaat tataacatag cattaaggtg gacagccaaa cagaagcttt attcgagaac    2040
aggtgaatca gttgaatttg tgtgtaaacg gggatatcgt ctttcatcac gttctcacac    2100
attgcgaaca acatgttggg atgggaaact ggagtatcca acttgtgcaa aaagatag     2158
```

<210> SEQ ID NO 48
<211> LENGTH: 701
<212> TYPE: PRT
<213> ORGANISM: Artificial Sequence
<220> FEATURE:
<223> OTHER INFORMATION: hFH 1-4.678.17-20

<400> SEQUENCE: 48

```
Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
                20                  25                  30

Leu Thr Gly Ser Trp Ser Asp Gln Thr Tyr Pro Glu Gly Thr Gln Ala
            35                  40                  45

Ile Tyr Lys Cys Arg Pro Gly Tyr Arg Ser Leu Gly Asn Ile Ile Met
        50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
            100                 105                 110

Thr Cys Asn Glu Gly Tyr Gln Leu Leu Gly Glu Ile Asn Tyr Arg Glu
        115                 120                 125

Cys Asp Thr Asp Gly Trp Thr Asn Asp Ile Pro Ile Cys Glu Val Val
    130                 135                 140

Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe
                165                 170                 175

Val Cys Asn Ser Gly Tyr Lys Ile Glu Gly Asp Glu Glu Met His Cys
            180                 185                 190

Ser Asp Asp Gly Phe Trp Ser Lys Glu Lys Pro Lys Cys Val Glu Ile
        195                 200                 205

Ser Cys Lys Ser Pro Asp Val Ile Asn Gly Ser Pro Ile Ser Gln Lys
    210                 215                 220

Ile Ile Tyr Lys Glu Asn Glu Arg Phe Gln Tyr Lys Cys Asn Met Gly
225                 230                 235                 240
```

```
Tyr Glu Tyr Ser Glu Arg Gly Asp Ala Val Cys Thr Glu Ser Gly Trp
                245                 250                 255

Arg Pro Leu Pro Ser Cys Glu Lys Ser Thr Leu Lys Pro Cys Asp
        260                 265                 270

Tyr Pro Asp Ile Lys His Gly Leu Tyr His Glu Asn Met Arg Arg
        275                 280                 285

Pro Tyr Phe Pro Val Ala Val Gly Lys Tyr Tyr Ser Tyr Tyr Cys Asp
    290                 295                 300

Glu His Phe Glu Thr Pro Ser Gly Ser Tyr Trp Asp His Ile His Cys
305                 310                 315                 320

Thr Gln Asp Gly Trp Ser Pro Ala Val Pro Cys Leu Arg Lys Cys Tyr
                325                 330                 335

Phe Pro Tyr Leu Glu Asn Gly Tyr Asn Gln Asn Tyr Gly Arg Lys Phe
            340                 345                 350

Val Gln Gly Lys Ser Ile Asp Val Ala Cys His Pro Gly Tyr Ala Leu
            355                 360                 365

Pro Lys Ala Gln Thr Thr Val Thr Cys Met Glu Asn Gly Trp Ser Pro
    370                 375                 380

Thr Pro Arg Cys Ile Arg Val Lys Thr Cys Ser Lys Ser Ser Ile Asp
385                 390                 395                 400

Ile Glu Asn Gly Phe Ile Ser Glu Ser Gln Tyr Thr Tyr Ala Leu Lys
                405                 410                 415

Glu Lys Ala Lys Tyr Gln Cys Lys Leu Gly Tyr Val Thr Ala Asp Gly
            420                 425                 430

Glu Thr Ser Gly Ser Ile Thr Cys Gly Lys Asp Gly Trp Ser Ala Gln
            435                 440                 445

Pro Thr Cys Ile Lys Ser Ile Lys Thr Asp Cys Leu Ser Leu Pro Ser
    450                 455                 460

Phe Glu Asn Ala Ile Pro Met Gly Glu Lys Lys Asp Val Tyr Lys Ala
465                 470                 475                 480

Gly Glu Gln Val Thr Tyr Thr Cys Ala Thr Tyr Tyr Lys Met Asp Gly
                485                 490                 495

Ala Ser Asn Val Thr Cys Ile Asn Ser Arg Trp Thr Gly Arg Pro Thr
            500                 505                 510

Cys Arg Asp Thr Ser Cys Val Asn Pro Pro Thr Val Gln Asn Ala Tyr
        515                 520                 525

Ile Val Ser Arg Gln Met Ser Lys Tyr Pro Ser Gly Glu Arg Val Arg
    530                 535                 540

Tyr Gln Cys Arg Ser Pro Tyr Glu Met Phe Gly Asp Glu Glu Val Met
545                 550                 555                 560

Cys Leu Asn Gly Asn Trp Thr Glu Pro Pro Gln Cys Lys Asp Ser Thr
                565                 570                 575

Gly Lys Cys Gly Pro Pro Pro Ile Asp Asn Gly Asp Ile Thr Ser
            580                 585                 590

Phe Pro Leu Ser Val Tyr Ala Pro Ala Ser Ser Val Glu Tyr Gln Cys
            595                 600                 605

Gln Asn Leu Tyr Gln Leu Glu Gly Asn Lys Arg Ile Thr Cys Arg Asn
    610                 615                 620

Gly Gln Trp Ser Glu Pro Pro Lys Cys Leu His Pro Cys Val Ile Ser
625                 630                 635                 640

Arg Glu Ile Met Glu Asn Tyr Asn Ile Ala Leu Arg Trp Thr Ala Lys
                645                 650                 655
```

```
Gln Lys Leu Tyr Ser Arg Thr Gly Glu Ser Val Glu Phe Val Cys Lys
            660                 665                 670

Arg Gly Tyr Arg Leu Ser Ser Arg Ser His Thr Leu Arg Thr Thr Cys
        675                 680                 685

Trp Asp Gly Lys Leu Glu Tyr Pro Thr Cys Ala Lys Arg
    690                 695                 700

<210> SEQ ID NO 49
<211> LENGTH: 27
<212> TYPE: DNA
<213> ORGANISM: Artificial sequence
<220> FEATURE:
<223> OTHER INFORMATION: hfHdSCR5R truncation variant primer

<400> SEQUENCE: 49
tgatttttct tcacatgaag gcaacgg                                       27

<210> SEQ ID NO 50
<211> LENGTH: 28
<212> TYPE: DNA
<213> ORGANISM: Artificial Sequence
<220> FEATURE:
<223> OTHER INFORMATION: hfHdSCR5F truncation primer

<400> SEQUENCE: 50
accttgaaac cttgtgatta tccagaca                                      28

<210> SEQ ID NO 51
<211> LENGTH: 24
<212> TYPE: DNA
<213> ORGANISM: Artificial Sequence
<220> FEATURE:
<223> OTHER INFORMATION: hfHdSCR9-18R truncation variant primer

<400> SEQUENCE: 51
agatttaatg cacgtgggtt gagc                                          24

<210> SEQ ID NO 52
<211> LENGTH: 26
<212> TYPE: DNA
<213> ORGANISM: Artificial Sequence
<220> FEATURE:
<223> OTHER INFORMATION: hfHdSCR9-18F truncation variant primer

<400> SEQUENCE: 52
aaagattcta caggaaaatg tgggcc                                        26

<210> SEQ ID NO 53
<211> LENGTH: 24
<212> TYPE: DNA
<213> ORGANISM: Artificial Sequence
<220> FEATURE:
<223> OTHER INFORMATION: hfHdSCR9-16R  truncation variant primer

<400> SEQUENCE: 53
agatttaatg cacgtgggtt gagc                                          24

<210> SEQ ID NO 54
<211> LENGTH: 31
<212> TYPE: DNA
<213> ORGANISM: Artificial sequence
<220> FEATURE:
<223> OTHER INFORMATION: hfHdSCR9-16F truncation variant primer

<400> SEQUENCE: 54
```

-continued

<210> SEQ ID NO 55
<211> LENGTH: 34
<212> TYPE: DNA
<213> ORGANISM: Artificial sequence
<220> FEATURE:
<223> OTHER INFORMATION: pCBAGhfH-ORF F truncation variant primer

<400> SEQUENCE: 55
ttttggcaaa gaattggacg ttgtgaacag agtt      34

<210> SEQ ID NO 56
<211> LENGTH: 36
<212> TYPE: DNA
<213> ORGANISM: Artificial sequence
<220> FEATURE:
<223> OTHER INFORMATION: CCTGAGGAGTGAATTCTATCTTTTTGCACAAGTTGG

<400> SEQUENCE: 56
cctgaggagt gaattctatc tttttgcaca agttgg      36

<210> SEQ ID NO 57
<211> LENGTH: 32
<212> TYPE: DNA
<213> ORGANISM: Artificial Sequence
<220> FEATURE:
<223> OTHER INFORMATION: dSCR5R

<400> SEQUENCE: 57
tctcttttct tcacagaaag gctgagaact cc      32

<210> SEQ ID NO 58
<211> LENGTH: 30
<212> TYPE: DNA
<213> ORGANISM: Artificial sequence
<220> FEATURE:
<223> OTHER INFORMATION: dSCR5F truncation varient primer

<400> SEQUENCE: 58
accttgaaac catgtgaatt tccacaattc      30

<210> SEQ ID NO 59
<211> LENGTH: 23
<212> TYPE: DNA
<213> ORGANISM: Artificial sequence
<220> FEATURE:
<223> OTHER INFORMATION: dSCR9-18F truncation varient primer

<400> SEQUENCE: 59
cgagactcaa cagggaaatg tgg      23

<210> SEQ ID NO 60
<211> LENGTH: 25
<212> TYPE: DNA
<213> ORGANISM: Artificial sequence
<220> FEATURE:
<223> OTHER INFORMATION: dSCR9-18R truncation primer

<400> SEQUENCE: 60
agacttaatg catgagggtt gaggt      25

<210> SEQ ID NO 61
<211> LENGTH: 140
<212> TYPE: DNA
<213> ORGANISM: Artificial sequence

<220> FEATURE:
<223> OTHER INFORMATION: AAV 5' ITR

<400> SEQUENCE: 61
ctgcgcgctc gctcgctcac tgaggccgcc cgggcaaagc ccgggcgtcg ggcgaccttt    60
ggtcgcccgg cctcagtgag cgagcgagcg cgcagagagg gagtggccaa ctccatcact   120
aggggttcct tgtagttaat                                              140

<210> SEQ ID NO 62
<211> LENGTH: 140
<212> TYPE: DNA
<213> ORGANISM: Artificial sequence
<220> FEATURE:
<223> OTHER INFORMATION: AAV 3' ITR

<400> SEQUENCE: 62
attaactaca aggaacccct agtgatggag ttggccactc cctctctgcg cgctcgctcg    60
ctcactgagg ccgggcgacc aaaggtcgcc cgacgcccgg gctttgcccg gcggcctca   120 gtgagcgagc gagcgcgcag                                              140

<210> SEQ ID NO 63
<211> LENGTH: 36
<212> TYPE: DNA
<213> ORGANISM: Artificial sequence
<220> FEATURE:
<223> OTHER INFORMATION: Hinc II 5'ITR F insertion primer

<400> SEQUENCE: 63
aagtgccacc tggtcgacgc tgcgcgctcg ctcgct                              36

<210> SEQ ID NO 64
<211> LENGTH: 38
<212> TYPE: DNA
<213> ORGANISM: Artificial sequence
<220> FEATURE:
<223> OTHER INFORMATION: Hinc II 5'ITR R insertion primer

<400> SEQUENCE: 64
tcaataatca atgtcgacat taactacaag gaacccct                            38

<210> SEQ ID NO 65
<211> LENGTH: 40
<212> TYPE: DNA
<213> ORGANISM: Artificial sequence
<220> FEATURE:
<223> OTHER INFORMATION: Pst I 3'ITR F insertion primer

<400> SEQUENCE: 65
gaagatccct cgacctgcag attaactaca aggaacccct                          40

<210> SEQ ID NO 66
<211> LENGTH: 38
<212> TYPE: DNA
<213> ORGANISM: Artificial sequence
<220> FEATURE:
<223> OTHER INFORMATION: Pst I 3'ITR R insertion primer

<400> SEQUENCE: 66
acgccaagct tgggctgcag ctgcgcgctc gctcgctc                            38

<210> SEQ ID NO 67
<211> LENGTH: 29
<212> TYPE: DNA

```
<213> ORGANISM: Artificial sequence
<220> FEATURE:
<223> OTHER INFORMATION: mFH primer 21st exon + intron

<400> SEQUENCE: 67
gcggccgccc tatccattag tgagtgtgg                                     29

<210> SEQ ID NO 68
<211> LENGTH: 27
<212> TYPE: DNA
<213> ORGANISM: Artificial sequence
<220> FEATURE:
<223> OTHER INFORMATION: R primer mFH 21st exon + intron

<400> SEQUENCE: 68
ctcgaggaca gcgatgtaag aacaatc                                       27

<210> SEQ ID NO 69
<211> LENGTH: 33
<212> TYPE: DNA
<213> ORGANISM: Artificial sequence
<220> FEATURE:
<223> OTHER INFORMATION: F primer mFH SCR20 (exon 22)

<400> SEQUENCE: 69
ggtaccaagc ttattgacca gctacagaca gta                                33

<210> SEQ ID NO 70
<211> LENGTH: 26
<212> TYPE: DNA
<213> ORGANISM: Artificial sequence
<220> FEATURE:
<223> OTHER INFORMATION: R primer mFH SCR20 (exon 22)

<400> SEQUENCE: 70
ggtaccctca ctcaggtgta ttactc                                        26

<210> SEQ ID NO 71
<211> LENGTH: 38
<212> TYPE: DNA
<213> ORGANISM: Artificial sequence
<220> FEATURE:
<223> OTHER INFORMATION: F primer W1183R mutation hFH

<400> SEQUENCE: 71
ggaatcacac aatataattc tcaaaaggag acacactg                           38

<210> SEQ ID NO 72
<211> LENGTH: 38
<212> TYPE: DNA
<213> ORGANISM: Artificial sequence
<220> FEATURE:
<223> OTHER INFORMATION: R primer W1183R mutation

<400> SEQUENCE: 72
cagtgtgtct ccttttgaga attatattgt gtgattcc                           38

<210> SEQ ID NO 73
<211> LENGTH: 21
<212> TYPE: DNA
<213> ORGANISM: Artificial sequence
<220> FEATURE:
<223> OTHER INFORMATION: F Primer for 480 bp 3' probe

<400> SEQUENCE: 73
agtgttgact cgtggagacc a                                             21
```

<210> SEQ ID NO 74
<211> LENGTH: 20
<212> TYPE: DNA
<213> ORGANISM: Artificial sequence
<220> FEATURE:
<223> OTHER INFORMATION: Neo-4 primer

<400> SEQUENCE: 74
cttgggtgga gaggctattc                                           20

<210> SEQ ID NO 75
<211> LENGTH: 20
<212> TYPE: DNA
<213> ORGANISM: Artificial sequence
<220> FEATURE:
<223> OTHER INFORMATION: Neo-5 primer

<400> SEQUENCE: 75
aggtgagatg acaggagatc                                           20

<210> SEQ ID NO 76

<400> SEQUENCE: 76

000

<210> SEQ ID NO 77
<211> LENGTH: 21
<212> TYPE: DNA
<213> ORGANISM: Artificial sequence
<220> FEATURE:
<223> OTHER INFORMATION: NEO-specific

<400> SEQUENCE: 77
gggtgggatt agataaatgc c                                         21

<210> SEQ ID NO 78
<211> LENGTH: 21
<212> TYPE: DNA
<213> ORGANISM: Artificial sequence
<220> FEATURE:
<223> OTHER INFORMATION: WR4 (FH-specific)

<400> SEQUENCE: 78
tactgtctgt agctggtcaa t                                         21

<210> SEQ ID NO 79
<211> LENGTH: 3759
<212> TYPE: DNA
<213> ORGANISM: Mus musculus
<220> FEATURE:
<221> NAME/KEY: CDS
<222> LOCATION: (1)..(3759)

<400> SEQUENCE: 79 atg gta cag cac aga ttt ctc ttg gag tca gtt ggt ccc aga aag atc      48
Met Val Gln His Arg Phe Leu Leu Glu Ser Val Gly Pro Arg Lys Ile
1               5                   10                  15 caa att atg aga ctg tca gca aga att att tgg ctt ata tta tgg act      96
Gln Ile Met Arg Leu Ser Ala Arg Ile Ile Trp Leu Ile Leu Trp Thr
                20                  25                  30 gtt tgt gca gca gaa gat tgt aaa ggt cct cct cca aga gaa aat tca     144
Val Cys Ala Ala Glu Asp Cys Lys Gly Pro Pro Pro Arg Glu Asn Ser
            35                  40                  45

```
gaa att ctc tca ggc tcg tgg tca gaa caa cta tat cca gaa ggc acc      192
Glu Ile Leu Ser Gly Ser Trp Ser Glu Gln Leu Tyr Pro Glu Gly Thr
        50                  55                  60 cag gct acc tac aaa tgc cgc cct gga tac cga aca ctt ggc act att      240
Gln Ala Thr Tyr Lys Cys Arg Pro Gly Tyr Arg Thr Leu Gly Thr Ile
65                  70                  75                  80 gta aaa gta tgc aag aat gga aaa tgg gtg gcg tct aac cca tcc agg      288
Val Lys Val Cys Lys Asn Gly Lys Trp Val Ala Ser Asn Pro Ser Arg
                85                  90                  95 ata tgt cgg aaa aag cct tgt ggg cat ccc gga gac aca ccc ttt ggg      336
Ile Cys Arg Lys Lys Pro Cys Gly His Pro Gly Asp Thr Pro Phe Gly
            100                 105                 110 tcc ttt agg ctg gca gtt gga tct caa ttt gag ttt ggt gca aag gtt      384
Ser Phe Arg Leu Ala Val Gly Ser Gln Phe Glu Phe Gly Ala Lys Val
        115                 120                 125 gtt tat acc tgt gat gat ggg tat caa cta tta ggt gaa att gat tac      432
Val Tyr Thr Cys Asp Asp Gly Tyr Gln Leu Leu Gly Glu Ile Asp Tyr
130                 135                 140 cgt gaa tgt ggt gca gat ggg tgg atc aat gat att cca cta tgt gaa      480
Arg Glu Cys Gly Ala Asp Gly Trp Ile Asn Asp Ile Pro Leu Cys Glu
145                 150                 155                 160 gtt gtg aag tgt cta cct gtg aca gaa ctc gag aat gga aga att gtg      528
Val Val Lys Cys Leu Pro Val Thr Glu Leu Glu Asn Gly Arg Ile Val
                165                 170                 175 agt ggt gca gca gaa aca gac cag gaa tac tat ttt gga cag gtg gtg      576
Ser Gly Ala Ala Glu Thr Asp Gln Glu Tyr Tyr Phe Gly Gln Val Val
            180                 185                 190 cgg ttt gaa tgc aat tca ggc ttc aag att gaa gga cat aag gaa att      624
Arg Phe Glu Cys Asn Ser Gly Phe Lys Ile Glu Gly His Lys Glu Ile
        195                 200                 205 cat tgc tca gaa aat ggc ctt tgg agc aat gaa aag cca cga tgt gtg      672
His Cys Ser Glu Asn Gly Leu Trp Ser Asn Glu Lys Pro Arg Cys Val
210                 215                 220 gaa att ctc tgc aca cca ccg cga gtg gaa aat gga gat ggt ata aat      720
Glu Ile Leu Cys Thr Pro Pro Arg Val Glu Asn Gly Asp Gly Ile Asn
225                 230                 235                 240 gtg aaa cca gtt tac aag gag aat gaa aga tac cac tat aag tgt aag      768
Val Lys Pro Val Tyr Lys Glu Asn Glu Arg Tyr His Tyr Lys Cys Lys
                245                 250                 255 cat ggt tat gtg ccc aaa gaa aga ggg gat gcc gtc tgc aca ggc tct      816
His Gly Tyr Val Pro Lys Glu Arg Gly Asp Ala Val Cys Thr Gly Ser
            260                 265                 270 gga tgg agt tct cag cct ttc tgt gaa gaa aag aga tgc tca cct cct      864
Gly Trp Ser Ser Gln Pro Phe Cys Glu Glu Lys Arg Cys Ser Pro Pro
        275                 280                 285 tat att cta aat ggt atc tac aca cct cac agg att ata cac aga agt      912
Tyr Ile Leu Asn Gly Ile Tyr Thr Pro His Arg Ile Ile His Arg Ser
290                 295                 300 gat gat gaa atc aga tat gaa tgt aat tat ggc ttc tat cct gta act      960
Asp Asp Glu Ile Arg Tyr Glu Cys Asn Tyr Gly Phe Tyr Pro Val Thr
305                 310                 315                 320 gga tca act gtt tca aag tgt aca ccc act ggc tgg atc cct gtt cca     1008
Gly Ser Thr Val Ser Lys Cys Thr Pro Thr Gly Trp Ile Pro Val Pro
                325                 330                 335 aga tgt acc ttg aaa cca tgt gaa ttt cca caa ttc aaa tat gga cgt     1056
Arg Cys Thr Leu Lys Pro Cys Glu Phe Pro Gln Phe Lys Tyr Gly Arg
            340                 345                 350 ctg tat tat gaa gag agc ctg aga ccc aac ttc cca gta tct ata gga     1104
Leu Tyr Tyr Glu Glu Ser Leu Arg Pro Asn Phe Pro Val Ser Ile Gly
        355                 360                 365
```

```
aat aag tac agc tat aag tgt gac aac ggg ttt tca cca cct tct ggg    1152
Asn Lys Tyr Ser Tyr Lys Cys Asp Asn Gly Phe Ser Pro Pro Ser Gly
    370             375                 380 tat tcc tgg gac tac ctt cgt tgc aca gca caa ggg tgg gag cct gaa    1200
Tyr Ser Trp Asp Tyr Leu Arg Cys Thr Ala Gln Gly Trp Glu Pro Glu
385             390                 395                 400 gtc cca tgc gtc agg aaa tgt gtt ttc cat tat gtg gag aat gga gac    1248
Val Pro Cys Val Arg Lys Cys Val Phe His Tyr Val Glu Asn Gly Asp
                405                 410                 415 tct gca tac tgg gaa aaa gta tat gtg cag ggt cag tct tta aaa gtc    1296
Ser Ala Tyr Trp Glu Lys Val Tyr Val Gln Gly Gln Ser Leu Lys Val
        420                 425                 430 cag tgt tac aat ggc tat agt ctt caa aat ggt caa gac aca atg aca    1344
Gln Cys Tyr Asn Gly Tyr Ser Leu Gln Asn Gly Gln Asp Thr Met Thr
            435                 440                 445 tgt aca gag aat ggc tgg tcc cct cct ccc aaa tgc atc cgt atc aag    1392
Cys Thr Glu Asn Gly Trp Ser Pro Pro Pro Lys Cys Ile Arg Ile Lys
    450                 455                 460 aca tgt tca gca tca gat ata cac att gac aat gga ttt ctt tct gaa    1440
Thr Cys Ser Ala Ser Asp Ile His Ile Asp Asn Gly Phe Leu Ser Glu
465                 470                 475                 480 tct tct tct ata tat gct cta aat aga gaa aca tcc tat aga tgt aag    1488
Ser Ser Ser Ile Tyr Ala Leu Asn Arg Glu Thr Ser Tyr Arg Cys Lys
                485                 490                 495 cag gga tat gtg aca aat act gga gaa ata tca gga tca ata act tgc    1536
Gln Gly Tyr Val Thr Asn Thr Gly Glu Ile Ser Gly Ser Ile Thr Cys
        500                 505                 510 ctt caa aat gga tgg tca cct caa ccc tca tgc att aag tct tgt gat    1584
Leu Gln Asn Gly Trp Ser Pro Gln Pro Ser Cys Ile Lys Ser Cys Asp
            515                 520                 525 atg cct gta ttt gag aat tct ata act aag aat act agg aca tgg ttt    1632
Met Pro Val Phe Glu Asn Ser Ile Thr Lys Asn Thr Arg Thr Trp Phe
    530                 535                 540 aag ctc aat gac aaa tta gac tat gaa tgt ctc gtt gga ttt gaa aat    1680
Lys Leu Asn Asp Lys Leu Asp Tyr Glu Cys Leu Val Gly Phe Glu Asn
545                 550                 555                 560 gaa tat aaa cat acc aaa ggc tct ata aca tgt act tat tat gga tgg    1728
Glu Tyr Lys His Thr Lys Gly Ser Ile Thr Cys Thr Tyr Tyr Gly Trp
                565                 570                 575 tct gat aca ccc tca tgt tat gaa aga gaa tgc agt gtt ccc act cta    1776
Ser Asp Thr Pro Ser Cys Tyr Glu Arg Glu Cys Ser Val Pro Thr Leu
        580                 585                 590 gac cga aaa cta gtc gtt tcc ccc aga aaa gaa aaa tac aga gtt gga    1824
Asp Arg Lys Leu Val Val Ser Pro Arg Lys Glu Lys Tyr Arg Val Gly
            595                 600                 605 gat ttg ttg gaa ttc tcc tgc cat tca gga cac aga gtt ggg cca gat    1872
Asp Leu Leu Glu Phe Ser Cys His Ser Gly His Arg Val Gly Pro Asp
    610                 615                 620 tca gtg caa tgc tac cac ttt gga tgg tct cct ggt ttc cct aca tgt    1920
Ser Val Gln Cys Tyr His Phe Gly Trp Ser Pro Gly Phe Pro Thr Cys
625                 630                 635                 640 aaa ggt caa gta gca tca tgt gca cca cct ctt gaa att ctt aat ggg    1968
Lys Gly Gln Val Ala Ser Cys Ala Pro Pro Leu Glu Ile Leu Asn Gly
                645                 650                 655 gaa att aat gga gca aaa aaa gtt gaa tac agc cat ggt gaa gtg gtg    2016
Glu Ile Asn Gly Ala Lys Lys Val Glu Tyr Ser His Gly Glu Val Val
        660                 665                 670 aaa tat gat tgc aaa cct aga ttc cta ctg aag gga ccc aat aaa atc    2064
Lys Tyr Asp Cys Lys Pro Arg Phe Leu Leu Lys Gly Pro Asn Lys Ile
```

-continued

```
                675                 680                 685
cag tgt gtt gat ggg aat tgg aca acc ttg cct gta tgt att gag gag    2112
Gln Cys Val Asp Gly Asn Trp Thr Thr Leu Pro Val Cys Ile Glu Glu
690                 695                 700 gag aga aca tgt gga gac att cct gaa ctt gaa cat ggc tct gcc aag    2160
Glu Arg Thr Cys Gly Asp Ile Pro Glu Leu Glu His Gly Ser Ala Lys
705                 710                 715                 720 tgt tct gtt cct ccc tac cac cat gga gat tca gtg gag ttc att tgt    2208
Cys Ser Val Pro Pro Tyr His His Gly Asp Ser Val Glu Phe Ile Cys
                725                 730                 735 gaa gaa aac ttc aca atg att gga cat ggg tca gtt tct tgc att agt    2256
Glu Glu Asn Phe Thr Met Ile Gly His Gly Ser Val Ser Cys Ile Ser
            740                 745                 750 gga aaa tgg acc cag ctt cct aaa tgt gtt gca aca gac caa ctg gag    2304
Gly Lys Trp Thr Gln Leu Pro Lys Cys Val Ala Thr Asp Gln Leu Glu
        755                 760                 765 aag tgt aga gtg ctg aag tca act ggc ata gaa gca ata aaa cca aaa    2352
Lys Cys Arg Val Leu Lys Ser Thr Gly Ile Glu Ala Ile Lys Pro Lys
770                 775                 780 ttg act gaa ttt acg cat aac tcc acc atg gat tac aaa tgt aga gac    2400
Leu Thr Glu Phe Thr His Asn Ser Thr Met Asp Tyr Lys Cys Arg Asp
785                 790                 795                 800 aag cag gag tac gaa cgc tca atc tgt atc aat gga aaa tgg gat cct    2448
Lys Gln Glu Tyr Glu Arg Ser Ile Cys Ile Asn Gly Lys Trp Asp Pro
                805                 810                 815 gaa cca aac tgt aca agc aaa aca tcc tgc cct cct cca ccg cag att    2496
Glu Pro Asn Cys Thr Ser Lys Thr Ser Cys Pro Pro Pro Gln Ile
            820                 825                 830 cca aat acc caa gtg att gaa acc acc gtg aaa tac ttg gat gga gaa    2544
Pro Asn Thr Gln Val Ile Glu Thr Thr Val Lys Tyr Leu Asp Gly Glu
        835                 840                 845 aaa tta tct gtt ctt tgc caa gac aat tac cta act cag gac tca gaa    2592
Lys Leu Ser Val Leu Cys Gln Asp Asn Tyr Leu Thr Gln Asp Ser Glu
850                 855                 860 gaa atg gtg tgc aaa gat gga agg tgg cag tca tta cct cgc tgc att    2640
Glu Met Val Cys Lys Asp Gly Arg Trp Gln Ser Leu Pro Arg Cys Ile
865                 870                 875                 880 gaa aaa att cca tgt tcc cag ccc cct aca ata gaa cat gga tct att    2688
Glu Lys Ile Pro Cys Ser Gln Pro Pro Thr Ile Glu His Gly Ser Ile
                885                 890                 895 aat tta ccc aga tct tca gaa gaa agg aga gat tcc att gag tcc agc    2736
Asn Leu Pro Arg Ser Ser Glu Glu Arg Arg Asp Ser Ile Glu Ser Ser
            900                 905                 910 agt cat gaa cat gga act aca ttc agc tat gtc tgt gat gat ggt ttc    2784
Ser His Glu His Gly Thr Thr Phe Ser Tyr Val Cys Asp Asp Gly Phe
        915                 920                 925 agg ata cct gaa gaa aat agg ata acc tgc tac atg gga aaa tgg agc    2832
Arg Ile Pro Glu Glu Asn Arg Ile Thr Cys Tyr Met Gly Lys Trp Ser
930                 935                 940 act cca cct cgc tgt gtt gga ctt cct tgt gga cct cca cct tca att    2880
Thr Pro Pro Arg Cys Val Gly Leu Pro Cys Gly Pro Pro Pro Ser Ile
945                 950                 955                 960 cct ctt ggt act gtt tct ctt gag cta gag agt tac caa cat ggg gaa    2928
Pro Leu Gly Thr Val Ser Leu Glu Leu Glu Ser Tyr Gln His Gly Glu
                965                 970                 975 gag gtt aca tac cat tgt tct aca ggc ttt gga att gat gga cca gca    2976
Glu Val Thr Tyr His Cys Ser Thr Gly Phe Gly Ile Asp Gly Pro Ala
            980                 985                 990 ttt att ata tgc gaa gga gga aag  tgg tct gac cca cca  aaa tgc ata   3024
```

```
                Phe Ile Ile Cys Glu Gly Gly Lys  Trp Ser Asp Pro Pro  Lys Cys Ile
                                995                1000               1005 aaa acg gat tgt gac gtt tta  ccc aca gtt aaa aat  gcc ata ata              3069
Lys Thr Asp Cys Asp Val Leu  Pro Thr Val Lys Asn  Ala Ile Ile
1010                1015                    1020 aga gga aag agc aaa aaa tca  tat agg aca gga gaa  caa gtg aca              3114
Arg Gly Lys Ser Lys Lys Ser  Tyr Arg Thr Gly Glu  Gln Val Thr
1025                1030                    1035 ttc aga tgt caa tct cct tat  caa atg aat ggc tca  gac act gtg              3159
Phe Arg Cys Gln Ser Pro Tyr  Gln Met Asn Gly Ser  Asp Thr Val
1040                1045                    1050 aca tgt gtt aat agt cgg tgg  att gga cag cca gta  tgc aaa gat              3204
Thr Cys Val Asn Ser Arg Trp  Ile Gly Gln Pro Val  Cys Lys Asp
1055                1060                    1065 aat tcc tgt gtg gat cca cca  cat gtg cca aat gct  act ata gta              3249
Asn Ser Cys Val Asp Pro Pro  His Val Pro Asn Ala  Thr Ile Val
1070                1075                    1080 aca agg acc aag aat aaa tat  cta cat ggt gac aga  gta cgt tat              3294
Thr Arg Thr Lys Asn Lys Tyr  Leu His Gly Asp Arg  Val Arg Tyr
1085                1090                    1095 gaa tgt aat aaa cct ttg gaa  cta ttt ggg caa gtg  gaa gtg atg              3339
Glu Cys Asn Lys Pro Leu Glu  Leu Phe Gly Gln Val  Glu Val Met
1100                1105                    1110 tgt gaa aat ggg ata tgg aca  gaa aaa cca aag tgc  cga gac tca              3384
Cys Glu Asn Gly Ile Trp Thr  Glu Lys Pro Lys Cys  Arg Asp Ser
1115                1120                    1125 aca ggg aaa tgt ggg cct cct  cca cct att gac aat  gga gac atc              3429
Thr Gly Lys Cys Gly Pro Pro  Pro Pro Ile Asp Asn  Gly Asp Ile
1130                1135                    1140 acc tcc ttg tca tta cca gta  tat gaa cca tta tca  tca gtt gaa              3474
Thr Ser Leu Ser Leu Pro Val  Tyr Glu Pro Leu Ser  Ser Val Glu
1145                1150                    1155 tat caa tgc cag aag tat tat  ctc ctt aag gga aag  aag aca ata              3519
Tyr Gln Cys Gln Lys Tyr Tyr  Leu Leu Lys Gly Lys  Lys Thr Ile
1160                1165                    1170 aca tgt aga aat gga aag tgg  tct gag cca cca aca  tgc tta cat              3564
Thr Cys Arg Asn Gly Lys Trp  Ser Glu Pro Pro Thr  Cys Leu His
1175                1180                    1185 gca tgt gta ata cca gaa aac  att atg gaa tca cac  aat ata att              3609
Ala Cys Val Ile Pro Glu Asn  Ile Met Glu Ser His  Asn Ile Ile
1190                1195                    1200 ctc aaa tgg aga cac act gaa  aag att tat tcc cat  tca ggg gag              3654
Leu Lys Trp Arg His Thr Glu  Lys Ile Tyr Ser His  Ser Gly Glu
1205                1210                    1215 gat att gaa ttt gga tgt aaa  tat gga tat tat aaa  gca aga gat              3699
Asp Ile Glu Phe Gly Cys Lys  Tyr Gly Tyr Tyr Lys  Ala Arg Asp
1220                1225                    1230 tca ccg cca ttt cgt aca aag  tgc att aat ggc acc  atc aat tat              3744
Ser Pro Pro Phe Arg Thr Lys  Cys Ile Asn Gly Thr  Ile Asn Tyr
1235                1240                    1245 ccc act tgt gta taa                                                         3759
Pro Thr Cys Val
    1250

<210> SEQ ID NO 80
<211> LENGTH: 1252
<212> TYPE: PRT
<213> ORGANISM: Mus musculus

<400> SEQUENCE: 80
```

```
Met Val Gln His Arg Phe Leu Leu Glu Ser Val Gly Pro Arg Lys Ile
 1               5                  10                  15

Gln Ile Met Arg Leu Ser Ala Arg Ile Ile Trp Leu Ile Leu Trp Thr
             20                  25                  30

Val Cys Ala Ala Glu Asp Cys Lys Gly Pro Pro Arg Glu Asn Ser
         35                  40                  45

Glu Ile Leu Ser Gly Ser Trp Ser Glu Gln Leu Tyr Pro Glu Gly Thr
 50                  55                  60

Gln Ala Thr Tyr Lys Cys Arg Pro Gly Tyr Arg Thr Leu Gly Thr Ile
 65                  70                  75                  80

Val Lys Val Cys Lys Asn Gly Lys Trp Val Ala Ser Asn Pro Ser Arg
                 85                  90                  95

Ile Cys Arg Lys Lys Pro Cys Gly His Pro Gly Asp Thr Pro Phe Gly
             100                 105                 110

Ser Phe Arg Leu Ala Val Gly Ser Gln Phe Glu Phe Gly Ala Lys Val
         115                 120                 125

Val Tyr Thr Cys Asp Asp Gly Tyr Gln Leu Leu Gly Glu Ile Asp Tyr
     130                 135                 140

Arg Glu Cys Gly Ala Asp Gly Trp Ile Asn Asp Ile Pro Leu Cys Glu
145                 150                 155                 160

Val Val Lys Cys Leu Pro Val Thr Glu Leu Glu Asn Gly Arg Ile Val
                 165                 170                 175

Ser Gly Ala Ala Glu Thr Asp Gln Glu Tyr Tyr Phe Gly Gln Val Val
             180                 185                 190

Arg Phe Glu Cys Asn Ser Gly Phe Lys Ile Glu Gly His Lys Glu Ile
         195                 200                 205

His Cys Ser Glu Asn Gly Leu Trp Ser Asn Glu Lys Pro Arg Cys Val
     210                 215                 220

Glu Ile Leu Cys Thr Pro Pro Arg Val Glu Asn Gly Asp Gly Ile Asn
225                 230                 235                 240

Val Lys Pro Val Tyr Lys Glu Asn Glu Arg Tyr His Tyr Lys Cys Lys
                 245                 250                 255

His Gly Tyr Val Pro Lys Glu Arg Gly Asp Ala Val Cys Thr Gly Ser
             260                 265                 270

Gly Trp Ser Ser Gln Pro Phe Cys Glu Glu Lys Arg Cys Ser Pro Pro
         275                 280                 285

Tyr Ile Leu Asn Gly Ile Tyr Thr Pro His Arg Ile Ile His Arg Ser
     290                 295                 300

Asp Asp Glu Ile Arg Tyr Glu Cys Asn Tyr Gly Phe Tyr Pro Val Thr
305                 310                 315                 320

Gly Ser Thr Val Ser Lys Cys Thr Pro Thr Gly Trp Ile Pro Val Pro
                 325                 330                 335

Arg Cys Thr Leu Lys Pro Cys Glu Phe Pro Gln Phe Lys Tyr Gly Arg
             340                 345                 350

Leu Tyr Tyr Glu Glu Ser Leu Arg Pro Asn Phe Pro Val Ser Ile Gly
         355                 360                 365

Asn Lys Tyr Ser Tyr Lys Cys Asp Asn Gly Phe Ser Pro Pro Ser Gly
     370                 375                 380

Tyr Ser Trp Asp Tyr Leu Arg Cys Thr Ala Gln Gly Trp Glu Pro Glu
385                 390                 395                 400

Val Pro Cys Val Arg Lys Cys Val Phe His Tyr Val Glu Asn Gly Asp
                 405                 410                 415

Ser Ala Tyr Trp Glu Lys Val Tyr Val Gln Gly Gln Ser Leu Lys Val
```

```
                420             425             430
Gln Cys Tyr Asn Gly Tyr Ser Leu Gln Asn Gly Gln Asp Thr Met Thr
            435             440             445

Cys Thr Glu Asn Gly Trp Ser Pro Pro Lys Cys Ile Arg Ile Lys
450             455             460

Thr Cys Ser Ala Ser Asp Ile His Ile Asp Asn Gly Phe Leu Ser Glu
465             470             475             480

Ser Ser Ser Ile Tyr Ala Leu Asn Arg Glu Thr Ser Tyr Arg Cys Lys
            485             490             495

Gln Gly Tyr Val Thr Asn Thr Gly Glu Ile Ser Gly Ser Ile Thr Cys
            500             505             510

Leu Gln Asn Gly Trp Ser Pro Gln Pro Ser Cys Ile Lys Ser Cys Asp
            515             520             525

Met Pro Val Phe Glu Asn Ser Ile Thr Lys Asn Thr Arg Thr Trp Phe
            530             535             540

Lys Leu Asn Asp Lys Leu Asp Tyr Glu Cys Leu Val Gly Phe Glu Asn
545             550             555             560

Glu Tyr Lys His Thr Lys Gly Ser Ile Thr Cys Thr Tyr Tyr Gly Trp
            565             570             575

Ser Asp Thr Pro Ser Cys Tyr Glu Arg Glu Cys Ser Val Pro Thr Leu
            580             585             590

Asp Arg Lys Leu Val Val Ser Pro Arg Lys Glu Lys Tyr Arg Val Gly
            595             600             605

Asp Leu Leu Glu Phe Ser Cys His Ser Gly His Arg Val Gly Pro Asp
            610             615             620

Ser Val Gln Cys Tyr His Phe Gly Trp Ser Pro Gly Phe Pro Thr Cys
625             630             635             640

Lys Gly Gln Val Ala Ser Cys Ala Pro Pro Leu Glu Ile Leu Asn Gly
            645             650             655

Glu Ile Asn Gly Ala Lys Lys Val Glu Tyr Ser His Gly Glu Val Val
            660             665             670

Lys Tyr Asp Cys Lys Pro Arg Phe Leu Leu Lys Gly Pro Asn Lys Ile
            675             680             685

Gln Cys Val Asp Gly Asn Trp Thr Thr Leu Pro Val Cys Ile Glu Glu
            690             695             700

Glu Arg Thr Cys Gly Asp Ile Pro Glu Leu Glu His Gly Ser Ala Lys
705             710             715             720

Cys Ser Val Pro Pro Tyr His His Gly Asp Ser Val Glu Phe Ile Cys
            725             730             735

Glu Glu Asn Phe Thr Met Ile Gly His Gly Ser Val Ser Cys Ile Ser
            740             745             750

Gly Lys Trp Thr Gln Leu Pro Lys Cys Val Ala Thr Asp Gln Leu Glu
            755             760             765

Lys Cys Arg Val Leu Lys Ser Thr Gly Ile Glu Ala Ile Lys Pro Lys
            770             775             780

Leu Thr Glu Phe Thr His Asn Ser Thr Met Asp Tyr Lys Cys Arg Asp
785             790             795             800

Lys Gln Glu Tyr Glu Arg Ser Ile Cys Ile Asn Gly Lys Trp Asp Pro
            805             810             815

Glu Pro Asn Cys Thr Ser Lys Thr Ser Cys Pro Pro Pro Gln Ile
            820             825             830

Pro Asn Thr Gln Val Ile Glu Thr Thr Val Lys Tyr Leu Asp Gly Glu
            835             840             845
```

-continued

Lys Leu Ser Val Leu Cys Gln Asp Asn Tyr Leu Thr Gln Asp Ser Glu
850                 855                 860

Glu Met Val Cys Lys Asp Gly Arg Trp Gln Ser Leu Pro Arg Cys Ile
865                 870                 875                 880

Glu Lys Ile Pro Cys Ser Gln Pro Pro Thr Ile Glu His Gly Ser Ile
                885                 890                 895

Asn Leu Pro Arg Ser Ser Glu Glu Arg Arg Asp Ser Ile Glu Ser Ser
                900                 905                 910

Ser His Glu His Gly Thr Thr Phe Ser Tyr Val Cys Asp Asp Gly Phe
        915                 920                 925

Arg Ile Pro Glu Glu Asn Arg Ile Thr Cys Tyr Met Gly Lys Trp Ser
930                 935                 940

Thr Pro Pro Arg Cys Val Gly Leu Pro Cys Gly Pro Pro Pro Ser Ile
945                 950                 955                 960

Pro Leu Gly Thr Val Ser Leu Glu Leu Glu Ser Tyr Gln His Gly Glu
                965                 970                 975

Glu Val Thr Tyr His Cys Ser Thr Gly Phe Gly Ile Asp Gly Pro Ala
                980                 985                 990

Phe Ile Ile Cys Glu Gly Gly Lys Trp Ser Asp Pro Pro Lys Cys Ile
        995                 1000                1005

Lys Thr Asp Cys Asp Val Leu Pro Thr Val Lys Asn Ala Ile Ile
    1010                1015                1020

Arg Gly Lys Ser Lys Lys Ser Tyr Arg Thr Gly Glu Gln Val Thr
    1025                1030                1035

Phe Arg Cys Gln Ser Pro Tyr Gln Met Asn Gly Ser Asp Thr Val
    1040                1045                1050

Thr Cys Val Asn Ser Arg Trp Ile Gly Gln Pro Val Cys Lys Asp
    1055                1060                1065

Asn Ser Cys Val Asp Pro Pro His Val Pro Asn Ala Thr Ile Val
    1070                1075                1080

Thr Arg Thr Lys Asn Lys Tyr Leu His Gly Asp Arg Val Arg Tyr
    1085                1090                1095

Glu Cys Asn Lys Pro Leu Glu Leu Phe Gly Gln Val Glu Val Met
    1100                1105                1110

Cys Glu Asn Gly Ile Trp Thr Glu Lys Pro Lys Cys Arg Asp Ser
    1115                1120                1125

Thr Gly Lys Cys Gly Pro Pro Pro Pro Ile Asp Asn Gly Asp Ile
    1130                1135                1140

Thr Ser Leu Ser Leu Pro Val Tyr Glu Pro Leu Ser Ser Val Glu
    1145                1150                1155

Tyr Gln Cys Gln Lys Tyr Tyr Leu Leu Lys Gly Lys Lys Thr Ile
    1160                1165                1170

Thr Cys Arg Asn Gly Lys Trp Ser Glu Pro Pro Thr Cys Leu His
    1175                1180                1185

Ala Cys Val Ile Pro Glu Asn Ile Met Glu Ser His Asn Ile Ile
    1190                1195                1200

Leu Lys Trp Arg His Thr Glu Lys Ile Tyr Ser His Ser Gly Glu
    1205                1210                1215

Asp Ile Glu Phe Gly Cys Lys Tyr Gly Tyr Tyr Lys Ala Arg Asp
    1220                1225                1230

Ser Pro Pro Phe Arg Thr Lys Cys Ile Asn Gly Thr Ile Asn Tyr
    1235                1240                1245

```
Pro Thr Cys Val
    1250

<210> SEQ ID NO 81
<211> LENGTH: 1800
<212> TYPE: DNA
<213> ORGANISM: Artificial sequence
<220> FEATURE:
<223> OTHER INFORMATION: mfH1-4.678.19-20
<220> FEATURE:
<221> NAME/KEY: CDS
<222> LOCATION: (1)..(1800)

<400> SEQUENCE: 81 atg gta cag cac aga ttt ctc ttg gag tca gtt ggt ccc aga aag atc      48
Met Val Gln His Arg Phe Leu Leu Glu Ser Val Gly Pro Arg Lys Ile
1               5                   10                  15 caa att atg aga ctg tca gca aga att att tgg ctt ata tta tgg act      96
Gln Ile Met Arg Leu Ser Ala Arg Ile Ile Trp Leu Ile Leu Trp Thr
            20                  25                  30 gtt tgt gca gca gaa gat tgt aaa ggt cct cct cca aga gaa aat tca     144
Val Cys Ala Ala Glu Asp Cys Lys Gly Pro Pro Pro Arg Glu Asn Ser
        35                  40                  45 gaa att ctc tca ggc tcg tgg tca gaa caa cta tat cca gaa ggc acc     192
Glu Ile Leu Ser Gly Ser Trp Ser Glu Gln Leu Tyr Pro Glu Gly Thr
    50                  55                  60 cag gct acc tac aaa tgc cgc cct gga tac cga aca ctt ggc act att     240
Gln Ala Thr Tyr Lys Cys Arg Pro Gly Tyr Arg Thr Leu Gly Thr Ile
65                  70                  75                  80 gta aaa gta tgc aag aat gga aaa tgg gtg gcg tct aac cca tcc agg     288
Val Lys Val Cys Lys Asn Gly Lys Trp Val Ala Ser Asn Pro Ser Arg
                85                  90                  95 ata tgt cgg aaa aag cct tgt ggg cat ccc gga gac aca ccc ttt ggg     336
Ile Cys Arg Lys Lys Pro Cys Gly His Pro Gly Asp Thr Pro Phe Gly
            100                 105                 110 tcc ttt agg ctg gca gtt gga tct caa ttt gag ttt ggt gca aag gtt     384
Ser Phe Arg Leu Ala Val Gly Ser Gln Phe Glu Phe Gly Ala Lys Val
        115                 120                 125 gtt tat acc tgt gat gat ggg tat caa cta tta ggt gaa att gat tac     432
Val Tyr Thr Cys Asp Asp Gly Tyr Gln Leu Leu Gly Glu Ile Asp Tyr
    130                 135                 140 cgt gaa tgt ggt gca gat ggg tgg atc aat gat att cca cta tgt gaa     480
Arg Glu Cys Gly Ala Asp Gly Trp Ile Asn Asp Ile Pro Leu Cys Glu
145                 150                 155                 160 gtt gtg aag tgt cta cct gtg aca gaa ctc gag aat gga aga att gtg     528
Val Val Lys Cys Leu Pro Val Thr Glu Leu Glu Asn Gly Arg Ile Val
                165                 170                 175 agt ggt gca gca gaa aca gac cag gaa tac tat ttt gga cag gtg gtg     576
Ser Gly Ala Ala Glu Thr Asp Gln Glu Tyr Tyr Phe Gly Gln Val Val
            180                 185                 190 cgg ttt gaa tgc aat tca ggc ttc aag att gaa gga cat aag gaa att     624
Arg Phe Glu Cys Asn Ser Gly Phe Lys Ile Glu Gly His Lys Glu Ile
        195                 200                 205 cat tgc tca gaa aat ggc ctt tgg agc aat gaa aag cca cga tgt gtg     672
His Cys Ser Glu Asn Gly Leu Trp Ser Asn Glu Lys Pro Arg Cys Val
    210                 215                 220 gaa att ctc tgc aca cca ccg cga gtg gaa aat gga gat ggt ata aat     720
Glu Ile Leu Cys Thr Pro Pro Arg Val Glu Asn Gly Asp Gly Ile Asn
225                 230                 235                 240 gtg aaa cca gtt tac aag gag aat gaa aga tac cac tat aag tgt aag     768
Val Lys Pro Val Tyr Lys Glu Asn Glu Arg Tyr His Tyr Lys Cys Lys
                245                 250                 255
```

-continued

```
cat ggt tat gtg ccc aaa gaa aga ggg gat gcc gtc tgc aca ggc tct    816
His Gly Tyr Val Pro Lys Glu Arg Gly Asp Ala Val Cys Thr Gly Ser
            260                 265                 270 gga tgg agt tct cag cct ttc tgt gaa gaa aag aga acc ttg aaa cca    864
Gly Trp Ser Ser Gln Pro Phe Cys Glu Glu Lys Arg Thr Leu Lys Pro
        275                 280                 285 tgt gaa ttt cca caa ttc aaa tat gga cgt ctg tat tat gaa gag agc    912
Cys Glu Phe Pro Gln Phe Lys Tyr Gly Arg Leu Tyr Tyr Glu Glu Ser
    290                 295                 300 ctg aga ccc aac ttc cca gta tct ata gga aat aag tac agc tat aag    960
Leu Arg Pro Asn Phe Pro Val Ser Ile Gly Asn Lys Tyr Ser Tyr Lys
305                 310                 315                 320 tgt gac aac ggg ttt tca cca cct tct ggg tat tcc tgg gac tac ctt   1008
Cys Asp Asn Gly Phe Ser Pro Pro Ser Gly Tyr Ser Trp Asp Tyr Leu
                325                 330                 335 cgt tgc aca gca caa ggg tgg gag cct gaa gtc cca tgc gtc agg aaa   1056
Arg Cys Thr Ala Gln Gly Trp Glu Pro Glu Val Pro Cys Val Arg Lys
            340                 345                 350 tgt gtt ttc cat tat gtg gag aat gga gac tct gca tac tgg gaa aaa   1104
Cys Val Phe His Tyr Val Glu Asn Gly Asp Ser Ala Tyr Trp Glu Lys
        355                 360                 365 gta tat gtg cag ggt cag tct tta aaa gtc cag tgt tac aat ggc tat   1152
Val Tyr Val Gln Gly Gln Ser Leu Lys Val Gln Cys Tyr Asn Gly Tyr
    370                 375                 380 agt ctt caa aat ggt caa gac aca atg aca tgt aca gag aat ggc tgg   1200
Ser Leu Gln Asn Gly Gln Asp Thr Met Thr Cys Thr Glu Asn Gly Trp
385                 390                 395                 400 tcc cct cct ccc aaa tgc atc cgt atc aag aca tgt tca gca tca gat   1248
Ser Pro Pro Pro Lys Cys Ile Arg Ile Lys Thr Cys Ser Ala Ser Asp
                405                 410                 415 ata cac att gac aat gga ttt ctt tct gaa tct tct tct ata tat gct   1296
Ile His Ile Asp Asn Gly Phe Leu Ser Glu Ser Ser Ser Ile Tyr Ala
            420                 425                 430 cta aat aga gaa aca tcc tat aga tgt aag cag gga tat gtg aca aat   1344
Leu Asn Arg Glu Thr Ser Tyr Arg Cys Lys Gln Gly Tyr Val Thr Asn
        435                 440                 445 act gga gaa ata tca gga tca ata act tgc ctt caa aat gga tgg tca   1392
Thr Gly Glu Ile Ser Gly Ser Ile Thr Cys Leu Gln Asn Gly Trp Ser
    450                 455                 460 cct caa ccc tca tgc att aag tct cga gac tca aca ggg aaa tgt ggg   1440
Pro Gln Pro Ser Cys Ile Lys Ser Arg Asp Ser Thr Gly Lys Cys Gly
465                 470                 475                 480 cct cct cca cct att gac aat gga gac atc acc tcc ttg tca tta cca   1488
Pro Pro Pro Pro Ile Asp Asn Gly Asp Ile Thr Ser Leu Ser Leu Pro
                485                 490                 495 gta tat gaa cca tta tca tca gtt gaa tat caa tgc cag aag tat tat   1536
Val Tyr Glu Pro Leu Ser Ser Val Glu Tyr Gln Cys Gln Lys Tyr Tyr
            500                 505                 510 ctc ctt aag gga aag aag aca ata aca tgt aga aat gga aag tgg tct   1584
Leu Leu Lys Gly Lys Lys Thr Ile Thr Cys Arg Asn Gly Lys Trp Ser
        515                 520                 525 gag cca cca aca tgc tta cat gca tgt gta ata cca gaa aac att atg   1632
Glu Pro Pro Thr Cys Leu His Ala Cys Val Ile Pro Glu Asn Ile Met
    530                 535                 540 gaa tca cac aat ata att ctc aaa tgg aga cac act gaa aag att tat   1680
Glu Ser His Asn Ile Ile Leu Lys Trp Arg His Thr Glu Lys Ile Tyr
545                 550                 555                 560 tcc cat tca ggg gag gat att gaa ttt gga tgt aaa tat gga tat tat   1728
Ser His Ser Gly Glu Asp Ile Glu Phe Gly Cys Lys Tyr Gly Tyr Tyr
```

```
                       565                 570                 575
aaa gca aga gat tca ccg cca ttt cgt aca aag tgc att aat ggc acc       1776
Lys Ala Arg Asp Ser Pro Pro Phe Arg Thr Lys Cys Ile Asn Gly Thr
            580                 585                 590 atc aat tat ccc act tgt gta taa                                       1800
Ile Asn Tyr Pro Thr Cys Val
            595
```

<210> SEQ ID NO 82
<211> LENGTH: 599
<212> TYPE: PRT
<213> ORGANISM: Artificial sequence
<220> FEATURE:
<223> OTHER INFORMATION: Synthetic Construct

<400> SEQUENCE: 82

```
Met Val Gln His Arg Phe Leu Leu Glu Ser Val Gly Pro Arg Lys Ile
1               5                   10                  15

Gln Ile Met Arg Leu Ser Ala Arg Ile Ile Trp Leu Ile Leu Trp Thr
            20                  25                  30

Val Cys Ala Ala Glu Asp Cys Lys Gly Pro Pro Arg Glu Asn Ser
        35                  40                  45

Glu Ile Leu Ser Gly Ser Trp Ser Glu Gln Leu Tyr Pro Glu Gly Thr
    50                  55                  60

Gln Ala Thr Tyr Lys Cys Arg Pro Gly Tyr Arg Thr Leu Gly Thr Ile
65                  70                  75                  80

Val Lys Val Cys Lys Asn Gly Lys Trp Val Ala Ser Asn Pro Ser Arg
                85                  90                  95

Ile Cys Arg Lys Lys Pro Cys Gly His Pro Gly Asp Thr Pro Phe Gly
            100                 105                 110

Ser Phe Arg Leu Ala Val Gly Ser Gln Phe Glu Phe Gly Ala Lys Val
        115                 120                 125

Val Tyr Thr Cys Asp Asp Gly Tyr Gln Leu Leu Gly Glu Ile Asp Tyr
    130                 135                 140

Arg Glu Cys Gly Ala Asp Gly Trp Ile Asn Asp Ile Pro Leu Cys Glu
145                 150                 155                 160

Val Val Lys Cys Leu Pro Val Thr Glu Leu Glu Asn Gly Arg Ile Val
                165                 170                 175

Ser Gly Ala Ala Glu Thr Asp Gln Glu Tyr Tyr Phe Gly Gln Val Val
            180                 185                 190

Arg Phe Glu Cys Asn Ser Gly Phe Lys Ile Glu Gly His Lys Glu Ile
        195                 200                 205

His Cys Ser Glu Asn Gly Leu Trp Ser Asn Glu Lys Pro Arg Cys Val
    210                 215                 220

Glu Ile Leu Cys Thr Pro Pro Arg Val Glu Asn Gly Asp Gly Ile Asn
225                 230                 235                 240

Val Lys Pro Val Tyr Lys Glu Asn Glu Arg Tyr His Tyr Lys Cys Lys
                245                 250                 255

His Gly Tyr Val Pro Lys Glu Arg Gly Asp Ala Val Cys Thr Gly Ser
            260                 265                 270

Gly Trp Ser Ser Gln Pro Phe Cys Glu Glu Lys Arg Thr Leu Lys Pro
        275                 280                 285

Cys Glu Phe Pro Gln Phe Lys Tyr Gly Arg Leu Tyr Tyr Glu Glu Ser
    290                 295                 300

Leu Arg Pro Asn Phe Pro Val Ser Ile Gly Asn Lys Tyr Ser Tyr Lys
305                 310                 315                 320
```

-continued

```
Cys Asp Asn Gly Phe Ser Pro Pro Ser Gly Tyr Ser Trp Asp Tyr Leu
                325                 330                 335

Arg Cys Thr Ala Gln Gly Trp Glu Pro Glu Val Pro Cys Val Arg Lys
            340                 345                 350

Cys Val Phe His Tyr Val Glu Asn Gly Asp Ser Ala Tyr Trp Glu Lys
        355                 360                 365

Val Tyr Val Gln Gly Gln Ser Leu Lys Val Gln Cys Tyr Asn Gly Tyr
    370                 375                 380

Ser Leu Gln Asn Gly Gln Asp Thr Met Thr Cys Thr Glu Asn Gly Trp
385                 390                 395                 400

Ser Pro Pro Pro Lys Cys Ile Arg Ile Lys Thr Cys Ser Ala Ser Asp
                405                 410                 415

Ile His Ile Asp Asn Gly Phe Leu Ser Glu Ser Ser Ser Ile Tyr Ala
            420                 425                 430

Leu Asn Arg Glu Thr Ser Tyr Arg Cys Lys Gln Gly Tyr Val Thr Asn
        435                 440                 445

Thr Gly Glu Ile Ser Gly Ser Ile Thr Cys Leu Gln Asn Gly Trp Ser
    450                 455                 460

Pro Gln Pro Ser Cys Ile Lys Ser Arg Asp Ser Thr Gly Lys Cys Gly
465                 470                 475                 480

Pro Pro Pro Pro Ile Asp Asn Gly Asp Ile Thr Ser Leu Ser Leu Pro
                485                 490                 495

Val Tyr Glu Pro Leu Ser Ser Val Glu Tyr Gln Cys Gln Lys Tyr Tyr
            500                 505                 510

Leu Leu Lys Gly Lys Lys Thr Ile Thr Cys Arg Asn Gly Lys Trp Ser
        515                 520                 525

Glu Pro Pro Thr Cys Leu His Ala Cys Val Ile Pro Glu Asn Ile Met
    530                 535                 540

Glu Ser His Asn Ile Ile Leu Lys Trp Arg His Thr Glu Lys Ile Tyr
545                 550                 555                 560

Ser His Ser Gly Glu Asp Ile Glu Phe Gly Cys Lys Tyr Gly Tyr Tyr
                565                 570                 575

Lys Ala Arg Asp Ser Pro Pro Phe Arg Thr Lys Cys Ile Asn Gly Thr
            580                 585                 590

Ile Asn Tyr Pro Thr Cys Val
        595

<210> SEQ ID NO 83
<211> LENGTH: 21
<212> TYPE: DNA
<213> ORGANISM: Artificial sequence
<220> FEATURE:
<223> OTHER INFORMATION: 480bp 3' probel R primer

<400> SEQUENCE: 83
agtgttgact cgtggagacc a                                              21
```